(12) United States Patent
Balog et al.

(10) Patent No.: US 9,675,571 B2
(45) Date of Patent: Jun. 13, 2017

(54) INHIBITORS OF INDOLEAMINE 2,3-DIOXYGENASE (IDO)

(71) Applicant: BRISTOL-MYERS SQUIBB COMPANY, Princeton, NJ (US)

(72) Inventors: James Aaron Balog, Lambertville, NJ (US); Audris Huang, New Hope, PA (US); Bin Chen, Lambertville, NJ (US); Libing Chen, Newtown, PA (US); Steven P. Seitz, Swarthmore, PA (US); Amy C. Hart, Ewing, NJ (US); Jay A. Markwalder, Lahaska, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/776,035

(22) PCT Filed: Mar. 12, 2014

(86) PCT No.: PCT/US2014/023948
§ 371 (c)(1),
(2) Date: Sep. 14, 2015

(87) PCT Pub. No.: WO2014/150677
PCT Pub. Date: Sep. 25, 2014

(65) Prior Publication Data
US 2016/0022619 A1    Jan. 28, 2016

Related U.S. Application Data

(60) Provisional application No. 61/791,224, filed on Mar. 15, 2013.

(51) Int. Cl.
| | |
|---|---|
| A61K 31/135 | (2006.01) |
| A61K 31/196 | (2006.01) |
| C07C 255/44 | (2006.01) |
| C07C 255/57 | (2006.01) |
| C07D 213/84 | (2006.01) |
| C07C 275/42 | (2006.01) |
| C07D 317/66 | (2006.01) |
| C07C 311/51 | (2006.01) |
| C07D 239/42 | (2006.01) |
| C07D 241/42 | (2006.01) |
| C07D 257/04 | (2006.01) |
| C07D 261/08 | (2006.01) |
| C07C 233/55 | (2006.01) |
| C07D 261/14 | (2006.01) |
| C07C 235/38 | (2006.01) |
| C07D 271/12 | (2006.01) |
| C07D 213/56 | (2006.01) |
| A61K 31/18 | (2006.01) |
| A61K 31/216 | (2006.01) |
| A61K 31/27 | (2006.01) |
| A61K 31/36 | (2006.01) |
| A61K 31/41 | (2006.01) |

(Continued)

(52) U.S. Cl.
CPC ........... *A61K 31/196* (2013.01); *A61K 31/18* (2013.01); *A61K 31/216* (2013.01); *A61K 31/27* (2013.01); *A61K 31/36* (2013.01); *A61K 31/41* (2013.01); *A61K 31/42* (2013.01); *A61K 31/4245* (2013.01); *A61K 31/44* (2013.01); *A61K 31/498* (2013.01); *A61K 31/505* (2013.01); *A61K 45/06* (2013.01); *A61N 5/10* (2013.01); *C07C 69/743* (2013.01); *C07C 233/55* (2013.01); *C07C 235/38* (2013.01); *C07C 255/44* (2013.01); *C07C 255/57* (2013.01); *C07C 271/28* (2013.01); *C07C 275/42* (2013.01); *C07C 311/47* (2013.01); *C07C 311/51* (2013.01); *C07D 213/56* (2013.01); *C07D 213/75* (2013.01); *C07D 213/84* (2013.01); *C07D 239/42* (2013.01); *C07D 241/42* (2013.01); *C07D 257/04* (2013.01); *C07D 261/08* (2013.01); *C07D 261/14* (2013.01); *C07D 271/12* (2013.01); *C07D 317/66* (2013.01); *C07B 2200/07* (2013.01); *C07C 2101/02* (2013.01); *C07C 2101/08* (2013.01); *C07C 2101/14* (2013.01); *C07C 2102/42* (2013.01)

(58) Field of Classification Search
USPC ................. 514/183, 185, 188, 613, 624
See application file for complete search history.

(56) References Cited

U.S. PATENT DOCUMENTS

| | | | | |
|---|---|---|---|---|
| 2013/0177590 A1* | 7/2013 | Combs | ................ | C07D 271/08 424/204.1 |
| 2016/0060237 A1* | 3/2016 | Balog | ................ | C07C 275/42 514/249 |

FOREIGN PATENT DOCUMENTS

| | | |
|---|---|---|
| CN | 101429151 A | 5/2009 |
| WO | WO02/46146 A1 | 6/2002 |

(Continued)

OTHER PUBLICATIONS

Kong, L. et al., "Recent advances of IDO Inhibitors", Chinese Journal of Medicinal Chemistry, vol. 19 (2), p. 147-154 (2009), abstract considered.

(Continued)

*Primary Examiner* — Pancham Bakshi
(74) *Attorney, Agent, or Firm* — Elliott Korsen; Maureen S. Gibbons; Serena Farquharson-Torres

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or inflammatory disorders utilizing the compounds of the invention.

11 Claims, No Drawings

(51) Int. Cl.
*A61K 31/42* (2006.01)
*A61K 31/4245* (2006.01)
*A61K 31/44* (2006.01)
*A61K 31/498* (2006.01)
*A61K 31/505* (2006.01)
*A61K 45/06* (2006.01)
*A61N 5/10* (2006.01)
*C07C 69/743* (2006.01)
*C07C 271/28* (2006.01)
*C07C 311/47* (2006.01)
*C07D 213/75* (2006.01)

(56) References Cited

FOREIGN PATENT DOCUMENTS

| WO | WO2007/075598 A2 | 7/2007 |
| WO | WO2008/058178 A1 | 5/2008 |
| WO | WO2013/107164 A | 7/2013 |
| WO | WO2014/150646 A1 | 9/2014 |

OTHER PUBLICATIONS

Lancellotti, S. et al., "Biochemical Properties of Indoleamine 2,3-dioxygenase: From Structure to Optimized Design of Inhibitors", Current Medicinal Chemistry, vol. 18, pp. 2205-2214 (2011).

\* cited by examiner

INHIBITORS OF INDOLEAMINE 2,3-DIOXYGENASE (IDO)

CROSS-REFERENCE TO RELATED APPLICATIONS

This application claims the benefit of U.S. Provisional Application No. 61/791,224, filed Mar. 15, 2013, the disclosure of which is incorporated herein by reference in its entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Tryptophan is an amino acid which is essential for cell proliferation and survival. Indoleamine-2,3-dioxygenase is a heme-containing intracellular enzyme that catalyzes the first and rate-determining step in the degradation of the essential amino acid L-tryptophan to N-formyl-kynurenine. N-formyl-kynurenine is then metabolized by multiple steps to eventually produce nicotinamide adenine dinucleotide (NAD+). Tryptophan catabolites produced from N-formyl-kynurenine, such as kynurenine, are known to be preferentially cytotoxic to T-cells. Thus an overexpression of IDO can lead to increased tolerance in the tumor microenvironment. IDO overexpression has been shown to be an independent prognostic factor for decreased survival in patients with melanoma, pancreatic, colorectal and endometrial cancers among others. Moreover, IDO has been found to be implicated in neurologic and psychiatric disorders including mood idsorders as well as other chronic diseases characterized by IDO activation and tryptophan depletiion, such as viral infections, for example AIDS, Alzheimer's disease, cancers including T-cell leukemia and colon cancer, autimmune diseases, diseases of the eye such as cataracts, bacterial infections such as Lyme disease, and streptococcal infections.

Accordingly, an agent which is safe and effective in inhibiting production of IDO would be a most welcomed addition to the physician's armamentarium.

SUMMARY OF THE INVENTION

The present invention provides compounds and/or pharmaceutically acceptable salts thereof, stereoisomers thereof or tautomers thereof, methods of modulating or inhibiting the enzymatic activity of IDO, and methods for treating various medical conditions using said compounds.

The present invention also provides processes and intermediates for making the compounds of the present invention and/or pharmaceutically acceptable salts thereof or stereoisomers thereof or tautomers thereof.

The present invention also provides pharmaceutical compositions comprising a pharmaceutically acceptable carrier and one or more of the compounds of the present invention and/or pharmaceutically acceptable salts thereof or stereoisomers thereof or tautomers thereof.

The compounds of the invention and/or pharmaceutically acceptable salts thereof or stereoisomers thereof or tautomers thereof may be used in the treatment and/or prophylaxis of multiple diseases or disorders associated with enzymatic activity of IDO inhibition, such as cancer, viral infections, autoimmune diseases, and other maladies.

The compounds of the invention and/or pharmaceutically acceptable salts thereof or stereoisomers thereof or tautomers thereof may be used in therapy.

The compounds of the invention and/or pharmaceutically acceptable salts thereof or stereoisomers thereof or tautomers thereof may be used for the manufacture of a medicament for the treatment and/or prophylaxis of multiple diseases or disorders associated with enzymatic activity of IDO.

The compounds of the invention and/or pharmaceutically acceptable salts thereof or stereoisomers thereof or tautomers thereof can be used alone, in combination with other compounds of the present invention and/or pharmaceutically acceptable salts thereof or stereoisomers thereof or tautomers thereof, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides compounds of Formula (I)

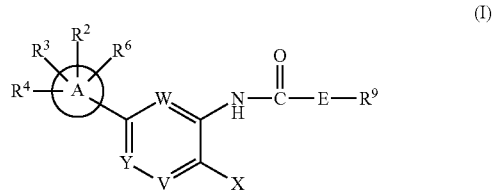

where
X is

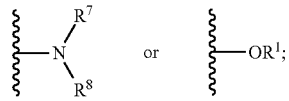

E is NH or $CH_2$;
W is N or $CR^{10}$;
Y is N or $CR^{11}$;
V is N or $CR^{12}$;

is an optionally substituted $C_3$-$C_8$ cycloalkyl;
$R^1$ is optionally substituted aryl, optionally substituted aryl-$C_1$-$C_{10}$-alkyl, or optionally substituted $C_1$-$C_{10}$ alkyl;
$R^2$ is COOH, optionally substituted heteroaryl or optionally substituted —$CONHSO_2R^{14}$;
$R^3$ is H, optionally substituted $C_1$-$C_{10}$ alkyl or halo;

$R^4$ is H, optionally substituted $C_1$-$C_{10}$ alkyl, or halo;
$R^6$ is H;
$R^7$ and $R^8$ are independently selected from optionally substituted $C_1$-$C_{10}$ alkyl, optionally substituted $C_1$-$C_{10}$ alkoxy, optionally substituted $C_1$-$C_{10}$-alkoxy-$C_1$-$C_{10}$-alkyl, optionally substituted $C_3$-$C_8$ cycloalkyl, optionally substituted aryl, optionally substituted aryl-$C_1$-$C_{10}$-alkyl, optionally substituted heteroaryl, optionally substituted $C_2$-$C_{10}$ alkenyl, optionally substituted $C_2$-$C_{10}$ alkynyl, or optionally substituted $C_4$-$C_8$ cycloalkenyl;

$R^9$ is optionally substituted aryl, optionally substituted $C_1$-$C_{10}$ alkylaryl, optionally substituted $C_3$-$C_8$ cycloalkylaryl, optionally substituted $C_1$-$C_{10}$ alkoxyaryl, optionally substituted $C_1$-$C_{10}$ alkyl heteroaryl, optionally substituted heteroaryl, or optionally substituted

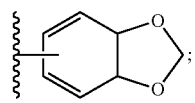

$R^{10}$ is H or halo;
$R^{11}$ is H or halo; and
$R^{12}$ is H, optionally substituted $C_1$-$C_{10}$ alkyl, or optionally substituted $C_2$-$C_{10}$ alkenyl;
$R^{14}$ is $CF_3$, optionally substituted $C_3$-$C_8$ cycloalkyl or optionally substituted $C_1$-$C_{10}$ alkyl;
and/or a stereoisomer, tautomer or a pharmaceutically acceptable salt thereof.

In a second aspect, the invention provides a compound of Formula (II) within the scope of the first aspect of the structure

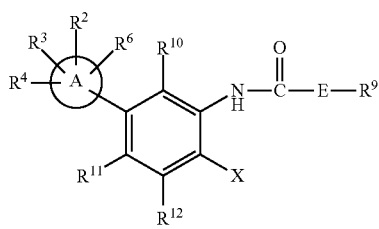

(II)

where
X is

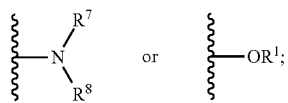

E is NH or $CH_2$;

is an optionally substituted $C_3$-$C_8$ cycloalkyl;
$R^1$ is optionally substituted aryl, optionally substituted aryl-$C_1$-$C_{10}$-alkyl, or optionally substituted $C_1$-$C_{10}$ alkyl;
$R^2$ is COOH, optionally substituted heteroaryl or optionally substituted —CONHSO$_2$R$^{14}$;

$R^3$ is H, optionally substituted $C_1$-$C_{10}$ alkyl or halo;
$R^4$ is H, $C_1$-$C_{10}$ alkyl, or halo;
$R^7$ and $R^8$ are independently selected from optionally substituted $C_1$-$C_{10}$ alkyl, optionally substituted $C_1$-$C_{10}$ alkoxy, optionally substituted $C_1$-$C_{10}$-alkoxy-$C_1$-$C_{10}$-alkyl, optionally substituted $C_3$-$C_8$ cycloalkyl, optionally substituted aryl, optionally substituted aryl-$C_1$-$C_{10}$-alkyl, optionally substituted heteroaryl, optionally substituted $C_2$-$C_{10}$ alkenyl, optionally substituted $C_2$-$C_{10}$ alkynyl, or optionally substituted $C_4$-$C_8$ cycloalkenyl,
each $R^7$ and $R^8$ group being optionally substituted, where possible, with 1 or 2 groups independently selected from optionally substituted $C_1$-$C_{10}$ alkyl, optionally substituted $C_2$-$C_{10}$ alkenyl, halo, CN, or OR$^{20}$,
where $R^{20}$ is H or optionally substituted $C_1$-$C_{10}$ alkyl;
$R^9$ is optionally substituted aryl, optionally substituted $C_1$-$C_{10}$ alkylaryl, optionally substituted $C_3$-$C_8$ cycloalkylaryl, optionally substituted $C_1$-$C_{10}$ alkoxyaryl, optionally substituted $C_1$-$C_{10}$ alkyl heteroaryl, optionally substituted heteroaryl, or optionally substituted

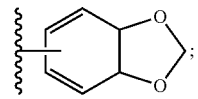

$R^{10}$ is H or halo;
$R^{11}$ is H or halo; and
$R^{12}$ is H, optionally substituted $C_1$-$C_{10}$ alkyl, or optionally substituted $C_2$-$C_{10}$ alkenyl;
$R^{14}$ is $CF_3$, optionally substituted $C_3$-$C_8$ cycloalkyl or optionally substituted $C_1$-$C_{10}$ alkyl;
and/or a stereoisomer, tautomer or a pharmaceutically acceptable salt thereof In a third aspect, the invention provides a compound of Formula (I) or (II) within the scope of the first or second aspect wherein E is NH.

In a fourth aspect, the invention provides a compound of Formula (I) or (II) within the scope of one or more of the previous aspects wherein E is $CH_2$.

In a fifth aspect, the invention provides a compound of Formula (I) or (II) within the scope of one or more of the previous aspects wherein

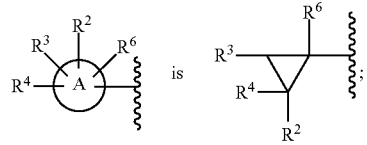

X is NR$^7$R$^8$;
E is NH;
$R^2$ is COOH, or —CONHSO$_2$R$^{14}$;
$R^3$ is H or $C_1$-$C_6$ alkyl;
$R^4$ is H, $C_1$-$C_6$ alkyl, or halo;
$R^6$ is H;

$R^7$ and $R^8$ are independently selected from $C_1$-$C_6$ alkyl, $C_1$-$C_6$ alkoxy, $C_3$-$C_8$ cycloalkyl, or $C_1$-$C_6$-alkoxy-$C_1$-$C_6$-alkyl;

$R^9$ is optionally substituted aryl, optionally substituted $C_1$-$C_6$ alkylaryl, optionally substituted $C_3$-$C_8$ cycloalkylaryl, optionally substituted $C_1$-$C_6$ alkoxyaryl, optionally substituted heteroaryl, optionally substituted $C_1$-$C_6$ alkyl heteroaryl, or

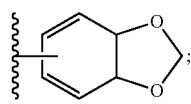

$R^{10}$ is H;

$R^{11}$ is halo or H; and $R^{12}$ is H;

$R^{14}$ is $CF_3$, optionally substituted $C_3$-$C_6$ cycloalkyl or optionally substituted $C_1$-$C_6$ alkyl;

and/or a stereoisomer, tautomer or a pharmaceutically acceptable salt thereof.

In a sixth aspect, the invention provides a compound of Formula (I) or (II) within the scope of one or more of the previous aspects wherein $R^7$ and $R^8$ are independently selected from

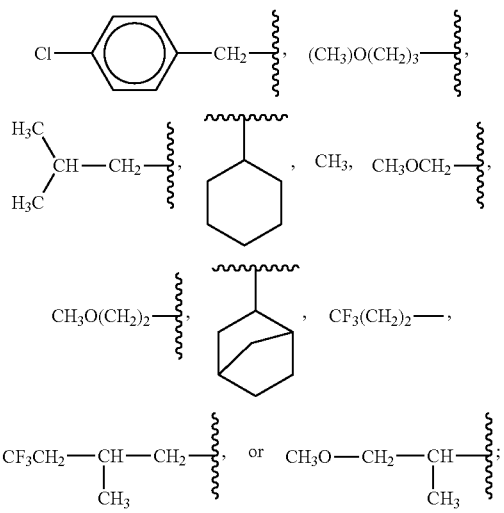

$R^9$ is

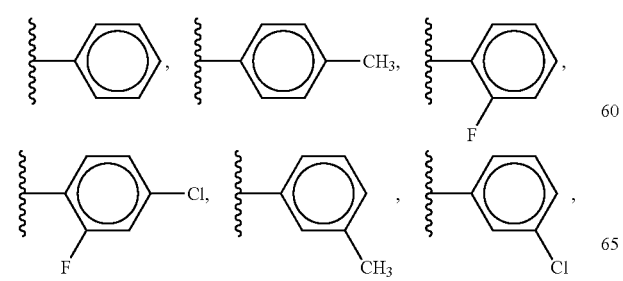

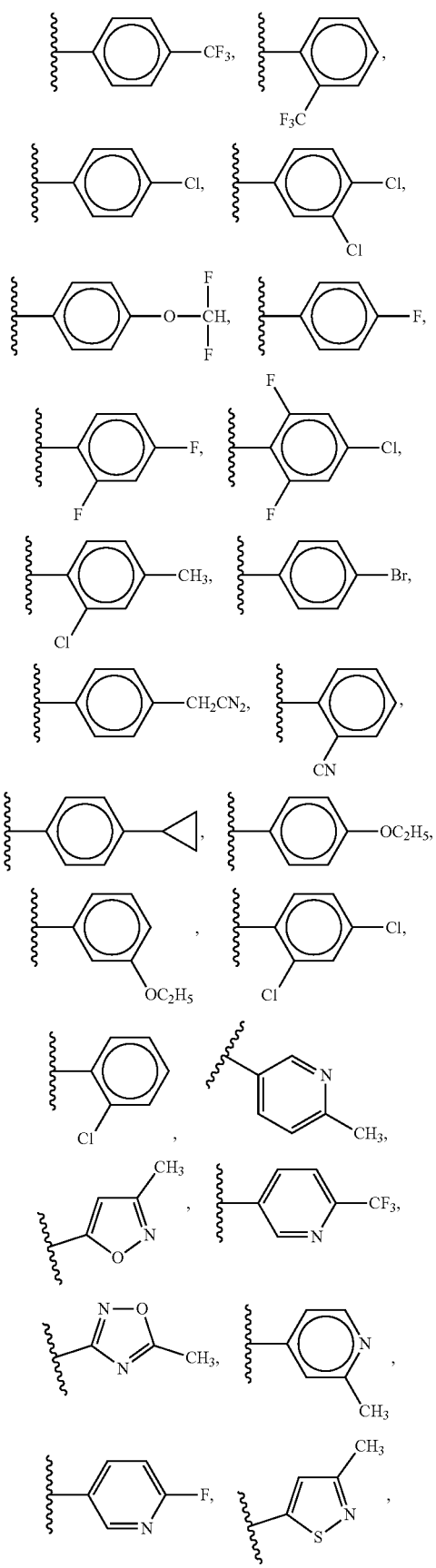

-continued

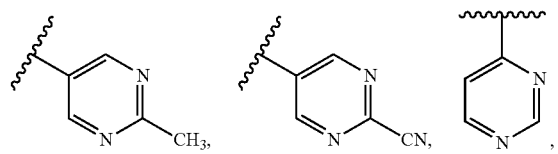

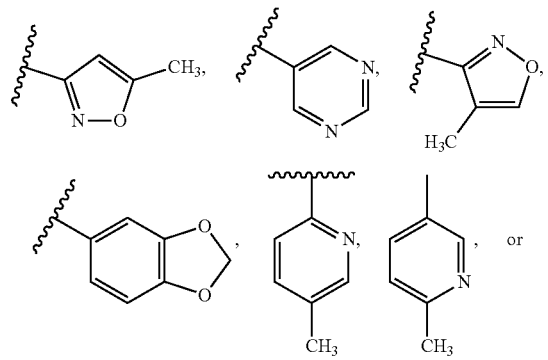

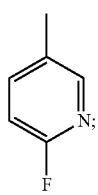

and/or a stereoisomer, tautomer or a pharmaceutically acceptable salt thereof

In another aspect, the invention provides a compound of Formula (I) or (II) within the scope of one or more of the previous aspects wherein

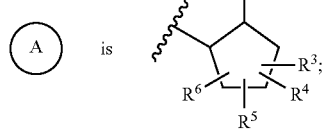

E is NH;
X is

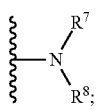

$R^2$ is COOH;
$R^3$, $R^4$, $R^5$ and $R^6$ are H;
$R^7$ and $R^8$ are independently selected from $C_1$-$C_{10}$ alkyl;
$R^9$ is $C_1$-$C_{10}$ alkylaryl;

and/or a stereoisomer, tautomer or a pharmaceutically acceptable salt thereof.

In another aspect, the invention provides a compound of Formula (I) or (II) within the scope of one or more of the previous aspects wherein $R^7$ and $R^8$ are each

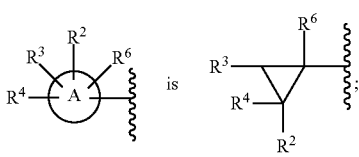

and
$R^9$ is

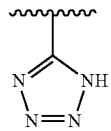

and/or a stereoisomer, tautomer or a pharmaceutically acceptable salt thereof.

In another aspect, the invention provides a compound of Formula (I) or (II) within the scope of one or more of the previous aspects wherein

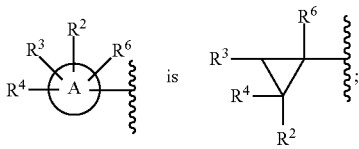

X is $OR^1$;
E is NH;
$R^2$ is COOH,

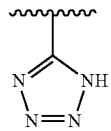

or —$CONHSO_2R^{14}$;
$R^3$, $R^4$, $R^5$ and $R^6$ are H;
$R^1$ is optionally substituted aryl, optionally substituted aryl-$C_1$-$C_6$-alkyl, or optionally substituted $C_1$-$C_6$ alkyl;
$R^9$ is optionally substituted aryl or $C_1$-$C_6$ alkylaryl;
$R^{12}$ is H, $C_1$-$C_6$ alkyl, $C_2$-$C_6$ alkenyl, or halo;
and/or a stereoisomer, tautomer or a pharmaceutically acceptable salt thereof.

In another aspect, the invention provides a compound of Formula (I) or (II) within the scope of one or more of the previous aspects wherein E is $CH_2$;

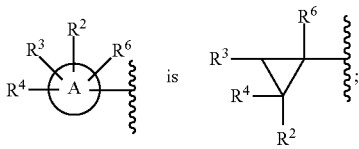

X is —$NR^7R^8$;
$R^2$ is COOH;
$R^7$ and $R^8$ are independently selected from $C_1$-$C_6$ alkyl;
$R^9$ is $C_1$-$C_6$ alkyl 5- to 7-membered monocyclic heteroaryl or $C_1$-$C_6$ alkylaryl;

and/or a stereoisomer, tautomer or a pharmaceutically acceptable salt thereof.

In another aspect, the invention provides a compound of Formula (I) or (II) within the scope of one or more of the previous aspects wherein $R^2$ is COOH;

$R^7$ and $R^8$ are independently selected from

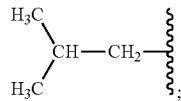

$R^9$ is

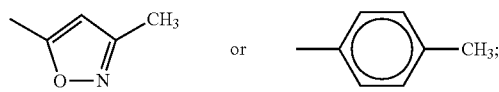

and/or a stereoisomer, tautomer or a pharmaceutically acceptable salt thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another embodiment, the compounds of the invention have human IDO $IC_{50}$ values ≤250 nM.

In another embodiment, the compounds of the invention have human IDO $IC_{50}$ values ≤50 nM.

In another embodiment, the compounds of the invention have human IDO $IC_{50}$ values ≤20 nM.

In another embodiment, the compounds of the invention have human IDO $IC_{50}$ values ≤10 nM.

II. Other Embodiments of the Invention

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising: a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

III. Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity by forming a covalent bond with the enzyme.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as *pemphigus vulgaris*, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-10 or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas (I) and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141 W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

DEFINITIONS

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms.

Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

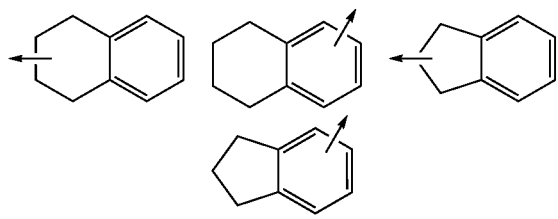

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl$)_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group (s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

General Experimental

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using prepacked REDISEP® $R_f$ silica gel columns on a CombiFlash Companion machine.

Air- or moisture-sensitive reactions were generally performed under an atmosphere of nitrogen or argon in anhydrous solvents (EMD DRISOLV®). Zinc (-325 mesh) for nitro group reduction was obtained from Alfa Aesar. Reaction concentrations indicated in the tables and procedures are given in units of molar and are approximate. Temperatures are given in degrees Celsius. Reactions were monitored for completeness by thin layer chromatography (TLC) or tandem liquid chromatography-mass spectroscopy (LCMS). For TLC, 0.25 mm plates coated with Silica60/F254 were used with visualization by UV light at ~254 nM, exposure to iodine vapor, or heating with PMA (phosphomolybdic acid solution), ninhydrin in ethanol, anisaldehyde solution, or ceric ammonium molybdate solution.

Unless otherwise specified, "dried" refers to the addition of anhydrous $MgSO_4$ followed by filtration and rinsing the residual solids with an appropriate organic solvent. "Stripped" means concentration under reduced pressure, generally on a rotary evaporator. "Silica gel chromatography", "flash chromatography", or "chromatographed on silica gel" refers to glass column chromatography performed in a manner similar to that described by Still (*J. Org. Chem.*, 43:2923 (1978)). Typically silica gel 60 (EMD, 230-400 mesh ASTM) is used with solvents from JT Baker or Mallinckrodt. HPLC refers to purification by reverse-phase high-performance liquid chromatography using the stated columns and mobile phases. Analytical HPLC runs were performed using the columns, flow rates, and mobile phases indicated. It is understood that analytical HPLC retention times ($T_r$) may be dependent on temperature, pH, and other factors. ISCO refers to chromatography on pre-packed silica gel cartridges using automated systems marketed by Teledyne Isco. For all chromatographic purifications the isolation of product by concentration of the appropriate fractions by evaporation at or below ambient pressure is implied. Melting points were determined on a Thomas-Hoover Uni-Melt apparatus and are uncorrected. Generally, mass spectral results are reported as the $(M+H)^+$ value. For halogenated compounds where two or more peaks are significant, m/z for one peak in the cluster, generally the most intense, is reported. $^1$H NMR spectra were recorded on dilute solutions at 400 or 500 MHz on VARIAN® or JEOL® instruments in the solvents indicated. Chemical shifts are reported in parts per million (ppm) downfield from internal tetramethylsilane (TMS) or from the position of TMS inferred by the deuterated NMR solvent. Apparent multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities.

Preparative Reverse Phase HPLC was performed with a linear gradient elution using $H_2O$/MeOH or $H_2O$/MeCN mixtures buffered with 0.1% trifluoroacetic acid or 10 mM $NH_4OAc$ and detection at 220 nm on one of the following columns: Shimadzu Sunfire S10 30×250 mm (flow rate=40 mL/min), or C18 PHENOMENEX® Luna 55 ODS 21×100 mm (flow rate=20 mL/min), or YMC 55 ODS 20×100 mm (flow rate=20 mL/min) or Waters XBridge C18 19×250 mm (flow rate=20 mL/min). Preparative Supercritical Fluid Chromatography (SFC) was performed using 78% $CO_2$/MeOH buffered with 0.1% diethylamine and detection at 220 nm on a CHIRALPAK® AS-H IDS 25×3 cm column (flow rate=85 mL/min).

Unless otherwise specified, the various substituents of the compounds as employed herein are defined in the same manner as compounds of the invention of Formula (I).

For ease of reference, the following abbreviations are used herein.

ABBREVIATIONS

AcOH acetic acid
$Ac_2O$ acetic anhydride
ADDP 1,1'-(azodicarbonyl)dipiperidine
aq. aqueous
Bn benzyl
Boc t-butyl carbamate
$Boc_2O$ di-t-butyl dicarbonate
Bu butyl
Cbz benzyl carbamate
conc. concentrated
DCE dichloroethane
DCM dichloromethane
DIAD diisopropyl azodicarboxylate
DIEA diisopropylethylamine
DMAP 4-N,N-dimethylaminopyridine
DMF dimethyl formamide
DMSO dimethyl sulfoxide
DMT-MM 4-(4,6-dimethoxy-1,3,5-triazin-2-yl)-4-methylmorpholinium chloride
EDC 1-(dimethylaminopropyl)-3-ethylcarbodiimide hydrochloride
Et ethyl
EtOAc ethyl acetate
EtOH ethanol
$Et_2O$ diethyl ether
$Et_3N$ triethylamine
Fmoc 9-fluorenylmethyl carbamate
h hour(s)
HATU O-(7-azabenzotriazol-1-yl)-N,N,N',N'-tetramethyluronium hexafluorophosphate
HOAt 1-hydroxy-7-azabenzotriazole
HPLC high pressure liquid chromatography
i-PrOH isopropanol
KOAc potassium acetate
min minute(s)
Me methyl
MeCN acetonitrile
MeOH methanol
$Me_2NH$ dimethyl amine
NaHMDS sodium bis(trimethylsilyl)amide
$Na(OAc)_3BH$ sodium triacetoxyborohydride
n-BuLi n-butyl lithium
NCS N-chlorosuccinimide
NMM N-methylmorpholine
NMP n-methylpyrrolidinone
NMR nuclear magnetic resonance
OTf trifluoromethylsulfonyloxy
Pd/C palladium on carbon
$Pd(dppf)_2Cl_2$ [1,1'-bis(diphenylphosphino)ferrocene]dichloropalladium(II)
$Pd(OAc)_2$ palladium acetate
$Pd(PPh_3)_4$ tetrakis(triphenylphosphine)palladium
$Pd_2(dba)_3$ tris(dibenzylideneacetone)dipalladium(0)
Ph phenyl
PhMe toluene
$Ph_2TfN$ 1,1,1-trifluoro-N-phenyl-N-(trifluoromethyl)sulfonyl methanesulfonamide
$PPh_3$ triphenyl phosphorus
rt room temperature
sat. saturated
t-Bu tertiary butyl
t-BuOH tertiary butanol
TFA trifluoroacetic acid
$Tf_2O$ trifluoromethylsulfonic anhydride
THF tetrahydrofuran
TMS trimethylsilyl
TsO p-toluenesulfonyl Synthesis The Compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Greene, T. W. et al., *Protecting Groups in Organic Synthesis*, 3rd Edition, Wiley (1999)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry: Reactions, Mechanisms, and Structure*. 4th Edition, Wiley & Sons, New York, N.Y. (1992); Katritzky, A. R. et al., eds., *Comprehensive Organic Functional Groups Transformations*, 1st Edition, Elsevier Science Inc., Tarrytown, N.Y. (1995); Larock, R. C., *Comprehensive Organic Transformations*, VCH Publishers, Inc., New York, N.Y. (1989), and references therein.

Methods for synthesis of enantiopure cis-iodocyclopropyl acid see Organic Process Research & Development 2004, 8, 353-359

Compounds of the invention I may be prepared according to the following schemes utilizing chemical transformations familiar to anyone of ordinary proficiency in the art of organic/medicinal chemistry. References to many of these transformations can be found in March's Advanced Organic Chemistry Reactions, Mechanisms, and Structure, Fifth Edition by Michael B. Smith and Jerry March, Wiley-Interscience, New York, 2001, or other standard texts on the topic of synthetic organic chemistry.

Compounds (i) where Z is Cl, Br, or I and Q is a halogen are commercially available or can be prepared utilizing standard transformations known to those of ordinary proficiency in the art of organic/medicinal chemistry. Treatment of an alcohol or phenol $R_1OH$ and a base of suitable strength to deprotonate it, ideally in a solvent such as THF, DMF, NMP followed by (i), affords adducts (ii). Depending upon the steric requirements and the degree of nucleophilicity of the alkoxide, heating may be required. Suitable bases for alcohols include, but are not be limited to, sodium hydride and organometallics such as Grignard or alkyllithium reagents. Typically, phenols are deprotonated with bases like sodium or potassium carbonate. Reduction of the nitro group in compounds (ii) to afford anilines (iii) can be effected by various means including catalytic hydrogenation and dissolving metal reductions both in their various forms. See: Modern Synthetic Reactions, Second Edition by Herbert O. House, Benjamin Cummings, Menlo Park, Calif., 1972. A preferred method for effecting this reduction without removal of the halogen substituent Z involves stirring a solution of (ii) in a wet alcoholic solvent with an acid such as ammonium chloride and finely divided zinc. The aniline (iii) can be coupled with boronate ester dimers such as bis(neopentylglycolato)diboron by heating in a solvent such as DMSO, dioxane or DMF in the presence of a base such as potassium acetate and a catalyst such as $Cl_2Pd(dppf)$ to give aryl boronate esters (iv). Coupling of the boronic acid or ester (iv) with substituted cyclopropyl iodide of structure (v), preferably under the conditions of Suzuki (See: Kotha, S. et al., *Tetrahedron*, 58:9633-9695 (2002)) affords compounds of general structure (vi). Typically, this reaction is performed by heating to around 95° C. the halide and the boronic acid or ester with a base such as aqueous tribasic sodium or potassium phosphate or sodium or potassium carbonate in a solvent such as dioxane, DMF, THF, or NMP using a catalyst such as tetrakis(triphenylphosphine)palladium or $Cl_2Pd(dppf)$. Many variations on this reaction involving the use of different temperatures, solvents, bases, anhydrous conditions, catalysts, boronate derivatives, and halide surrogates such as triflates are known to those skilled in the art of organic/medicinal chemistry. Recently, mild conditions have been reported for the coupling of sensitive boronic acid derivatives. See: Kinzel, T.; Zhang, Y.; Buchwald, S. L. J. Am. Chem. Soc. 2010, 132(40), 14073-14075. Related coupling reactions for the conversion of (iv) and other intermediates described in later schemes into compounds of the invention include the Heck (olefin, See Heck, R. F. et al J. Org. Chem. 1979, (44), 4078), Stille (organostannane, See Stille, J. K. Angew. Chem. Int. Ed. Engl. 1986, (25), 508), Sonogashira (acetylene See: Sonogashira, K.; Tohda, Y.; Hagihara, N. Tetrahedron Lett. 1975, 16(50), 4467-4470.), and Negishi (organozinc) coupling reactions. Treatment of anilines (vi) with an isocyanate $R^9N{=}C{=}O$, affords urea compounds of the invention I (Z=OR). Typically, this reaction is performed in a solvent such as THF at a temperature between ambient and the boiling point of the solvent.

Scheme 1

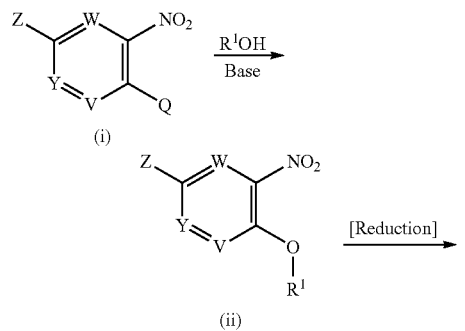

Scheme 2 describes a preparation of compounds of the invention I similar to that of Scheme 1 but with the transformations performed in a different order. In this scheme the Suzuki or related coupling is performed on intermediate (vii) to afford aniline (viii) which is derivatized by reaction of an isocyanate $R^9N{=}C{=}O$ to afford compounds of the invention I (Z=OR$^1$).

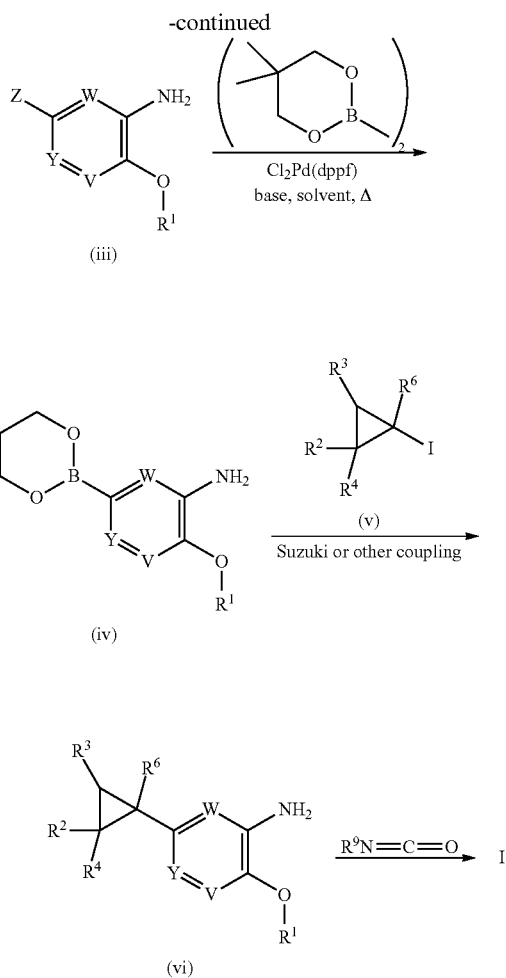

Scheme 2

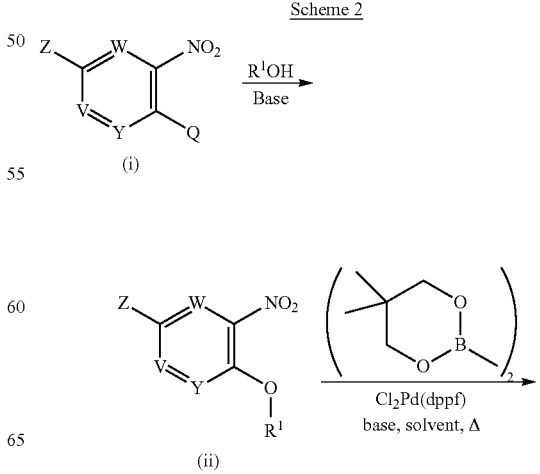

-continued

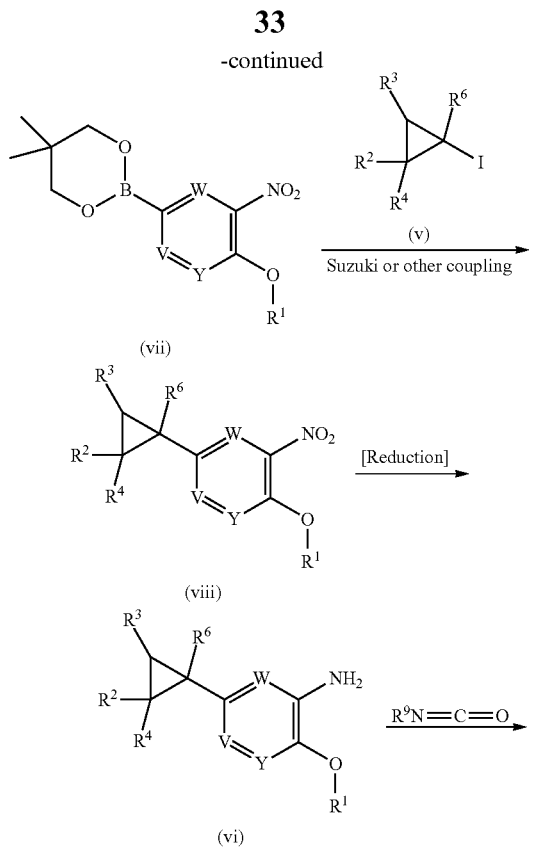

Treatment of compounds (i) with amines HNR⁷R⁸ (Scheme 4) and a suitable base in a solvent such as THF, DMF, NMP, or the like affords intermediates (ix). Generally heating is required. Suitable bases include, but are not limited to aliphatic tertiary amines or an excess of the reacting primary or secondary amine HNR⁷R⁸. Reduction of nitroaromatics (ix) under the conditions described above affords the primary anilines (x) which can be transformed into boronic acids and/or esters (xi) as in Scheme 1. Coupling of (xi) with a suitable cyclopropyliodide (v), furnishes compound (xii) which can be treated with an isocyanate as described in Scheme 1 to give compounds of the invention I (Z=NR⁷R⁸).

Scheme 3 was inadvertently omitted.

Scheme 4

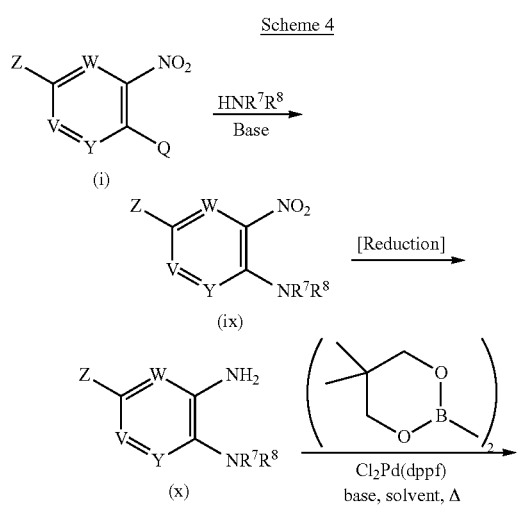

-continued

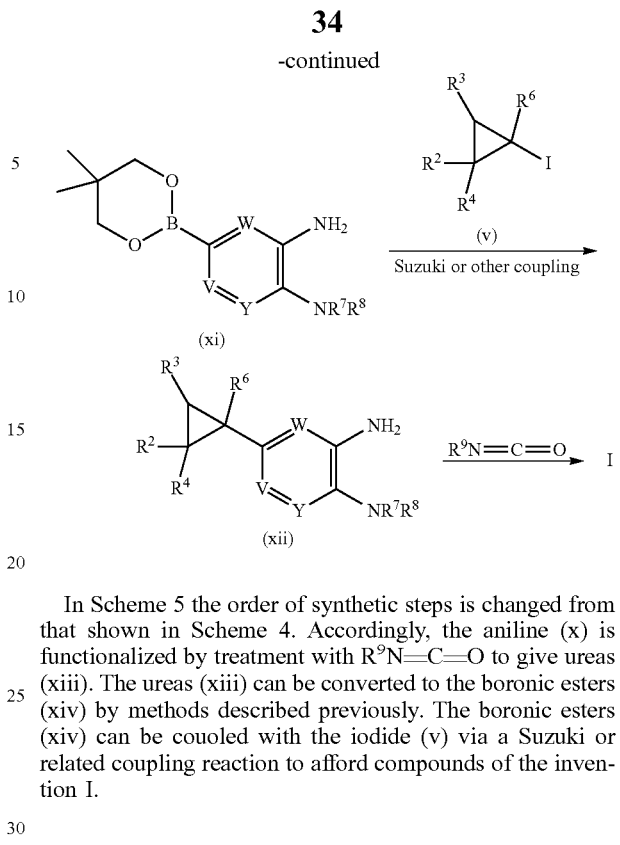

In Scheme 5 the order of synthetic steps is changed from that shown in Scheme 4. Accordingly, the aniline (x) is functionalized by treatment with R⁹N=C=O to give ureas (xiii). The ureas (xiii) can be converted to the boronic esters (xiv) by methods described previously. The boronic esters (xiv) can be couoled with the iodide (v) via a Suzuki or related coupling reaction to afford compounds of the invention I.

Scheme 5

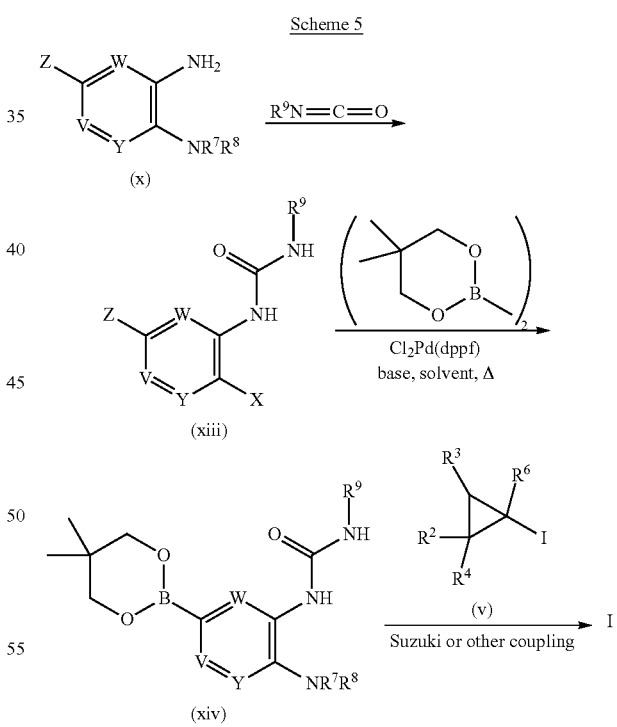

Scheme 6 describes an additional method for the preparation of compounds of the invention I. Alternately, (xv) can react with primary or secondary amines HNR₇R₈, either in excess or in the presence of a suitable base such as an aliphatic tertiary amine, optionally in the presence of a solvent such as DMF or NMP, at elevated temperature to provide adducts (xvi). Esters (xvi) may be converted to the corresponding carboxylic acids under various conditions familiar to those of ordinary skill in the art. Generally this is effected using an alkali metal hydroxide (MOH) in aqueous solution, preferably with an organic co-solvent such as methanol or THF. Carboxylic acids (xvii) can be converted to acyl azides which rearrange (Curtius rearrangement) upon heating to form isocyanates which can be trapped by alcohols R'OH to furnish carbamates (xviii). Many variations on the Curtius rearrangement are familiar to those skilled in the art of organic/medicinal chemistry which have utility for the transformation of carboxylic acids such as (xvii) into carbamates (xviii) or the related amines (x). Transformation of carbamates (xviii) into the corresponding anilines (x) is effected in a manner which depends upon the nature of the R' group. Typically, acidic conditions (~4M HCl in dioxane or ~1:1 TFA-CH$_2$Cl$_2$) are used for acid-labile carbamates (R'=t-Bu). Benzylic carbamates are generally cleaved to the corresponding anilines by exposure to hydrogen gas in the presence of a noble metal catalyst such as Pd or Pt or by phase transfer hydrogenolysis. Methods for transformation of anilines (x) into compounds of the invention I are described in previous schemes.

Scheme 6

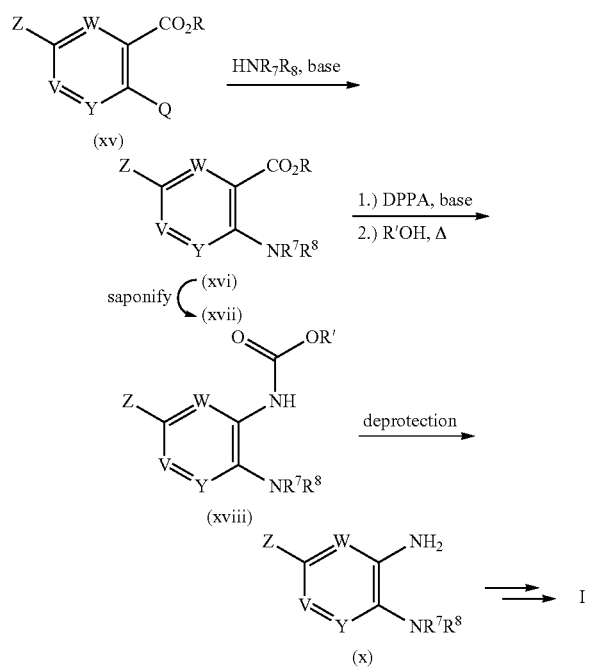

Scheme 7 describes a preparation of compounds of the invention I similar to that of Scheme 6 in which the intermediate isocyanate formed in the Curtius rearrangement is intercepted by an amine R$_9$NH$_2$ to generate urea intermediate (xiii). Intermediate (xiii) is further transformed using the Suzuki or related coupling into compounds of the invention I.

Scheme 7

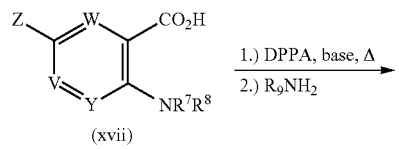

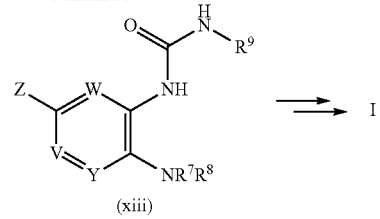

Intermediate (xii) is useful for preparation of further compounds of the invention as shown in Scheme 8. Treatment with a phenyl chloroformate derivative and a suitable base, generally in a solvent such as dichloromethane provides phenyl carbamate derivatives (xviii). Where greater reactivity than that available with derivatives of phenyl chloroformate (R=H) is required, the related carbamates where R is an electron-withdrawing substituent such as a p-nitro group may be employed. Suitable bases include but are not limited to pyridines and aliphatic tertiary amines. These derivatives may be isolated or used in the next reaction without isolation. In the event, they react with amines R$^9$NH$_2$ to give compounds of the invention I.

Scheme 8

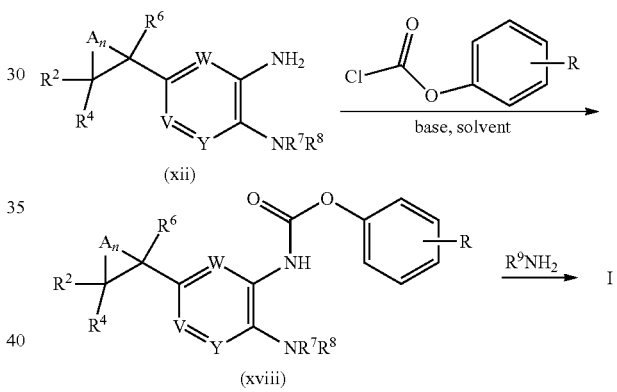

Intermediates prepared in the above schemes may require further elaboration in order to be converted into compounds of the invention. Examples of this are provided in the following schemes.

Scheme 9 illustrates the conversion of nitriles (xix) into tetrazole compounds of the invention I. Typically, the nitrile is prepared by chemistry described above and heated with an azide such as tributyltinazide in a solvent such as toluene at or near the boiling point. This methodology could be used to prepare various cycloalkyl tetrazole derivatives.

Scheme 9

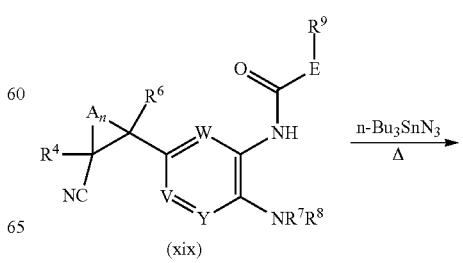

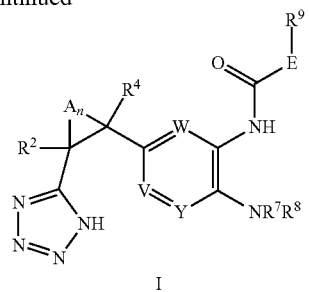

Scheme 10 illustrates the transformation of intermediates or compounds of the invention into further intermediates or compounds of the invention by functional group interconversions. The boronic ester (xxi) described previously, can be coupled to the iodide (xx) via a Suzuki or related coupling to give the ester (xxi). Hydroylsis of the ester (xxi) can be accomplished by treatment with hydroxide in aqueous or mixed aqueous/organic solvents to afford a compound of the invention I. Other conditions, (catalytic hydrogenation for benzylic esters, acid hydrolysis of t-butyl esters, for instance) may be selected by one of ordinary skill in the art. This methodology could be used to prepare heteroaromatic, cycloalkyl or cycloalkenyl, or aliphatic acylsulfonamide derivatives in addition to the phenyl derivatives shown.

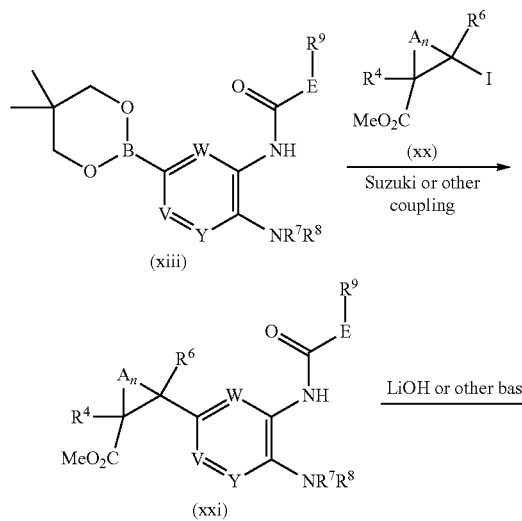

As shown in Scheme 11, compounds (xxii) (prepared by the methods described above) may be coupled with carboxylic acids using peptide coupling reagents such as Bop, Pybop, HATU or a similar reagent and a suitable base in a solvent such as THF, DMF, NMP, or the like to afford intermediates (xxiii). The use of such peptide coupling reagents has been reviewed by Han, S-Y et al., *Tetrahedron*, 60:2447-2467 (2004). Suitable bases include, but are not limited to aliphatic tertiary amines. Alternatively, amines (xxii) could react with acid chlorides of the formula R$^9$CH$_2$COCl to give amides (xxiii), again in a solvent in the presence of a base. Conversion of (xxiii) to compounds of the invention I is accomplished by hydrolysis of the ester by methods described previously to afford a compound of the invention I.

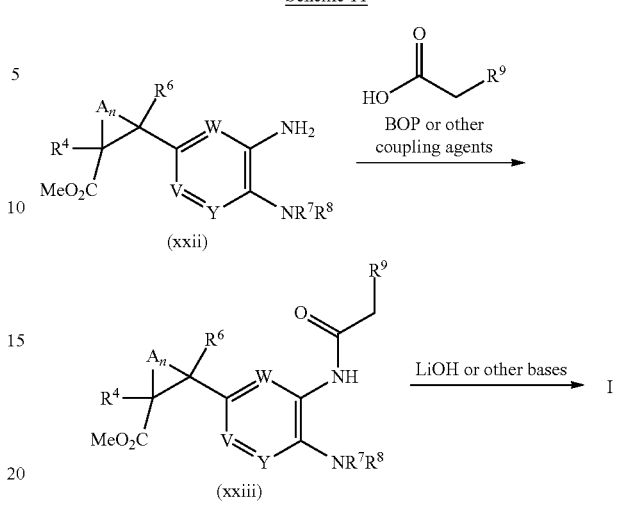

Scheme 12 describes methods to prepare cycloalkyl derivatives of 4-7 carbons. Cycloalkenes (xxiv) where n=1-4, can be prepared by many methods known to one skilled in the art or are commercially available, can be coupled to the previously bromide (x) via standard Heck coupling conditions to give the cycloalkene (xxv). The cycloalkene (xxv) can be reduced by several known methods, including by not limited to Pd/C and H$_2$ in a solvent such as ethyl acetate to give the cycloalkane (xxvi). The aniline (xxvi) can then be treated sequentially with the isocyanates R$^9$N═C═O and an aqueous base, such as but not limited to LiOH as described previously, to give a compound of the invention I.

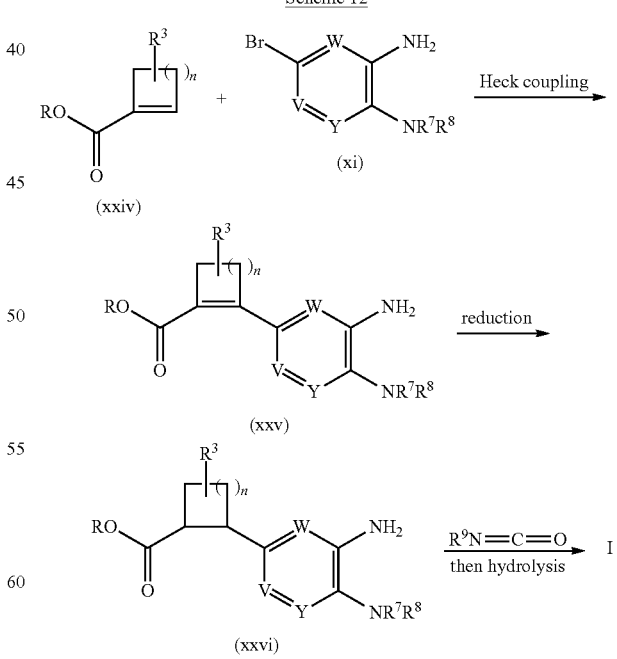

Scheme 13 demonstrates an alternative method to install a cyclopropyl on the aryl halide (ix). In scheme, the ethylene group can be installed via a Suzuki coupling of 2,4,6- trivinyl-1,3,5,2,4,6-trioxatriborinane and the aryl halide (ix) to give the styrene analog (xxxvii). The cyclopropyl ester (xxix) can be synthesized via a carbene generated with the diazoacetate (xxviii) and a Ru or Cu catalyst (reference). This will give a separable mixture of cis and trans cyclopropyl esters. Reduction of the nitro analog (xxix) will give the previously described aniline (xxii) which can be converted to a compound of formula I by methods previously described.

Scheme 13

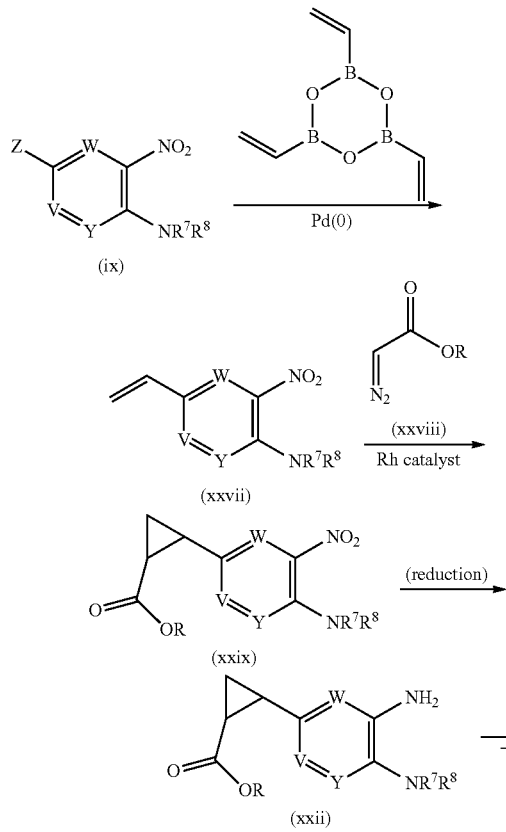

Carboxylic acids (xxix), which are compounds of the invention I can be further elaborated to acyl sulfonamides, which are also compounds of the invention I. Several methods are known to one skilled in the art for the preparation of acyl sulfonamides from carboxylic acids, including treatment with a sulfonamide (xxx) in presence of a coupling agent, such as EDC and a base such as TEA in a solvent such as DCM.

Scheme 14

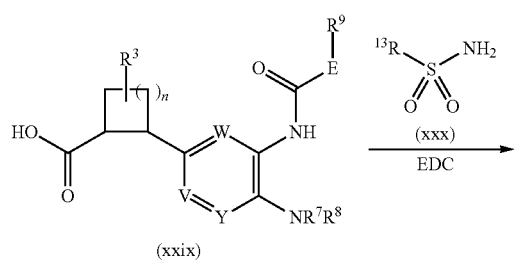

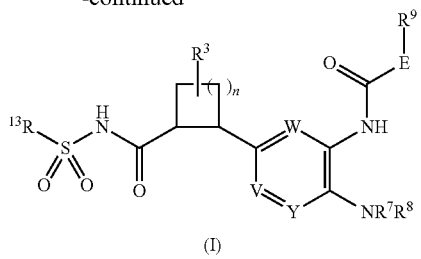

(I)

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS and Preparatory/Analytical HPLC Methods Employed in Characterization or Purification of Examples Analytical HPLC/MS was performed using the following methods:

Method A:
Shimadzu SCL-10A liquid chromatographs and Waters MICROMASS® ZQ Mass Spectrometers (Desalvation Gas: Nitrogen; Desalvation Temp. 250° C.; Ion Source Temp: 120° C.; Positive Electrospray conditions) using the following method: Linear Gradient of 0% to 100% solvent B over 4 min; UV visualization at 220 nm; Column: Waters Sunfire C18 2.1 mm×30 mm; 2.5 um particle (Heated to Temp. 40° C.); Flow rate: 1 ml/min; Mobile phase A: 10% MeOH, 90% Water, 0.1% TFA; Mobile phase B: 90% MeOH, 10% Water, 0.1% TFA;

Method B:
Waters Acquity SDS using the following method: Linear Gradient of 2% to 98% solvent B over 1.6 min; UV visualization at 220 nm; Column: BEH C18 2.1 mm×50 mm; 1.7 um particle (Heated to Temp. 50° C.); Flow rate: 1 ml/min; Mobile phase A: 100% Water, 0.05% TFA; Mobile phase B: 100% Acetonitrile, 0.05% TFA;

Method C:
Phenomenex-Luna C18 3 um 4.6×30 mm, 0% B-95% B with flow rate 4 mL/min and 2 min gradient time; Mobile phase A: 10% water/90% acetonitrile with 10 mM NH$_4$OAc; Mobile phase B: 10% water/90% acetonitrile with 10 mM NH$_4$OAc, wavelength 220 nM.

Method D:
Waters Acquity UPLC BEH C18, 2.1×50 mm, 1.7-μm particles; Mobile Phase A: water with 0.05% TFA; Mobile Phase B: acetonitrile with 0.05% TFA; Temperature: 50° C.; Gradient: 2-98% B over 1 minutes, then a 0.5-minute hold at 100% B; Flow: 0.8 mL/min.

Method E:
Phenomenex Luna C18, 2.0×30 mm, 5-μm particles; Mobile Phase A: 10:90 water:MeOH 0.1% TFA; Mobile Phase B: 10:90 water:MeOH 0.1% TFA; Temperature: RT; Gradient: 0-100% B over 2 minutes, then a 0.5-minute hold at 100% B; Flow: 1.5 mL/min.

Method F:

Phenomenex Luna C18, 2.0×30 mm, 5-μm particles; Mobile Phase A: 10:90 water:MeOH 0.1% TFA; Mobile Phase B: 10:90 water:MeOH 0.1% TFA; Temperature: RT; Gradient: 0% B for a 0.2 min hold, then 0-100% B over 2.5 minutes, then a 3-minute hold at 100% B; Flow: 1.5 mL/min.

Method G:

YMC S5 ODS, 4.6×50 mm, 1.7-μm particles; Mobile Phase A: 10% MeOH-90% $H_2O$-0.2% $H_3PO_4$; Mobile Phase B: 90% MeOH-10% $H_2O$-0.2% $H_3PO_4$; Temperature: 40° C.; Gradient: 0-100% B over 4 minutes, then a 1-minute hold at 100% B; Flow: 4 mL/min.

Preparatory chiral SFC chromatography was performed using the following method:

Method H:

Berger SFC MGII, UV visualization at 220 nm; Column: Chiral Whelk-O, 25×3 cm ID, 5 μm; Flow rate: 85.0 mL/min, Mobile Phase: 80/20, $CO_2$/MeOH.

Method I:

Thar 350, UV visualization at 220 nm; Column: AD-H, 5×25 cm ID, 5 μm; BPR pressure: 100 bars, Temperature: 40° C., Flow rate: 250 mL/min, Mobile Phase: 92/8, $CO_2$/MeOH.

Analytical chiral SFC chromatography was performed on an Berger Analytical SFC using the following method:

Method J:

UV visualization at 220 nm; Column: Chiral Whelk-O, 250×4.6 mm ID, 5 μm; Flow rate: 2 mL/min, Mobile Phase: 80/20, $CO_2$/MeOH.

Method K:

Thar analytical SFC, UV visualization at 220-400 nm; Column: AD-H, 0.46×25 cm ID, 5 μm; BPR pressure: 100 bars, Temperature: 35° C., Flow rate: 3 mL/min, Mobile Phase: 93/7, $CO_2$/MeOH.

Method L:

Waters Acquity UPLC Column: BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method M:

Waters Acquity UPLC Column: BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

NMR Employed in Characterization of Examples $^1$H NMR spectra (unless otherwise noted) were obtained with JEOL or Bruker FOURIER® transform spectrometers operating at 400 MHz or 500 MHz. $^1$H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

Example 1

Method A

Enantiomer 1 and Enantiomer 2

Enantiomer 1: (1R,2S)-2-(4-(diisobutylamino)-3-(3-(p-tolyl)ureido)phenyl)cyclopropanecarboxylic acid

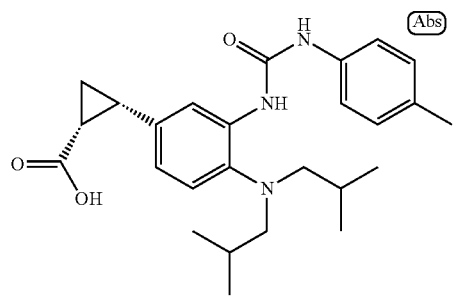 [SMILES: Cc1ccc(NC(=O)Nc2cc([C@H]3C[C@H]3C(=O)O)ccc2N(CC(C)C)CC(C)C)cc1]

Enantiomer 2: (1S,2R)-2-(4-(diisobutylamino)-3-(3-(p-tolyl)ureido)phenyl)cyclopropanecarboxylic acid

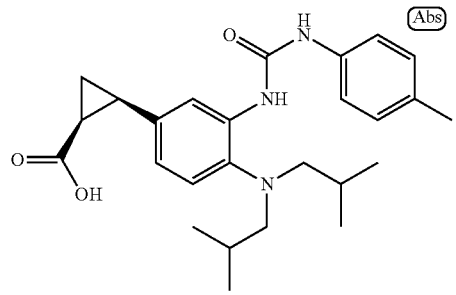 [SMILES: Cc1ccc(NC(=O)Nc2cc([C@@H]3C[C@@H]3C(=O)O)ccc2N(CC(C)C)CC(C)C)cc1]

1A. 4-bromo-N,N-diisobutyl-2-nitroaniline 4-bromo-1-fluoro-2-nitrobenzene (7 g, 31.8 mmol) and diisobutylamine (12.23 ml, 70.0 mmol) were heated at 130° C. for 3 h. It was then cooled to RT, purification via flash chromatography gave 1A (bright red solid, 8.19 g, 24.88 mmol, 78% yield) LC-MS Anal. Calc'd for $C_{14}H_{21}BrN_2O_2$ 328.08. found [M+3] 331.03, $T_r$=2.63 min (Method A).

1B. N,N-diisobutyl-2-nitro-4-vinylaniline

To a solution of 1A (1 g, 3.04 mmol) in ethanol (15.00 mL) and toluene (5 mL) (sonication to break up the solid) was added 2,4,6-trivinyl-1,3,5,2,4,6-trioxatriborinane pyridine complex (0.589 g, 3.64 mmol) followed by $K_3PO_4$ (1.289 g, 6.07 mmol) and water (2.000 mL). The reaction mixture was purged with Argon for 2 min and then Pd $(PPh_3)_4$(0.351 g, 0.304 mmol) was added. It was then heated at 80° C. in an oil bath for 8 h. LC-MS indicated completion. It was diluted with EtOAc (10 mL) and water (5 mL) and filtered through a pad of Celite, rinsed with EtOAc (2×30 mL). Aqueous layer was further extracted with EtOAc (2×30 mL), the combined extracts were washed with water, brine, dried over MgSO$_4$, filtered and concentrated. Purification via flash chromatography gave 1B (orange oil, 800 mg, 2.89 mmol, 95% yield). LC-MS Anal. Calc'd for C$_{16}$H$_{24}$N$_2$O$_2$ 276.18. found [M+H] 277.34, T$_r$=2.41 min (Method A). $^1$H NMR (400 MHz, CHLOROFORM-d) δ 7.73 (d, J=2.2 Hz, 1H), 7.44 (dd, J=8.8, 2.2 Hz, 1H), 7.08 (d, J=8.6 Hz, 1H), 6.60 (dd, J=17.5, 10.9 Hz, 1H), 5.63 (dd, J=17.6, 0.4 Hz, 1H), 5.20 (d, J=11.2 Hz, 1H), 3.00-2.89 (m, 4H), 1.99-1.85 (m, 2H), 0.84 (d, J=6.6 Hz, 12H)

1C. Racemic (1R,2S)-ethyl 2-(4-(diisobutylamino)-3 nitrophenyl) cyclopropanecarboxylate To a solution of 1B (800 mg, 2.61 mmol) in DCM (15 mL) was added rhodium(II) acetate dimer (230 mg, 0.521 mmol) followed by a slow addition of a solution of ethyl diazoacetate (0.811 mL, 7.82 mmol) in CH$_2$Cl$_2$ (5.00 mL) over a period of 2 h via a syringe pump. The reaction mixture turned into a dark red solution and it was stirred at RT for extra 1 h. LC-MS indicated the appearance of two peaks with the desired molecular mass, the solvent was removed in vacuo and purification via flash chromatography gave 1C (cis isomer) (yellow oil, 220 mg, 0.607 mmol, 23.30% yield) and trans isomer (yellow oil, 300 mg, 0.828 mmol, 31.8% yield). LC-MS Anal. Calc'd for C$_{20}$H$_{30}$N$_2$O$_4$ 362.22. found [M+H] 363.27, T$_r$=2.34 min (cis), 2.42 min (trans) (Method A). cis isomer: $^1$H NMR (400 MHz, CHLOROFORM-d) δ 7.62 (d, J=1.8 Hz, 1H), 7.30-7.25 (m, 1H), 7.02 (d, J=8.6 Hz, 1H), 3.95-3.86 (m, 2H), 2.89 (d, J=7.3 Hz, 4H), 2.53-2.44 (m, 1H), 2.07 (ddd, J=9.2, 7.9, 5.7 Hz, 1H), 1.87 (dquin, J=13.5, 6.8 Hz, 2H), 1.67 (dt, J=7.3, 5.5 Hz, 1H), 1.37-1.30 (m, 1H), 0.99 (t, J=7.0 Hz, 3H), 0.82 (d, J=6.6 Hz, 12H) trans isomer: $^1$H NMR (400 MHz, CHLOROFORM-d) δ 7.43 (d, J=2.2 Hz, 1H), 7.17-7.11 (m, 1H), 7.08-7.03 (m, 1H), 4.18 (q, J=7.3 Hz, 2H), 2.89 (d, J=7.3 Hz, 4H), 2.46 (ddd, J=9.2, 6.4, 4.2 Hz, 1H), 1.94-1.80 (m, 3H), 1.62-1.54 (m, 1H), 1.34-1.23 (m, 4H), 0.83 (d, J=6.6 Hz, 12H)

1D. Racemic (1R,2S)-ethyl 2-(3-amino-4-(diisobutylamino)phenyl) cyclopropanecarboxylate To a stirred solution of 1C (cis isomer) (220 mg, 0.607 mmol) in EtOAc (6 mL) was added palladium on carbon (64.6 mg, 0.061 mmol) and the suspension was hydrogenated (1 atm, balloon) at RT for 1 h. LC-MS indicated completion. The suspension was filtered through a pad of Celite and the filter cake was rinsed with EtOAc (2×30 mL). Combined filtrate and rinses were evaporated in vacuo. Purification via flash chromatography gave 1D (light yellow oil, 140 mg, 0.421 mmol, 69.4% yield). LC-MS Anal. Calc'd for C$_{20}$H$_{32}$N$_2$O$_2$ 332.25. found [M+H] 333.34, T$_r$=2.22 min (Method A). $^1$H NMR (400 MHz, CHLOROFORM-d) δ 6.95 (d, J=8.1 Hz, 1H), 6.65 (d, J=2.0 Hz, 1H), 6.64-6.59 (m, 1H), 4.06 (s, 2H), 3.87 (qd, J=7.1, 0.9 Hz, 2H), 2.56 (d, J=7.0 Hz, 4H), 2.47 (q, J=8.6 Hz, 1H), 2.01 (ddd, J=9.4, 7.8, 5.7 Hz, 1H), 1.78-1.61 (m, 3H), 1.24 (ddd, J=8.6, 7.9, 5.1 Hz, 1H), 0.92 (t, J=7.2 Hz, 3H), 0.89 (dd, J=6.6, 0.9 Hz, 12H)

Racemic Example 1

Racemic (1R,2S)-2-(4-(diisobutylamino)-3-(3-(p-tolyl)ureido)phenyl)cyclopropanecarboxylic acid To a solution of 1D (140 mg, 0.421 mmol) in THF (4 mL) was added 1-isocyanato-4-methylbenzene (0.079 mL, 0.632 mmol). The resulting solution was stirred at RT for 3 h. LC-MS indicated completion. The reaction mixture was concentrated and used without purification in the next step. The crude ester (180 mg, 0.387 mmol) was dissolved in THF (4 mL), NaOH (1N aqueous) (1.160 mL, 1.160 mmol) was added. Then MeOH (1 mL) was added to dissolve the precipitate and it turned into a clear yellow solution. After 60 h, reaction was complete by LC-MS. Most MeOH and THF was removed in vacuo and the crude was diluted with 2 mL of water, the pH was adjusted to ca. 2 using 1N aqueous HCl. The aqueous phase was then extracted with EtOAc (3×10 mL) and the combined organic phase was washed with brine, dried over Na$_2$SO$_4$ and concentrated. Purification via flash chromatography gave racemic example 1 (yellow foam, 110 mg, 0.251 mmol, 65.0% yield), LC-MS Anal. Calc'd for C$_{26}$H$_{35}$N$_3$O$_3$ 437.27. found [M+H] 438.29, T$_r$=4.22 min (Method A). $^1$H NMR (400 MHz, CHLOROFORM-d) δ 10.15 (br. s., 1H), 7.42-7.35 (m, 3H), 7.22-7.14 (m, 2H), 7.10 (d, J=8.1 Hz, 2H), 3.22 (d, J=6.6 Hz, 4H), 2.54 (q, J=8.6 Hz, 1H), 2.31 (s, 3H), 2.16-1.98 (m, 3H), 1.61 (dt, J=7.3, 5.6 Hz, 1H), 1.40 (td, J=8.3, 5.3 Hz, 1H), 1.01 (br. s., 12H)

Example 1, Enantiomer 1 and Enantiomer 2. Chiral separation of racemic example 1 (Method H) gave enantiomer 1 T$_r$=9.042 min (Method J). [α]$^{24}_D$=−11.11 (c 7.02 mg/mL, MeOH) and enantiomer 2 T$_r$=10.400 min (Method J). [α]$^{24}_D$=+11.17 (c 7.02 mg/mL, MeOH) as single enantiomers. Absolute stereochemistry was confirmed in example 1 method B.

Enantiomer 1: LC-MS Anal. Calc'd for C$_{26}$H$_{35}$N$_3$O$_3$ 437.27. found [M+H] 438.25, T$_r$=4.19 min (Method A). $^1$H NMR (400 MHz, CHLOROFORM-d) δ 8.12 (d, J=1.3 Hz, 1H), 7.97 (s, 1H), 7.20 (d, J=8.4 Hz, 2H), 7.14-7.07 (m, 2H), 7.02 (t, J=7.7 Hz, 2H), 6.89 (dd, J=8.1, 1.5 Hz, 1H), 2.60 (q, J=8.6 Hz, 1H), 2.50 (d, J=7.0 Hz, 4H), 2.32 (s, 3H), 2.13-2.04 (m, 1H), 1.71-1.55 (m, 3H), 1.35 (td, J=8.3, 5.1 Hz, 1H), 0.76 (dd, J=6.6, 2.2 Hz, 12H)

Enantiomer 2: LC-MS Anal. Calc'd for C$_{26}$H$_{35}$N$_3$O$_3$ 437.27. found [M+H] 438.24, T$_r$=4.18 min (Method A). $^1$H NMR (400 MHz, CHLOROFORM-d) δ 8.11 (d, J=1.5 Hz, 1H), 7.96 (s, 1H), 7.23-7.16 (m, 2H), 7.13-7.07 (m, 2H), 7.05-6.98 (m, 2H), 6.89 (dd, J=8.3, 1.7 Hz, 1H), 2.59 (q, J=8.7 Hz, 1H), 2.49 (d, J=7.3 Hz, 4H), 2.32 (s, 3H), 2.12-2.03 (m, 1H), 1.70-1.53 (m, 3H), 1.34 (td, J=8.2, 5.0 Hz, 1H), 0.75 (dd, J=6.6, 2.0 Hz, 12H)

Example 1

Method B

Enantiomer 1 and Enantiomer 2

Enantiomer 2: (1S,2R)-2-(4-(diisobutylamino)-3-(3-(p-tolyl)ureido)phenyl)cyclopropanecarboxylic acid

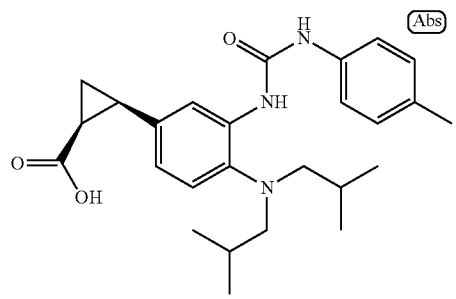 [SMILES: Cc1ccc(NC(=O)Nc2cc([C@@H]3C[C@@H]3C(=O)O)ccc2N(CC(C)C)CC(C)C)cc1]

1E. 4-(5,5-dimethyl-1,3,2-dioxaborinan-2-yl)-N,N-diisobutyl-2-nitroaniline 1A (10 g, 30.4 mmol), 5,5,5',5'-tetramethyl-2,2'-bi(1,3,2-dioxaborinane) (7.55 g, 33.4 mmol), PdCl$_2$(dppf)-CH$_2$Cl$_2$ adduct (0.556 g, 0.759 mmol) and potassium acetate (8.94 g, 91 mmol) were combined in a round bottom flask, and DMSO (100 mL) was added. It was vacuated and back-filled with N$_2$ three times, then heated at 80° C. for 8 h. Reaction was complete by LC-MS. Cooled to RT and passed through a short plug of silica gel, rinsed with a mixture of Hexane/EtOAc (5:1) (3×100 mL). After removing the solvent in vacuo, purification via flash chromatography gave 1E (orange oil, 9 g, 22.36 mmol, 73.6% yield), LC-MS Anal. Calc'd for C$_{19}$H$_{31}$BN$_2$O$_4$ 362.24. found [M+H] 295.18 (mass of boronic acid), T$_r$=3.65 min (Method A). $^1$H NMR (400 MHz, CHLOROFORM-d) δ 8.13 (d, J=1.8 Hz, 1H), 7.73 (dd, J=8.4, 1.5 Hz, 1H), 7.04 (d, J=8.6 Hz, 1H), 3.75 (s, 4H), 3.00-2.92 (m, 4H), 1.93 (dquin, J=13.5, 6.8 Hz, 2H), 1.02 (s, 6H), 0.93-0.79 (m, 12H)

1F. (1S,2R)-ethyl 2-(4-(diisobutylamino)-3-nitrophenyl) cyclopropanecarboxylate To 1E (9 g, 22.36 mmol) in a 500 mL round bottom flask was added 1,4-dioxane (60 mL). After it was dissolved, cesium carbonate (15.30 g, 47.0 mmol) was added. To the suspension was then added water (30 mL) slowly. It became an homogeneous solution. Enantiopure (1R,2R)-ethyl 2-iodocyclopropanecarboxylate (5.90 g, 24.59 mmol) (For synthesis see Organic Process Research & Development 2004, 8, 353-359) was then added. The resulting mixture was purged with nitrogen for 25 min. Then PdCl$_2$(dppf)-CH$_2$Cl$_2$ adduct (1.824 g, 2.236 mmol) was added. The reaction mixture was purged with nitrogen for another 10 min. It became dark brown colored solution. This mixture was then stirred under nitrogen at 87° C. for 22 h. LC-MS indicated product formation and depletion of starting material. It was then cooled to RT. After removing solvent under reduced pressure, it was diluted with EtOAc (50 mL) and water (50 mL). Organic layer was separated and the aqueous layer was further extracted with EtOAc (3×30 mL). The combined organic layers were washed with brine, dried over MgSO$_4$, filtered and concentrated. Purification via flash chromatography gave 1F (dark orange oil, 3.2 g, 8.83 mmol, 39.5% yield), LC-MS Anal. Calc'd for C$_{20}$H$_{30}$N$_2$O$_4$ 362.22. found [M+H] 363.3, T$_r$=3.89 min (Method A). $^1$H NMR (400 MHz, CHLOROFORM-d) δ 7.65-7.60 (m, 1H), 7.29 (d, J=2.2 Hz, 1H), 7.02 (d, J=8.6 Hz, 1H), 3.95-3.84 (m, 2H), 2.89 (d, J=7.3 Hz, 4H), 2.48 (q, J=8.6 Hz, 1H), 2.07 (ddd, J=9.2, 7.9, 5.7 Hz, 1H), 1.87 (dquin, J=13.5, 6.8 Hz, 2H), 1.67 (dt, J=7.3, 5.5 Hz, 1H), 1.38-1.28 (m, 1H), 0.99 (t, J=7.2 Hz, 3H), 0.82 (d, J=6.6 Hz, 12H

1G. (1S,2R)-ethyl 2-(3-amino-4-(diisobutylamino) phenyl) cyclopropanecarboxylate To a stirred solution of 1F (5.5 g, 15.17 mmol) in EtOAc (150 mL) was added palladium on carbon (1.615 g, 1.517 mmol) and the suspension was hydrogenated (1 atm, balloon) for 1.5 h. LC-MS indicated completion. The suspension was filtered through a pad of Celite and the filter cake was rinsed with EtOAc (2×50 mL). Combined filtrate and rinses were concentrated under reduced pressure. Purification via flash chromatography gave 1G (yellow oil, 4.5 g, 13.53 mmol, 89% yield). LC-MS Anal. Calc'd for C$_{20}$H$_{32}$N$_2$O$_2$ 332.25. found [M+H] 333.06, T$_r$=2.88 min (Method A). $^1$H NMR (400 MHz, CHLOROFORM-d) δ 6.95 (d, J=7.9 Hz, 1H), 6.68-6.58 (m, 2H), 4.06 (s, 2H), 3.93-3.81 (m, 2H), 2.57 (d, J=7.3 Hz, 4H), 2.47 (q, J=8.6 Hz, 1H), 2.01 (ddd, J=9.4, 7.8, 5.5 Hz, 1H), 1.78-1.59 (m, 3H), 1.30-1.18 (m, 1H), 0.92 (t, J=7.2 Hz, 3H), 0.89 (dd, J=6.6, 0.9 Hz, 12H)

Example 1 enantiomer 2 was prepared following the reduction, urea formation and basic saponification procedures in racemic example 1 method A except that saponification was carried out at 50° C. for 8 h instead of at RT. Chiral analytical analysis verified it was enantiomer 2 T$_r$=10.646 min (Method J). Absolute stereochemistry was confirmed by referring to reference: Organic Process Research & Development 2004, 8, 353-359.

Enantiomer 1 Method B: (1R,2S)-2-(4-(diisobutylamino)-3-(3-(p-tolyl)ureido)phenyl)cyclopropanecarboxylic acid

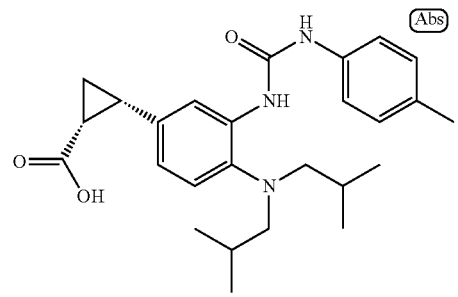 [SMILES: Cc1ccc(NC(=O)Nc2cc([C@H]3C[C@H]3C(=O)O)ccc2N(CC(C)C)CC(C)C)cc1]

1H. Single enantiomer (1R,2S)-ethyl 2-(3-amino-4-(diisobutylamino)phenyl) cyclopropanecarboxylate 1H was prepared following procedures in example 1 enantiomer 2 method B utilizing enantiopure (1S,2S)-ethyl 2-iodocyclopropanecarboxylate. This was obtained through chiral resolution modifying the procedure in Organic Process Research & Development 2004, 8, 353-359, using (R)-(+)-N-benzyl-α-methylbenzylamine instead of (S)-(−)-N-benzyl-α-methylbenzylamine). LC-MS Anal. Calc'd for C$_{20}$H$_{32}$N$_2$O$_2$ 332.25. found [M+H] 333.06, T$_r$=2.88 min (Method A). $^1$H NMR (400 MHz, CHLOROFORM-d) δ 6.95 (d, J=7.9 Hz, 1H), 6.68-6.58 (m, 2H), 4.06 (s, 2H), 3.93-3.81 (m, 2H), 2.57 (d, J=7.3 Hz, 4H), 2.47 (q, J=8.6 Hz, 1H), 2.01 (ddd, J=9.4, 7.8, 5.5 Hz, 1H), 1.78-1.59 (m, 3H), 1.30-1.18 (m, 1H), 0.92 (t, J=7.2 Hz, 3H), 0.89 (dd, J=6.6, 0.9 Hz, 12H).

Note:

1H was also made through chiral separation (Method I) of racemic (1R,2S)-ethyl 2-(3-amino-4-(diisobutylamino)phenyl)cyclopropanecarboxylate. Chiral analytical analysis (Method K) showed 1H as a single enantiomer (99% ee).

Example 1 enantiomer 1 was prepared following the reduction, urea formation and basic saponification procedures in racemic example 1 method A using 1H except that saponification was carried out at 50° C. for 8 h instead of at RT. Chiral analytical analysis verified it was enantiomer 1 with 97.8% ee (Method J).

Example 1—Method C

Enantiomer 1 (1R,2S)-2-(4-(diisobutylamino)-3-(3-(p-tolyl)ureido)phenyl)cyclopropanecarboxylic acid

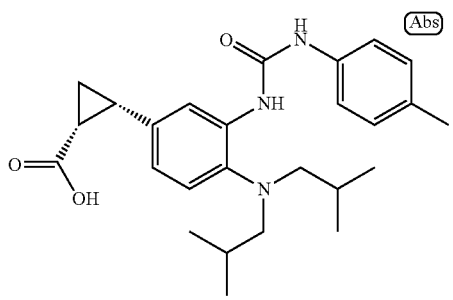 [SMILES: Cc1ccc(NC(=O)Nc2cc([C@H]3C[C@H]3C(=O)O)ccc2N(CC(C)C)CC(C)C)cc1]

1I. Diastereomer 1: (R)-4-benzyl-3-((1R,2S)-2-(4-(diisobutylamino)-3-nitrophenyl)cyclopropanecarbonyl)oxazolidin-2-one Diastereomer 2: (R)-4-benzyl-3-((1S,2R)-2-(4-(diisobutylamino)-3-nitrophenyl)cyclopropanecarbonyl)oxazolidin-2-one: 1C (1.2 g, 3.31 mmol) was dissolved in THF (20 mL), NaOH (1N aqueous) (8.28 mL, 8.28 mmol) was added. Saw precipitate formed, then MeOH (5.00 mL) was added and it turned into a clear yellow solution. The reaction was monitored by LC-MS. After 24 h, reaction was complete. Most MeOH and THF was removed in vacuo and the crude was diluted with 10 mL of water, the pH was adjusted to ca. 2 using 1N aqueous HCl. The aqueous phase was then extracted with EtOAc (3×30 mL) and the combined organic phase was washed with brine, dried over $Na_2SO_4$, filtered and concentrated to give 1.1 g of desired acid as an orange foam. This was used without purification in the subsequent step. To a solution of the crude acid from the previous step (1132 mg, 3.39 mmol) in THF (15 mL) cooled in an ice-water bath was added N-methylmorpholine (0.447 mL, 4.06 mmol) followed by slow addition of pivaloyl chloride (0.500 mL, 4.06 mmol). After stirring in an ice-water bath for 30 min, the reaction mixture was then cooled to −78° C. In a separate reaction flask, nBuLi (1.354 mL, 3.39 mmol) was added dropwise to a solution of (R)-4-benzyloxazolidin-2-one (600 mg, 3.39 mmol) in THF (15.00 mL). After 45 min at −78° C., the solution was cannulated into the −78° C. anhydride mixture. After 30 min, the cooling bath was removed and the solution was allowed to warm to RT. After 1 h, LC-MS indicated completion. The reaction was quenched by addition of saturated aqueous $NH_4Cl$. The solution was then partitioned between EtOAc and water. The organic phase was further extracted with EtOAc (2×30 mL). The combined organic extracts were washed with water, brine, dried over $MgSO_4$, filtered and concentrated. Purification via flash chromatography gave 1I Diastereomer 1 (yellow oil, 600 mg, 1.216 mmol, 35.9% yield). Diastereomer 2 (yellow oil, 450 mg, 0.912 mmol, 26.9% yield) LC-MS Anal. Calc'd for $C_{28}H_{35}N_3O_5$ 493.26. found: [M+H] 494.23, $T_r$=5.26 min (Diastereomer 1). $T_r$=5.25 min (Diastereomer 2) (Method A). Diastereomer 1: $^1$H NMR (400 MHz, CHLOROFORM-d) δ 7.56 (d, J=1.8 Hz, 1H), 7.35-7.23 (m, 4H), 7.18-7.12 (m, 2H), 7.03 (d, J=8.8 Hz, 1H), 4.37 (ddt, J=9.6, 7.3, 3.6 Hz, 1H), 4.11-4.06 (m, 2H), 3.48-3.40 (m, 1H), 3.22 (dd, J=13.4, 3.5 Hz, 1H), 2.89 (d, J=7.3 Hz, 4H), 2.77-2.66 (m, 2H), 1.97-1.81 (m, 3H), 1.52-1.44 (m, 1H), 0.82 (d, J=6.6 Hz, 12H); Diastereomer 2: $^1$H NMR (400 MHz, CHLOROFORM-d) δ 7.62 (d, J=2.0 Hz, 1H), 7.36-7.19 (m, 4H), 7.09-6.97 (m, 3H), 4.45 (ddt, J=10.2, 7.2, 3.0 Hz, 1H), 4.14-4.05 (m, 2H), 3.45-3.36 (m, 1H), 2.80 (d, J=7.3 Hz, 4H), 2.52 (dd, J=13.3, 3.2 Hz, 1H), 2.19 (dd, J=13.2, 10.3 Hz, 1H), 2.03 (dt, J=7.2, 5.8 Hz, 1H), 1.72 (dquin, J=13.4, 6.8 Hz, 2H), 1.45 (ddd, J=8.3, 7.3, 5.3 Hz, 1H), 0.64 (dd, J=6.6, 2.0 Hz, 12H)

1J. (1R,2S)-methyl 2-(4-(diisobutylamino)-3-nitrophenyl) cyclopropanecarboxylate To a solution of 1I Diastereomer 1 (460 mg, 0.932 mmol) in THF (6 mL) at 0° C. was added hydrogen peroxide (0.228 mL, 3.73 mmol). Then a solution of lithium hydroxide monohydrate (44.6 mg, 1.864 mmol) in water (2.000 mL) was added to the cold THF solution and stirred for 6 h. LC-MS indicated completion, then 2 mL of saturated aqueous $Na_2SO_3$ was added followed by 3 mL of saturated aqueous $NaHCO_3$. The mixture was concentrated to remove most of the THF. The solution was then diluted with 5 mL of water. The aqueous solution was acidified with 1 N aqueous HCl and extracted with EtOAc (3×20 mL). The combined organic extracts was washed with water, brine, dried over $MgSO_4$, filtered and concentrated to give 300 mg acid. To a solution of the crude acid from previous step (300 mg, 0.897 mmol) in MeOH (10 mL) was added 6 drops of concentrated $H_2SO_4$. The resulting solution was stirred at 50° C. for 6 h. After LC-MS indicated completion, solvent was removed under reduced pressure. It was then diluted with 5 mL of water, the aqueous layer was then extracted with EtOAc (3×20 mL) and the combined organic extracts were washed with water, brine, dried with $Na_2SO_4$, filtered and concentrated. Purification via flash chromatography gave 1J (orange oil, 260 mg, 0.746 mmol, 83% yield). LC-MS Anal. Calc'd for $C_{19}H_{28}N_2O_4$ 348.20. found: [M+H] 349.31, $T_r$=3.87 min (Method A). $^1$H NMR (400 MHz, CHLOROFORM-d) δ 7.66-7.61 (m, 1H), 7.31-7.25 (m, 1H), 7.04 (d, J=8.8 Hz, 1H), 3.47 (s, 3H), 2.90 (d, J=7.3 Hz, 4H), 2.54-2.44 (m, 1H), 2.14-2.04 (m, 1H), 1.89 (dquin, J=13.5, 6.8 Hz, 2H), 1.67 (dt, J=7.5, 5.5 Hz, 1H), 1.42-1.31 (m, 1H), 0.83 (dd, J=6.6, 1.1 Hz, 12H)

1K. (1R,2S)-methyl 2-(3-amino-4-(diisobutylamino) phenyl) cyclopropanecarboxylate To a stirred solution of 1J (100 mg, 0.287 mmol) in EtOAc (5 mL) was added palladium on carbon (30.5 mg, 0.029 mmol) and the suspension was hydrogenated (1 atm, balloon) for 2 h. LC-MS indicated completion. The suspension was filtered through a pad of Celite and the filter cake was rinsed with EtOAc (20 mL). Combined filtrate and rinses were concentrated. Purification via flash chromatography gave 1K (yellow oil, 90 mg, 0.287 mmol, 99% yield). LC-MS Anal. Calc'd for $C_{19}H_{30}N_2O_2$ 318.23. found: [M+H] 319.31, $T_r$=2.72 min (Method A). $^1$H NMR (400 MHz, CHLOROFORM-d) δ 6.95 (d, J=8.1 Hz, 1H), 6.65 (d, J=1.8 Hz, 1H), 6.60 (dd, J=8.1, 1.5 Hz, 1H), 4.08 (br. s., 2H), 3.42 (s, 3H), 2.58 (d, J=7.0 Hz, 4H), 2.52-2.42 (m, 1H), 2.09-1.98 (m, 1H), 1.79-1.59 (m, 3H), 1.32-1.22 (m, 1H), 0.94-0.84 (m, 12H)

Enantiomer 1 was prepared following the urea formation and saponification procedure in racemic example 1 method A. Chiral analytical analysis verified it was enantiomer 1 with 98.1% ee (Method J).

49
Example 1—Method C

Enantiomer 2 (1S,2R)-2-(4-(diisobutylamino)-3-(3-(p-tolyl)ureido)phenyl)cyclopropanecarboxylic acid

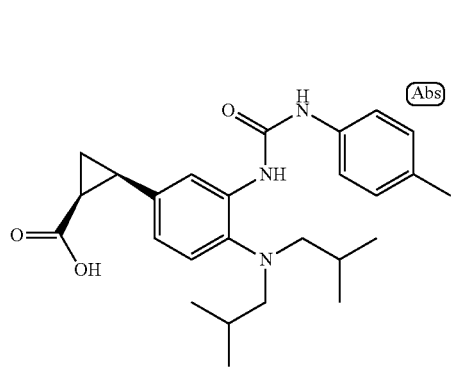 [SMILES: Cc1ccc(NC(=O)Nc2cc([C@@H]3C[C@@H]3C(=O)O)ccc2N(CC(C)C)CC(C)C)cc1]

Example 1 Enantiomer 2 was prepared following the procedure for Example 1 enantiomer 1 method C using diastereomer 2 instead of diastereomer 1. Chiral analytical analysis verified it was enantiomer 2 with 94.0% ee (Method J).

50
Example 2-16

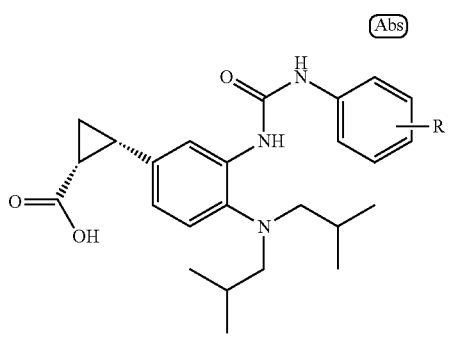

Examples 2-16 were prepared following the procedure for Example 1, Enantiomer 1 method C using the corresponding isocyanates.

| Ex. No. | Name | R | Tr (min) Method A | [M + H]$^+$ |
|---|---|---|---|---|
| 2 | (1R,2S)-2-(3-(3-(4-chlorophenyl)ureido)-4-(diisobutylamino)phenyl)cyclopropanecarboxylic acid | 4-Cl-C6H4 | 3.53 | 458.26 |
| 3 | (1R,2S)-2-(4-(diisobutylamino)-3-(3-(2-(trifluoromethyl)phenyl)ureido)phenyl)cyclopropanecarboxylic acid | 2-CF3-C6H4 | 3.39 | 492.32 |
| 4 | (1R,2S)-2-(3-(3-(2,4-dichlorophenyl)ureido)-4-(diisobutylamino)phenyl)cyclopropanecarboxylic acid | 2,4-Cl2-C6H3 | 3.64 | 492.25 |
| 5 | (1R,2S)-2-(4-(diisobutylamino)-3-(3-(4-(trifluoromethyl)phenyl)ureido)phenyl)cyclopropanecarboxylic acid | 4-CF3-C6H4 | 3.60 | 492.26 |
| 6 | (1R,2S)-2-(3-(3-(3,4-dichlorophenyl)ureido)-4-(diisobutylamino)phenyl)cyclopropanecarboxylic acid | 3,4-Cl2-C6H3 | 3.71 | 492.19 |
| 7 | (1R,2S)-2-(3-(3-(4-(difluoromethoxy)phenyl)ureido)-4-(diisobutylamino)phenyl)cyclopropanecarboxylic acid | 4-OCHF2-C6H4 | 3.27 | 490.31 |

-continued

| Ex. No. | Name | R | Tr (min) Method A | [M + H]+ |
|---|---|---|---|---|
| 8 | (1R,2S)-2-(4-(diisobutylamino)-3-(3-(4-fluorophenyl)ureido)phenyl)cyclopropanecarboxylic acid | 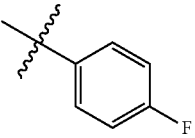 | 3.18 | 442.30 |
| 9 | (1R,2S)-2-(3-(3-(2-chlorophenyl)ureido)-4-(diisobutylamino)phenyl)cyclopropanecarboxylic acid | 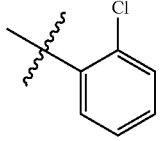 [SMILES: *c1ccccc1C(F)(F)F] | 3.31 | 458.26 |
| 10 | (1R,2S)-2-(3-(3-(2,4-difluorophenyl)ureido)-4-(diisobutylamino)phenyl)cyclopropanecarboxylic acid | 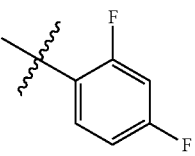 [SMILES: *c1ccc(F)cc1F] | 3.24 | 460.31 |
| 11 | (1R,2S)-2-(3-(3-(4-chloro-2,6-difluorophenyl)ureido)-4-(diisobutylamino)phenyl)cyclopropanecarboxylic acid | 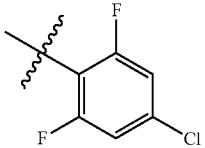 [SMILES: *c1c(F)cc(Cl)cc1F] | 3.42 | 494.26 |
| 12 | (1R,2S)-2-(4-(diisobutylamino)-3-(3-(2-fluorophenyl)ureido)phenyl)cyclopropanecarboxylic acid | 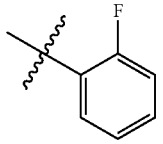 [SMILES: *c1ccccc1F] | 3.13 | 442.29 |
| 13 | (1R,2S)-2-(3-(3-(4-bromophenyl)ureido)-4-(diisobutylamino)phenyl)cyclopropanecarboxylic acid | 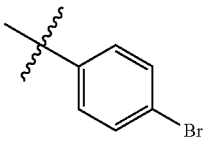 [SMILES: *c1ccc(Br)cc1] | 3.47 | 504.22 |
| 14 | (1R,2S)-2-(3-(3-(2-chloro-4-methylphenyl)ureido)-4-(diisobutylamino)phenyl)cyclopropanecarboxylic acid | 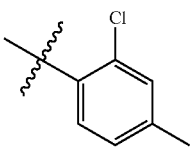 [SMILES: *c1ccc(C)cc1Cl] | 3.46 | 472.27 |
| 15 | (1R,2S)-2-(3-(3-(4-(cyanomethyl)phenyl)ureido)-4-(diisobutylamino)phenyl)cyclopropanecarboxylic acid | 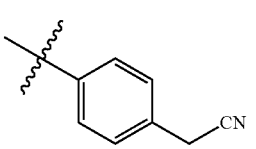 [SMILES: *c1ccc(CC#N)cc1] | 2.90 | 463.32 |
| 16 | (1R,2S)-2-(3-(3-(4-cyclopropylphenyl)ureido)-4-(diisobutylamino)phenyl)cyclopropanecarboxylic acid | 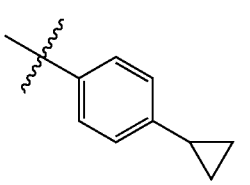 [SMILES: *c1ccc(C2CC2)cc1] | 3.43 | 464.32 |

Example 17-26

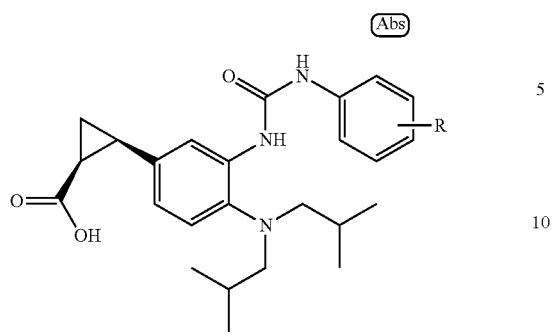

Examples 17-26 were prepared following the procedure for Example 1, Enantiomer 2 method C using the corresponding isocyanates.

| Ex. No. | Name | R | Tr (min) Method A | [M + H]⁺ |
|---|---|---|---|---|
| 17 | (1S,2R)-2-(4-(diisobutylamino)-3-(3-(4-(trifluoromethyl)phenyl)ureido)phenyl)cyclopropanecarboxylic acid | 4-CF₃-phenyl | 3.43 | 492.32 |
| 18 | (1S,2R)-2-(3-(3-(4-chlorophenyl)ureido)-4-(diisobutylamino)phenyl)cyclopropanecarboxylic acid | 4-Cl-phenyl | 3.44 | 458.28 |
| 19 | (1S,2R)-2-(4-(diisobutylamino)-3-(3-(m-tolyl)ureido)phenyl)cyclopropanecarboxylic acid | 3-methyl-phenyl | 3.26 | 438.35 |
| 20 | (1S,2R)-2-(3-(3-(4-cyclopropylphenyl)ureido)-4-(diisobutylamino)phenyl)cyclopropanecarboxylic acid | 4-cyclopropyl-phenyl | 3.43 | 464.36 |
| 21 | (1S,2R)-2-(3-(3-(2,4-difluorophenyl)ureido)-4-(diisobutylamino)phenyl)cyclopropanecarboxylic acid | 2,4-diF-phenyl | 3.24 | 460.30 |
| 22 | (1S,2R)-2-(4-(diisobutylamino)-3-(3-(2-fluorophenyl)ureido)phenyl)cyclopropanecarboxylic acid | 2-F-phenyl | 3.14 | 442.30 |
| 23 | (1S,2R)-2-(4-(diisobutylamino)-3-(3-phenylureido)phenyl)cyclopropanecarboxylic acid | phenyl | 3.10 | 424.34 |

-continued

| Ex. No. | Name | R | Tr (min) Method A | [M + H]+ |
|---|---|---|---|---|
| 24 | (1S,2R)-2-(4-(diisobutylamino)-3-(3-(4-ethoxyphenyl)ureido)phenyl)cyclopropanecarboxylic acid | 4-ethoxyphenyl (OEt) | 3.26 | 468.25 |
| 25 | (1S,2R)-2-(4-(diisobutylamino)-3-(3-(4-fluorophenyl)ureido)phenyl)cyclopropanecarboxylic acid | 4-fluorophenyl (F) | 3.18 | 442.19 |
| 26 | (1S,2R)-2-(3-(3-(4-chloro-2-fluorophenyl)ureido)-4-(diisobutylamino)phenyl)cyclopropanecarboxylic acid | 2-fluoro-4-chlorophenyl | 3.50 | 476.23 |

Example 27

(1S,2R)-2-(4-(diisobutylamino)-2-fluoro-5-(3-(p-tolyl)ureido)phenyl)cyclopropanecarboxylic acid Enantiomer 1 and Enantiomer 2

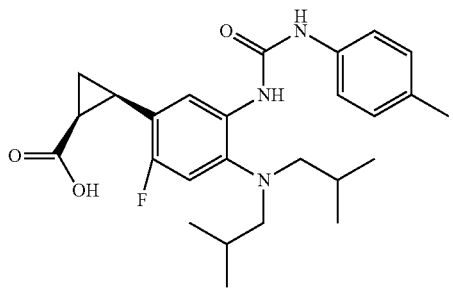 [SMILES: Cc1ccc(NC(=O)Nc2cc([C@@H]3C[C@@H]3C(=O)O)c(F)cc2N(CC(C)C)CC(C)C)cc1]

27A.
4-bromo-5-fluoro-N,N-diisobutyl-2-nitroaniline

To a solution of 1-bromo-2,4-difluoro-5-nitrobenzene (1 g, 4.20 mmol) in NMP (2 mL) was added diisobutylamine (0.597 g, 4.62 mmol) followed by Hunig's base (0.881 mL, 5.04 mmol). The resulting reaction mixture was heated at 140° C. for 2 h. LC-MS indicated completion. After cooling to RT, it was diluted with water (10 mL) and EtOAc (20 mL). The aqueous layer was further extracted with EtOAc (3×20 mL) and the combined organic layer was washed with water, brine, dried over $MgSO_4$, filtered and concentrated. Purification via flash chromatography gave 27A (yellow/orange solid, 0.8 g, 2.304 mmol, 54.8% yield). LC-MS Anal. Calc'd for $C_{14}H_{20}BrFN_2O_2$ 346.07. found [M+3H] 349.12. $T_r$=4.24 min (Method A). $^1$H NMR (400 MHz, CHLOROFORM-d) δ 8.01 (d, J=7.3 Hz, 1H), 6.83 (d, J=11.2 Hz, 1H), 2.92 (d, J=7.3 Hz, 4H), 1.94 (dquin, J=13.5, 6.8 Hz, 2H), 0.85 (d, J=6.4 Hz, 12H)

Racemic example 27 was prepared following the procedure for Example 1 method A using 27A. LC-MS Anal. Calc'd for $C_{26}H_{34}FN_3O_3$ 455.26. found [M+H] 456.34. $T_r$=3.72 min (Method A). $^1$H NMR (500 MHz, DMSO-$d_6$) δ 8.43 (s, 1H), 6.94 (d, J=8.4 Hz, 1H), 6.77 (s, 1H), 6.50 (d, J=8.4 Hz, 2H), 6.24 (d, J=7.9 Hz, 2H), 6.11 (d, J=11.4 Hz, 1H), 1.86-1.74 (m, 4H), 1.57 (q, J=8.3 Hz, 1H), 1.40 (s, 3H), 1.15 (td, J=7.8, 6.7 Hz, 1H), 0.78 (dquin, J=13.4, 6.7 Hz, 2H), 0.50-0.42 (m, 2H), -0.02 (dd, J=7.9, 6.9 Hz, 12H)

Example 27 enantiomer 1 and enantiomer 2 were obtained through chiral separation of racemic example 27 (Method H). Enantiomer 1, $T_r$=4.002 min, Enantiomer 2, $T_r$=5.297 min (Method J). 1: LC-MS Anal. Calc'd for $C_{26}H_{34}FN_3O_3$ 455.26. found [M+H] 456.26. $T_r$=3.71 min (Method A). $^1$H NMR (400 MHz, CHLOROFORM-d) δ 7.97 (d, J=8.1 Hz, 1H), 7.65 (s, 1H), 7.21-7.12 (m, 2H), 7.12-7.06 (m, 2H), 6.77 (d, J=11.2 Hz, 1H), 2.55-2.41 (m, 5H), 2.31 (s, 3H), 2.16-2.06 (m, 1H), 1.68-1.53 (m, 3H), 1.37 (td, J=8.3, 5.1 Hz, 1H), 0.73 (d, J=6.6 Hz, 12H). Enantiomer 2: LC-MS Anal. Calc'd for $C_{26}H_{34}FN_3O_3$ 455.26. found [M+H] 456.28. $T_r$=3.73 min (Method A). $^1$H NMR (400 MHz, CHLOROFORM-d) δ 7.94 (d, J=8.1 Hz, 1H), 7.64 (s, 1H), 7.21-7.14 (m, 2H), 7.13-7.05 (m, 2H), 6.77 (d, J=11.4 Hz, 1H), 2.55-2.40 (m, 5H), 2.31 (s, 3H), 2.14-2.04 (m, 1H), 1.67-1.53 (m, 3H), 1.35 (td, J=8.3, 5.0 Hz, 1H), 0.73 (d, J=6.6 Hz, 12H)

Example 28

Racemic (1S,2R)-2-(4-(diisobutylamino)-2-fluoro-5-(3-(6-methylpyridin-3-yl)ureido)phenyl)cyclopropanecarboxylic acid

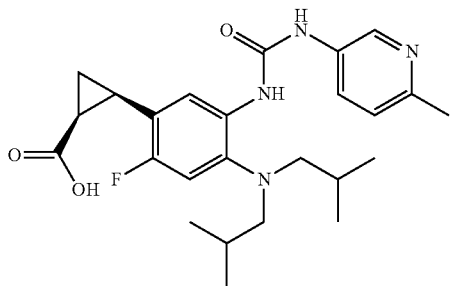 [SMILES: Cc1ccc(NC(=O)Nc2cc([C@@H]3C[C@@H]3C(=O)O)c(F)cc2N(CC(C)C)CC(C)C)cn1]

Racemic example 28 was prepared following the procedure for racemic example 27 except for using the following urea formation method: To a solution of triphosgene (21.95 mg, 0.074 mmol) in THF (2 mL) was added 6-methylpyridin-3-amine (20 mg, 0.185 mmol) and Hunig's base (0.068 mL, 0.388 mmol). After stirring for 1 h, (1S,2R)-ethyl 2-(5-amino-4-(diisobutylamino)-2-fluorophenyl)cyclopropanecarboxylate (97 mg, 0.277 mmol) in THF (2.000 mL) was added. The resulting solution was stirred at RT for 16 h. LC-MS indicated product formation. After removing solvent the crude ester was dissolved in THF (2.000 mL) and water (1.000 mL) then 1N aqueous sodium hydroxide (0.555 mL, 0.555 mmol) was added. Then MeOH (1 mL) was added to dissolve the precipitate and it turned into a clear yellow solution. The reaction was monitored by LC-MS. After 4 days, reaction was complete. Most MeOH and THF was removed in vacuo and the crude was diluted with 2 mL of water, the pH was adjusted to ca.4 using 1N aqueous HCl. The aqueous phase was then extracted with EtOAc (3×10 mL) and the combined organic phase were washed with brine, dried over $Na_2SO_4$, filtered and concentrated. Purification by preparative HPLC gave racemic example 28 (yellow solid, 12.8 mg, 0.028 mmol, 15.01% yield). LC-MS Anal. Calc'd for $C_{25}H_{33}FN_4O_3$ 456.25. found [M+H] 457.22 $T_r$=3.01 min (Method A). $^1$H NMR (500 MHz, DMSO-$d_6$) δ 9.51 (br. s., 1H), 8.47 (d, J=2.5 Hz, 1H), 7.92-7.66 (m, 3H), 7.16 (d, J=8.4 Hz, 1H), 6.97 (d, J=11.4 Hz, 1H), 2.72-2.59 (m, 4H), 2.45-2.34 (m, 4H), 2.05-1.94 (m, 1H), 1.63 (dquin, J=13.3, 6.6 Hz, 2H), 1.30 (t, J=7.2 Hz, 2H), 0.83 (t, J=6.9 Hz, 12H)

Example 29

Racemic (1S,2R)-2-(4-(diisobutylamino)-2-fluoro-5-(3-(3-methylisoxazol-5-yl)ureido)phenyl)cyclopropanecarboxylic acid

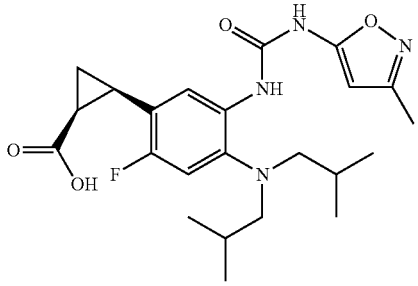 [SMILES: Cc1cc(NC(=O)Nc2cc([C@@H]3C[C@@H]3C(=O)O)c(F)cc2N(CC(C)C)CC(C)C)on1]

Racemic example 29 was prepared following the procedure for racemic example 27 except for using the following urea formation method: To a solution of rac-(1R,2S)-ethyl 2-(5-amino-4-(diisobutylamino)-2 fluorophenyl)cyclopropanecarboxylate (75 mg, 0.214 mmol) in THF (1 ml) at RT was added 4-nitrophenyl carbonochloridate (45.3 mg, 0.225 mmol). The mixture was stirred at RT for 30 min. To this reaction mixture were added 3-methylisoxazol-5-amine (63.0 mg, 0.642 mmol) and TEA (0.089 ml, 0.642 mmol). The reaction was heated at 50° C. for 16 h. Then it was allowed to cool to RT. The crude mixture was passed through a plug of silica gel, rinsed with EtOAc (3×20 mL). The organic phases were combined and concentrated to afford rac-(1R,2S)-ethyl 2-(4-(diisobutylamino)-2-fluoro-5-(3-(3-methylisoxazol-5-yl)ureido)phenyl) cyclopropanecarboxylate as a brown residue. A solution of the crude urea formed above was dissolved in THF (1.8 mL), then a solution of lithium hydroxide monohydrate (27.1 mg, 0.645 mmol) in water (0.6 mL) was added. MeOH (0.6 mL) was added to dissolve the precipitate and it turned into a clear yellow solution. The reaction was monitored by LC-MS. After 12 h, reaction was complete. Most MeOH and THF was removed in vacuo and the crude was diluted with 5 mL of water, the pH was adjusted to ca.4 using 1N aqueous HCl. The aqueous phase was then extracted with EtOAc (2×10 mL) and the combined organic extracts were washed with brine, dried over $Na_2SO_4$, filtered and concentrated. Purification by preparative HPLC gave racemic example 29 (yellow oil, 42 mg, 0.094 mmol, 43.8% yield). LC-MS Anal. Calc'd for $C_{23}H_{31}FN_4O_4$ 446.23. found [M+H] 447.4 $T_r$=1 min (Method B). $^1$H NMR (500 MHz, METHANOL-$d_4$) δ 7.89-7.77 (m, 1H), 6.88-6.74 (m, 1H), 6.04 (s, 1H), 2.72-2.57 (m, 4H), 2.52-2.37 (m, 1H), 2.25 (s, 3H), 2.14-2.04 (m, 1H), 1.78-1.66 (m, 2H), 1.63-1.54 (m, 1H), 1.42-1.31 (m, 1H), 0.87 (dd, J=7.9, 6.9 Hz, 12H)

Example 30

(1R,2S)-2-(4-(diisobutylamino)-3-(3-(3-methylisoxazol-5-yl)ureido)phenyl)cyclopropanecarboxylic acid

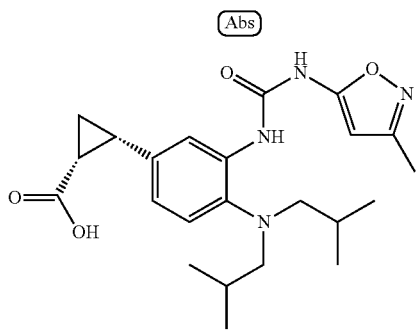 [SMILES: Cc1cc(NC(=O)Nc2cc([C@H]3C[C@H]3C(=O)O)ccc2N(CC(C)C)CC(C)C)on1]

Example 30 was prepared following the procedure for Example 29 using 1H and 3-methylisoxazol-5-amine. LC-MS Anal. Calc'd for $C_{23}H_{32}N_4O_4$ 428.24. found [M+H] 429.4 $T_r$=0.9 min (Method B). $^1$H NMR (400 MHz, METHANOL-$d_4$) δ 7.97 (d, J=1.8 Hz, 1H), 7.16 (d, J=8.4 Hz, 1H), 7.00 (dd, J=8.1, 1.5 Hz, 1H), 6.07 (s, 1H), 2.69 (d, J=7.0 Hz, 4H), 2.61 (d, J=8.4 Hz, 1H), 2.26 (s, 3H), 2.14-2.05 (m, 1H), 1.76-1.58 (m, 3H), 1.41-1.31 (m, 1H), 0.90 (dd, J=6.6, 1.1 Hz, 12H)

Example 31

(1S,2R)-2-(4-(diisobutylamino)-3-(3-(3-methylisoxazol-5-yl)ureido)phenyl)cyclopropanecarboxylic acid

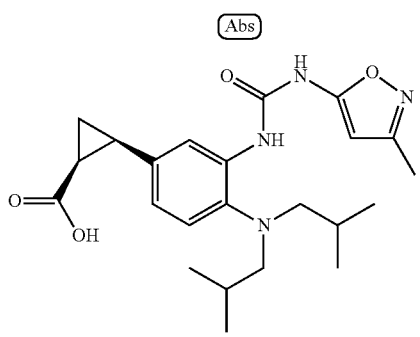 [SMILES: Cc1cc(NC(=O)Nc2cc([C@@H]3C[C@@H]3C(=O)O)ccc2N(CC(C)C)CC(C)C)on1]

Example 31 was prepared following the procedure for example 29 using 1G and 3-methylisoxazol-5-amine. LC-MS Anal. Calc'd for $C_{23}H_{32}N_4O_4$ 428.24. found [M+H] 429.4 $T_r$=0.9 min (Method B). $^1$H NMR (400 MHz, METHANOL-$d_4$) δ 7.97 (d, J=1.8 Hz, 1H), 7.16 (d, J=8.4 Hz, 1H), 7.00 (dd, J=8.3, 1.7 Hz, 1H), 6.07 (s, 1H), 2.69 (d, J=7.0 Hz, 4H), 2.65-2.57 (m, 1H), 2.26 (s, 3H), 2.09 (ddd, J=9.4, 7.8, 5.3 Hz, 1H), 1.76-1.58 (m, 3H), 1.36 (ddd, J=8.6, 7.7, 4.8 Hz, 1H), 0.90 (dd, J=6.6, 1.1 Hz, 12H)

Example 32

Racemic (1S,2R)-2-(4-(diisobutylamino)-3-(3-(6-(trifluoromethyl)pyridin-3-yl)ureido)phenyl)cyclopropanecarboxylic acid

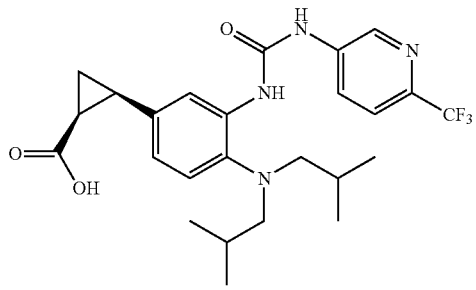 [SMILES: CC(C)CN(CC(C)C)c1ccc([C@@H]2C[C@@H]2C(=O)O)cc1NC(=O)Nc1ccc(C(F)(F)F)nc1]

Example 32 was prepared following the procedure for example 29 using 1G and 6-(trifluoromethyl)pyridin-3-amine. LC-MS Anal. Calc'd for $C_{25}H_{31}F_3N_4O_3$ 492.23. found [M+H] 493.5 $T_r$=0.97 min (Method B). $^1$H NMR (500 MHz, METHANOL-$d_4$) δ 8.68 (d, J=2.0 Hz, 1H), 8.33 (dd, J=8.7, 2.2 Hz, 1H), 7.92 (d, J=1.5 Hz, 1H), 7.68 (d, J=8.4 Hz, 1H), 7.09 (d, J=7.9 Hz, 1H), 6.97 (dd, J=8.2, 1.7 Hz, 1H), 2.70-2.61 (m, 4H), 2.60 (d, J=7.9 Hz, 1H), 2.06 (s, 1H), 1.76-1.59 (m, 3H), 1.35 (d, J=5.0 Hz, 1H), 0.89 (d, J=6.9 Hz, 12H)

Example 33

Racemic (1S,2R)-2-(4-(diisobutylamino)-3-(3-(6-fluoropyridin-3-yl)ureido)phenyl)cyclopropanecarboxylic acid

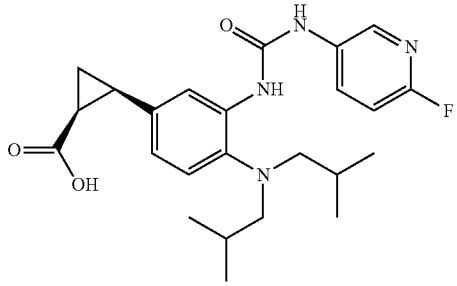 [SMILES: CC(C)CN(CC(C)C)c1ccc([C@@H]2C[C@@H]2C(=O)O)cc1NC(=O)Nc1ccc(F)nc1]

Example 33 was prepared following the procedure for example 29 using 1G and 6-fluoropyridin-3-amine. LC-MS Anal. Calc'd for $C_{24}H_{31}FN_4O_3$ 442.24. found [M+H] 443.5 $T_r$=0.87 min (Method B). $^1$H NMR (500 MHz, METHANOL-$d_4$) δ 8.22 (d, J=2.0 Hz, 1H), 8.14 (br. s., 1H), 7.88 (d, J=1.5 Hz, 1H), 7.08 (d, J=8.4 Hz, 1H), 7.00-6.92 (m, 2H), 2.63 (d, J=6.9 Hz, 4H), 2.59 (d, J=7.9 Hz, 1H), 2.13-1.98 (m, 1H), 1.78-1.59 (m, 3H), 1.34 (d, J=4.5 Hz, 1H), 0.93-0.84 (m, 12H)

Example 34

(1R,2S)-2-(3-(3-(3-cyclopropylisoxazol-5-yl)ureido)-4-(diisobutylamino)phenyl)cyclopropanecarboxylic acid

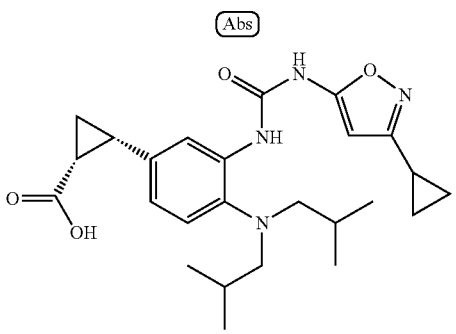 [SMILES: CC(C)CN(CC(C)C)c1ccc([C@H]2C[C@H]2C(=O)O)cc1NC(=O)Nc1cc(C2CC2)no1]

Example 34 was prepared following the procedure for Example 29 utilizing 1H and 3-cyclopropylisoxazol-5-amine. LC-MS Anal. Calc'd for $C_{25}H_{34}N_4O_4$ 454.26. found [M+H] 455.4 $T_r$=0.94 min (Method B). $^1$H NMR (500 MHz, METHANOL-$d_4$) δ 7.96 (d, J=1.5 Hz, 1H), 7.08 (d, J=7.9 Hz, 1H), 6.96 (dd, J=8.2, 1.7 Hz, 1H), 5.87 (s, 1H), 2.67-2.61 (m, 4H), 2.58 (d, J=8.4 Hz, 1H), 2.10-2.01 (m, 1H), 1.97-1.90 (m, 1H), 1.74-1.60 (m, 3H), 1.34 (dd, J=8.4, 3.0 Hz, 1H), 1.08-1.00 (m, 2H), 0.91-0.85 (m, 12H), 0.85-0.81 (m, 2H)

Example 35

(1S,2R)-2-(3-(3-(3-cyclopropylisoxazol-5-yl)ureido)-4-(diisobutylamino)phenyl)cyclopropanecarboxylic acid

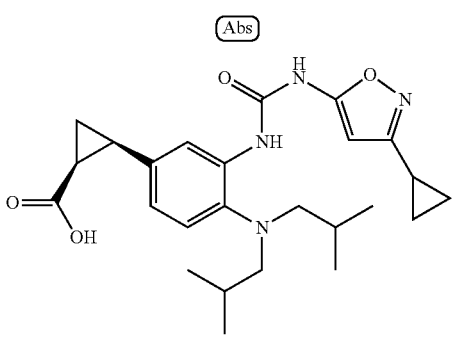 [SMILES: CC(C)CN(CC(C)C)c1ccc([C@@H]2C[C@@H]2C(=O)O)cc1NC(=O)Nc1cc(C2CC2)no1]

Example 35 was prepared following the procedure for example 29 utilising the 1G and 3-cyclopropylisoxazol-5-amine. LC-MS Anal. Calc'd for $C_{25}H_{34}N_4O_4$ 454.26. found [M+H] 455.23 $T_r$=3.47 min (Method A). $^1$H NMR (400 MHz, CHLOROFORM-d) δ 8.26 (br. s., 1H), 7.92 (s, 1H), 7.55 (d, J=3.5 Hz, 1H), 7.11 (d, J=8.1 Hz, 1H), 7.04-6.95 (m, 1H), 5.88 (s, 1H), 2.71-2.53 (m, 5H), 2.16-2.05 (m, 1H), 2.03-1.93 (m, 1H), 1.77-1.64 (m, 3H), 1.42 (td, J=8.3, 5.1 Hz, 1H), 1.11-1.00 (m, 2H), 0.90 (dd, J=6.6, 2.0 Hz, 12H), 0.88-0.83 (m, 2H)

Example 36

(1R,2S)-2-(4-(diisobutylamino)-3-(3-(3-(trifluoromethyl)isoxazol-5-yl)ureido)phenyl)cyclopropanecarboxylic acid

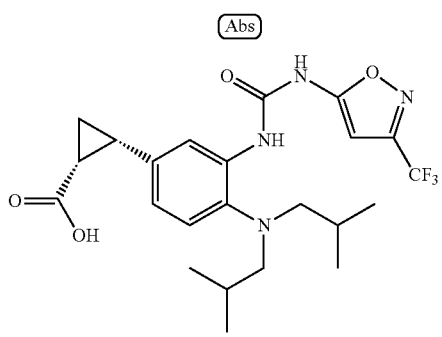 [SMILES: CC(C)CN(CC(C)C)c1ccc([C@H]2C[C@H]2C(=O)O)cc1NC(=O)Nc1cc(C(F)(F)F)no1]

Example 36 was prepared following the procedure for Example 29 utilising 1H and 3-(trifluoromethyl)isoxazol-5-amine. LC-MS Anal. Calc'd for $C_{23}H_{29}F_3N_4O_4$ 482.21. found [M+H] 483.4 $T_r$=1.04 min (Method B). $^1$H NMR (500 MHz, METHANOL-$d_4$) δ 7.99 (d, J=1.5 Hz, 1H), 7.10 (d, J=8.4 Hz, 1H), 6.98 (dd, J=8.4, 2.0 Hz, 1H), 6.48 (s, 1H), 2.68-2.62 (m, 4H), 2.59 (d, J=8.4 Hz, 1H), 2.11-2.00 (m, 1H), 1.74-1.61 (m, 3H), 1.40-1.30 (m, 1H), 0.88 (dd, J=6.7, 1.2 Hz, 12H)

Example 37

(1S,2R)-2-(4-(diisobutylamino)-3-(3-(3-(trifluoromethyl)isoxazol-5-yl)ureido)phenyl)cyclopropanecarboxylic acid

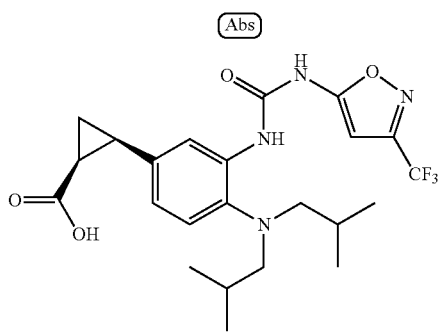 [SMILES: CC(C)CN(CC(C)C)c1ccc([C@@H]2C[C@@H]2C(=O)O)cc1NC(=O)Nc1cc(C(F)(F)F)no1]

Example 37 was prepared following the procedure for example 29 utilising 1G and 3-(trifluoromethyl)isoxazol-5-amine. LC-MS Anal. Calc'd for $C_{23}H_{29}F_3N_4O_4$ 482.21. found [M+H] 483.3 $T_r$=1.03 min (Method B). $^1$H NMR (500 MHz, DMSO-$d_6$) δ 8.35-8.18 (m, 1H), 8.03-7.82 (m, 1H), 7.26-7.07 (m, 1H), 6.96-6.79 (m, 1H), 2.71-2.58 (m, 4H), 2.56-2.52 (m, 1H), 2.11-1.86 (m, 1H), 1.68-1.52 (m, 2H), 1.47-1.35 (m, 1H), 1.33-1.18 (m, 1H), 0.85 (dd, J=6.9, 3.0 Hz, 12H)

Example 38

(1R,2S)-2-(4-(diisobutylamino)-3-(3-(3-phenylisoxazol-5-yl)ureido)phenyl)cyclopropanecarboxylic acid

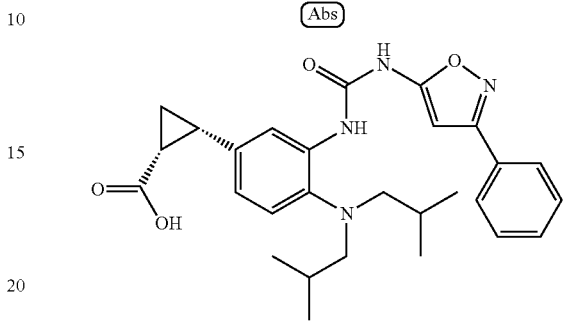

Example 38 was prepared following the procedure for Example 29 utilizing 1H and 3-phenylisoxazol-5-amine. LC-MS Anal. Calc'd for $C_{28}H_{34}N_4O_4$ 490.26. found [M+H] 491.5 $T_r$=1.02 min (Method B). $^1$H NMR (500 MHz, METHANOL-$d_4$) δ 8.01 (d, J=2.0 Hz, 1H), 7.84-7.75 (m, 2H), 7.51-7.41 (m, 3H), 7.10 (d, J=8.4 Hz, 1H), 6.99 (d, J=2.0 Hz, 1H), 6.58 (s, 1H), 2.65 (d, J=6.9 Hz, 4H), 2.61-2.55 (m, 1H), 2.11-2.03 (m, 1H), 1.76-1.59 (m, 3H), 1.40-1.31 (m, 1H), 0.89 (dd, J=6.7, 1.2 Hz, 12H)

Example 39

(1R,2S)-2-(4-(diisobutylamino)-3-(3-(3,4-dimethylisoxazol-5-yl)ureido)phenyl)cyclopropanecarboxylic acid

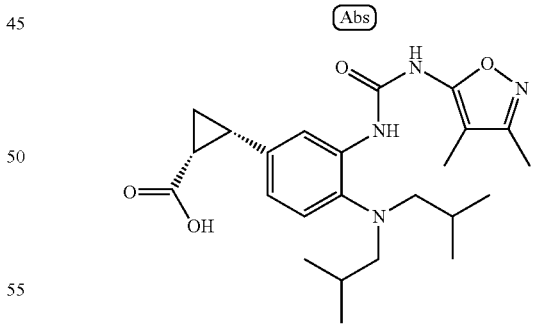

Example 39 was prepared following the procedure for Example 29 utilizing 1H and 3,4-dimethylisoxazol-5-amine. LC-MS Anal. Calc'd for $C_{24}H_{34}N_4O_4$ 442.26. found [M+H] 443.4 $T_r$=0.90 min (Method B). $^1$H NMR (500 MHz, METHANOL-$d_4$) δ 7.94 (d, J=1.5 Hz, 1H), 7.08 (d, J=7.9 Hz, 1H), 6.97 (d, J=2.0 Hz, 1H), 2.60 (d, J=6.9 Hz, 4H), 2.57-2.51 (m, 1H), 2.21 (s, 3H), 2.09-1.99 (m, 1H), 1.91 (s, 3H), 1.73-1.56 (m, 3H), 1.35-1.27 (m, 1H), 0.86 (d, J=6.9 Hz, 12H)

Example 40

Racemic (1S,2R)-2-(5-(3-(4-chloro-2-fluorophenyl)ureido)-4-(diisobutylamino)-2-fluorophenyl)cyclopropanecarboxylic acid

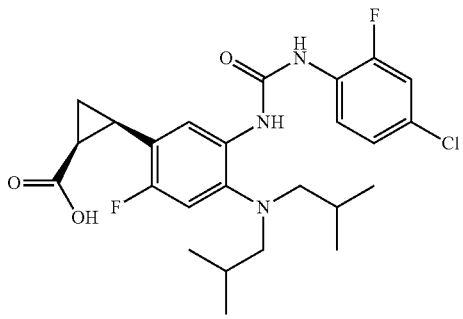 [SMILES: CC(C)CN(CC(C)C)c1cc(F)c([C@@H]2C[C@@H]2C(=O)O)cc1NC(=O)Nc1ccc(Cl)cc1F]

Racemic example 40 was prepared following the procedure for Example 27 utilizing the corresponding isocyanate. LC-MS Anal. Calc'd for $C_{25}H_{30}ClF_2N_3O_3$ 493.19. found [M+H] 494.12. $T_r$=3.91 min (Method A). $^1$H NMR (500 MHz, DMSO-$d_6$) δ 8.11 (td, J=8.9, 5.0 Hz, 1H), 7.94 (s, 1H), 7.64 (dt, J=8.2, 2.8 Hz, 1H), 7.43 (dd, J=11.1, 2.2 Hz, 1H), 7.21 (dd, J=10.2, 1.2 Hz, 1H), 6.91 (d, J=11.9 Hz, 1H), 2.75-2.60 (m, 4H), 2.40 (q, J=8.1 Hz, 1H), 2.03-1.94 (m, 1H), 1.66 (dquin, J=13.4, 6.7 Hz, 2H), 1.30 (t, J=7.4 Hz, 2H), 0.82 (dd, J=11.1, 6.7 Hz, 12H)

Example 41

Racemic (1S,2R)-2-(4-(diisobutylamino)-2-fluoro-5-(3-(2-fluorophenyl)ureido)phenyl)cyclopropanecarboxylic acid

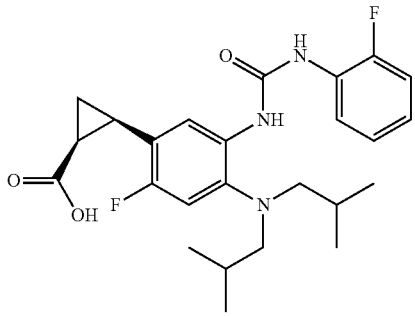 [SMILES: CC(C)CN(CC(C)C)c1cc(F)c([C@@H]2C[C@@H]2C(=O)O)cc1NC(=O)Nc1ccccc1F]

Racemic example 41 was prepared following the procedure for Example 27 utilizing the corresponding isocyanate. LC-MS Anal. Calc'd for $C_{25}H_{31}F_2N_3O_3$ 459.23. found [M+H] 460.19. $T_r$=3.65 min (Method A). $^1$H NMR (500 MHz, DMSO-$d_6$) δ 9.25 (s, 1H), 8.10-8.01 (m, 1H), 7.98-7.87 (m, 1H), 7.65 (dt, J=8.2, 3.1 Hz, 1H), 7.23 (ddd, J=11.5, 8.3, 1.5 Hz, 1H), 7.17-7.09 (m, 1H), 7.06-6.98 (m, 1H), 6.92 (d, J=11.4 Hz, 1H), 2.76-2.61 (m, 4H), 2.41 (q, J=8.4 Hz, 1H), 2.05-1.93 (m, 1H), 1.66 (dquin, J=13.4, 6.7 Hz, 2H), 1.35-1.24 (m, 2H), 0.83 (dd, J=11.6, 6.7 Hz, 12H)

Example 42

Racemic (1S,2R)-2-(4-(diisobutylamino)-3-(3-(6-methylpyridin-3-yl)ureido)phenyl)cyclopropanecarboxylic acid

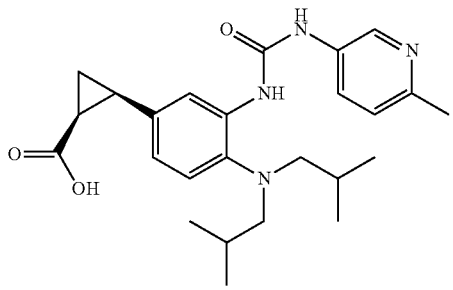 [SMILES: Cc1ccc(NC(=O)Nc2cc([C@@H]3C[C@@H]3C(=O)O)ccc2N(CC(C)C)CC(C)C)cn1]

Racemic example 42 was prepared following the procedure for Example 28 utilizing 1G and 3-amino-6-methylpyridine. LC-MS Anal. Calc'd for $C_{25}H_{34}N_4O_3$ 438.26. found [M+H] 439.19. $T_r$=2.63 min (Method A). $^1$H NMR (500 MHz, DMSO-$d_6$) δ 8.48 (d, J=2.0 Hz, 1H), 8.01-7.89 (m, 2H), 7.87-7.77 (m, 1H), 7.22-7.13 (m, 2H), 7.09 (d, J=7.9 Hz, 1H), 6.81 (dd, J=8.2, 1.7 Hz, 1H), 2.68-2.58 (m, 4H), 2.43-2.32 (m, 4H), 2.01-1.92 (m, 1H), 1.61 (dquin, J=13.3, 6.6 Hz, 2H), 1.42-1.34 (m, 1H), 1.28-1.20 (m, 1H), 0.84 (dd, J=6.7, 3.2 Hz, 12H)

Example 43

(1R,2S)-2-(4-((4-chlorobenzyl)(2-methoxyethyl)amino)-3-(3-(p-tolyl)ureido)phenyl)cyclopropanecarboxylic acid Enantiomer 1 and Enantiomer 2

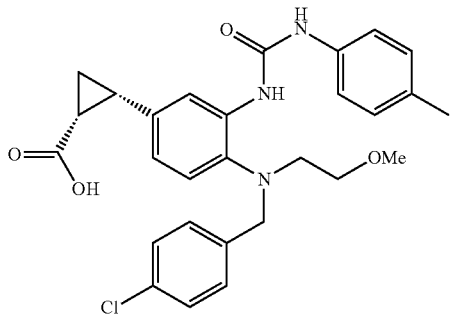 [SMILES: COCCN(Cc1ccc(Cl)cc1)c1ccc([C@H]2C[C@H]2C(=O)O)cc1NC(=O)Nc1ccc(C)cc1]

43A. 4-((4-chlorobenzyl)(2-methoxyethyl)amino)-3-nitrobenzaldehyde

To a flask containing 4-fluoro-3-nitrobenzaldehyde (258 mg, 1.525 mmol) in DMF (6 mL) was added N-(4-chlorobenzyl)-2-methoxyethanamine hydrochloride (300 mg, 1.270 mmol) and cesium carbonate (497 mg, 1.525 mmol). The reaction mixture was heated at 100° C. for 2 h. LC-MS indicated product formation. After cooling to RT, it was diluted with EtOAc (20 mL) and water (10 mL). Aqueous layer was further extracted with EtOAc (3×20 mL), the combined extracts were washed with water, brine, dried over MgSO$_4$, filtered and concentrated. Purification via flash chromatography gave 43A (yellow oil, 360 mg, 1.032 mmol, 81% yield). LC-MS Anal. Calc'd for C$_{17}$H$_{17}$ClN$_2$O$_4$ 348.09. found [M+H] 349.18. T$_r$=3.46 min (Method A). $^1$H NMR (400 MHz, CHLOROFORM-d) δ 9.85 (s, 1H), 8.24 (d, J=2.0 Hz, 1H), 7.88 (dd, J=8.8, 2.0 Hz, 1H), 7.40-7.18 (m, 5H), 4.57 (s, 2H), 3.59-3.50 (m, 2H), 3.48-3.39 (m, 2H), 3.27 (s, 3H)

43B. N-(4-chlorobenzyl)-N-(2-methoxyethyl)-2-nitro-4-vinylaniline

To a solution of methyltriphenylphosphonium iodide (0.627 g, 1.755 mmol) in THF (8 mL) cooled to −78° C. was added nBuLi (0.619 mL, 1.548 mmol). The suspension turned into orange/brown suspension, after it was stirred in an ice-water bath for 1 h. Then 43A (0.36 g, 1.032 mmol) in THF (4.00 mL) was added dropwise to the reaction mixture at −78° C. and warmed up to RT over 3 h. It was diluted with water (10 mL) and EtOAc (20 mL). The aqueous layer was further extracted with EtOAc (3×20 mL) and the combined organic layer was washed with brine, dried over MgSO4, filtered and concentrated. Purification via flash chromatography gave 43B (yellow oil, 0.16 g, 0.461 mmol, 44.7% yield). LC-MS Anal. Calc'd for C$_{18}$H$_{19}$ClN$_2$O$_3$ 346.11. found [M+H] 347.17. T$_r$=3.91 min (Method A). $^1$H NMR (400 MHz, CHLOROFORM-d) δ 7.72 (d, J=2.0 Hz, 1H), 7.44 (dd, J=8.6, 2.2 Hz, 1H), 7.27 (s, 4H), 7.16 (d, J=8.6 Hz, 1H), 6.62 (dd, J=17.6, 10.8 Hz, 1H), 5.69 (d, J=17.6 Hz, 1H), 5.28 (d, J=11.0 Hz, 1H), 4.38 (s, 2H), 3.50-3.42 (m, 2H), 3.30-3.22 (m, 5H)

43C. Racemic (1R,2S)-2-(4-((4-chlorobenzyl)(2-methoxyethyl)amino)-3-(3-(p-tolyl)ureido)phenyl)cyclopropanecarboxylic acid 43C was prepared following the procedure for Example 1 method A using 43B. LC-MS Anal. Calc'd for C$_{28}$H$_{30}$ClN$_3$O$_4$ 507.19. found [M+H] 508.27. T$_r$=3.61 min (Method A). $^1$H NMR (500 MHz, DMSO-d$_6$) δ 11.80 (br. s., 1H), 9.32 (s, 1H), 8.25 (s, 1H), 8.05-7.89 (m, 2H), 7.38 (d, J=7.9 Hz, 2H), 7.31-7.23 (m, 3H), 7.10 (d, J=8.4 Hz, 2H), 7.05 (d, J=7.9 Hz, 1H), 6.70 (dd, J=7.9, 1.5 Hz, 1H), 4.15 (s, 2H), 3.17 (s, 3H), 3.03 (t, J=5.7 Hz, 2H), 2.48-2.42 (m, 1H), 2.25 (s, 3H), 1.95 (td, J=7.8, 6.7 Hz, 1H), 1.40-1.33 (m, 1H), 1.22 (td, J=7.9, 4.5 Hz, 1H) (Note: one triplet of CH$_2$ is buried under the water peak)

Enantiomer 1 and Enantiomer 2 (1R,2S)-2-(4-((4-chlorobenzyl)(2-methoxyethyl)amino)-3-(3-(p-tolyl)ureido)phenyl)cyclopropanecarboxylic acid Chiral separation of 43C gave Enantiomer 1 and Enatiomer 2 as single enantiomers (Method H). Enantiomer 1 T$_r$=12.736 min and Enantiomer 2 T$_r$=14.547 min (Method J). Enantiomer 1: LC-MS Anal. Calc'd for C$_{28}$H$_{30}$ClN$_3$O$_4$ 507.19. found [M+H] 508.13. T$_r$=3.60 min (Method A). $^1$H NMR (400 MHz, CHLOROFORM-d) δ 8.39 (s, 1H), 8.21 (d, J=1.8 Hz, 1H), 7.25 (s, 1H), 7.20-7.08 (m, 4H), 7.00 (d, J=8.4 Hz, 2H), 6.93 (d, J=8.1 Hz, 1H), 6.80 (dd, J=8.3, 1.7 Hz, 1H), 3.96 (s, 2H), 3.31-3.23 (m, 5H), 2.95 (t, J=5.0 Hz, 2H), 2.58 (q, J=8.6 Hz, 1H), 2.32 (s, 3H), 2.09-1.98 (m, 1H), 1.62 (dt, J=7.5, 5.4 Hz, 1H), 1.32 (td, J=8.3, 5.1 Hz, 1H) Enantiomer 2: LC-MS Anal. Calc'd for C$_{28}$H$_{30}$ClN$_3$O$_4$ 507.19. found [M+H] 508.10. T$_r$=3.61 min. $^1$H NMR (400 MHz, CHLOROFORM-d) δ 8.38 (s, 1H), 8.22 (s, 1H), 7.25-7.19 (m, 2H), 7.18-7.08 (m, 4H), 6.99 (d, J=8.1 Hz, 2H), 6.92 (d, J=8.1 Hz, 1H), 6.84-6.75 (m, 1H), 3.95 (s, 2H), 3.32-3.18 (m, 5H), 2.94 (t, J=5.0 Hz, 2H), 2.57 (q, J=8.5 Hz, 1H), 2.32 (s, 3H), 2.09-1.97 (m, 1H), 1.66-1.56 (m, 1H), 1.32 (td, J=8.1, 5.2 Hz, 1H)

Example 44

Racemic (1R,2S)-2-(4-((4-chlorobenzyl)(2-methoxyethyl)amino)-3-(3-(2-fluorophenyl)ureido)phenyl)cyclopropanecarboxylic acid

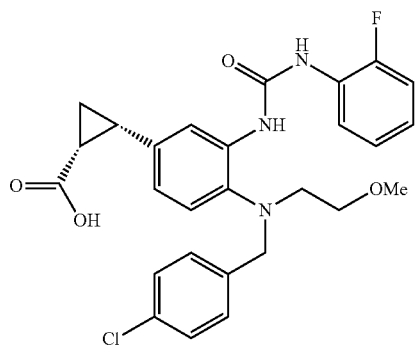 [SMILES: COCCN(Cc1ccc(Cl)cc1)c1ccc([C@H]2C[C@H]2C(=O)O)cc1NC(=O)Nc1ccccc1F]

Racemic example 44 was prepared following the procedure for Example 43 utilizing the corresponding isocyanate. LC-MS Anal. Calc'd for C$_{27}$H$_{27}$ClFN$_3$O$_4$ 511.17. found [M+H] 512.22. T$_r$=3.58 min (Method A). $^1$H NMR (500 MHz, DMSO-d$_6$) δ 9.33 (d, J=1.0 Hz, 1H), 8.62 (s, 1H), 8.12 (td, J=8.3, 1.7 Hz, 1H), 7.97 (d, J=2.0 Hz, 1H), 7.36-7.22 (m, 5H), 7.20-7.09 (m, 1H), 7.06-6.95 (m, 2H), 6.73 (dd, J=8.4, 2.0 Hz, 1H), 4.17 (s, 2H), 3.18 (s, 3H), 3.05 (t, J=5.9 Hz, 2H), 2.43 (q, J=8.4 Hz, 1H), 1.93 (ddd, J=9.3, 7.6, 5.9 Hz, 1H), 1.40-1.30 (m, 1H), 1.20 (td, J=8.2, 4.5 Hz, 1H) (Note: one triplet CH$_2$ buried under solvent peak)

Example 45

Racemic (1S,2R)-2-(4-(cyclohexyl)isobutyl)amino)-3-(3-(p-tolyl)ureido)phenyl)cyclopropanecarboxylic acid

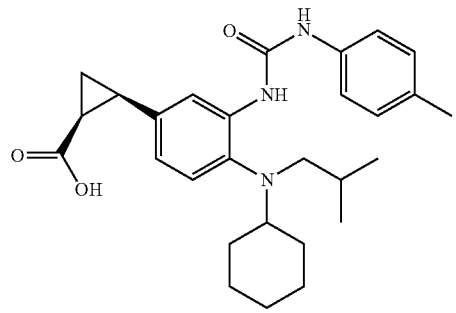 [SMILES: Cc1ccc(NC(=O)Nc2cc([C@@H]3C[C@@H]3C(=O)O)ccc2N(CC(C)C)C2CCCCC2)cc1]

45A. 4-bromo-N-cyclohexyl-N-isobutyl-2-nitroaniline

To a solution of cyclohexanamine (2.309 mL, 20.17 mmol) in CH$_2$Cl$_2$ (100 mL) cooled to 0° C. was added triethylamine (4.22 mL, 30.2 mmol). The mixture was stirred at 0° C. for 5 min before isobutyryl chloride (2.54 mL, 24.20 mmol) was added dropwise. The mixture was stirred and allowed to warm to RT slowly. After 2 h, LC-MS indicated completion. The reaction mixture was quenched with saturated aqueous NaHCO$_3$ then extracted with CH$_2$Cl$_2$ (3×30 mL). The combined organic extracts were washed with 1N aqueous HCl, brine then dried over Na$_2$SO$_4$, filtered and concentrated in vacuo to afford 2.3 g white solid and this was used without purification in the next step. To a solution of crude N-cyclohexylisobutyramide obtained in the previous step (2.3 g, 13.59 mmol) in THF (50 mL) was slowly added lithium aluminum hydride (27.2 mL, 27.2 mmol). The resulting solution was refluxed at 70° C. for 16 h. LC-MS indicated depletion of starting material. After Fieser quenching, the solid was filtered out. After separating two layers, the aqueous layer was further extracted with EtOAc (3×30 mL) and the combined organic layer was washed with water, brine, dried over MgSO$_4$, filtered and concentrated to give 2 g white solid. A suspension containing 4-bromo-1-fluoro-2-nitrobenzene (1.417 g, 6.44 mmol), cesium carbonate (4.20 g, 12.88 mmol) and above obtained crude N-isobutylcyclohexanamine (1 g, 6.44 mmol) in DMF (6 mL) was heated at 120° C. for 12 h. LC-MS showed desired product. The mixture was concentrated under reduced pressure and directly purified by flash chromatography to give 45A (orange solid, 1.5 g, 3.38 mmol, 52.4% yield). LC-MS Anal. Calc'd for C$_{16}$H$_{23}$BrN$_2$O$_2$ 354.09. found [M+3H] 356.91. T$_r$=4.40 min (Method A).

45B. Racemic (1S,2R)-2-(4-(cyclohexyl(isobutyl) amino)-3-(3-(p-tolyl)ureido)phenyl)cyclopropanecarboxylic acid 45B was prepared following the procedure for Example 1 Method A using 45A. LC-MS Anal. Calc'd for C$_{28}$H$_{37}$N$_3$O$_3$ 463.28. found [M+H] 464.25. T$_r$=3.29 min (Method A). $^1$H NMR (500 MHz, DMSO-d$_6$) δ 8.00 (s, 1H), 7.95 (d, J=5.9 Hz, 1H), 7.41-7.27 (m, 2H), 7.08 (d, J=8.4 Hz, 2H), 7.03 (d, J=7.9 Hz, 1H), 6.77 (dd, J=7.9, 2.0 Hz, 1H), 3.37 (br. s., 3H), 2.24 (s, 3H), 2.01-1.92 (m, 1H), 1.91-1.79 (m, 2H), 1.67 (d, J=11.9 Hz, 2H), 1.50 (d, J=11.9 Hz, 1H), 1.42-1.34 (m, 1H), 1.33-0.93 (m, 7H), 0.80 (d, J=6.4 Hz, 6H) (one proton buried under DMSO peak)

Example 46

Racemic (1S,2R)-2-(4-(cyclohexyl(isobutyl)amino)-3-(3-(3-methylisoxazol-5-yl)ureido)phenyl)cyclopropanecarboxylic acid

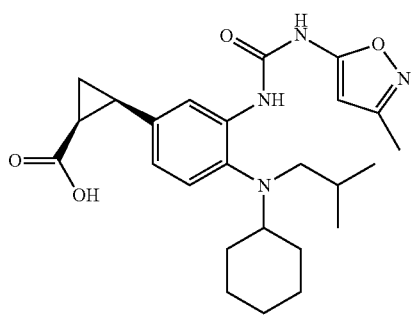 [SMILES: Cc1cc(NC(=O)Nc2cc([C@@H]3C[C@@H]3C(=O)O)ccc2N(CC(C)C)C2CCCCC2)on1]

Racemic example 46 was prepared following the procedure for Example 45 utilizing 3-methylisoxazol-5-amine following the urea formation method from example 29.

LC-MS Anal. Calc'd for C$_{25}$H$_{34}$N$_4$O$_4$ 454.26. found [M+H] 455.3. T$_r$=0.91 min (Method B). $^1$H NMR (500 MHz, METHANOL-d$_4$) δ 8.11-7.98 (m, 1H), 7.18-6.82 (m, 2H), 6.05 (s, 1H), 2.86-2.72 (m, 2H), 2.64-2.49 (m, 2H), 2.25 (s, 3H), 2.12-2.01 (m, 1H), 1.95-1.82 (m, 2H), 1.79-1.69 (m, 2H), 1.68-1.62 (m, 1H), 1.60-1.51 (m, 1H), 1.46-1.32 (m, 2H), 1.30-1.22 (m, 2H), 1.20-1.10 (m, 2H), 1.09-1.00 (m, 1H), 0.82 (br. s., 6H)

Example 47

(1S,2R)-2-(4-(1-phenylpropoxy)-3-(3-(p-tolyl) ureido)phenyl)cyclopropanecarboxylic acid Racemic Mixture of Four Diastereomers

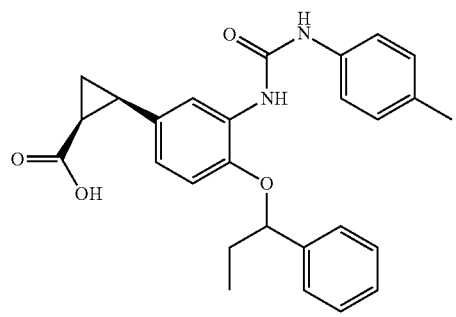 [SMILES: CCC(Oc1ccc([C@@H]2C[C@@H]2C(=O)O)cc1NC(=O)Nc1ccc(C)cc1)c1ccccc1]

47A. 4-bromo-1-(methoxymethoxy)-2-nitrobenzene

To a solution of 4-bromo-2-nitrophenol (1 g, 4.59 mmol) in CH$_2$Cl$_2$ (30 mL) was added Hunig's Base (1.202 mL, 6.88 mmol) followed by chloromethyl methyl ether (MOM-Cl) (0.418 mL, 5.50 mmol). The resulting solution was stirred at RT for 4 h. LC-MS indicated completion, it was diluted with CH$_2$Cl$_2$ (10 mL) and water (10 mL), the aqueous layer was further extracted with CH$_2$Cl$_2$ (2×20 mL), the combined extracts were washed with water, brine, dried over MgSO$_4$, filtered and concentrated. Purification via flash chromatography gave 47A (yellow oil, 1.1 g, 4.20 mmol, 92% yield). LC-MS Anal. Calc'd for C$_8$H$_8$BrNO$_4$ 260.96, T$_r$=2.89 min (Method A). $^1$H NMR (400 MHz, CHLOROFORM-d) δ 7.95 (d, J=2.4 Hz, 1H), 7.61 (dd, J=9.0, 2.4 Hz, 1H), 7.24 (d, J=8.8 Hz, 1H), 5.28 (s, 2H), 3.53 (s, 3H)

47B. 1-(methoxymethoxy)-2-nitro-4-vinylbenzene

To a solution of 48A (1.1 g, 4.20 mmol) in ethanol (10.0 mL) and toluene (5.00 mL), was added 2,4,6-trivinyl-1,3,5, 2,4,6-trioxatriborinane pyridine complex (0.814 g, 5.04 mmol) followed by K$_3$PO$_4$ (1.337 g, 6.30 mmol) and water (2.000 mL). The reaction mixture was purged with nitrogen for 10 min and then palladium tetrakis (0.243 g, 0.210 mmol) was added. It was then heated under nitrogen at 80° C. in an oil bath for 8 h. LC-MS showed completion. It was diluted with EtOAc (20 mL) and filtered through a pad of Celite, rinsed with EtOAc. Then it was diluted with 20 mL of water, the aqueous layer was further extracted with EtOAc (2×20 mL), the combined extracts were washed with water, brine, dried over MgSO$_4$, filtered and concentrated. Purification via flash chromatography gave 47B (yellow oil, 750 mg, 3.59 mmol, 85% yield). LC-MS Anal. Calc'd for C$_{10}$H$_{11}$NO$_4$ 209.07. T$_r$=2.87 min (Method A). $^1$H NMR (400

MHz, CHLOROFORM-d) δ 7.86 (d, J=2.2 Hz, 1H), 7.55 (dd, J=8.9, 2.1 Hz, 1H), 7.38-7.20 (m, 1H), 6.68 (dd, J=17.6, 11.0 Hz, 1H), 5.82-5.64 (m, 1H), 5.37-5.28 (m, 3H), 3.55 (s, 3H)

47C. racemic (1S,2R)-ethyl 2-(4-(methoxymethoxy)-3-nitrophenyl) cyclopropanecarboxylate To a solution of 47B (740 mg, 3.54 mmol) in $CH_2Cl_2$ (18 mL) was added Rodium acetate dimer (235 mg, 0.531 mmol) followed by a slow addition of a solution of ethyl diazoacetate (0.734 mL, 7.07 mmol) in $CH_2Cl_2$ (3.00 mL) over a period of 1 h via a syringe pump. The reaction mixture turned into a dark green solution. After stirring at RT for 2 days, LC-MS indicated completion. The reaction was filtered through a pad of Celite, rinsed with $CH_2Cl_2$ (2×30 mL). The solvent was removed in vacuo and purification via flash chromatography gave 47C (orange oil, 280 mg, 0.759 mmol, 21.45% yield) and the trans isomer of 47C (orange oil, 350 mg, 1.185 mmol, 33.5% yield). LC-MS Anal. Calc'd for: $C_{14}H_{17}NO_6$ 295.11. found [M+H] 252.15 (mass of the corresponding phenol). $T_r$=2.80 min (Method A). $^1$H NMR (400 MHz, CHLOROFORM-d) δ 7.72 (d, J=2.0 Hz, 1H), 7.45-7.37 (m, 1H), 7.21 (d, J=8.8 Hz, 1H), 5.25 (d, J=2.0 Hz, 2H), 3.94 (qd, J=7.1, 1.9 Hz, 2H), 3.51 (s, 3H), 2.58-2.47 (m, 1H), 2.11 (ddd, J=9.1, 8.0, 5.6 Hz, 1H), 1.66 (dt, J=7.4, 5.4 Hz, 1H), 1.44-1.35 (m, 1H), 1.06 (t, J=7.2 Hz, 3H)

47D. Racemic (1S,2R)-ethyl 2-(4-hydroxy-3-nitrophenyl) cyclopropanecarboxylate To a flask containing 47C (280 mg, 0.759 mmol) was added HCl in dioxane (3414 µl, 13.65 mmol). The resulting reaction mixture was heated at 60° C. for 12 h. After cooling to RT, it was diluted with EtOAc (10 mL) and water (10 mL). The aqueous layer was further extracted with EtOAc (2×20 mL), the combined extracts were washed with water, brine, dried over $MgSO_4$, filtered and concentrated. Purification via flash chromatography gave 47D (yellow oil, 140 mg, 0.474 mmol, 62.4% yield). LC-MS Anal. Calc'd for $C_{12}H_{13}NO_5$ 251.08. found [M+H] 252.15 (mass of the corresponding phenol). $T_r$=2.69 min (Method A). $^1$H NMR (400 MHz, CHLOROFORM-d) δ 8.08-7.96 (m, 1H), 7.56-7.45 (m, 1H), 7.06 (d, J=8.8 Hz, 1H), 4.03-3.85 (m, 2H), 2.60-2.44 (m, 1H), 2.11 (ddd, J=9.0, 7.9, 5.7 Hz, 1H), 1.67 (dt, J=7.3, 5.5 Hz, 1H), 1.47-1.35 (m, 1H), 1.08 (t, J=7.2 Hz, 3H)

47E. Racemic Mixture of Diastereomers (1S,2R)-2-(4-(1-phenylpropoxy)-3-(3-(p-tolyl)ureido)phenyl) cyclopropanecarboxylic acid To a solution of triphenylphosphine (70.5 mg, 0.269 mmol) in THF (1 mL) was added DIAD (0.052 mL, 0.269 mmol). The reaction mixture was stirred for 10 min. Then a solution of 47D (45 mg, 0.179 mmol) and 1-phenylpropan-1-ol (24.39 mg, 0.179 mmol) in THF (1.000 mL) was added dropwise. The reaction mixture was then stirred at rt for 16 h. LC-MS indicated a new nonpolar peak, it was diluted with EtOAc (10 mL) and water (5 mL). The aqueous layer was extracted with EtOAc (2×20 mL) and the combined organic extracts were washed with water, brine, dried over $Na_2SO_4$, filtered and concentrated. Purification via flash chromatography gave (1S,2R)-ethyl 2-(3-nitro-4-(1-phenylpropoxy) phenyl)cyclopropanecarboxylate (yellow oil, 70 mg, 0.133 mmol, 74.1% yield) with ca. 70% purity. This was used without further purification in subsequent step. To a stirred solution of the product obtained above (70 mg, 0.133 mmol) in ethyl acetate (4.00 mL) was added palladium on carbon (28.2 mg, 0.027 mmol) and the suspension was hydrogenated (1 atm, balloon) for 1 h. LC-MS indicated completion. The suspension was then filtered through a pad of Celite. The filter cake was rinsed with EtOAc (2×20 mL). Combined filtrate and rinses were evaporated in vacuo. Purification via flash chromatography gave 40 mg aniline. To a solution of this crude aniline in THF (2 mL) was added 1-isocyanato-4-methylbenzene (26.5 mg, 0.199 mmol). The resulting solution was stirred at rt for 2 h. LC-MS indicated completion. The reaction mixture was concentrated then the crude ester was dissolved in THF (2.000 mL) and water (1.000 mL) then sodium hydroxide (1N aqueous) (0.398 mL, 0.398 mmol) was added. MeOH (1 mL) was added to dissolve the precipitate and it turned into a clear yellow solution. After 60 h, reaction was complete. Most MeOH and THF was removed in vacuo and the crude was diluted with 2 mL of water, the pH was adjusted to ca.4 using 1N aqueous HCl. The aqueous phase was then extracted with EtOAc (3×20 mL) and the combined organic phase was washed with brine, dried over $Na_2SO_4$ and concentrated. Preparative HPLC gave racemic 47E (yellow solid, 21.3 mg, 0.048 mmol, 36.1% yield), as a diastereomeric mixture LC-MS Anal. Calc'd for: $C_{27}H_{28}N_2O_4$ 444.20. found [M+H] 445.17. $T_r$=3.59 min (Method A). $^1$H NMR (500 MHz, MeOD) δ 7.98 (s, 1H), 7.38-7.24 (m, 6H), 7.20 (td, J=6.1, 2.7 Hz, 1H), 7.11 (d, J=7.9 Hz, 2H), 6.68 (dt, J=8.4, 2.7 Hz, 1H), 6.57 (dd, J=8.4, 1.5 Hz, 1H), 5.08-4.96 (m, 1H), 2.47 (q, J=8.8 Hz, 1H), 2.29 (s, 3H), 2.03 (dt, J=14.4, 7.2 Hz, 1H), 1.99-1.92 (m, 1H), 1.91-1.79 (m, 1H), 1.58-1.47 (m, 1H), 1.28-1.18 (m, 1H), 0.96 (t, J=7.2 Hz, 3H)

Example 48

(1S,2R)-2-(4-(1-(4-chlorophenyl)butoxy)-3-(3-(p-tolyl)ureido) phenyl)cyclopropanecarboxylic acid Racemic Mixture of Four Diastereomers

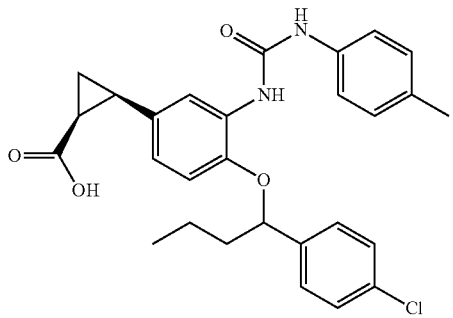 [SMILES: CCCC(Oc1ccc([C@@H]2C[C@@H]2C(=O)O)cc1NC(=O)Nc1ccc(C)cc1)c1ccc(Cl)cc1]

48A. 4-bromo-1-(1-(4-chlorophenyl)butoxy)-2-nitrobenzene

To a solution of triphenylphosphine (1704 mg, 6.50 mmol) in THF (20 mL) was added DIAD (1.263 mL, 6.50 mmol). The reaction mixture was stirred for 10 min. Then a solution of 4-bromo-2-nitrophenol (944 mg, 4.33 mmol) and 1-(4-chlorophenyl)butan-1-ol (800 mg, 4.33 mmol) in THF (10.00 mL) was added dropwise. The reaction mixture was then stirred at RT for 1 h. LC-MS indicated completion, it was diluted with EtOAc (10 mL) and water (5 mL). The aqueous layer was extracted with EtOAc (2×10 mL) and the combined organic layer was washed with water, brine and dried over $Na_2SO_4$. Purification via flash chromatography gave 48A (yellow oil, 1.3 g, 3.38 mmol, 78% yield). LC-MS Anal. Calc'd for $C_{16}H_{15}BrClNO_3$ 382.99. found [M+H] 252.15 (mass of the corresponding phenol). $T_r$=4.22 min (Method A). $^1$H NMR (400 MHz, CHLOROFORM-d) δ 7.91 (d, J=2.4 Hz, 1H), 7.43 (dd, J=8.9, 2.5 Hz, 1H), 7.37-7.27 (m, 4H), 6.75 (d, J=9.0 Hz, 1H), 5.24-5.20 (m, 1H), 2.11-1.97 (m, 1H), 1.83 (ddt, J=14.0, 10.1, 5.6 Hz, 1H), 1.58-1.48 (m, 1H), 0.95 (t, J=7.4 Hz, 3H) (one proton buried under impurity peak)

48B. Racemic (1S,2R)-2-(4-(1-(4-chlorophenyl)butoxy)-3-(3-(p-tolyl)ureido)phenyl)cyclopropanecarboxylic acid 48B was obtained following the procedure of Example 47 using 48 A. LC-MS Anal. Calc'd for $C_{28}H_{29}ClN_2O_4$ 492.18. found [M+H] 493.25. $T_r$=3.90 min (Method A). $^1$H NMR (400 MHz, DMSO-$d_6$) δ 9.32 (s, 1H), 8.04 (t, J=2.2 Hz, 1H), 8.00 (s, 1H), 7.51-7.43 (m, 2H), 7.42-7.34 (m, 4H), 7.11 (d, J=8.4 Hz, 2H), 6.72 (d, J=8.6 Hz, 1H), 6.65-6.54 (m, 1H), 5.37 (t, J=5.6 Hz, 1H), 2.41 (q, J=7.8 Hz, 1H), 2.26 (s, 3H), 2.10-1.99 (m, 1H), 1.95-1.85 (m, 1H), 1.83-1.71 (m, 1H), 1.53-1.42 (m, 1H), 1.39-1.27 (m, 2H), 1.22-1.12 (m, 1H), 0.92 (t, J=7.4 Hz, 3H)

Example 49

(1S,2R)-2-(4-(1-phenylbutoxy)-3-(3-(p-tolyl)ureido)phenyl)cyclopropanecarboxylic acid Racemic Mixture of Diastereomers

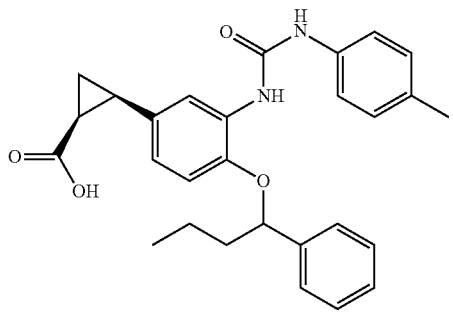 [SMILES: CCCC(Oc1ccc([C@@H]2C[C@@H]2C(=O)O)cc1NC(=O)Nc1ccc(C)cc1)c1ccccc1]

Example 49 was prepared following the procedure for example 47 utilizing 1-phenylbutan-1-ol. LC-MS Anal. Calc'd for $C_{28}H_{30}N_2O_4$ 458.22. found [M+H] 459.19. $T_r$=3.73 min (Method A). $^1$H NMR (500 MHz, MeOD) δ 7.97 (s, 1H), 7.34-7.24 (m, 6H), 7.20 (td, J=5.8, 2.7 Hz, 1H), 7.11 (d, J=8.4 Hz, 2H), 6.68 (dt, J=8.4, 2.7 Hz, 1H), 6.57 (dd, J=8.7, 1.7 Hz, 1H), 5.10 (ddd, J=8.2, 5.2, 3.5 Hz, 1H), 2.47 (q, J=8.4 Hz, 1H), 2.29 (s, 3H), 2.06-1.90 (m, 2H), 1.82-1.69 (m, 1H), 1.57-1.41 (m, 2H), 1.39-1.27 (m, 1H), 1.27-1.18 (m, 1H), 0.91 (t, J=7.4 Hz, 3H)

Example 50

2-(4-(diisobutylamino)-3-(3-(p-tolyl)ureido)phenyl)-1-methylcyclopropanecarboxylic acid Racemic

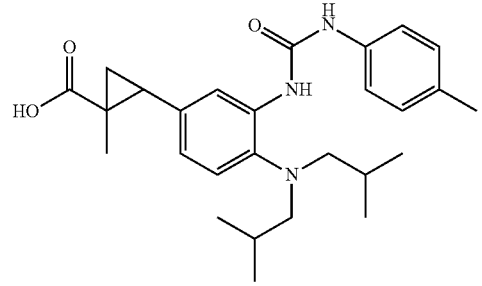 [SMILES: Cc1ccc(NC(=O)Nc2cc(C3CC3(C)C(=O)O)ccc2N(CC(C)C)CC(C)C)cc1]

50A. (E)-ethyl 3-(4-(diisobutylamino)-3-nitrophenyl)-2-methylacrylate

To a solution of sodium hydride (25.9 mg, 0.647 mmol) in 2 mL of THF at 0° C. was added ethyl 2-(diethoxyphosphoryl)propanoate (154 mg, 0.647 mmol) dropwise. The resulting suspension turned into a clear solution. After stirring at the same temperature for 30 min, a solution of 4-(diisobutylamino)-3-nitrobenzaldehyde in 3 mL THF (150 mg, 0.539 mmol) was added slowly and the resulting solution was warmed up to RT and stirred for 4 h. LC-MS showed product formation, it was diluted with EtOAc (10 mL) and water (10 mL). Aqueous layer was further extracted with EtOAc (2×10 mL), the combined extracts were washed with water, brine, dried over $MgSO_4$, filtered and concentrated. Purification via flash chromatography gave 50A (yellow oil, 50 mg, 0.138 mmol, 25.6% yield). LC-MS Anal. Calc'd for $C_{20}H_{30}N_2O_4$ 362.22. found [M+H] 363.24. $T_r$=4.23 min (Method A).

50B. Racemic 2-(4-(diisobutylamino)-3-(3-(p-tolyl)ureido)phenyl)-1 methylcyclopropanecarboxylic acid Diazomethane was prepared as following: To a solution of 40% aqueous KOH (1 mL, 0.138 mmol) and diethyl ether (2 mL) at 0° C. was added 1-methyl-1-nitrosourea (85 mg, 0.414 mmol). The urea dissolved very slowly; A plastic Erlenmeyer flask was used; large surface area between $Et_2O$ and $H_2O$ layers appears to improve extraction of diazomethane. The solution was swirled briefly, then the yellow ether layer was added to a solution of 51A (50 mg, 0.138 mmol) and Palladium acetate (2.478 mg, 0.011 mmol) in diethyl ether (2 mL) at 0° C. After 1 h, LC-MS indicated the desired peak, reaction mixture was quenched with 2 drops of acetic acid and diluted with 5 mL water. The aqueous layer was extracted with EtOAc (2×10 mL) and the combined organic extracts were washed with saturated aqueous $NaHCO_3$, water, brine, dried over $Na_2SO_4$, filtered and concentrated. Purification via flash chromatography (0-50% EtOAc in Hexanes, 12 g) gave 20 mg product contaminated with starting material. 50B was then obtained using the above material following the hydrogenation, urea formation and basic hydrolysis procedures for example 1 method A. LC-MS Anal. Calc'd for $C_{27}H_{37}N_3O_3$ 451.28. found [M+H]

452.32. T$_r$=3.65 min (Method A). $^1$H NMR (500 MHz, MeOD) δ 7.85 (d, J=1.5 Hz, 1H), 7.26 (d, J=8.4 Hz, 2H), 7.07 (dd, J=11.4, 8.4 Hz, 3H), 6.80 (dd, J=8.4, 2.0 Hz, 1H), 2.76-2.70 (m, 1H), 2.58 (dd, J=6.9, 1.5 Hz, 4H), 2.28 (s, 3H), 1.70-1.56 (m, 3H), 1.15 (dd, J=6.9, 4.5 Hz, 1H), 0.99 (s, 3H), 0.82 (dd, J=6.7, 2.2 Hz, 12H)

Example 51

Racemic 3-(4-(diisobutylamino)-3-(3-(p-tolyl)ureido)phenyl)-2,2-difluorocyclopropanecarboxylic acid

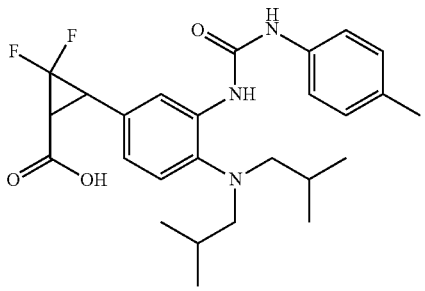 [SMILES: Cc1ccc(NC(=O)Nc2cc(C3C(C(=O)O)C3(F)F)ccc2N(CC(C)C)CC(C)C)cc1]

51A: (Z)-ethyl 3-(4-(diisobutylamino)-3-nitrophenyl)acrylate

A pressure vial was charged with (4-(diisobutylamino)-3-nitrophenyl)boronic acid (1.7 g, 5.78 mmol), (Z)-ethyl 3-iodoacrylate (1.306 g, 5.78 mmol) and potassium carbonate (1.702 g, 17.34 mmol) in DMF (10 mL) and water (1 mL). The slurry was degassed with nitrogen for 1 min. Pd(Ph$_3$P)$_4$ (0.668 g, 0.578 mmol) was added, degassed with nitrogen for another 1 min and the vial was sealed and heated to 90° C. overnight. After cooling to RT, it was filtered through a pad of Celite and the rinses were concentrated. Purification via flash chromatography gave 51A (orange oil, 1.09 g, 3.13 mmol, 54.1% yield). LC-MS Anal. Calc'd for C$_{19}$H$_{28}$N$_2$O$_4$ 348.20. found [M+H] 349.3. T$_r$=1.27 min (Method B). $^1$H NMR (400 MHz, CHLOROFORM-d) δ 7.90 (dd, J=8.9, 2.3 Hz, 1H), 7.29 (s, 1H), 7.06 (d, J=9.0 Hz, 1H), 6.76 (d, J=12.8 Hz, 1H), 5.87 (d, J=12.8 Hz, 1H), 4.24 (q, J=7.3 Hz, 2H), 3.06-2.90 (m, 4H), 2.05-1.86 (m, 2H), 1.42-1.21 (m, 3H), 0.91-0.76 (m, 12H)

51B: Racemic Ethyl 3-(3-amino-4-(diisobutylamino)phenyl)-2,2-difluorocyclopropanecarboxylate A two necked round bottom flask equipped with a refluxing condenser, was charged with sodium fluoride (8.44 mg, 0.201 mmol) and 51A (0.7 g, 2.009 mmol) in dimethylacetone (0.532 ml, 5.02 mmol). It was heated at 105° C. under nitrogen, while trimethylsilyl 2,2-difluoro-2-(fluorosulfonyl)acetate (1.006 g, 4.02 mmol) was slowly added using a syringe pump via a Teflon needle over a period of 5 h. Upon completion of the addition, the reaction mixture was stirred for extra 20 min, then cooled to RT and diluted with 30 ml EtOAc. The solution was washed with water, 5% aqueous sodium bicarbonate, brine, dried over Na$_2$SO$_4$. The solvent was removed under reduced pressure. To the above obtained crude product (16 mg, 0.040 mmol) in MeOH (3 mL) under a nitrogen atmosphere was added 10% Pd/C (0.427 mg, 4.02 μmol). The reaction mixture was stirred under hydrogen atmosphere (hydrogen balloon) for 2 h. The reaction mixture was filtered through a pad of Celite and concentrated to obtain ethyl 3-(3-amino-4-(diisobutylamino)phenyl)-2,2-difluorocyclopropanecarboxylate (light yellow oil, 11 mg, 0.030 mmol, 74.3% yield). To this crude amine (11 mg, 0.030 mmol) in THF (1 mL) was added 1-isocyanato-4-methylbenzene (7.95 mg, 0.060 mmol). The solution was stirred at RT for 2 h. Concentrated in vacuo and the crude product was carried to next step without purification. This crude ester was dissolved in THF (1 mL), a solution of LiOH (2.62 mg, 0.110 mmol) in water (0.1 mL) was added, then methanol (0.3 mL) was added and it turned into a clear yellow solution. The reaction was monitored by LC-MS. After 2 h, reaction was complete. Most MeOH and THF was removed in vacuo and the crude was diluted with 2 mL of water, the pH was adjusted to ca.4 using 1N aqueous HCl. The aqueous phase was then extracted with EtOAc (3×5 mL) and the combined organic phase was washed with brine, dried over Na$_2$SO$_4$ and concentrated. Purified via preparative HPLC gave 51B (4.8 mg, 10.14 μmol, 27.8% yield). LC-MS Anal. Calc'd for C$_{26}$H$_{33}$F$_2$N$_3$O$_3$ 473.25. found [M+H] 474.5. T$_r$=1.05 min (Method B). $^1$H NMR (500 MHz, METHANOL-d$_4$) δ 7.94 (d, J=2.0 Hz, 1H), 7.29 (d, J=8.4 Hz, 2H), 7.12 (t, J=8.2 Hz, 3H), 6.88 (dd, J=8.4, 2.0 Hz, 1H), 3.45-3.35 (m, 1H), 2.72 (dd, J=14.4, 7.9 Hz, 1H), 2.62 (d, J=6.9 Hz, 4H), 2.31 (s, 3H), 1.77-1.61 (m, 2H), 0.84 (d, J=6.4 Hz, 12H)

Example 52

Enantiomer 1: 1-(5-((1R,2S)-2-(1H-tetrazol-5-yl)cyclopropyl)-2-(diisobutylamino)phenyl)-3-(p-tolyl)urea

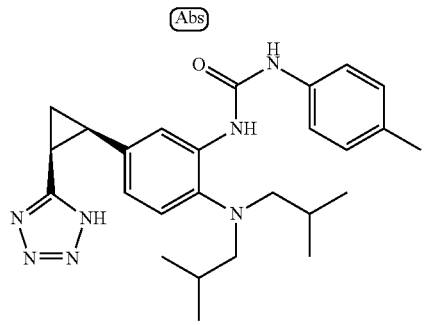 [SMILES: Cc1ccc(NC(=O)Nc2cc([C@@H]3C[C@@H]3c3nnn[nH]3)ccc2N(CC(C)C)CC(C)C)cc1]

Enantiomer 2: 1-(5-((1S,2R)-2-(1H-tetrazol-5-yl)cyclopropyl)-2-(diisobutylamino)phenyl)-3-(p-tolyl)urea

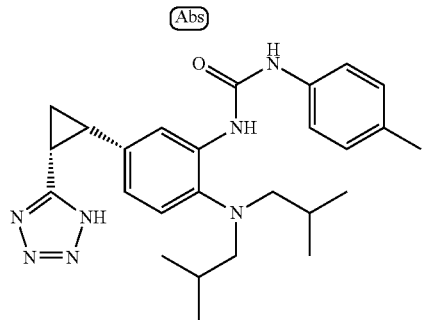

52A: (1S,2R)—N-(2-cyanoethyl)-2-(4-(diisobutylamino)-3-nitrophenyl)cyclopropanecarboxamide 1D (1.2 g, 3.31 mmol) was dissolved in THF (9 mL), a solution of LiOH (0.238 g, 9.93 mmol) in water (3 mL) was added. Methanol (3 mL) was added to dissolve the solid and it turned into a clear yellow solution. The reaction was stirred at RT overnight, then most MeOH and THF was removed in vacuo and the crude was diluted with 2 mL of water, the pH was adjusted to ca.2 using 1N aqueous HCl. The aqueous phase was then extracted with EtOAc (3×10 mL) and the combined organic extracts were washed with brine, dried over $Na_2SO_4$ and concentrated. To a solution of above obtained crude acid (1.1 g, 3.29 mmol) in DCM (9 mL) was added oxalyl chloride (0.576 mL, 6.58 mmol) and DMF (2.55 μl, 0.033 mmol), the reaction mixture was stirred at RT for 2 h. It was concentrated in vacuo, dried under high vacuum for 1 h. To a solution of above obtained acid chloride in THF (9.00 mL) at 0° C. was added 3-aminopropanenitrile (0.277 g, 3.95 mmol) and TEA (1.375 mL, 9.87 mmol). The solution was stirred at RT for 2 h. Then water (20 ml) was added and the aqeous layer was extracted with EtOAc (3×20 ml). The combined organic extracts were washed with brine, dried over $MgSO_4$, filtered and concentrated. Purification via flash chromatography gave 52A (light yellow oil, 1.03 g, 2.67 mmol, 81% yield). LC-MS Anal. Calc'd for $C_{21}H_{30}N_4O_3$ 386.23. found [M+H] 387.6. $T_r$=1.05 min (Method B). $^1$H NMR (400 MHz, CHLOROFORM-d) δ 7.61 (d, J=1.8 Hz, 1H), 7.35-7.24 (m, 1H), 7.06 (d, J=8.8 Hz, 1H), 6.10 (s, 1H), 3.54-3.38 (m, 1H), 3.34-3.19 (m, 1H), 2.90 (dd, J=7.2, 1.0 Hz, 4H), 2.51-2.21 (m, 3H), 2.02-1.82 (m, 3H), 1.73 (dt, J=7.2, 5.4 Hz, 1H), 1.39-1.30 (m, 1H), 0.93-0.76 (m, 12H)

52B: 4-((1R,2S)-2-(1H-tetrazol-5-yl)cyclopropyl)-N,N-diisobutyl-2-nitroaniline 52A (1.03 g, 2.67 mmol), triphenylphosphine (1.398 g, 5.33 mmol), DEAD (2.423 mL, 5.33 mmol), trimethylsilyl azide (0.707 mL, 5.33 mmol) and THF (20 mL) were mixed and stirred at RT under nitrogen. After 24 h LC-MS indicated ca. 50% completion, added another equivalent of triphenylphosphine, DEAD and trimethylsilyl azide, stirred at RT for another 24 h. LC-MS indicated ca.70% completion. The solvent and excess trimethylsilyl azide were cautiously removed in vacuo behind the shield. After removing solvent in vacuo, the residue was dissolved in THF (10 mL), and 1N aqueous NaOH (2.67 mL, 2.67 mmol) was added. After stirring at RT for 24 h, the reaction was about 40% completed. Additional 0.5 equivalent of 1N aqueous NaOH was added and stirred at RT for another 24 h. LC-MS indicated completion, then the solvent was removed in vacuo, the residue was diluted with water (10 mL) and extracted with diethyl ether (2×20 ml). The aqueous layer was acidified with 1N aqueous HCl until pH=2, then extracted with EtOAc (3×20 mL), the organic layer was washed with water, brine and dried over $MgSO_4$, filtered and concentrated to give 52B (0.399 g, 1.113 mmol, 41.8% yield). LC-MS Anal. Calc'd for $C_{18}H_{26}N_6O_2$ 358.21. found [M+H] 359.2. $T_r$=1.03 min (Method B). $^1$H NMR (400 MHz, CHLOROFORM-d) δ 7.61 (d, J=2.0 Hz, 1H), 7.12 (dd, J=8.8, 2.2 Hz, 1H), 6.94 (d, J=8.6 Hz, 1H), 2.87 (d, J=7.3 Hz, 4H), 2.83-2.70 (m, 2H), 1.97 (q, J=6.2 Hz, 1H), 1.91-1.73 (m, 3H), 0.79 (d, J=6.6 Hz, 12H).

52C: racemic 1-(5-((1R,2S)-2-(1H-tetrazol-5-yl)cyclopropyl)-2-(diisobutylamino)phenyl)-3-(p-tolyl)urea 52C was obtained following the hydrogenation and urea formation procedures in example 1 method A. LC-MS Anal. Calc'd for $C_{26}H_{35}N_7O$, 461.29. found [M+H] 462.5. $T_r$=0.93 min (Method B). $^1$H NMR (400 MHz, METHANOL-$d_4$) δ 8.05-7.92 (m, 1H), 7.76 (d, J=2.0 Hz, 1H), 7.32 (d, J=8.6 Hz, 2H), 7.14 (d, J=8.1 Hz, 2H), 6.95 (d, J=8.4 Hz, 1H), 6.64-6.51 (m, 1H), 2.80-2.64 (m, 2H), 2.60 (dd, J=7.0, 3.1 Hz, 4H), 2.33 (s, 3H), 1.92-1.83 (m, 1H), 1.74-1.64 (m, 1H), 1.64-1.51 (m, 2H), 0.82 (dd, J=6.6, 2.0 Hz, 12H).

52D: Chiral separation (Method G) of 52C gave faster eluting enantiomer 1: 1-(5-((1R,2S)-2-(1H-tetrazol-5-yl)cyclopropyl)-2-(diisobutylamino)phenyl)-3-(p-tolyl)urea: LC-MS Anal. Calc'd for $C_{26}H_{35}N_7O$, 461.29. found [M+H] 462.5. $T_r$=0.93 min (Method B). $^1$H NMR (400 MHz, METHANOL-$d_4$) δ 7.73 (d, J=2.0 Hz, 1H), 7.40-7.25 (m, 2H), 7.13 (d, J=8.1 Hz, 2H), 6.90 (d, J=8.4 Hz, 1H), 6.57 (dd, J=8.4, 2.0 Hz, 1H), 2.66-2.52 (m, 6H), 2.32 (s, 3H), 1.84 (q, J=6.2 Hz, 1H), 1.65-1.53 (m, 3H), 0.82 (d, J=6.6 Hz, 12H). Slower eluting enantiomer 2: 1-(5-((1S,2R)-2-(1H-tetrazol-5-yl)cyclopropyl)-2-(diisobutylamino)phenyl)-3-(p-tolyl)urea: LC-MS Anal. Calc'd for $C_{26}H_{35}N_7O$, 461.29. found [M+H] 462.5. $T_r$=0.93 min. $^1$H NMR (400 MHz, METHANOL-$d_4$) δ 7.74 (d, J=2.0 Hz, 1H), 7.40-7.24 (m, 2H), 7.13 (d, J=8.1 Hz, 2H), 6.90 (d, J=8.4 Hz, 1H), 6.58 (dd, J=8.3, 2.1 Hz, 1H), 2.70-2.50 (m, 6H), 2.32 (s, 3H), 1.90-1.78 (m, 1H), 1.68-1.50 (m, 3H), 0.82 (d, J=6.6 Hz, 12H).

Example 53

Racemic (1R,3R)-3-(4-(diisobutylamino)-3-(3-(p-tolyl)ureido)phenyl)-2,2-dimethylcyclopropanecarboxylic acid

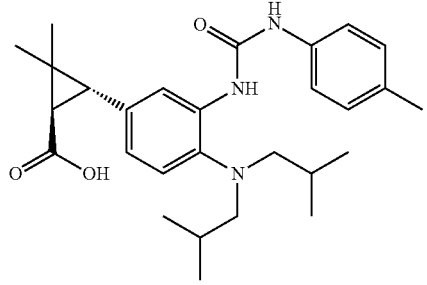 [SMILES: Cc1ccc(NC(=O)Nc2cc([C@@H]3[C@@H](C(=O)O)C3(C)C)ccc2N(CC(C)C)CC(C)C)cc1]

Racemic (1R,3S)-3-(4-(diisobutylamino)-3-(3-(p-tolyl)ureido)phenyl)-2,2-dimethylcyclopropanecarboxylic acid

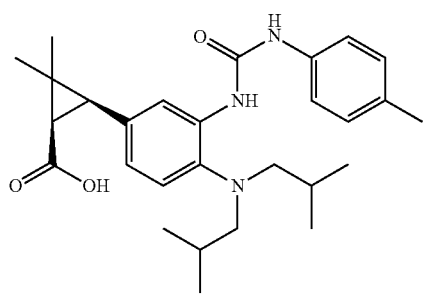 [SMILES: Cc1ccc(NC(=O)Nc2cc([C@H]3[C@@H](C(=O)O)C3(C)C)ccc2N(CC(C)C)CC(C)C)cc1]

53A: N,N-diisobutyl-4-(2-methylprop-1-en-1-yl)-2-nitroaniline

To a solution of isopropyltriphenylphosphonium iodide (4.54 g, 10.51 mmol) in DMF (11 ml) was slowly added a solution of potassium tert-butoxide (1.258 g, 11.21 mmol) in DMF (9 ml) at 0° C. with stirring, and the resulting mixture was stirred for 30 min. Then a solution of 4-(diisobutylamino)-3-nitrobenzaldehyde (1.95 g, 7.01 mmol) in DMF (5 ml) was added at the same temperature. The reaction mixture was warmed up to RT slowly and stirred for 1 h. After LC-MS indicated completion, a solution of saturated aqueous ammonium chloride (10 mL) was added to the reaction mixture to quench the reaction, and the resulting mixture was poured into water (10 mL) and extracted with EtOAc (2×15 mL). The combined extracts were washed with brine, dried over $MgSO_4$, filtered and concentrated. Purification via flash chromatography gave 53A (yellow oil, 1.05 g, 3.45 mmol, 49.2% yield). LC-MS Anal. Calc'd for $C_{18}H_{28}N_2O_2$ 304.22. found [M+H] 305.5. $T_r$=1.33 min (Method B).

53B: Mixture of cis and trans ethyl 3-(4-(diisobutylamino)-3-nitrophenyl)-2,2-dimethylcyclopropanecarboxylate To a solution of 53A (0.59 g, 1.938 mmol) in DCM (10 mL) was added Rhodium(II) acetate dimer (0.086 g, 0.194 mmol) followed by a slow addition of a solution of ethyl diazoacetate (0.402 mL, 3.88 mmol) in DCM (1 mL) over a period of 4 h via a syringe pump. The reaction mixture turned into a dark red color. LC-MS indicated only 20% conversion, the reaction mixture was then heated to 40° C. and another lot of ethyl diazoacetate (0.402 mL, 3.88 mmol) in DCM (1 mL) was added over a period of 4 h via a syringe pump. LC-MS indicated ca. 70% completion and the appearance of two peaks with the desired mass. The reaction mixture was filtered through a pad of Celite, rinsed with DCM (2×100 mL). The combined solvent was removed in vacuo and concentrated. to give crude. Purification via flash chromatography gave 53B as a mixture of two isomers (cis and trans) (light yellow oil, 400 mg, 1.024 mmol, 52.8% yield). LC-MS Anal. Calc'd for $C_{22}H_{34}N_2O_4$ 390.25. found [M+H] 391.25. $T_r$=4.22 and 4.30 min (Method A).

Example 53 as a mixture of trans and cis acids was obtained following the hydrogenation, urea formation and basic hydrolysis procedures in example 1 method A utilizing 53B. Then purification via preparative HPLC separated the two isomers. Trans isomer: Racemic (1R,3R)-3-(4-(diisobutylamino)-3-(3-(p-tolyl)ureido)phenyl)-2,2 dimethylcyclopropanecarboxylic acid: LC-MS Anal. Calc'd for $C_{28}H_{39}N_3O_3$ 465.30. found [M+H] 466.5. $T_r$=1.01 min (Method B). $^1$H NMR (500 MHz, METHANOL-d4) δ 7.85 (d, J=1.5 Hz, 1H), 7.28 (d, J=8.4 Hz, 2H), 7.09 (dd, J=18.3, 7.9 Hz, 3H), 6.88-6.71 (m, 1H), 2.60 (d, J=6.9 Hz, 4H), 2.36-2.19 (m, 4H), 1.94 (d, J=5.9 Hz, 1H), 1.77-1.55 (m, 2H), 1.37 (s, 3H), 0.98 (s, 3H), 0.84 (d, J=6.9 Hz, 12H); Cis isomer: Racemic (1R,3S)-3-(4-(diisobutylamino)-3-(3-(p-tolyl)ureido)phenyl)-2,2-dimethylcyclopropanecarboxylic acid: LC-MS Anal. Calc'd for $C_{28}H_{39}N_3O_3$ 465.30. found [M+H] 466.4. $T_r$=1.00 min (Method B). $^1$H NMR (500 MHz, METHANOL-$d_4$) δ 7.76 (s, 1H), 7.27 (d, J=8.4 Hz, 2H), 7.11 (d, J=7.9 Hz, 2H), 7.04 (d, J=8.4 Hz, 1H), 6.85-6.76 (m, 1H), 2.58 (d, J=6.9 Hz, 4H), 2.48-2.38 (m, 1H), 2.30 (s, 3H), 1.81 (d, J=9.4 Hz, 1H), 1.75-1.59 (m, 2H), 1.32 (d, J=11.4 Hz, 6H), 0.84 (d, J=6.4 Hz, 12H).

Example 54

Racemic (1R,3R)-3-(4-(diisobutylamino)-3-(3-(2-fluorophenyl)ureido)phenyl)-2,2-dimethylcyclopropanecarboxylic acid

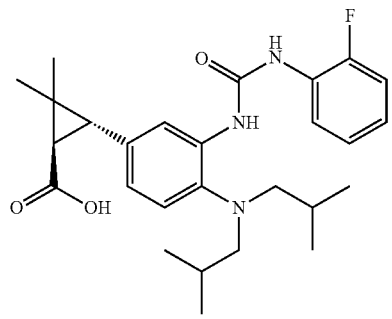 [SMILES: CC(C)CN(CC(C)C)c1ccc([C@@H]2[C@@H](C(=O)O)C2(C)C)cc1NC(=O)Nc1ccccc1F]

Racemic (1R,3S)-3-(4-(diisobutylamino)-3-(3-(2-fluorophenyl)ureido)phenyl)-2,2-dimethylcyclopropanecarboxylic acid

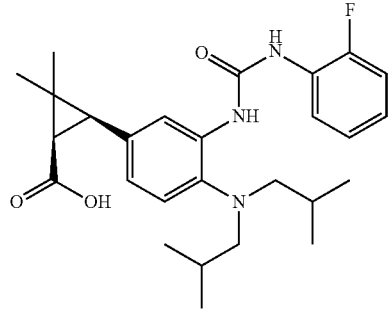 [SMILES: CC(C)CN(CC(C)C)c1ccc([C@H]2[C@@H](C(=O)O)C2(C)C)cc1NC(=O)Nc1ccccc1F]

Example 54 was obtained following the same procedure in example 53 utilizing the corresponding isocyanate: Trans isomer: Racemic (1R,3R)-3-(4-(diisobutylamino)-3-(3-(2-fluorophenyl)ureido)phenyl)-2,2-dimethylcyclopropanecarboxylic acid: LC-MS Anal. Calc'd for $C_{27}H_{36}N_3O_3$ 469.27. found [M+H] 470.4. $T_r$=1.01 min (Method B). $^1$H NMR (500 MHz, METHANOL-$d_4$) δ 7.91-7.85 (m, 1H), 7.80 (d, J=1.5 Hz, 1H), 7.16-7.02 (m, 4H), 6.86-6.79 (m, 1H), 2.71-2.53 (m, 5H), 2.01-1.88 (m, 1H), 1.71 (s, 2H), 1.37 (s, 3H), 0.99 (s, 3H), 0.87 (d, J=6.4 Hz, 12H); Cis isomer: racemic (1R,3S)-3-(4-(diisobutylamino)-3-(3-(2-fluorophenyl)ureido)phenyl)-2,2-dimethylcyclopropanecarboxylic acid: LC-MS Anal. Calc'd for $C_{27}H_{36}N_3O_3$ 469.27. found [M+H] 470.4. $T_r$=0.98 min (Method B). $^1$H NMR (500 MHz, METHANOL-$d_4$) δ 7.85 (d, J=1.5 Hz, 1H), 7.73 (d, J=1.0 Hz, 1H), 7.19-6.97 (m, 4H), 6.83 (d, J=1.0 Hz, 1H), 2.62 (d, J=6.9 Hz, 4H), 2.43 (d, J=8.9 Hz, 1H), 1.81 (d, J=8.9 Hz, 1H), 1.76-1.62 (m, 2H), 1.32 (d, J=12.4 Hz, 6H), 0.87 (d, J=6.9 Hz, 12H)

Example 55

Racemic (1S,2R)-2-(3-butyl-5-(3-(p-tolyl)ureido)-4-(4,4,4-trifluorobutoxy)phenyl) cyclopropanecarboxylic acid

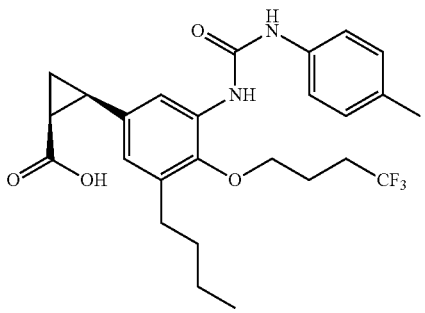 [SMILES: CCCCc1cc([C@@H]2C[C@@H]2C(=O)O)cc(NC(=O)Nc2ccc(C)cc2)c1OCCCC(F)(F)F]

Racemic (1S,2S)-2-(3-butyl-5-(3-(p-tolyl)ureido)-4-(4,4,4-trifluorobutoxy)phenyl) cyclopropanecarboxylic acid

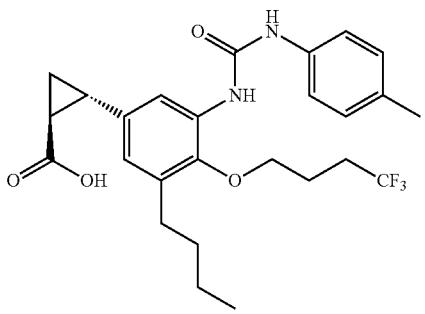 [SMILES: CCCCc1cc([C@H]2C[C@@H]2C(=O)O)cc(NC(=O)Nc2ccc(C)cc2)c1OCCCC(F)(F)F]

55A: 4-bromo-1-(but-3-en-2-yloxy)-2-nitrobenzene

To a stirred solution of but-3-en-2-ol (6.56 g, 91 mmol) in THF (5 mL) at −78° C. was added n-Butyllithium (27.3 mL, 68.2 mmol) dropwise. The solution was warmed to 0° C. and stirred for 10 min. Then it was re-cooled to −78° C., 4-bromo-1-fluoro-2-nitrobenzene (10 g, 45.5 mmol) was added and allowed to warm to RT with stirring. Then the reaction mixture was heated to 50° C. for 20 min. After cooling to RT, the reaction mixture was transferred into 10 mL of 1N aqueous HCl. After separating the layers, the aqueous layer was extracted with EtOAc (2×30 mL). The combined extracts were washed with brine, dried over $MgSO_4$, filtered and concentrated. Purification via flash chromatography gave 55A (yellow oil, 8.45 g, 31.1 mmol, 68.3% yield). LC-MS Anal. Calc'd for $C_{10}H_{10}BrNO_3$ 270.98, did not show desired mass. $T_r$=1.05 min (Method B). $^1$H NMR (400 MHz, CHLOROFORM-d) δ 7.93 (d, J=2.4 Hz, 1H), 7.58 (dd, J=8.9, 2.5 Hz, 1H), 7.06-6.88 (m, 1H), 6.03-5.76 (m, 1H), 5.42-5.12 (m, 2H), 4.89 (t, J=6.4 Hz, 1H), 1.52 (d, J=6.4 Hz, 3H)

55B: (E)-4-bromo-2-(but-2-en-1-yl)-6-nitrophenol

A solution of 55A (8 g, 29.4 mmol) in 10 mL diglyme was placed under nitrogen and heated to 150° C. for 5 h. After cooling to RT, purification via flash chromatography gave 55B (yellow solid, 7.07 g, 26.0 mmol, 88% yield). LC-MS Anal. Calc'd for $C_{10}H_{10}BrNO_3$ 270.98. $T_r$=1.16 min (Method B). $^1$H NMR (400 MHz, METHANOL-$d_4$) δ 8.05 (d, J=2.4 Hz, 1H), 7.64-7.48 (m, 1H), 5.80-5.40 (m, 2H), 3.44-3.26 (m, 2H), 1.80-1.58 (m, 3H).

55C: (E)-5-bromo-1-(but-2-en-1-yl)-3-nitro-2-(4,4,4-trifluorobutoxy)benzene

Triphenylphosphine (1.446 g, 5.51 mmol) and diisopropyl azodicarboxylate (1.072 mL, 5.51 mmol) were added to a solution of (E)-4-bromo-2-(but-2-en-1-yl)-6-nitrophenol (1 g, 3.68 mmol) and 4,4,4-trifluorobutan-1-ol (0.706 g, 5.51 mmol) in THF (3 mL). The reaction mixture was stirred overnight under nitrogen. After concentration, purification via flash chromatography gave 55C (1.01 g, 2.64 mmol, 71.9% yield). LC-MS Anal. Calc'd for $C_{14}H_{15}BrF_3NO_3$ 381.02. $T_r$=1.22 min (Method B).

55D: (E)-1-(but-2-en-1-yl)-3-nitro-2-(4,4,4-trifluorobutoxy)-5-vinylbenzene

To a solution of 55C (1.5 g, 3.92 mmol) in ethanol (12 mL) and toluene (4 mL) (sonication to break up the solid) was added 2,4,6-trivinyl-1,3,5,2,4,6-trioxatriborinane pyridine complex (1.01 g, 6.25 mmol) followed by potassium phosphate (tribasic) (1.250 g, 5.89 mmol) and water (1.6 mL). The reaction mixture was purged with nitrogen for 2 min and then Pd(Ph$_3$P)$_4$ (0.454 g, 0.392 mmol) was added, purged with nitrogen for another 1 min. It was then heated at 80° C. for 8 h. It was diluted with EtOAc (10 mL) and filtered through a pad of silica gel, rinsed with EtOAc (3×20 mL). The combined rinses were concentrated and purification via flash chromatography gave 55D (orange oil, 0.913 g, 2.77 mmol, 70.6% yield). LC-MS Anal. Calc'd for $C_{16}H_{18}F_3NO_3$ 329.12. $T_r$=3.89 min (Method A). $^1$H NMR (400 MHz, CHLOROFORM-d) δ 7.78-7.66 (m, 1H), 7.53-7.41 (m, 1H), 6.76-6.56 (m, 1H), 5.86-5.69 (m, 1H), 5.65-5.48 (m, 2H), 5.45-5.33 (m, 1H), 4.11-3.93 (m, 2H), 3.47-3.33 (m, 2H), 2.52-2.24 (m, 2H), 2.18-1.98 (m, 2H), 1.82-1.65 (m, 3H)

55E: (E)-ethyl 2-(3-(but-2-en-1-yl)-5-nitro-4-(4,4,4-trifluorobutoxy)phenyl) cyclopropanecarboxylate To a solution of 55D (0.9 g, 2.73 mmol) in DCM (12 mL) was added rodium(II) acetate dimer (0.121 g, 0.273 mmol) followed by a slow addition of a solution of ethyl diazoacetate (0.567 mL, 5.47 mmol) in DCM (1.2 mL) over a period of 6 h via a syringe pump at RT. The reaction mixture turned into a dark red solution. LC-MS indicated ca. 65% completion. The reaction was filtered through a pad of Celite, rinsed with DCM (2×20 mL). The solvent was removed in vacuo and concentrated. Purification via flash chromatography gave 55E as a mixture of cis and trans isomers (yellow oil, 0.591 g, 1.423 mmol, 52.1% yield). LC-MS Anal. Calc'd for $C_{20}H_{24}F_3NO_5$ 415.16. found [M+H] 416.18. $T_r$=4.09 min (Method A).

55F: ethyl 2-(3-amino-5-butyl-4-(4,4,4-trifluorobutoxy)phenyl) cyclopropanecarboxylate 55E (30 mg, 0.072 mmol) was taken up in methanol (5 mL) and water (0.5 mL), zinc (47.2 mg, 0.722 mmol) and ammonium chloride (38.6 mg, 0.722 mmol) were added. It was stirred at RT for 30 min, LC-MS indicated completion.

It was diluted with DCM (20 mL) passed through a pad of Celite. Rinses were concentrated and used in the subsequent step without purification. To a solution of the crude aniline obtained above (0.2 g, 0.481 mmol) in methanol (10 ml) under a nitrogen atmosphere was added 10% Pd on C (0.051 g, 0.048 mmol). The mixture was stirred under hydrogen atmosphere (hydrogen ballon) for 1 h. The reaction mixture was then filtered through a pad of Celite and concentrated to obtain 55F as a light yellow oil. The crude was carried to the next step without purification. LC-MS Anal. Calc'd for $C_{20}H_{28}F_3NO_3$ 387.20. found [M+H] 388.26. $T_r$=3.36 and 3.58 min (Method A).

55G: A mixture of trans and cis acids was obtained following the hydrogenation, urea formation and basic hydrolysis procedures in example 1 method A using 55F. Then purification via preparative HPLC separated the two isomers. Cis isomer: racemic (1S,2R)-2-(3-butyl-5-(3-(p-tolyl)ureido)-4-(4,4,4-trifluorobutoxy)phenyl) cyclopropanecarboxylic acid (5.4 mg, 10.96 μmol, 11.42% yield) LC-MS Anal. Calc'd for $C_{26}H_{31}N_2O_4$ 492.22. found [M+H] 493.4. $T_r$=1.09 min (Method B). $^1$H NMR (500 MHz, METHANOL-$d_4$) δ 7.67-7.52 (m, 1H), 7.30 (d, J=8.4 Hz, 2H), 7.12 (d, J=8.4 Hz, 2H), 6.66 (d, J=2.0 Hz, 1H), 3.81 (t, J=6.4 Hz, 2H), 2.59-2.51 (m, 2H), 2.46-2.32 (m, 3H), 2.30 (s, 3H), 2.10-2.00 (m, 2H), 1.87-1.78 (m, 1H), 1.58 (s, 3H), 1.38 (d, J=7.4 Hz, 3H), 0.95 (t, J=7.2 Hz, 3H); Trans isomer: racemic (1S,2S)-2-(3-butyl-5-(3-(p-tolyl)ureido)-4-(4,4,4-trifluorobutoxy)phenyl)cyclopropanecarboxylic acid (11.7 mg, 0.024 mmol, 24.73% yield) LC-MS Anal. Calc'd for $C_{26}H_{31}N_2O_4$ 492.22. found [M+H] 493.4. $T_r$=1.09 min (Method B). $^1$H NMR (500 MHz, METHANOL-$d_4$) δ 7.70 (s, 1H), 7.31 (d, J=8.4 Hz, 2H), 7.11 (d, J=8.4 Hz, 2H), 6.86-6.74 (m, 1H), 3.82 (s, 2H), 2.61-2.49 (m, 3H), 2.45-2.33 (m, 2H), 2.30 (s, 3H), 2.10-1.95 (m, 3H), 1.64-1.51 (m, 3H), 1.44-1.22 (m, 3H), 0.95 (t, J=7.2 Hz, 3H)

Example 56 rac-(1S,2R)-2-(3-butyl-5-(3-(2-fluorophenyl)ureido)-4-(4,4,4-trifluorobutoxy) phenyl)cyclopropanecarboxylic acid

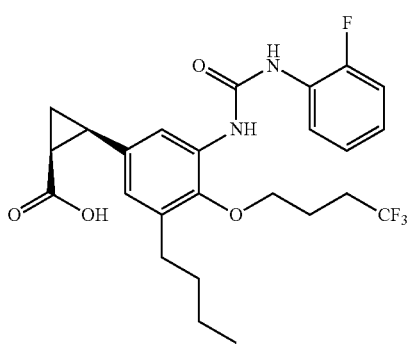 [SMILES: CCCCc1cc([C@@H]2C[C@@H]2C(=O)O)cc(NC(=O)Nc2ccccc2F)c1OCCCC(F)(F)F]

Example 56 was obtained following the same procedure in Example 55 with the corresponding isocyanate. Only cis isomer was isolated. LC-MS Anal. Calc'd for $C_{25}H_{28}F_4N_2O_4$ 496.20. found [M+H] 497.4. $T_r$=1.07 min (Method B). $^1$H NMR (500 MHz, DMSO-$d_6$) δ 8.23-8.09 (m, 1H), 7.70-7.57 (m, 1H), 7.29-7.21 (m, 1H), 7.17-7.10 (m, 1H), 7.08-6.93 (m, 1H), 6.76-6.58 (m, 1H), 3.85-3.69 (m, 2H), 2.60-2.45 (m, 6H), 2.36-2.24 (m, 1H), 2.14-1.94 (m, 2H), 1.77-1.67 (m, 1H), 1.60-1.17 (m, 4H), 0.98-0.88 (m, 3H)

Example 57

Racemic (1S,2R)-2-(3-butyl-5-(3-(2-fluorophenyl) ureido)-4-propoxyphenyl) cyclopropanecarboxylic acid

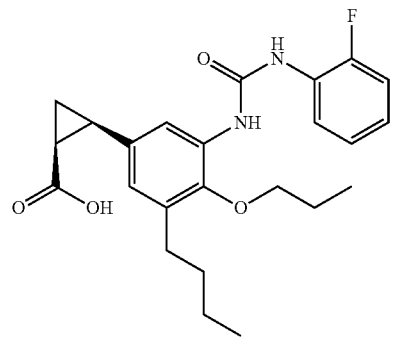 [SMILES: CCCCc1cc([C@@H]2C[C@@H]2C(=O)O)cc(NC(=O)Nc2ccccc2F)c1OCCC]

Example 57 was obtained following the same procedure in example 55 utilizing 1-iodopropane and 2-fluorophenylisocyanate. Only cis isomer was isolated. LC-MS Anal. Calc'd for $C_{24}H_{29}FN_2O_4$ 428.21. found [M+H] 429.3. $T_r$=1.06 min (Method B). $^1$H NMR (500 MHz, METHANOL-$d_4$) δ 8.11-8.02 (m, 1H), 7.76 (d, J=1.5 Hz, 1H), 7.10 (s, 3H), 6.83 (d, J=1.5 Hz, 1H), 3.74 (t, J=6.9 Hz, 2H), 2.62-2.46 (m, 3H), 2.07-1.98 (m, 1H), 1.84 (d, J=7.4 Hz, 2H), 1.65-1.53 (m, 3H), 1.38 (d, J=7.4 Hz, 3H), 1.04 (t, J=7.4 Hz, 3H), 0.94 (t, J=7.4 Hz, 3H)

Example 58

Racemic 1-(5-((1R,2S)-2-(1H-tetrazol-5-yl)cyclopropyl)-3-butyl-2-propoxyphenyl)-3-(p-tolyl)urea

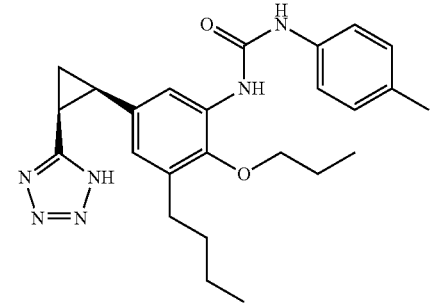 [SMILES: CCCCc1cc([C@@H]2C[C@@H]2c2nnn[nH]2)cc(NC(=O)Nc2ccc(C)cc2)c1OCCC]

58A: racemic (1S,2R)-2-(3-((E)-but-2-en-1-yl)-5-nitro-4-propoxyphenyl)-N-(2-cyanoethyl)cyclopropanecarboxamide A solution of racemic (1R,2S)-2-(3-((E)-but-2-en-1-yl)-5-nitro-4-propoxyphenyl)cyclopropanecarboxylic acid (intermediate from example 57) (1 g, 3.13 mmol) in DCM (9 mL) was added oxalyl chloride (0.548 mL, 6.26 mmol) and DMF (2.425 μl, 0.031 mmol), the reaction mixture was stirred at RT for 2 h. LC-MS indicated completion. It was concentrated in vacuo, dried under high vacuum for 1 h. To a solution of above obtained acid chloride in THF (9.00 mL) at 0° C. was added 3-aminopropanenitrile (0.263 g, 3.76 mmol) and TEA (1.309 mL, 9.39 mmol). The solution was stirred at RT for 12 h. Reaction was complete by LC-MS, then water (20 mL) was added and the aqueous layer was extracted with EtOAc (3×20 mL). The combined extracts were washed with brine, dried over MgSO$_4$, filtered and concentrated. Purification via flash chromatography gave 58A (light yellow oil, 0.793 g, 2.135 mmol, 68.2% yield) LC-MS Anal. Calc'd for C$_{20}$H$_{25}$N$_3$O$_4$ 371.18. found [M+H] 372.2. T$_r$=1.00 min (Method B). $^1$H NMR (400 MHz, CHLOROFORM-d) δ 7.52 (d, J=2.0 Hz, 1H), 7.35-7.24 (m, 1H), 6.69-6.50 (m, 1H), 5.63-5.42 (m, 2H), 3.94-3.77 (m, 2H), 3.49-3.33 (m, 3H), 3.31-3.20 (m, 1H), 2.50-2.20 (m, 3H), 2.05-1.90 (m, 1H), 1.79 (sxt, J=7.1 Hz, 2H), 1.72-1.58 (m, 4H), 1.32 (td, J=8.3, 5.2 Hz, 1H), 1.01 (t, J=7.4 Hz, 3H)

58B: Racemic 5-((1R,2S)-2-(1H-tetrazol-5-yl)cyclopropyl)-3-butyl-2-propoxyaniline 58A (550 mg, 1.481 mmol), triphenylphosphine (1165 mg, 4.44 mmol), DIAD (0.864 mL, 4.44 mmol), trimethylsilyl azide (0.590 mL, 4.44 mmol) and THF (20 mL) were mixed and stirred at RT under nitrogen. After 48 h, LC-MS indicated the reaction was complete. The solvent and excess trimethylsilyl azide were cautiously removed in vacuo behind the shield. The residue was dried under vacuum overnight and was then dissolved in THF (20 mL), then 1N aqueous NaOH (1.481 mL, 1.481 mmol) was added. After stirring at RT for 24 h, the reaction was about 40% complete, then additional 0.5equiv. of 1N aqueous NaOH was added and stirred at RT for another 24 h. LC-MS indicated the reaction was complete, the solvent was removed in vacuo. The aqueous layer was acidified with 1N aqueous HCl until pH=ca.2, then extracted with EtOAc (3×20 mL). The combined extracts were washed with brine, dried over MgSO$_4$, filtered and concentrated. Purification via preparative HPLC gave 5-((1S,2R)-2-(3-((E)-but-2-en-1-yl)-5-nitro-4-propoxyphenyl)cyclopropyl)-1H-tetrazole (317 mg, 0.923 mmol, 62.3% yield). LC-MS Anal. Calc'd for C$_{17}$H$_{21}$N$_5$O$_3$ 343.16. found [M+H] 344.1. T$_r$=1.00 min (Method B). To a solution of above obtained nitro compound (317 mg, 0.923 mmol) in MeOH (5 ml) was added 10% Pd on Carbon (98 mg, 0.092 mmol). The mixture was stirred under hydrogen atmosphere (hydrogen ballon) for 2 h. Then the reaction mixture was filtered through a pad of Celite and concentrated to give 58B (yellow oil, 255 mg, 0.808 mmol, 88% yield). LC-MS Anal. Calc'd for C$_{17}$H$_{25}$N$_5$O, 315.21. found [M+H] 316.2. T$_r$=0.79 min (Method B).

Example 58. To a solution of 58B (30 mg, 0.095 mmol) in THF (1 mL) was added 1-isocyanato-4-methylbenzene (0.0306 ml, 0.243 mmol). The solution was stirred at RT for 12 h. It was then concentrated in vacuo and purification by preparative HPLC gave example 58 (14 mg, 0.031 mmol, 32.8% yield). LC/MS, m/z 449.4 (M+1). LC-MS Anal. Calc'd for C$_{25}$H$_{32}$N$_6$O$_2$ 448.26. found [M+H] 449.4. T$_r$=1.06 min (Method B). $^1$H NMR (500 MHz, METHANOL-d$_4$) δ 7.68 (d, J=2.0 Hz, 1H), 7.33 (d, J=8.4 Hz, 2H), 7.13 (d, J=8.4 Hz, 2H), 6.38 (d, J=2.0 Hz, 1H), 3.64 (d, J=5.0 Hz, 2H), 2.66 (s, 2H), 2.48-2.37 (m, 2H), 2.31 (s, 3H), 1.85 (d, J=6.9 Hz, 1H), 1.76 (d, J=6.9 Hz, 2H), 1.67 (d, J=5.9 Hz, 1H), 1.41-1.30 (m, 2H), 1.26-1.15 (m, 2H), 1.00 (t, J=7.4 Hz, 3H), 0.88 (t, J=7.4 Hz, 3H).

Example 59

Racemic 1-(5-((1R,2S)-2-(1H-tetrazol-5-yl)cyclopropyl)-3-butyl-2-propoxyphenyl)-3-(2-fluorophenyl)urea

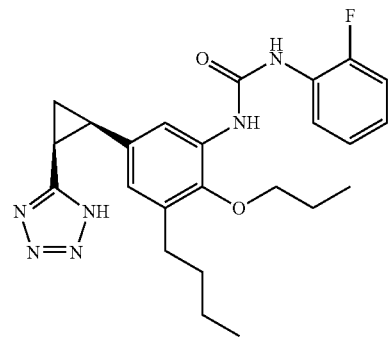 [SMILES: CCCCc1cc([C@@H]2C[C@@H]2c2nnn[nH]2)cc(NC(=O)Nc2ccccc2F)c1OCCC]

Example 59 was obtained following the same procedure in example 58 utilizing 2-fluorophenylisocyanate. LC-MS Anal. Calc'd for C$_{24}$H$_{29}$N$_6$O$_2$ 452.23. found [M+H] 453.4. T$_r$=1.04 min (Method B). $^1$H NMR (500 MHz, METHANOL-d$_4$) δ 8.15-8.04 (m, 1H), 8.01-7.91 (m, 1H), 7.17-7.08 (m, 2H), 7.07-6.97 (m, 1H), 6.41 (d, J=2.0 Hz, 1H), 3.68 (d, J=3.0 Hz, 2H), 2.81-2.59 (m, 2H), 2.49-2.33 (m, 2H), 1.81 (d, J=6.9 Hz, 3H), 1.73-1.63 (m, 1H), 1.44-1.31 (m, 2H), 1.23 (s, 2H), 1.02 (t, J=7.4 Hz, 3H), 0.90 (t, J=7.4 Hz, 3H)

Example 60

(1R,2S)-2-(4-(diisobutylamino)-3-(2-(p-tolyl)acetamido)phenyl)cyclopropanecarboxylic acid

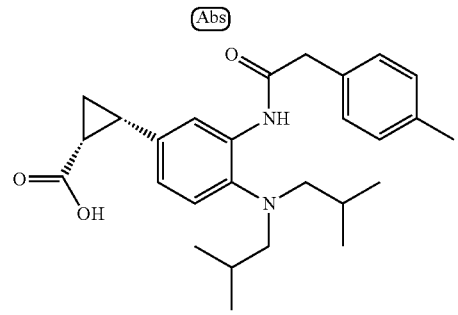 [SMILES: Cc1ccc(CC(=O)Nc2cc([C@H]3C[C@H]3C(=O)O)ccc2N(CC(C)C)CC(C)C)cc1]

To a solution of 1H (22.0 mg, 0.0660 mmol) in DMF (1 mL) at RT was added 2-(p-tolyl)acetic acid (19.9 mg, 0.132 mmol), followed by EDC (25.4 mg, 0.132 mmol),1-Hydroxybenzotriazole hydrate (20.3 mg, 0.132 mmol) and Hunig's Base (0.0350 mL, 0.199 mmol). The mixture was stirred at RT for 1 h. The reaction mixture was diluted with EtOAc and water. Organic phase was separated and washed with 1N aqueous NaOH, 1N aqueous HCl, water, brine, dried over MgSO$_4$, filtered and concentrated. Purification via flash chromatography gave (1R,2S)-ethyl 2-(4-(diisobutylamino)-3-(2-(p-tolyl)acetamido)phenyl)cyclopropanecarboxylate (colorless oil, 16 mg, 0.662 mmol, 52% yield). To a flask containing above obtained ester (16.0 mg, 0.0340 mmol) was added lithium hydroxide monohydrate (27.8 mg, 0.662 mmol), followed by water (0.300 mL) and MeOH (0.400 mL). The mixture was stirred at 50° C. for 1 h. The reaction mixture was cooled to RT and the pH was adjusted to ca. 2 using 1N aqueous HCl. The aqueous phase was then extracted with EtOAc (3×10 mL) and the combined organic phase was washed with brine, dried over $Na_2SO_4$ and concentrated. Purification via preparative HPLC gave Example 60 (9.70 mg, 0.0220 mmol, 33.6% yield). LC-MS Anal. Calc'd for $C_{27}H_{36}N_2O_3$ 436.27. found [M+H] 437.2, $T_r$=3.02 min (Method G). $^1$H NMR (500 MHz, METHANOL-$d_4$) δ 8.30 (d, J=1.5 Hz, 1H), 7.18-7.14 (m, J=7.9 Hz, 2H), 7.14-7.10 (m, J=7.9 Hz, 2H), 7.05 (d, J=8.4 Hz, 1H), 6.94 (dd, J=8.2, 1.7 Hz, 1H), 3.65 (s, 2H), 2.52 (d, J=8.4 Hz, 1H), 2.46 (d, J=7.4 Hz, 4H), 2.30 (s, 3H), 2.05-1.99 (m, 1H), 1.61-1.48 (m, 3H), 1.29 (td, J=8.2, 5.0 Hz, 1H), 0.77-0.71 (m, 12H).

Example 61

(1R,2S)-2-(4-(diisobutylamino)-3-(2-(3-methylisoxazol-5yl)acetamido)phenyl) cyclopropanecarboxylic acid

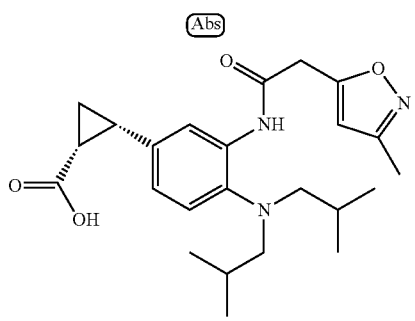 [SMILES: Cc1cc(CC(=O)Nc2cc([C@H]3C[C@H]3C(=O)O)ccc2N(CC(C)C)CC(C)C)on1]

Example 61 was prepared following the procedure for Example 60 using 1H and 2-(3-methylisoxazol-5-yl)acetic acid. LC-MS Anal. Calc'd for $C_{24}H_{33}N_3O_4$ 427.25. found [M+H] 428.4, $T_r$=3.80 min (Method G). $^1$H NMR (500 MHz, METHANOL-$d_4$) δ 8.30 (d, J=1.5 Hz, 1H), 7.14 (d, J=7.9 Hz, 1H), 7.02 (dd, J=8.4, 2.0 Hz, 1H), 6.23 (s, 1H), 3.87 (s, 2H), 2.62-2.49 (m, 5H), 2.29 (s, 3H), 2.06 (ddd, J=9.2, 7.7, 5.4 Hz, 1H), 1.71-1.51 (m, 3H), 1.33 (td, J=8.2, 5.0 Hz, 1H), 0.94-0.79 (m, 12H)

Example 62

(1S,2R)-2-(4-(diisobutylamino)-3-(2-(p-tolyl)acetamido)phenyl)cyclopropanecarboxylic acid

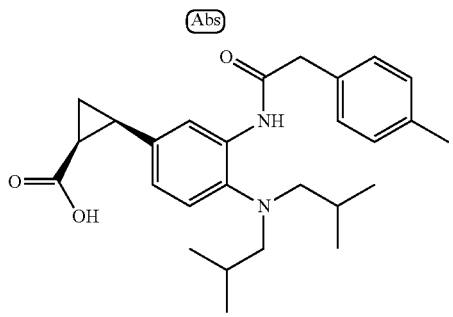 [SMILES: Cc1ccc(CC(=O)Nc2cc([C@@H]3C[C@@H]3C(=O)O)ccc2N(CC(C)C)CC(C)C)cc1]

Example 62 was prepared following the procedure for Example 60 utilizing 1G and 2-(p-tolyl)acetic acid. LC-MS Anal. Calc'd for $C_{27}H_{36}N_2O_3$ 436.27. found [M] 436.0, $T_r$=2.96 min (Method G). $^1$H NMR (500 MHz, METHANOL-$d_4$) δ 8.33 (d, J=1.5 Hz, 1H), 7.22-7.13 (m, 4H), 7.07 (d, J=7.9 Hz, 1H), 6.99-6.92 (m, 1H), 3.67 (s, 2H), 2.60-2.52 (m, 1H), 2.48 (d, J=7.4 Hz, 4H), 2.33 (s, 3H), 2.09-1.97 (m, 1H), 1.66-1.48 (m, 3H), 1.32 (td, J=8.2, 5.0 Hz, 1H), 0.81-0.73 (m, 12H)

Example 63

(1S,2R)-2-(4-(diisobutylamino)-3-(2-(3-methylisoxazol-5-yl)acetamido)phenyl) cyclopropanecarboxylic acid

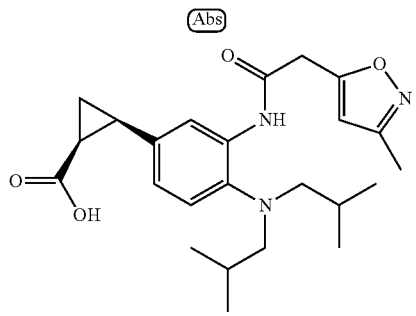 [SMILES: Cc1cc(CC(=O)Nc2cc([C@@H]3C[C@@H]3C(=O)O)ccc2N(CC(C)C)CC(C)C)on1]

Example 63 was prepared following the procedure for Example 60 using 1G and 2-(3-methylisoxazol-5-yl)acetic acid. LC-MS Anal. Calc'd for $C_{24}H_{33}N_3O_4$ 427.25. found [M+H] 427.5, $T_r$=1.53 min (Method D). $^1$H NMR (400 MHz, CHLOROFORM-d) δ 7.65 (s, 1H), 7.37-7.08 (m, 2H), 6.19 (s, 1H), 4.08 (s, 2H), 3.20 (d, J=6.4 Hz, 4H), 2.63 (q, J=8.4 Hz, 1H), 2.31 (s, 3H), 2.20-2.05 (m, 1H), 1.90 (dt, J=13.4, 6.6 Hz, 2H), 1.71-1.61 (m, 1H), 1.55-1.44 (m, 1H), 0.92 (d, J=6.6 Hz, 12H)

Example 64

(1R,2S)-2-(4-(diisobutylamino)-3-(3-(pyrimidin-5-yl)ureido)phenyl) cyclopropanecarboxylic acid

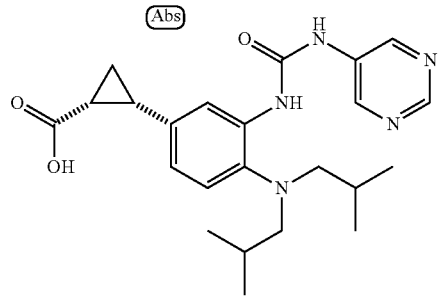

Example 64 was prepared following the procedure for Example 29 using 1H and 5-aminopyrmidine. LC-MS Anal. Calc'd for $C_{23}H_{31}N_5O_3$ 425.24. found [M+H] 426.3, $T_r$=1.85 min (Method E). $^1$H NMR (500 MHz, DMSO-$d_6$) δ 9.89 (s, 1H), 8.94 (s, 2H), 8.82 (s, 1H), 8.10 (s, 1H), 7.92 (d, J=2.0 Hz, 1H), 7.13 (d, J=8.4 Hz, 1H), 6.86 (dd, J=8.2, 1.7 Hz, 1H), 2.66 (dd, J=6.7, 1.2 Hz, 4H), 2.03-1.94 (m, 1H), 1.62 (dquin, J=13.4, 6.7 Hz, 2H), 1.45-1.35 (m, 1H), 1.25 (td, J=7.9, 4.5 Hz, 1H), 0.85 (dd, J=6.4, 3.0 Hz, 12H).

Example 65

(1S,2R)-2-(4-(diisobutylamino)-3-(3-(pyrimidin-5-yl)ureido)phenyl)cyclopropanecarboxylic acid

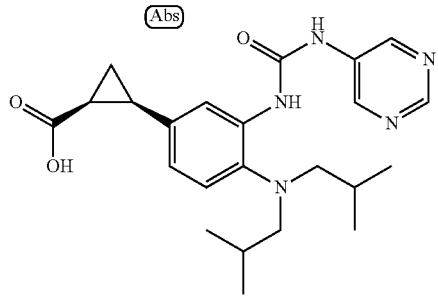 [SMILES: CC(C)CN(CC(C)C)c1ccc([C@@H]2C[C@@H]2C(=O)O)cc1NC(=O)Nc1cncnc1]

Example 65 was prepared following the procedure for Example 29 using the 1G and 5-aminopyrmidine. LC-MS Anal. Calc'd for $C_{23}H_{31}N_5O_3$ 425.24. found [M+H] 426.3, $T_r$=1.76 min (Method E) $^1$H NMR (500 MHz, DMSO-d$_6$) δ 9.86 (s, 1H), 8.94 (s, 2H), 8.83 (s, 1H), 8.10 (s, 1H), 7.93 (d, J=2.0 Hz, 1H), 7.13 (d, J=7.9 Hz, 1H), 6.86 (dd, J=8.2, 1.7 Hz, 1H), 2.66 (d, J=6.9 Hz, 4H), 2.06-1.92 (m, 1H), 1.72-1.54 (m, 2H), 1.49-1.35 (m, 1H), 1.32-1.19 (m, 1H), 0.85 (dd, J=6.7, 3.2 Hz, 12H).

Example 66

(1S,2R)-2-(4-(diisobutylamino)-3-(3-(quinoxalin-6-yl)ureido)phenyl)cyclopropanecarboxylic acid

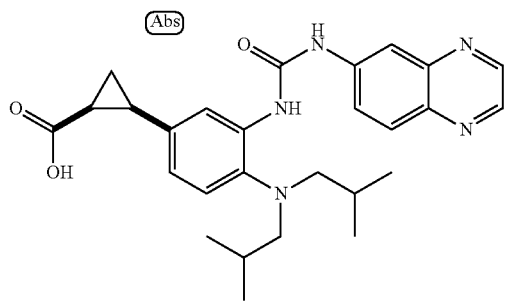

Example 66 was prepared following the procedure for Example 29 using 1G and quinoxalin-6-amine. Anal. Calc'd for $C_{27}H_{33}N_5O_3$ 475.26. found [M+H] 476.4, $T_r$=1.40 min (Method C). $^1$H NMR (500 MHz, METHANOL-d$_4$) δ 8.78 (d, J=1.5 Hz, 1H), 8.71 (d, J=2.0 Hz, 1H), 8.26 (d, J=2.0 Hz, 1H), 7.61 (s, 2H), 7.09 (d, J=8.4 Hz, 1H), 6.98 (dd, J=8.2, 1.7 Hz, 1H), 2.66 (d, J=6.9 Hz, 4H), 2.64-2.56 (m, 1H), 2.15-2.01 (m, 1H), 1.73 (dquin, J=13.4, 6.8 Hz, 2H), 1.65 (dt, J=7.4, 5.2 Hz, 1H), 1.35 (td, J=8.2, 5.0 Hz, 1H), 0.90 (d, J=6.4 Hz, 12H).

Example 67

(1S,2R)-2-(4-(diisobutylamino)-3-(3-(5-methylisoxazol-3-yl)ureido)phenyl)cyclopropanecarboxylic acid

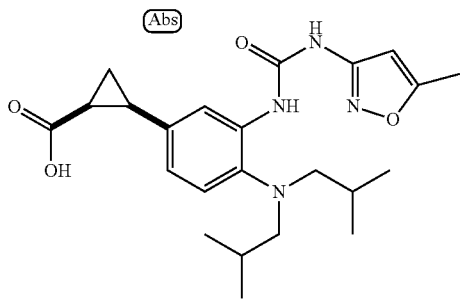

Example 67 was prepared following the procedure for Example 29 using 1G and 5-methylisoxazol-3-amine. Anal. Calc'd for $C_{23}H_{32}N_4O_4$ 428.24. found [M+H] 429.4, $T_r$=1.54 min (Method C). $^1$H NMR (500 MHz, DMSO-d$_6$) δ 10.36 (s, 1H), 8.53 (br. s., 1H), 7.93 (d, J=2.0 Hz, 1H), 7.11 (d, J=7.9 Hz, 1H), 6.84 (dd, J=8.4, 2.0 Hz, 1H), 6.45 (s, 1H), 2.64 (dd, J=6.9, 1.5 Hz, 4H), 2.36 (s, 3H), 2.04-1.91 (m, 1H), 1.61 (dt, J=13.4, 6.7 Hz, 2H), 1.43-1.34 (m, 1H), 1.24 (td, J=8.2, 4.5 Hz, 1H), 0.83 (dd, J=6.4, 2.5 Hz, 12H)

Example 68

(1R,2S)-2-(4-(diisobutylamino)-3-(3-(5-methylisoxazol-3-yl)ureido)phenyl)cyclopropanecarboxylic acid

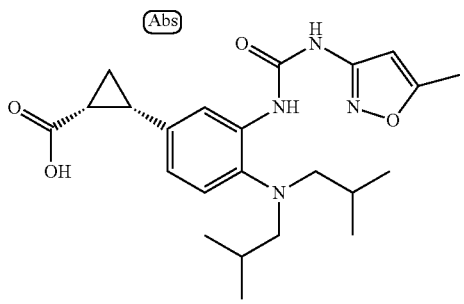 [SMILES: Cc1cc(NC(=O)Nc2cc([C@H]3C[C@H]3C(=O)O)ccc2N(CC(C)C)CC(C)C)no1]

Example 68 was prepared following the procedure for Example 29 using 1H and 5-methylisoxazol-3-amine Anal. Calc'd for $C_{23}H_{32}N_4O_4$ 428.24. found [M+H] 429.5, $T_r$=2.02 min (Method E). $^1$H NMR (500 MHz, DMSO-d$_6$) δ 10.35 (br s, 1H), 8.52 (br s, 1H), 7.92 (br s, 1H), 7.09 (dd, J=8.4, 3.5 Hz, 1H), 6.85 (d, J=7.4 Hz, 1H), 6.45 (br s, 1H), 2.63 (d, J=5.4 Hz, 4H), 2.36 (app d, J=3.0 Hz, 3H), 1.94 (d, J=7.4 Hz, 1H), 1.66-1.56 (m, 2H), 1.35 (br s, 1H), 1.24-1.16 (m, 1H), 0.97-0.70 (m, 12H).

Example 69

(1S,2R)-2-(3-(3-(6-cyanopyridin-3-yl)ureido)-4-(diisobutylamino)phenyl)cyclopropanecarboxylic acid

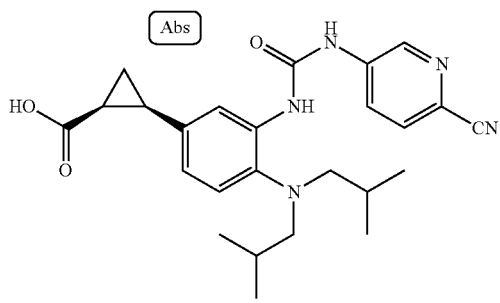 [SMILES: CC(C)CN(CC(C)C)c1ccc([C@@H]2C[C@@H]2C(=O)O)cc1NC(=O)Nc1ccc(C#N)nc1]

Example 69 was prepared following the procedure for Example 29 using 1G except for using the following urea formation method: In a one dram sample vial equipped with a stir bar was placed the enantiomer of 1I (0.02 g, 0.060 mmol) and TEA (0.084 ml, 0.602 mmol). To this stirred solution was added 5-isocyanatopicolinonitrile (0.026 g, 0.180 mmol) as a suspension in THF (0.7 mL) and DCM (0.7 mL), and the reaction was stirred for 30 min at rt. The reaction mixture was concentrated under a stream of nitrogen, then diluted with water and extracted with EtOAc (3×1 mL). The combined organic layers were dried under a stream of nitrogen to give (1S,2R)-ethyl 2-(3-(3-(6-cyanopyridin-3-yl)ureido)-4-(diisobutylamino)phenyl)cyclopropanecarboxylate. (1S,2R)-ethyl 2-(3-(3-(6-cyanopyridin-3-yl)ureido)-4-(diisobutylamino)phenyl)cyclopropanecarboxylate was dissolved in THF (0.626 ml) and MeOH (0.626 ml). Lithium hydroxide (0.60 mmol, 0.3 mL) was added as a 2 N aqueous solution and the mixture was stirred overnight at rt, then heated at 40° C. for 5.5 h. The reaction was cooled to rt and the crude product was adjusted to neutral pH with HCl/dioxane then dried under a stream of nitrogen. Purification by preparative HPLC gave example 69 (7.2 mg, 0.015 mmol, 25%). Anal. Calc'd for $C_{25}H_{31}N_5O_3$ 449.24. found [M+H] 450.4, $T_r$=3.87 min (Method F). $^1$H NMR (500 MHz, DMSO-$d_6$) δ 10.29 (br. s, 1H), 8.77 (d, J=2.5 Hz, 1H), 8.23-8.18 (m, 1H), 8.17 (s, 1H), 7.94 (d, J=8.9 Hz, 1H), 7.88 (d, J=1.5 Hz, 1H), 7.12 (d, J=7.9 Hz, 1H), 6.88 (dd, J=8.2, 1.7 Hz, 1H), 2.66 (dd, J=6.7, 2.2 Hz, 4H), 2.04-1.87 (m, 1H), 1.61 (dquin, J=13.2, 6.6 Hz, 2H), 1.42-1.35 (m, 1H), 1.24 (td, J=7.9, 4.5 Hz, 1H), 0.84 (dd, J=6.4, 3.5 Hz, 12H).

Example 70

(1S,2R)-2-(3-(3-(benzo[c][1,2,5]oxadiazol-5-yl)ureido)-4-(diisobutylamino)phenyl)cyclopropanecarboxylic acid

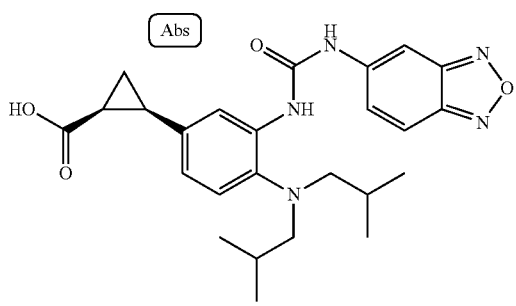 [SMILES: CC(C)CN(CC(C)C)c1ccc([C@@H]2C[C@@H]2C(=O)O)cc1NC(=O)Nc1ccc2nonc2c1]

Example 70 was prepared following the procedure for Example 29 using 1G and benzo[c][1,2,5]oxadiazol-5-amine. Anal. Calc'd for $C_{23}H_{32}N_4O_4$ 428.24. found [M+H] 429.2, $T_r$=2.39 min (Method D). $^1$H NMR (500 MHz, DMSO-$d_6$) δ 10.37 (br s, 1H), 8.24 (br. s., 1H), 8.20 (d, J=2.5 Hz, 1H), 7.99 (dd, J=9.9, 4.0 Hz, 1H), 7.95 (d, J=3.5 Hz, 1H), 7.86 (br s, 1H), 7.48 (dd, J=9.9, 3.0 Hz, 1H), 7.09 (dd, J=8.2, 3.7 Hz, 1H), 6.89 (d, J=7.9 Hz, 1H), 2.89 (d, J=4.5 Hz, 2H), 2.73 (d, J=4.5 Hz, 2H), 2.01-1.91 (m, 1H), 1.85 (br s, 1H), 1.69-1.55 (m, 2H), 1.38 (br, s, 1H), 1.22 (dd, J=7.7, 4.2 Hz, 1H), 0.90-0.77 (m, 12H).

Example 71

(1S,2R)-2-(4-(diisobutylamino)-3-(3-(4-((ethoxycarbonyl)amino)phenyl)ureido)phenyl)cyclopropanecarboxylic acid

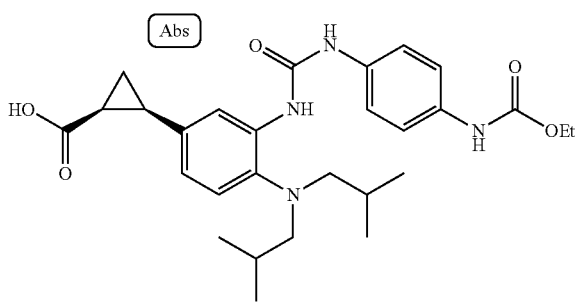 [SMILES: CCOC(=O)Nc1ccc(NC(=O)Nc2cc([C@@H]3C[C@@H]3C(=O)O)ccc2N(CC(C)C)CC(C)C)cc1]

Example 71 was prepared following the procedure for Example 29 using 1G and ethyl (4-aminophenyl)carbamate. Anal. Calc'd for $C_{28}H_{38}N_4O_5$ 510.28. found [M+H] 511.1, $T_r$=1.62 min (Method L) $^1$H NMR (500 MHz, DMSO-$d_6$) δ 9.48 (br s, 1H), 9.31 (br s, 1H), 7.92 (br s, 1H), 7.82 (br s, 1H), 7.37 (br s, 4H), 7.08 (dd, J=8.2, 3.2 Hz, 1H), 6.79 (d, J=8.4 Hz, 1H), 4.11 (qd, J=6.9, 3.5 Hz, 2H), 2.89 (d, J=3.0 Hz, 1H), 2.74 (d, J=3.0 Hz, 1H), 2.62 (d, J=5.9 Hz, 4H), 1.97 (d, J=7.4 Hz, 1H), 1.68-1.51 (m, 2H), 1.38 (br s, 1H), 1.24 (td, J=6.9, 3.5 Hz, 3H), 0.90-0.78 (m, 12H).

Example 72

(1S,2R)-2-(4-(diisobutylamino)-3-(3-(4-(2,2,2-trifluoroethoxy)phenyl)ureido)phenyl)cyclopropanecarboxylic acid

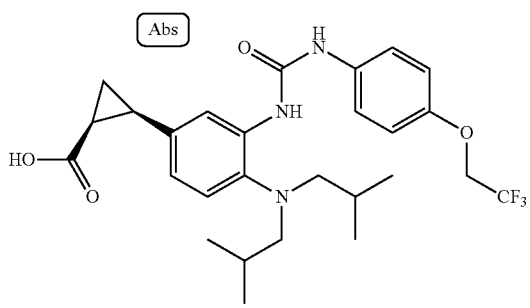 [SMILES: CC(C)CN(CC(C)C)c1ccc([C@@H]2C[C@@H]2C(=O)O)cc1NC(=O)Nc1ccc(OCC(F)(F)F)cc1]

Example 72 was prepared following the procedure for Example 29 using 1G and 4-(2,2,2-trifluoroethoxy)aniline in the urea formation. Anal. Calc'd for $C_{27}H_{34}F_3N_3O_4$ 521.25.

found [M+H] 522.1, $T_r$=1.81 min (Method L). $^1$H NMR (500 MHz, METHANOL-$d_4$) δ 7.90 (d, J=1.5 Hz, 1H), 7.61 (s, 2H), 7.39 (d, J=8.9 Hz, 2H), 7.07 (d, J=7.9 Hz, 1H), 6.99-6.89 (app m, 3H), 4.41 (q, J=8.1 Hz, 2H), 3.02 (s, 1H), 2.90 (s, 1H), 2.6 (d, J=6.9, 4H), 2.06 (ddd, J=9.2, 7.7, 5.9 Hz, 1H), 1.74-1.57 (app m, 3H), 1.33 (td, J=8.2, 5.0 Hz, 1H), 0.86 (d, J=6.4 Hz, 12H).

Example 73

(1R,2S)-2-(4-(cyclohexyl(4,4,4-trifluorobutyl) amino)-3-(3-(p-tolyl)ureido)phenyl)cyclopropanecarboxylic acid

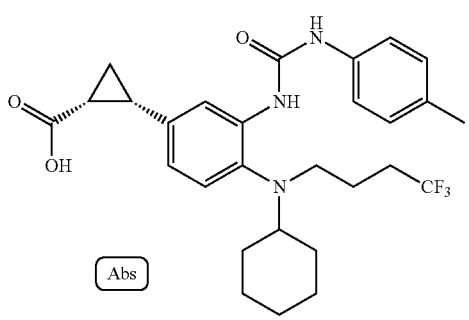 [SMILES: Cc1ccc(NC(=O)Nc2cc([C@H]3C[C@H]3C(=O)O)ccc2N(CCCC(F)(F)F)C2CCCCC2)cc1]

73A. N-cyclohexyl-4,4,4-trifluorobutanamide

In a 100 mL round-bottom flask with stir bar, was placed cyclohexanamine (2.096 ml, 18.30 mmol) and 4,4,4-trifluorobutanoic acid (2 g, 14.08 mmol) in DMF (15.64 ml). Triethylamine (3.92 ml, 28.2 mmol) and BOP (6.85 g, 15.48 mmol) were added and the brown, clear solution was stirred at rt overnight. The reaction mixture was diluted with 20 mL of water and a white precipitate formed upon stirring. The precipitate was filtered and washed with water (3×10 mL). The solid was dried under reduced pressure to give 73A (white solid, 2.994 g, 12.74 mmol, 91% yield). LC-MS Anal. Calc'd for $C_{10}H_{16}F_3NO$ 223.12. found [M+H] 224.3. $T_r$=2.99 min (Method F). $^1$H NMR (400 MHz, CHLOROFORM-d) δ 5.30 (br s, 1H), 3.85-3.70 (m, 1H), 2.56-2.42 (m, 2H), 2.41-2.33 (m, 2H), 1.98-1.85 (m, 2H), 1.77-1.66 (m, 2H), 1.66-1.56 (m, 1H), 1.46-1.29 (m, 3H), 1.25-1.00 (m, 3H).

73B. N-(4,4,4-trifluorobutyl)cyclohexylamine

In a 100 mL round-bottom flask with stir bar was placed lithium aluminum hydride (26.8 ml, 26.8 mmol) as a 1 M solution in THF. 73A (2.994 g, 13.41 mmol) was added in portions and a reflux condenser was installed. The apparatus was evacuated and back-filled with nitrogen three times, then the reaction mixture was stirred at reflux in a oil bath. The reaction mixture was heated at reflux overnight, then cooled in an ice bath. One mL of water was added dropwise with stirring, followed by 1 mL of 15% NaOH solution, followed by 3 mL of water. Additional THF was added to aid stirring and anhydrous $MgSO_4$ was added. The mixture was filtered and concentrated under reduced pressure to give 73B (colorless oil, 2.49 g, 11.9 mmol, 89% yield). LC-MS Anal. Calc'd for $C_{10}H_{18}F_3N$, 209.14. found [M+H] 210.2. $T_r$=0.58 min (Method D). $^1$H NMR (400 MHz, DMSO-$d_6$) δ 3.67-3.58 (m, 1H), 3.32 (br s, 1H), 2.61-2.55 (m, 2H), 2.37-2.20 (m, 2H), 1.85-1.75 (m, 2H), 1.72-1.63 (m, 2H), 1.62-1.51 (m, 3H), 1.29-1.10 (m, 3H), 1.07-0.90 (m, 2H).

73C. 4-bromo-N-cyclohexyl-2-nitro-N-(4,4,4-trifluorobutyl)aniline

A neat solution of 4-bromo-1-fluoro-2-nitrobenzene (0.061 ml, 0.500 mmol) and 73B (0.115 g, 0.550 mmol) was heated at 130° C. for 2 h, then allowed to cool to rt. Purification by flash chromatography gave 73C (orange oil, 0.113 g, 0.193 mmol, 39% yield). LC-MS Anal. Calc'd for $C_{16}H_{20}BrF_3N_2O_2$ 408.07. found [M+H] 409.1. $T_r$=2.14 min (Method C). $^1$H NMR (400 MHz, CHLOROFORM-d) δ 7.77 (d, J=2.4 Hz, 1H), 7.53 (dd, J=8.8, 2.4 Hz, 1H), 7.10 (d, J=8.8 Hz, 1H), 3.15 (t, J=6.5 Hz, 2H), 2.82 (tt, J=11.4, 3.3 Hz, 1H), 2.20-2.07 (m, 2H), 1.83-1.71 (m, 4H), 1.67-1.55 (m, 3H), 1.40-1.25 (m, 2H), 1.25-1.12 (m, 2H), 1.10-0.97 (m, 1H).

73D. N-cyclohexyl-4-(5,5-dimehtyl-1,3,2-dioxaborinan-2-yl)-2-nitro-N-(4,4,4-trifluorobutyl)aniline In a two-dram sample vial with stir bar was placed potassium acetate (0.432 g, 4.40 mmol), 2-(2,2-dimethyl-1,3,5-dioxaborinan-5-yl)-5,5-dimethyl-1,3,2-dioxaborinane (0.431 g, 1.906 mmol), 73C (0.600 g, 1.466 mmol) and $PdCl_2$(dppf) (0.032 g, 0.044 mmol). The vial was evacuated and backfilled with nitrogen (3×), then DMSO (2.094 ml) was added. The reaction mixture was sparged with nitrogen for 20 min. The mixture was heated at 80° C. overnight, then cooled to rt. The reaction was diluted with $H_2O$ and extracted with EtOAc (4×10 mL). The separated organic layer was washed with water, then brine and dried over anhydrous $MgSO_4$. The dried organics were filtered and concentrated under reduced pressure. The crude material was dissolved in a minimal amount of DCM and purified by flash chromatography to give 73D (orange oil, 0.55 g, 1.24 mmol, 75% yield). Anal. Calc'd for $C_{21}H_{30}BF_3N_2O_4$ 442.23. found [M+H] 375.4 (mass of boronic acid), $T_r$=2.84 min (Method F). $^1$H NMR (400 MHz, CHLOROFORM-d) δ 8.04 (d, J=1.5 Hz, 1H), 7.80 (dd, J=8.3, 1.4 Hz, 1H), 7.14 (d, J=8.4 Hz, 1H), 3.75 (s, 4H), 3.20 (t, J=6.5 Hz, 2H), 2.89 (ft, J=11.5, 3.3 Hz, 1H), 2.23-2.07 (m, 2H), 1.86-1.70 (m, 4H), 1.69-1.52 (m, 3H), 1.41-1.12 (m, 5H), 1.01 (s, 6H).

73E. (1R,2S)-ethyl 2-(4-(cyclohexyl(4,4,4-trifluorobutyl)amino)-3-nitrophenyl)cyclopropanecarboxylate A two-dram sample vial equipped with a stir bar and pressure relief cap, was charged with 73D (0.370 g, 0.837 mmol), (1S,2S)-ethyl 2-iodocyclopropanecarboxylate (0.241 g, 1.004 mmol), which was obtained through chiral resolution following the procedure in Organic Process Research & Development 2004, 8, 353-359, cesium carbonate (0.572 g, 1.757 mmol), and $PdCl_2$(dppf) (0.122 g, 0.167 mmol). The vial was evacuated and backfilled with nitrogen (3×), then dioxane (2.145 ml) and water (1.073 ml) were added. The reaction mixture was sparged with nitrogen for 15 min, then heated at 85° C. for 24 h. The vial was allowed to cool to rt, diluted with water and extracted with EtOAc. The combined organic layers were washed with brine, dried over anhydrous $MgSO_4$, filtered and concentrated under reduced pressure. Purification by flash chromatography gave 73E (orange oil, 0.137 g, 0.310 mmol, 37% yield). LC-MS Anal. Calc'd for $C_{22}H_{29}F_3N_2O_4$ 442.21. found [M+H] 443.3, $T_r$=2.99 min (Method F). $^1$H NMR (400 MHz, CHLOROFORM-d) δ 7.53 (d, J=2.0 Hz, 1H), 7.34 (dd, J=8.5, 1.9 Hz, 1H), 7.14 (d, J=8.6 Hz, 1H), 3.90 (qd, J=7.1, 0.9 Hz, 2H), 3.14 (t, J=6.5 Hz, 2H), 2.84-2.77 (m, 1H), 2.51 (q, J=8.6 Hz, 1H), 2.21-2.03 (m, 3H), 1.84-1.64 (m, 5H), 1.62-1.51 (m, 3H), 1.42-1.33 (m, 1H), 1.32-1.23 (m, 2H), 1.23-1.10 (m, 2H), 1.09-0.99 (m, 1H), 0.96 (t, J=7.2 Hz, 3H).

73F. (1R,2S)-ethyl 2-(3-amino-4-(cyclohexyl(4,4,4-trifluorobutyl)amino)phenyl) cyclopropanecarboxylate In a 10 mL round-bottom flask with stir bar was placed ammonium chloride (0.099 g, 1.858 mmol) and water (0.194 ml). The mixture was stirred to dissolve the ammonium chloride, then 73E (0.137 g, 0.310 mmol) was added as a solution in ethanol (1.355 ml). The reaction mixture was cooled in an ice bath and zinc flake (0.162 g, 2.477 mmol) was added in one portion. The reaction was allowed to warm to rt. After 10 min, the reaction mixture was filtered through packed Celite and concentrated under reduced pressure. Purification via flash chromatography gave 73F (pink oil, 0.070 g, 0.172 mmol, 55% yield). LC-MS Anal. Calc'd for $C_{22}H_{31}F_3N_2O_2$ 412.23. found [M+H] 413.3, $T_r$=2.42 min (Method F). $^1$H NMR (400 MHz, CHLOROFORM-d) δ 6.91 (d, J=8.1 Hz, 1H), 6.66 (d, J=1.8 Hz, 1H), 6.61 (dd, J=8.1, 1.5 Hz, 1H), 3.98 (br. s., 2H), 3.92-3.77 (m, 2H), 3.02 (t, J=6.7 Hz, 2H), 2.71-2.58 (m, 1H), 2.47 (q, J=8.7 Hz, 1H), 2.10-1.90 (m, 3H), 1.82 (d, J=10.8 Hz, 2H), 1.73 (d, J=12.5 Hz, 2H), 1.65 (dt, J=7.3, 5.4 Hz, 1H), 1.58 (d, J=12.3 Hz, 1H), 1.54-1.45 (m, 2H), 1.35-1.11 (m, 5H), 1.06 (tt, J=12.2, 3.1 Hz, 1H), 0.90 (t, J=7.2 Hz, 3H).

73G. (1R,2S)-2-(3-amino-4-(cyclohexyl(4,4,4-trifluorobutyl)amino) phenyl)cyclopropanecarboxylic acid In a one-dram sample vial with stir bar was placed LiOH (41.2 mg, 1.719 mmol) and water (172 μl). The mixture was stirred to dissolve the LiOH, then 73F (70.9 mg, 0.172 mmol) was added as a solution in MeOH (172 μl) and THF (86 μl). The reaction mixture was warmed to 45° C. for 3 h, stirred at rt for 3 d, and at 35° C. for 18 h. The reaction was neutralized with 4 N HCl in dioxane (430 μl, 1.719 mmol) and concentrated under a stream of nitrogen. Water was added and the crude product was isolated by extraction with EtOAc (5×1 mL). The combined organic layers were dried under a stream of nitrogen to give 73G (brown solid, 0.065 g, 0.169 mmol, 98% yield). LC-MS Anal. Calc'd for $C_{20}H_{27}F_3N_2O_2$ 384.20. found [M+H] 385.4, $T_r$=0.77 min (Method D).

Example 73

(1R,2S)-2-(4-(cyclohexyl(4,4,4-trifluorobutyl)amino)-3-(3-(p-tolyl)ureido)phenyl)cyclopropanecarboxylic acid In a one-dram sample vial equipped with a stirbar was placed 73G (25 mg, 0.065 mmol) and THF (0.5 mL). Then 1-isocyanato-4-methylbenzene (0.014 mL, 0.111 mmol) was added to the stirred solution and the mixture was stirred at 50° C. After 10 min, the mixture was dried under a stream of nitrogen and purification via preparative HPLC gave Example 73 (21.4 mg, 0.041 mmol, 62.9% yield). LC-MS Anal. Calc'd for $C_{28}H_{34}F_3N_3O_3$ 517.26. found [M+H] 518.3, $T_r$=2.61 min (Method F). $^1$H NMR (500 MHz, METHANOL-d$_4$: CHLOROFORM-d) δ 8.09 (d, J=1.5 Hz, 1H), 7.29 (d, J=8.4 Hz, 2H), 7.15 (d, J=7.9 Hz, 2H), 7.05 (d, J=7.9 Hz, 1H), 6.92 (dd, J=8.2, 1.7 Hz, 1H), 2.99 (t, J=7.4 Hz, 2H), 2.58 (q, J=8.4 Hz, 2H), 2.33 (s, 3H), 2.11-1.95 (m, 3H), 1.69 (d, J=12.4 Hz, 4H), 1.66-1.61 (m, 1H), 1.57 (d, J=12.4 Hz, 1H), 1.46 (quin, J=7.7 Hz, 2H), 1.33 (td, J=8.2, 5.0 Hz, 1H), 1.18-1.08 (m, 4H), 1.08-0.99 (m, 1H).

Example 74

(1R,2S)-2-(4-(cyclohexyl(4,4,4-trifluorobutyl)amino)-3-(3-(5-methylisoxazol-3-yl)ureido)phenyl)cyclopropanecarboxylic acid

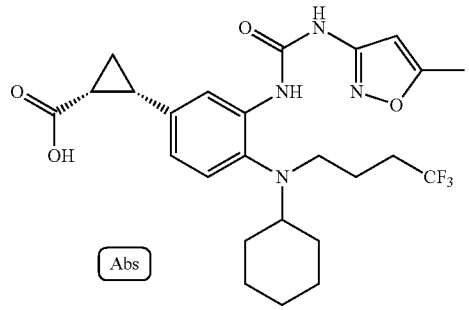 [SMILES: Cc1cc(NC(=O)Nc2cc([C@H]3C[C@H]3C(=O)O)ccc2N(CCCC(F)(F)F)C2CCCCC2)no1]

74A. 4-nitrophenyl (5-methylisoxazole-3-yl)carbamate

In a one-dram sample vial with stir bar was placed 5-methylisoxazol-3-amine (10.20 mg, 0.104 mmol) in THF (0.520 ml). To this stirred solution was added 4-nitrophenyl carbonochloridate (0.023 g, 0.114 mmol) and the mixture was stirred at rt for 20 min. The crude product (white suspension) was used without purification. LC-MS Anal. Calc'd for $C_{11}H_9N_3O_5$ 263.05. found [M+H] 264.2, $T_r$=2.08 min (Method F).

Example 74. Example 74 was prepared following the procedure for Example 1 with exception of the urea formation step: 73G (22 mg, 0.057 mmol) was added to a stirred suspension of 74A (15.06 mg, 0.057 mmol) in THF (0.5 mL). Triethylamine (0.024 mL, 0.172 mmol) was added and the reaction mixture was warmed to 50° C. while stirring. After 10 minutes of stirring, the mixture was dried under a stream of nitrogen and purified by preparative HPLC to give Example 74 (11.6 mg, 0.022 mmol, 37.9% yield). LC-MS Anal. Calc'd for $C_{25}H_{31}F_3N_4O_4$ 508.23. found [M+H] 509.4, $T_r$=0.96 min (Method D). $^1$H NMR (500 MHz, METHANOL-d$_4$: CHLOROFORM-d) δ 8.17 (d, J=1.5 Hz, 1H), 7.60 (s, 1H), 7.11 (d, J=7.9 Hz, 1H), 6.97 (dd, J=7.9, 1.5 Hz, 1H), 6.21 (br. s., 1H), 3.08 (t, J=6.9 Hz, 2H), 2.73-2.65 (m, 1H), 2.60 (q, J=8.6 Hz, 1H), 2.40 (s, 3H), 2.19-2.02 (m, 3H), 1.90 (d, J=10.4 Hz, 2H), 1.72 (d, J=12.4 Hz, 2H), 1.66 (dt, J=7.4, 5.4 Hz, 1H), 1.57 (d, J=12.4 Hz, 1H), 1.54-1.46 (m, 2H), 1.35 (td, J=8.2, 5.0 Hz, 1H), 1.30-1.11 (m, 4H), 1.10-1.05 (m, 1H).

Example 75

(1R,2S)-2-(4-(cyclohexyl(4,4,4-trifluorobutyl)amino)-3-(3-pyrimidine-5-yl)ureido)phenyl)cyclopropanecarboxylic acid

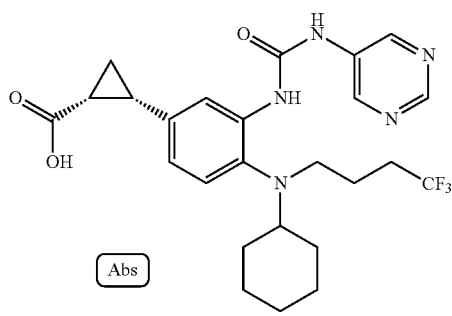 [SMILES: O=C(Nc1cncnc1)Nc1cc([C@H]2C[C@H]2C(=O)O)ccc1N(CCCC(F)(F)F)C1CCCCC1]

75A. (1R,2S)-ethyl 2-(4-(cyclohexyl(4,4,4-trifluorobutyl)amino)-3-(3-(pyrimidin-5-yl)ureido)phenyl)cyclopropanecarboxylate In a one-dram sample vial with stirbar was placed 73F (53.3 mg, 0.129 mmol) and THF (1988 µl). To this stirred solution was added 4-nitrophenyl carbonochloridate (27.3 mg, 0.136 mmol). The reaction was stirred at rt for 30 min. Pyrimidin-5-amine (36.9 mg, 0.388 mmol) and triethylamine (54.0 µl, 0.388 mmol) were added and the reaction was heated at 50° C. After 17 h, the reaction was cooled to rt, then dried under a stream of nitrogen. The concentrate was diluted with water and extracted with EtOAc (3×). The combined organic layers were washed with brine, dried over anhydrous $MgSO_4$, filtered and concentrated under a reduced pressure to give 75A. The crude product was used directly in the subsequent procedure. Anal. Calc'd for $C_{27}H_{34}F_3N_5O_3$ 533.26. found [M+H] 534.4, $T_r$=2.15 min (Method E).

75. In a one-dram sample vial with stir bar was placed LiOH (30.9 mg, 1.290 mmol) and water (129 µl). The mixture was stirred until all of the LiOH was dissolved, then 75A (68.8 mg, 0.129 mmol) was as added as a solution in MeOH (129 µl) and THF (64.5 µl). The reaction mixture was warmed to 45° C. and monitored by LCMS. After 3 h, the reaction was neutralized with 4 N HCl in dioxane (323 µl, 1.290 mmol) and diluted with water. The mixture was extracted with EtOAc until no material was observed in the water layer. The combined organic layers were dried under a stream of nitrogen, then purified by preparative HPLC to give Example 75 (0.011 g, 0.021 mmol, 16.53% yield for two steps). LC-MS Anal. Calc'd for $C_{25}H_{30}F_3N_5O_3$ 505.23. found [M+H] 506.4, $T_r$=0.89 min (Method D). $^1$H NMR (500 MHz, METHANOL-$d_4$: CHLOROFORM-d) δ 9.04 (br. s., 1H), 8.83 (br. s., 1H), 8.11 (br. s., 1H), 7.62 (s, 1H), 7.12 (d, J=7.9 Hz, 1H), 6.98 (d, J=7.4 Hz, 1H), 4.35 (br. s., 1H), 3.08 (t, J=7.2 Hz, 2H), 2.71 (apparent br. s., 1H), 2.66-2.54 (m, 1H), 2.18-1.99 (m, 3H), 1.91 (br. s., 2H), 1.75 (d, J=9.4 Hz, 2H), 1.66 (br. s., 1H), 1.60 (d, J=12.4 Hz, 1H), 1.57-1.47 (m, 2H), 1.43-1.33 (m, 1H), 1.30-1.14 (m, 4H), 1.11-1.04 (m, 1H).

Example 76

(1S,2R)-2-(4-(cyclohexyl(4,4,4-trifluorobutyl)amino)-3-(3-(p-tolyl)ureido)phenyl)cyclopropanecarboxylic acid

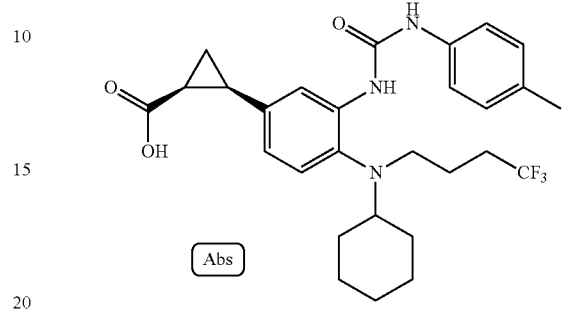

Example 76 was prepared following the procedure for Example 75 using the enantiomer of 73F and the corresponding amine. LC-MS Anal. Calc'd for $C_{28}H_{34}F_3N_3O_3$ 517.26. found [M+H] 518.3, $T_r$=1.70 min (Method C). $^1$H NMR (500 MHz, METHANOL-$d_4$:CHLOROFORM-d) δ 8.09 (s, 1H), 7.28 (d, J=8.4 Hz, 2H), 7.14 (d, J=7.9 Hz, 2H), 7.03 (d, J=7.9 Hz, 1H), 6.90 (dd, J=7.9, 1.5 Hz, 1H), 2.97 (t, J=7.2 Hz, 2H), 2.66-2.51 (m, 2H), 2.32 (s, 3H), 2.11-1.91 (m, 3H), 1.76-1.60 (m, 5H), 1.56 (d, J=12.4 Hz, 1H), 1.44 (quin, J=7.4 Hz, 2H), 1.33 (td, J=8.2, 5.0 Hz, 1H), 1.21-0.96 (m, 5H).

Example 77

(1S,2R)-2-(4-(diisobutylamino)-3-(3-(2-methylpyrimidin-5-yl)ureido)phenyl)cyclopropanecarboxylic acid

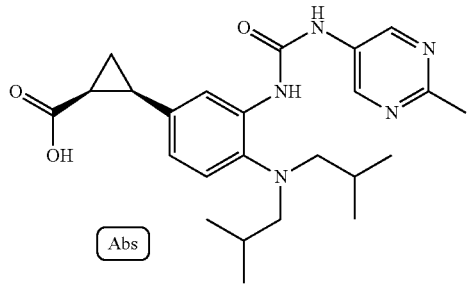 [SMILES: Cc1ncc(NC(=O)Nc2cc([C@@H]3C[C@@H]3C(=O)O)ccc2N(CC(C)C)CC(C)C)cn1]

77A. 2-methylpyrimidine-5-amine

A solution of 4,6-dichloro-2-methylpyrimidin-5-amine (2 g, 11.23 mmol) in ethyl ether (93 ml) was treated with sodium hydroxide (7.37 g, 184 mmol) in water (22.05 ml) and 10% palladium on carbon (0.161 g, 1.517 mmol). The mixture was shaken at rt on a Parr shaker under 50 psi of $H_2$ gas for 22 h. The reaction was filtered through Celite and the filter cake was washed with DCM. The solvent from the filtrate was evaporated to give a yellow residue. The suspension was re-dissolved in DCM and water. The aqueous layer was neutralized to approximately pH 6 with 4N HCl, then extracted with DCM (3×). The combined organic phases were dried over anhydrous $Na_2SO_4$, filtered, and concentrated to afford a yellow residue. The aqueous phase still contained product, so the water was evaporated to give a yellow solid. The solid was taken up in MeOH and DCM and filtered to remove all salts. The filtrate was evaporated to give a yellow residue. A total of two crops were obtained—one from the extraction and one from the aqueous layer. Each crop was purified by flash chromatography and combined to give 77A (off-white solid, 0.968 g, 8.87 mmol, 79% yield). $^1$H NMR (400 MHz, CHLOROFORM-d) δ 8.14 (s, 2H), 3.60 (br. s., 2H), 2.61 (s, 3H).

77. Example 77 was prepared following the procedure for Example 1 Method B, using the enantiomer of 1I, except for the urea formation and hydrolysis: To a solution of the enantiomer of 11 (0.0255 g, 0.077 mmol) in THF (1.180 ml) was added 4-nitrophenyl carbonochloridate (0.017 g, 0.084 mmol). The reaction was stirred at rt for 30 min. To this reaction mixture were added 77A (0.025 g, 0.230 mmol) and triethylamine (0.032 ml, 0.230 mmol). The reaction was heated at 50° C. overnight, then allowed to cool to rt. The reaction was diluted with $H_2O$ and diluted with EtOAc. The layers were separated and the aqueous phase was extracted with EtOAc (3×). The organic phases were combined, dried over anhydrous $Na_2SO_4$, filtered and concentrated to give (1S,2R)-ethyl 2-(4-(diisobutylamino)-3-(3-(2-methylpyrimidin-5-yl)ureido)phenyl)cyclopropanecarboxylate as a yellow residue. The crude product was used in the subsequent procedure. LC-MS Anal. Calc'd for $C_{26}H_{37}N_5O_3$ 467.29. found [M+H] 468.3, $T_r$=1.75 min (Method C). To a solution of (1S,2R)-ethyl 2-(4-(diisobutylamino)-3-(3-(2-methylpyrimidin-5-yl)ureido)phenyl)cyclopropanecarboxylate (0.036 g, 0.077 mmol) in tetrahydrofuran (0.171 ml) and MeOH (0.086 ml) was added 1.5M lithium hydroxide aqueous solution (0.513 ml, 0.770 mmol). The mixture was heated at 50° C. for 16 h. The reaction was neutralized with 1 N HCl (0.77 mL) and diluted with EtOAc. The layers were separated and the aqueous phase was extracted with EtOAc (3×). The organic phases were combined and the solvent was evaporated to give the crude product as a yellow residue. Purification by preparative HPLC gave Example 77 (0.017 g, 0.038 mmol, 50%). LC-MS Anal. Calc'd for $C_{24}H_{33}N_5O_3$ 439.26. found [M+H] 440.2, $T_r$=1.31 min (Method C). $^1$H NMR (500 MHz, METHANOL-$d_4$:CHLOROFORM-d) δ 8.89 (s, 2H), 7.91 (s, 1H), 7.10 (d, J=7.9 Hz, 1H), 6.98 (dd, J=8.4, 1.5 Hz, 1H), 2.69-2.63 (m, 6H), 2.63-2.56 (m, 1H), 2.12-2.03 (m, 1H), 1.77-1.60 (m, 3H), 1.35 (td, J=8.2, 5.0 Hz, 1H), 0.90 (d, J=6.9 Hz, 12H).

Example 78

(1S,2R)-2-(3-(3-(2-cyanopyrimidin-5-yl)ureido)-4-(diisobutylamino)phenyl)cyclopropanecarboxylic acid 78A. 5-Isocyanatopyrimidine-2-carbonitrile In a 25 mL scintillation vial equipped with a stir bar was placed sodium carbonate (0.212 g, 1.998 mmol) in DCM (2.69 ml). The mixture was cooled to 0° C. while stirring and phosgene (0.394 ml, 0.549 mmol) was added as a 15% solution in toluene. 5-Aminopyrimidine-2-carbonitrile (0.060 g, 0.500 mmol) was added dropwise over 5 min as a solution in THF (2.69 ml). After addition, the reaction was stirred at 0° C. for 10 min, then allowed to warm to rt. After 1 h, the reaction was filtered through a syringe filter and used without purification.

78B. (1S,2R)-2-(3-amino-4-(diisobutylamino)phenyl)cyclopropanecarboxylic acid

To a solution of 1G (0.085 g, 0.256 mmol) in tetrahydrofuran (0.568 ml) and MeOH (0.284 ml) was added lithium hydroxide aqueous solution (1.704 ml, 2.56 mmol). The mixture was heated at 50° C. overnight and the reaction allowed to cool to rt. The reaction was neutralized with 1 N HCl (2.56 mL) and diluted with EtOAc. The layers were separated and the aqueous phase was extracted with EtOAc (9×). The organic phases were combined and the solvent was evaporated to give 78B (brown oil, 0.078 g, 0.254 mmol, 99% yield). LC-MS Anal. Calc'd for $C_{18}H_{28}N_2O_2$ 304.22. found [M+H] 305.2, $T_r$=1.43 min (Method C). $^1$H NMR (500 MHz, CHLOROFORM-d) δ 6.93 (d, J=8.1 Hz, 1H), 6.69-6.54 (m, 2H), 2.67 (d, J=7.0 Hz, 4H), 2.50 (d, J=8.4 Hz, 1H), 2.02-1.91 (m, 1H), 1.76 (dquin, J=13.4, 6.7 Hz, 2H), 1.56 (dt, J=7.5, 5.4 Hz, 1H), 1.33-1.29 (m, 1H), 0.89 (d, J=6.6 Hz, 12H).

78. To a vial charged with 78B (0.023 g, 0.076 mmol) was added 78A (2.437 ml, 0.227 mmol) as a 0.093 M solution in DCM and THF followed by triethylamine (0.105 ml, 0.756 mmol). The reaction was allowed to stir at rt overnight. The reaction was diluted with water and EtOAc. The layers were separated and the aqueous phase was extracted with EtOAc (3×). The organic phases were combined and the solvent was evaporated to give the crude product as a yellow residue. Purification by preparative HPLC gave Example 78 (0.014 g, 030 mmol, 39% yield). LC-MS Anal. Calc'd for $C_{24}H_{30}N_6O_3$ 450.24. found [M+H] 451.2, $T_r$=1.49 min (Method C). $^1$H NMR (500 MHz, METHANOL-$d_4$:CHLOROFORM-d) δ 9.12 (s, 2H), 8.02-7.89 (m, 1H), 7.12 (d, J=7.9 Hz, 1H), 7.01 (dd, J=7.9, 1.5 Hz, 1H), 2.66 (d, J=7.4 Hz, 4H), 2.62-2.53 (m, 1H), 2.14-2.02 (m, 1H), 1.71 (dt, J=13.4, 6.7 Hz, 2H), 1.66-1.57 (m, 1H), 1.35 (td, J=8.2, 5.0 Hz, 1H), 0.90 (d, J=6.4 Hz, 12H).

Example 79

(1R,2S)-2-(3-(3-(2-cyanopyrimidin-5-yl)ureido)-4-(diisobutylamino)phenyl)cyclopropanecarboxylic acid

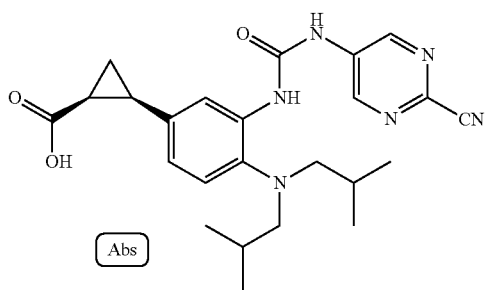 [SMILES: CC(C)CN(CC(C)C)c1ccc([C@@H]2C[C@@H]2C(=O)O)cc1NC(=O)Nc1cnc(C#N)nc1]

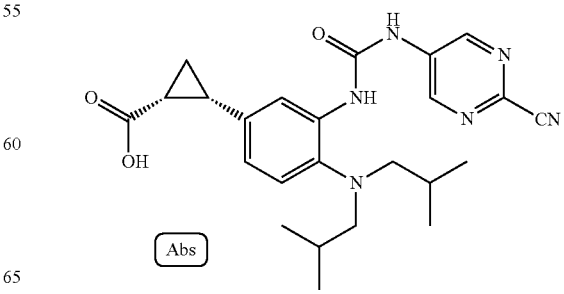

79A. (1R,2S)-ethyl 2-(4-(diisobutylamino)-3-nitrophenyl) cyclopropanecarboxylate To a solution of 1G (9.0 g, 24.84 mmol) in dioxane (50.2 ml) in a pressure tube was added cesium carbonate (17.81 g, 54.7 mmol), followed by water (25.09 ml) and (1S,2S)-ethyl 2-iodocyclopropanecarboxylate (5.96 g, 24.84 mmol), which was obtained through chiral resolution following the procedure in Organic Process Research & Development 2004, 8, 353-359. Nitrogen was bubbled through the mixture for 20 minutes followed by addition of $PdCl_2$(dppf)-$CH_2Cl_2$ adduct (2.029 g, 2.484 mmol). Sparging was continued for another 10 minutes and then the pressure tube was capped. The mixture was heated at 85° C. for 17 hours and then cooled to rt. After cooling to rt, the mixture was diluted with EtOAc and brine and then extracted three times with EtOAc. The combined organics were dried over anhydrous $MgSO_4$, filtered and concentrated to give the crude product as a brown oil. Purification via flash chromatography gave 79A (orange oil, 4.54 g, 12.4 mmol, 50% yield). LC-MS Anal. Calc'd for $C_{20}H_{30}N_2O_4$ 362.22. found [M+H] 363.3, $T_r$=1.22 min (Method D). $^1$H NMR (500 MHz, CHLOROFORM-d) δ 7.64 (dd, J=2.2, 0.7 Hz, 1H), 7.33-7.28 (m, 1H), 7.05 (d, J=8.6 Hz, 1H), 4.01-3.84 (m, 2H), 2.91 (d, J=7.3 Hz, 4H), 2.51 (q, J=8.6 Hz, 1H), 2.09 (ddd, J=9.1, 8.0, 5.6 Hz, 1H), 1.98-1.82 (m, 2H), 1.70 (dt, J=7.4, 5.4 Hz, 1H), 1.36 (ddd, J=8.7, 8.0, 5.3 Hz, 1H), 1.02 (t, J=7.2 Hz, 3H), 0.85 (d, J=6.6 Hz, 12H).

79B. (1R,2S)-ethyl 2-(3-amino-4-(diisobutylamino) phenyl) cyclopropanecarboxylate To a solution of 79A (0.580 g, 1.600 mmol) in Ethyl acetate (16.00 ml) was added palladium on carbon (0.170 g, 0.160 mmol). The flask was the evacuated with vacuum and back-filled two times with $H_2$ from a balloon. The reaction was stirred at rt for 1.5 h. The reaction was filtered through Celite and the filter cake washed with DCM. The solvent was evaporated and purification via flash chromatography gave 79B (brown oil, 0.308 g, 0.917 mmol, 57% yield). LC-MS Anal. Calc'd for $C_{20}H_{32}N_2O_2$ 332.48. found 333.3, $T_r$=1.86 min (Method C). $^1$H NMR (500 MHz, CHLOROFORM-d) δ 6.94 (d, J=7.9 Hz, 1H), 6.73-6.51 (m, 2H), 4.07 (br. s., 2H), 3.87 (qd, J=7.1, 0.8 Hz, 2H), 2.56 (d, J=7.3 Hz, 4H), 2.47 (q, J=8.6 Hz, 1H), 2.00 (ddd, J=9.3, 7.8, 5.6 Hz, 1H), 1.80-1.69 (m, 2H), 1.68-1.57 (m, 1H), 1.29-1.19 (m, 1H), 0.92 (t, J=7.2 Hz, 3H), 0.88 (dd, J=6.6, 0.9 Hz, 12H).

79C. (1R,2S)-2-(3-amino-4-(diisobutylamino)phenyl)cyclopropanecarboxylic acid To a solution of 79B (0.0308 g, 0.093 mmol) in tetrahydrofuran (0.206 ml) and MeOH (0.103 ml) was added 1.5 M lithium hydroxide aqueous solution (0.618 ml, 0.926 mmol). The mixture was heated at 50° C. overnight. The reaction was allowed to cool to rt. The reaction was neutralized with 1 N HCl (0.93 mL) and diluted with EtOAc. The layers were separated and the aqueous phase was extracted with EtOAc (9×). The organic phases were combined and the solvent was evaporated to give 79C (pink oil, 0.027 g, 0.086 mmol, 93% yield). LC-MS Anal. Calc'd for $C_{18}H_{28}N_2O_4$ 304.22. found [M+H] 305.2, $T_r$=1.51 min (Method C). $^1$H NMR (500 MHz, CHLOROFORM-d) δ 6.94 (d, J=8.1 Hz, 1H), 6.72-6.55 (m, 2H), 2.66 (d, J=7.0 Hz, 4H), 2.57-2.41 (m, 1H), 2.05-1.89 (m, 1H), 1.77 (dquin, J=13.4, 6.7 Hz, 1H), 1.57 (dt, J=7.5, 5.4 Hz, 1H), 1.35-1.23 (m, 1H), 0.90 (d, J=6.6 Hz, 12H).

79.

To a vial charged with 79C (0.0265 g, 0.087 mmol) was added 78A (1.729 ml, 0.261 mmol) as a 1.7 M solution in DCM and THF followed by triethylamine (0.121 ml, 0.870 mmol). The reaction was allowed to stir at rt overnight. The reaction was diluted with water and EtOAc. The layers were separated and the aqueous phase was extracted with EtOAc (3×). The organic phases were combined and the solvent was evaporated to give the crude product as a yellow residue. Purification by preparative HPLC gave Example 79 (0.006 g, 12.40 mmol, 50% yield). LC-MS Anal. Calc'd for $C_{24}H_{30}N_6O_3$ 450.24. found [M+H] 451.4, $T_r$=2.11 min (Method E). $^1$H NMR (500 MHz, METHANOL-$d_4$:CHLOROFORM-d) δ 9.12 (s, 2H), 8.02-7.89 (m, 1H), 7.12 (d, J=7.9 Hz, 1H), 7.01 (dd, J=7.9, 1.5 Hz, 1H), 2.66 (d, J=7.4 Hz, 4H), 2.62-2.53 (m, 1H), 2.14-2.02 (m, 1H), 1.71 (dt, J=13.4, 6.7 Hz, 2H), 1.66-1.57 (m, 1H), 1.35 (td, J=8.2, 5.0 Hz, 1H), 0.90 (d, J=6.4 Hz, 12H).

Example 80

(1R,2S)-2-(4-(cyclohexyl)isobutyl)amino)-3-(3-(5-methylisoxazol-3-yl)ureido)phenyl)cyclopropanecarboxylic acid

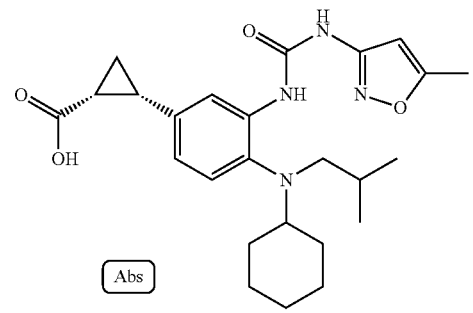 [SMILES: Cc1cc(NC(=O)Nc2cc([C@H]3C[C@H]3C(=O)O)ccc2N(CC(C)C)C2CCCCC2)no1]

80A. N-isobutylcyclohexanamine

A solution of cyclohexanamine (2.307 ml, 20.17 mmol) and isobutyraldehyde (1.933 ml, 21.17 mmol) in MeOH (40.3 ml) was heated at 40° C. for 1 h, then allowed to cool to rt. Sodium borohydride (1.144 g, 30.2 mmol) was added and the reaction was allowed to stir at rt overnight. The solvent was evaporated and the crude material taken up in EtOAc and $H_2O$. The layers were separated and the aqueous phase was extracted with EtOAc (2×). The combined organic phases were dried over anhydrous $Na_2SO_4$, filtered, and concentrated to afford 80A (clear, colorless oil, 2.60 g, 16.58 mmol, 82% yield). LC-MS Anal. Calc'd for $C_{10}H_{21}N$, 155.17. found [M+H] 156.2, $T_r$=1.16 min (Method C). $^1$H NMR (500 MHz, METHANOL-$d_4$:CHLOROFORM-d) δ 2.42 (d, J=6.8 Hz, 2H), 2.40-2.32 (m, 1H), 1.93-1.82 (m, 2H), 1.77-1.67 (m, 4H), 1.65-1.55 (m, 1H), 1.33-1.12 (m, 3H), 1.12-0.98 (m, 2H), 0.90 (d, J=6.6 Hz, 6H).

80B. 4-bromo-N-cyclohexyl-N-isobutyl-2-nitroaniline

A neat solution of 4-bromo-1-fluoro-2-nitrobenzene (1.931 ml, 15.89 mmol) and 80A (2.59 g, 16.68 mmol) was heated at 130° C. for 3 h, then allowed to cool to rt. Purification by flash chromatography gave 80B (orange oil, 2.56 g, 7.2 mmol, 45% yield). LC-MS Anal. Calc'd for $C_{16}H_{23}BrN_2O_2$ 354.09. found [M+H] 355.0, $T_r$=2.32 min (Method C). $^1$H NMR (500 MHz, METHANOL-$d_4$:CHLOROFORM-d) δ 7.78 (d, J=2.4 Hz, 1H), 7.46 (dd, J=8.8, 2.4 Hz, 1H), 7.04 (d, J=9.0 Hz, 1H), 2.91-2.81 (m, 3H), 1.86-1.71 (m, 4H), 1.59 (dt, J=13.4, 6.7 Hz, 2H), 1.46-1.31 (m, 2H), 1.27-1.12 (m, 2H), 1.11-0.96 (m, 1H), 0.85 (d, J=6.6 Hz, 6H)

80C. N-cyclohexyl-4-(5,5-dimethyl-1,3,2-dioxaborinan-2-yl)-N-isobutyl-2-nitroaniline A suspension of potassium acetate (1.774 g, 18.07 mmol), 2-(2,2-dimethyl-1,3,5-dioxaborinan-5-yl)-5,5-dimethyl-1,3,2-dioxaborinane (1.769 g, 7.83 mmol) and 80B (2.14 g, 6.02 mmol) in DMSO (9.02 ml) was sparged with nitrogen for 15 min, then treated with PdCl$_2$(dppf) (0.148 g, 0.181 mmol). The reaction was sparged with nitrogen for an additional 2 min. The mixture was heated to 80° C. overnight, then allowed to cool to rt. The reaction was diluted with H$_2$O and EtOAc. The layers were separated and the aqueous phase was extracted with EtOAc (2×). The combined organic phases were washed with H$_2$O (2×), then dried over Na$_2$SO$_4$, filtered, and concentrated to afford a black residue. Purification by flash chromatography gave 80C (orange oil, 1.50 g, 3.86 mmol, 63% yield). LC-MS Anal. Calc'd for $C_{21}H_{33}BN_2O_4$ 388.25. found [M+H] 321.2 (mass of boronic acid), $T_r$=1.78 min (Method C). $^1$H NMR (500 MHz, METHANOL-$d_4$:CHLOROFORM-d) δ 8.06 (d, J=1.3 Hz, 1H), 7.74 (dd, J=8.4, 1.5 Hz, 1H), 7.08 (d, J=8.4 Hz, 1H), 3.74 (s, 4H), 2.95 (tt, J=11.6, 3.4 Hz, 1H), 2.89 (d, J=7.3 Hz, 2H), 1.82 (d, J=11.4 Hz, 2H), 1.75 (d, J=13.0 Hz, 2H), 1.70-1.63 (m, 1H), 1.59 (d, J=12.5 Hz, 1H), 1.39 (qd, J=12.2, 3.0 Hz, 2H), 1.29-1.13 (m, 2H), 1.01 (s, 6H), 0.87 (d, J=6.6 Hz, 6H).

80D. (1R,2S)-ethyl 2-(4-(cyclohexyl(isobutyl)amino)-3-nitrophenyl) cyclopropanecarboxylate A vial containing a mixture of 80B (0.771 g, 1.986 mmol), (1S,2S)-ethyl 2-iodocyclopropanecarboxylate (0.500 g, 2.085 mmol), which was obtained through chiral resolution modifying the procedure in Organic Process Research & Development 2004, 8, 353-359 (see Example 1, 1H), and cesium carbonate (1.359 g, 4.17 mmol) in dioxane (5.09 ml) and water (2.55 ml) was sparged with nitrogen for 10 min, then PdCl$_2$(dppf) (0.324 g, 0.397 mmol) was added and the resulting mixture was sparged with nitrogen for an additional 2 min. The solution was heated at 85° C. for 24 h, then allowed to cool to rt. The reaction was diluted with water and extracted with EtOAc (4×). The organic layers were combined, dried over over Na$_2$SO$_4$, filtered, and concentrated to afford a dark brown residue. Purification by flash chromatography gave 80D (orange oil, 0.343 g, 0.883 mmol, 44% yield). LC-MS Anal. Calc'd for $C_{22}H_{32}N_2O_4$ 388.24. found [M+H] 389.2, $T_r$=2.15 min (Method C). $^1$H NMR (500 MHz, METHANOL-$d_4$:CHLOROFORM-d) δ 7.55 (d, J=2.2 Hz, 1H), 7.28 (dd, J=8.7, 2.3 Hz, 1H), 7.07 (d, J=8.6 Hz, 1H), 3.91 (q, J=7.1 Hz, 2H), 2.93-2.84 (m, 1H), 2.82 (d, J=7.3 Hz, 2H), 2.57-2.42 (m, 1H), 2.07 (ddd, J=9.2, 8.0, 5.7 Hz, 1H), 1.85-1.70 (m, 4H), 1.67 (dt, J=7.4, 5.4 Hz, 1H), 1.60-1.55 (m, 1H), 1.42-1.28 (m, 3H), 1.26-1.11 (m, 2H), 1.04 (tt, J=12.7, 3.4 Hz, 1H), 0.97 (t, J=7.0 Hz, 3H), 0.88 (t, J=6.8 Hz, 1H), 0.83 (d, J=6.6 Hz, 6H).

80E. (1R,2S)-ethyl 2-(3-amino-4-(cyclohexyl(isobutyl)amino)phenyl) cyclopropanecarboxylate To a solution of ammonium chloride (0.283 g, 5.30 mmol) in water (0.528 ml) was added ethanol (3.70 ml). The reaction vessel was cooled to 0° C., then charged with zinc flake 325 mesh (0.476 g, 7.27 mmol). The mixture was treated with 80D (0.343 g, 0.883 mmol) in THF (0.83 mL). The reaction mixture was allowed to warm to rt and stirred for 30 min. The reaction was filtered through Celite and the filter cake was washed with EtOAc and DCM. Purification via flash chromatography gave 80E (colorless oil, 296 mg, 0.826 mmol, 94% yield). LC-MS Anal. Calc'd for $C_{22}H_{34}N_2O_2$ 358.26. found [M+H] 359.2, $T_r$=2.30 min (Method C). $^1$H NMR (500 MHz, METHANOL-$d_4$:CHLOROFORM-d) δ 6.92 (d, J=8.1 Hz, 1H), 6.65 (d, J=1.8 Hz, 1H), 6.59 (dd, J=8.1, 1.8 Hz, 1H), 3.98 (br. s., 2H), 3.91-3.77 (m, 2H), 2.58 (tt, J=11.6, 3.4 Hz, 2H), 2.46 (q, J=8.7 Hz, 1H), 1.99 (ddd, J=9.3, 7.8, 5.6 Hz, 1H), 1.80 (d, J=11.4 Hz, 2H), 1.72 (d, J=12.1 Hz, 2H), 1.64 (dt, J=7.3, 5.4 Hz, 1H), 1.57 (d, J=11.9 Hz, 1H), 1.40 (td, J=13.4, 6.8 Hz, 2H), 1.35-1.28 (m, 1H), 1.27-1.18 (m, 2H), 1.18-1.11 (m, 1H), 1.10-0.99 (m, 2H), 0.88 (t, J=7.2 Hz, 3H), 0.79 (dd, J=6.6, 0.7 Hz, 6H)

80F. (1R,2S)-ethyl 2-(4-(cyclohexyl(isobutyl)amino)-3-(3-(5-methylisoxazol-3-yl)ureido)phenyl) cyclopropanecarboxylate To a solution of 80E (26.4 mg, 0.074 mmol) in THF (1133 μl) was added 4-nitrophenyl carbonochloridate (15.58 mg, 0.077 mmol). The reaction was stirred at rt for 30 min. To this reaction were added 5-methylisoxazol-3-amine (21.67 mg, 0.221 mmol) and triethylamine (30.8 μl, 0.221 mmol). The reaction was heated at 50° C. for 3 d, then allowed to cool to rt. The solvent was evaporated with a stream of nitrogen to give 80F as a yellow residue. This material was used in the subsequent reaction without purification. LC-MS Anal. Calc'd for $C_{27}H_{38}N_4O_4$ 482.29. found [M+H] 483.3, $T_r$=2.27 min (Method E).

80: To a solution of 80F (35.5 mg, 0.074 mmol) in tetrahydrofuran (123 μl) and MeOH (61.3 μl) was added 1.5M lithium hydroxide aqueous solution (490 μl, 0.736 mmol). The mixture was heated at 50° C. for 16 h. The reaction was neutralized with 1 N HCl (0.91 mL) and diluted with EtOAc. The layers were separated and the aqueous phase was extracted with EtOAc (3×). The organic phases were combined and the solvent was evaporated to give the crude product as a yellow residue. Purification by preparative HPLC gave Example 80 (7.8 mg, 0.016 mmol, 22% yield). LC-MS Anal. Calc'd for $C_{25}H_{34}N_4O_4$ 454.26. found [M+H] 455.2, $T_r$=2.03 min (Method E). $^1$H NMR (500 MHz, METHANOL-$d_4$:CHLOROFORM-d) δ 8.04 (br. s., 1H), 7.07 (d, J=8.4 Hz, 1H), 6.94 (d, J=7.4 Hz, 1H), 6.26 (s, 1H), 2.79 (br. s., 2H), 2.64-2.53 (m, 2H), 2.39 (s, 3H), 2.10-2.02 (m, 1H), 1.89 (d, J=11.4 Hz, 2H), 1.71 (d, J=12.4 Hz, 2H), 1.64 (dt, J=7.6, 5.4 Hz, 1H), 1.56 (d, J=11.9 Hz, 1H), 1.45-1.21 (m, 4H), 1.19-0.99 (m, 3H), 0.82 (d, J=6.4 Hz, 6H).

Example 81

(1S,2R)-2-(4-(cyclohexyl(isobutyl)amino)-3-(3-(5-methylisoxazol-3-yl)ureido)phenyl)cyclopropanecarboxylic acid

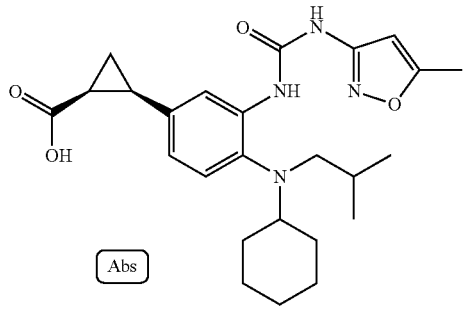 [SMILES: Cc1cc(NC(=O)Nc2cc([C@@H]3C[C@@H]3C(=O)O)ccc2N(CC(C)C)C2CCCCC2)no1]

81A. Example 81 was prepared following the procedure for 80, using single enantiomer (1R,2R)-ethyl 2-iodocyclopropanecarboxylate (Organic Process Research & Development 2004, 8, 353-359). LC-MS Anal. Calc'd for $C_{25}H_{34}N_4O_4$ 454.26. found [M+H] 455.2, $T_r$=2.04 min (Method E). $^1$H NMR (500 MHz, METHANOL-$d_4$:CHLOROFORM-d) δ 8.06 (d, J=1.5 Hz, 1H), 7.08 (d, J=8.4 Hz, 1H), 6.95 (dd, J=8.2, 1.7 Hz, 1H), 6.27 (s, 1H), 2.81 (br. s., 1H), 2.66-2.51 (m, 2H), 2.4 (s, 3H), 2.12-2.02 (m, 1H), 1.90 (d, J=10.9 Hz, 2H), 1.71 (d, J=12.9 Hz, 2H), 1.65 (dt, J=7.4, 5.2 Hz, 1H), 1.56 (d, J=11.9 Hz, 1H), 1.46-1.22 (m, 5H), 1.20-1.00 (m, 3H), 0.83 (d, J=6.4 Hz, 6H).

Example 82

(1R,2S)-2-(4-(cyclohexyl(isobutyl)amino)-3-(3-(pyrimidin-5-yl)ureido)phenyl)cyclopropanecarboxylic acid

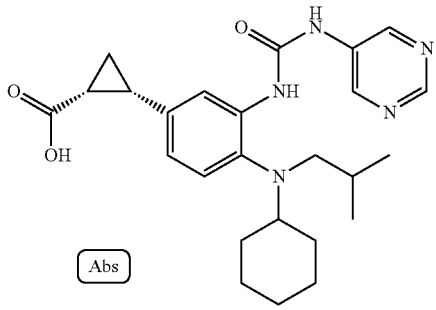 [SMILES: CC(C)CN(c1ccc([C@H]2C[C@H]2C(=O)O)cc1NC(=O)Nc1cncnc1)C1CCCCC1]

Example 82 was prepared following the procedure for 80 and the urea was formed using pyrimidin-5-amine. LC-MS Anal. Calc'd for $C_{25}H_{33}N_5O_3$ 451.26. found [M+H] 452.3, $T_r$=1.77 min (Method E). $^1$H NMR (500 MHz, METHANOL-$d_4$:CHLOROFORM-d) δ 9.05 (br. s., 2H), 8.82 (br. s., 1H), 8.01 (br. s., 1H), 7.09 (d, J=7.9 Hz, 1H), 6.95 (d, J=7.9 Hz, 1H), 2.81 (br. s., 2H), 2.67-2.50 (m, 2H), 1.90 (d, J=11.4 Hz, 2H), 1.74 (d, J=12.9 Hz, 2H), 1.68-1.51 (m, 2H), 1.48-1.23 (m, 5H), 1.22-0.99 (m, 3H), 0.84 (d, J=6.4 Hz, 6H).

Example 83

(1S,2R)-2-(4-(cyclohexyl(isobutyl)amino)-3-(3-(pyrimidin-5-yl)ureido)phenyl)cyclopropanecarboxylic acid

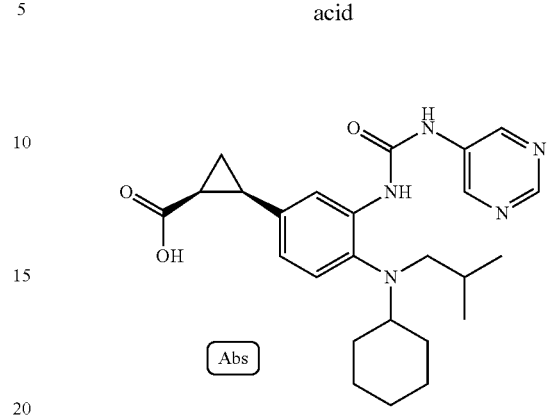

Example 83 was prepared following the procedure for Example 82, using single enantiomer (1R,2R)-ethyl 2-iodocyclopropanecarboxylate. LC-MS Anal. Calc'd for $C_{25}H_{33}N_5O_3$ 451.26. found [M+H] 452.2, $T_r$=1.77 min (Method E). $^1$H NMR (500 MHz, METHANOL-$d_4$:CHLOROFORM-d) δ 9.02 (s, 2H), 8.79 (s, 1H), 8.02 (d, J=1.5 Hz, 1H), 7.09 (d, J=8.4 Hz, 1H), 6.97 (dd, J=8.2, 1.7 Hz, 1H), 2.82 (br. s., 1H), 2.68-2.52 (m, 2H), 2.12-2.04 (m, 1H), 1.91 (d, J=11.4 Hz, 2H), 1.75 (d, J=12.9 Hz, 2H), 1.66 (dt, J=7.4, 5.4 Hz, 1H), 1.59 (d, J=12.4 Hz, 1H), 1.48-1.25 (m, 5H), 1.24-0.99 (m, 3H), 0.85 (d, J=6.4 Hz, 6H).

Example 84

(1R,2S)-2-(4-(((1R,2R,4S)-bicyclo[2.2.1]heptan-2-yl)isobutyl)amino)-3-(3-(p-tolyl)ureido)phenyl) cyclopropanecarboxylic acid

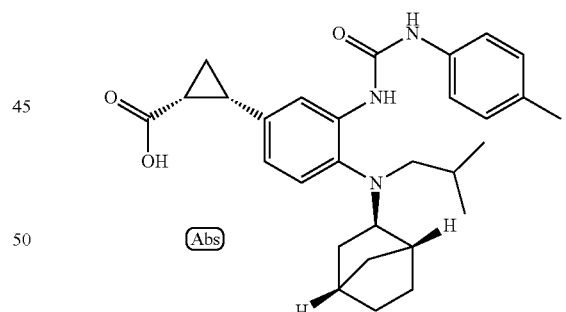

84A. N-((1R,2R,4S)-bicyclo[2.2.1]heptan-2-yl)isobutyramide

To a mixture of (1R,2R,4S)-bicyclo[2.2.1]heptan-2-amine (0.57 mL, 4.81 mmol) in DCM (9.62 mL) cooled to 0° C., was added triethylamine (0.737 mL, 5.29 mmol). The mixture was stirred at 0° C. for 15 min, then isobutyryl chloride (0.504 mL, 4.81 mmol) was added. The reaction was allowed to slowly warm to rt and stirred overnight. The reaction was quenched with sat. aq. NaHCO3 and diluted with DCM. The bi-phasic layers were separated and the aqueous phase was extracted with DCM (2×). The organic phases were combined, dried over anhydrous $Na_2SO_4$, filtered, and concentrated to afford 84A (yellow solid, 0.872 g, 4.76 mmol, 99% yield). LC-MS Anal. Calc'd for $C_{11}H_{19}NO$ 181.15. found [M+H] 182.1, $T_r$=1.10 min (Method C). $^1H$ NMR (500 MHz, CHLOROFORM-d) δ 5.29 (br. s., 1H), 3.72 (td, J=7.4, 3.6 Hz, 1H), 2.37-2.22 (m, 2H), 2.18 (d, J=3.5 Hz, 1H), 1.81 (ddd, J=13.1, 8.0, 2.4 Hz, 1H), 1.68 (br. s., 1H), 1.57-1.40 (m, 2H), 1.34-1.17 (m, 3H), 1.14 (dd, J=6.8, 1.5 Hz, 6H).

84B. (1R,2R,4S)—N-isobutylbicyclo[2.2.1]heptan-2-amine

To a solution of 84A (0.872 g, 4.81 mmol) in THF (20.38 ml) was added a 1 M THF solution of LAH (9.62 ml, 9.62 mmol) at rt. The resulting solution was heated at 70° C. for 3 h. The reaction was allowed to cool to rt, then further cooled to 0° C. and quenched with water (0.2 mL), 15% NaOH (0.4 mL), and water (0.6 mL). The resulting slurry was allowed to warm to rt, then filtered. The filtered reaction mixture was partitioned between EtOAc and water. The bi-phasic layers were separated and the aqueous phase was extracted with EtOAc (3×). The organic phases were combined, dried over anhydrous $Na_2SO_4$, filtered, and concentrated to afford 84B (colorless oil, 0.569 g, 3.37 mmol, 70% yield). LC-MS Anal. Calc'd for $C_{11}H_{21}N$, 167.17. found [M+H] 168.2, $T_r$=0.94 min (Method C). $^1H$ NMR (500 MHz, CHLOROFORM-d) δ 2.54 (dd, J=6.9, 3.2 Hz, 1H), 2.44-2.32 (m, 2H), 2.20 (br. s., 1H), 2.15 (d, J=3.5 Hz, 1H), 1.71 (dquin, J=13.4, 6.7 Hz, 1H), 1.57 (ddd, J=12.4, 7.6, 2.2 Hz, 1H), 1.52-1.38 (m, 3H), 1.14-1.02 (m, 4H), 0.90 (d, J=6.8 Hz, 6H).

84C. (1R,2R,4S)—N-(4-bromo-2-nitrophenyl)-N-isobutylbicyclo[2.2.1]heptan-2-amine A neat solution of 4-bromo-1-fluoro-2-nitrobenzene (0.345 ml, 2.84 mmol) and 84B (0.498 g, 2.98 mmol) was heated at 130° C. for 3 h, then allowed to cool to rt. Purification by flash chromatography gave 84C (orange oil, 0.532 g, 1.434 mmol, 51% yield). LC-MS Anal. Calc'd for $C_{17}H_{23}BrN_2O_2$ 366.09. found [M−H] 365.3, $T_r$=1.30 min (Method C). $^1H$ NMR (500 MHz, CHLOROFORM-d) δ 7.77 (d, J=2.4 Hz, 1H), 7.50 (dd, J=8.8, 2.4 Hz, 1H), 7.10 (d, J=8.8 Hz, 1H), 3.17 (dd, J=6.7, 3.6 Hz, 1H), 2.92 (dd, J=13.8, 5.8 Hz, 1H), 2.59 (dd, J=13.9, 8.1 Hz, 1H), 2.30 (d, J=4.2 Hz, 1H), 2.22 (br. s., 1H), 1.76-1.66 (m, 1H), 1.66-1.60 (m, 1H), 1.52-1.40 (m, 3H), 1.38-1.30 (m, 1H), 1.16-1.02 (m, 3H), 0.78 (d, J=6.6 Hz, 3H), 0.73 (d, J=6.6 Hz, 3H).

84D. (1R,2R,4S)—N-(4-(5,5-dimethyl-1,3,2-dioxaborinan-2-yl)-2-nitrophenyl)-N-isobutylbicyclo[2.2.1]heptan-2-amine A suspension of potassium acetate (0.426 g, 4.35 mmol), 2-(2,2-dimethyl-1,3,5-dioxaborinan-5-yl)-5,5-dimethyl-1,3,2-dioxaborinane (0.425 g, 1.883 mmol) and 84C (0.532 g, 1.448 mmol) in DMSO (2.168 ml) was sparged with nitrogen for 15 min, then treated with $PdCl_2(dppf)$ (0.035 g, 0.043 mmol). The reaction was sparged with nitrogen for an additional 2 min. The mixture was heated to 80° C. overnight, then allowed to cool to rt. The reaction was diluted with water and EtOAc. The layers were separated and the aqueous phase was extracted with EtOAc (2×). The combined organic phases were washed with $H_2O$ (2×), then dried over anhydrous $Na_2SO_4$, filtered, and concentrated to afford a black residue. Purification via flash chromatography gave 84D. LC-MS Anal. Calc'd for $C_{22}H_{33}BN_2O_4$ 400.3. found [M+H] 333.2 (mass of boronic acid), $T_r$=1.81 min (Method C). $^1H$ NMR (500 MHz, CHLOROFORM-d) δ 8.06 (d, J=1.5 Hz, 1H), 7.76 (dd, J=8.4, 1.5 Hz, 1H), 7.13 (d, J=8.1 Hz, 1H), 3.75 (s, 4H), 3.27 (dd, J=6.7, 3.9 Hz, 1H), 3.00 (dd, J=13.9, 5.5 Hz, 1H), 2.62 (dd, J=13.9, 8.4 Hz, 1H), 2.36 (d, J=4.2 Hz, 1H), 2.20 (br. s., 1H), 1.84-1.70 (m, 1H), 1.66 (d, J=9.7 Hz, 1H), 1.60-1.33 (m, 5H), 1.17-1.05 (m, 2H), 1.01 (s, 6H), 0.77 (d, J=6.8 Hz, 3H), 0.71 (d, J=6.4 Hz, 3H)

84E. (1R,2S)-ethyl 2-(4-((1R,2R,4S)-bicyclo[2.2.1]heptan-2-yl)isobutyl)amino)-3-nitrophenyl)cyclopropanecarboxylate A vial containing a mixture of 84D (0.174 g, 0.435 mmol), (1S,2S)-ethyl 2-iodocyclopropanecarboxylate (0.110 g, 0.456 mmol), which was obtained through chiral resolution following the procedure in Organic Process Research & Development 2004, 8, 353-359, and cesium carbonate (0.297 g, 0.913 mmol) in dioxane (1.114 ml) and water (0.557 ml) was sparged with nitrogen for 10 min, then $PdCl_2$(dppf)-$CH_2Cl_2$ adduct (0.071 g, 0.087 mmol) was added and the resulting mixture was sparged for an additional 2 min. The solution was heated at 85° C. for 24 h, then allowed to cool to rt. The reaction was diluted with water and extracted with EtOAc (4×). The organic layers were combined, dried over over anhydrous $Na_2SO_4$, filtered, and concentrated to afford a dark brown residue. Purification via flash chromatography gave 84E (orange oil, 0.080 g, 0.197 mmol, 45% yield). LC-MS Anal. Calc'd for $C_{23}H_{32}N_2O_4$ 400.2. found [M+H] 401.3, $T_r$=2.23 min (Method C). $^1H$ NMR (500 MHz, CHLOROFORM-d) δ 7.50 (d, J=2.0 Hz, 1H), 7.32 (dd, J=8.5, 2.1 Hz, 1H), 7.15 (d, J=8.6 Hz, 1H), 3.97-3.80 (m, 2H), 3.15-3.07 (m, 1H), 2.83 (ddd, J=13.4, 5.9, 2.9 Hz, 1H), 2.60 (ddd, J=13.6, 7.9, 1.5 Hz, 1H), 2.51 (q, J=8.4 Hz, 1H), 2.21 (d, J=17.4 Hz, 2H), 2.13-2.00 (m, 1H), 1.74-1.60 (m, 3H), 1.53-1.41 (m, 2H), 1.40-1.24 (m, 3H), 1.11-1.02 (m, 3H), 1.02-0.94 (m, 3H), 0.80-0.67 (m, 6H).

84F. (1R,2S)-ethyl 2-(3-amino-4-01R,2R,4S)-bicyclo[2.2.1]heptan-2-yl)isobutyl)amino)phenyl)cyclopropanecarboxylate To a solution of ammonium chloride (63.7 mg, 1.191 mmol) in water (119 µl) was added ethanol (831 µl). The reaction vessel was cooled to 0° C., then charged with zinc flake 325 mesh (107 mg, 1.636 mmol). The mixture was treated with 84E (79.5 mg, 0.198 mmol) in THF (0.83 mL). The reaction mixture was allowed to warm to rt and stirred for 1 h. The reaction was filtered through Celite and the filter cake was washed with EtOAc and $CH_2Cl_2$. Purification via flash chromatography gave 84F (yellow oil, 0.051 g, 0.136 mmol, 68% yield). LC-MS Anal. Calc'd for $C_{23}H_{34}N_2O_2$ 370.26. found [M+H] 371.2, $T_r$=2.20 min (Method C). $^1H$ NMR (500 MHz, CHLOROFORM-d) δ 7.00 (apparent br. s., 1H), 6.61 (apparent br. s., 2H), 4.09 (apparent br. s., 2H), 3.99-3.67 (m, 2H), 2.70 (apparent br. s., 1H), 2.54-2.42 (m, 1H), 2.25 (apparent br. s., 1H), 2.09 (apparent br. s., 1H), 2.00 (ddd, J=9.4, 7.8, 5.7 Hz, 1H), 1.74 (apparent br. s., 1H), 1.70-1.60 (m, 1H), 1.55 (s, 4H), 1.49-1.30 (m, 2H), 1.23 (td, J=8.2, 5.2 Hz, 2H), 1.14-0.98 (m, 3H), 0.98-0.82 (m, 6H), 0.71 (apparent br. s., 3H).

84G. (1R,2S)-ethyl 2-(4-((1R,2R,4S)-bicyclo[2.2.1]heptan-2-yl)isobutyl)amino)-3-(3-(p-tolyl)ureido)phenyl)cyclopropanecarboxylate To a solution of 84F (17 mg, 0.046 mmol) in THF (706 µl) was added 4-nitrophenyl carbonochloridate (9.71 mg, 0.048 mmol). The reaction was stirred at rt for 30 min. To this reaction were added p-toluidine (14.75 mg, 0.138 mmol) and triethylamine (19.18 μl, 0.138 mmol). The reaction was heated at 50° C. for 3 d, then allowed to cool to rt. The solvent was evaporated with a stream of $N_2$ to give 84G as a yellow oil. The crude product was used directly in the subsequent step without purification. LC-MS Anal. Calc'd for $C_{31}H_{41}N_3O_3$ 503.32. found [M+H] 504.3, $T_r$=2.20 min (Method C).

Example 84. To a solution of 84G (23 mg, 0.046 mmol) in tetrahydrofuran (152 μl) and MeOH (76 μl) was added (concentration) lithium hydroxide aqueous solution (304 μl, 0.457 mmol). The mixture was heated at 50° C. overnight. The reaction was neutralized with 1 N HCl (0.46 mL) and diluted with EtOAc. The layers were separated and the aqueous phase was extracted with EtOAc (3×). The organic phases were combined and the solvent was evaporated to give the crude product as a yellow residue. Purification by preparative HPLC gave Example 84 (0.014 g, 0.028 mmol, 61% yield). LC-MS Anal. Calc'd for $C_{29}H_{37}N_3O_3$ 475.28. found [M+H] 476.3, $T_r$=1.85 min (Method C). $^1$H NMR (500 MHz, METHANOL-$d_4$:CHLOROFORM-d) δ 8.04 (br. s., 1H), 7.30 (d, J=8.4 Hz, 2H), 7.15-7.06 (m, 3H), 6.92 (d, J=7.9 Hz, 1H), 4.33 (br. s., 2H), 2.72 (br. s., 1H), 2.65-2.47 (m, 3H), 2.31 (s, 3H), 2.05 (br. s., 1H), 1.63 (br. s., 2H), 1.52-1.21 (m, 6H), 1.11-0.93 (m, 3H), 0.93-0.60 (m, 6H).

Example 85

(1R,2S)-2-(4-((1R,2R,4S)-bicyclo[2.2.1]heptan-2-yl) isobutyl)amino)-3-(3-(pyrimidin-5-yl)ureido)phenyl) cyclopropanecarboxylic acid

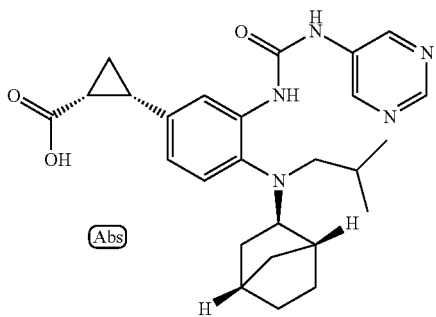 [SMILES: CC(C)CN(c1ccc([C@H]2C[C@H]2C(=O)O)cc1NC(=O)Nc1cncnc1)[C@@H]1C[C@H]2CC[C@@H]1C2]

Example 85 was prepared following the procedure for Example 84 and the urea was formed using 5-aminopyrimidine. LC-MS Anal. Calc'd for $C_{26}H_{33}N_5O_3$ 463.26. found [M+H] 464.2, $T_r$=1.41 min (Method C). $^1$H NMR (500 MHz, METHANOL-$d_4$:CHLOROFORM-d) δ 9.01 (br. s., 2H), 8.78 (s, 1H), 8.08 (br. s., 1H), 7.14 (d, J=7.9 Hz, 1H), 6.99 (d, J=7.4 Hz, 1H), 4.30 (br. s., 4H), 2.72-2.52 (m, 3H), 2.15-2.01 (m, 1H), 1.71-1.57 (m, 3H), 1.42 (apparent br. s., 1H), 1.35 (td, J=8.2, 5.0 Hz, 3H), 1.07 (d, J=6.9 Hz, 2H), 0.99-0.58 (m, 7H).

Example 86

(1R,2S)-2-(4-((1R,2R,4S)-bicyclo[2.2.1]heptan-2-yl) isobutyl)amino)-3-(3-(5-methylisoxazole-3-yl) ureido)phenyl)cyclopropanecarboxylic acid

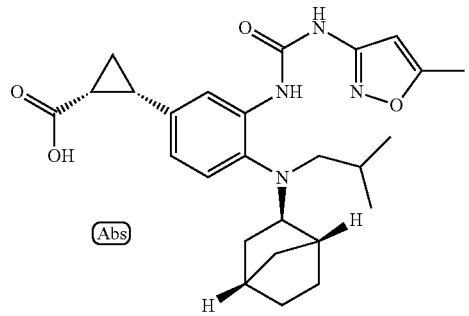 [SMILES: Cc1cc(NC(=O)Nc2cc([C@H]3C[C@H]3C(=O)O)ccc2N(CC(C)C)[C@@H]2C[C@H]3CC[C@@H]2C3)no1]

Example 86 was prepared following the procedure for Example 84 and the urea was formed using 3-amino-5-methylisoxazole. LC-MS Anal. Calc'd for $C_{26}H_{34}N_4O_4$ 466.57. found [M+H] 467.3, $T_r$=1.68 min (Method C). $^1$H NMR (500 MHz, METHANOL-$d_4$:CHLOROFORM-d) δ 8.13 (br. s., 1H), 7.14 (d, J=8.4 Hz, 1H), 6.98 (d, J=7.4 Hz, 1H), 6.28 (br. s., 1H), 2.68-2.56 (m, 3H), 2.40 (s, 3H), 2.12-2.03 (m, 1H), 1.79-1.52 (m, 4H), 1.48-1.22 (m, 5H), 1.15-0.63 (m, 11H).

Example 87

(1R,2S)-2-(4-(cyclohexyl(3,3,3-trifluoropropyl) amino)-3-(3-(pyrimidin-5-yl)ureido)phenyl)cyclo-propanecarboxylic acid

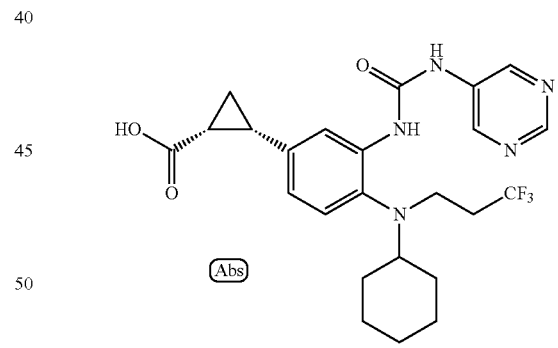

87A. N-cyclohexyl-3,3,3-trifluoropropanamide

In a 200 mL round bottom flask equipped with a stir bar was placed 3,3,3-trifluoropropanoic acid (6 g, 46.9 mmol) in DMF (52.1 mL) under nitrogen. BOP (21.14 g, 47.8 mmol) was added followed by triethylamine (13.06 ml, 94 mmol). The mixture was stirred for 15 min at rt, then cyclohexanamine (6.98 ml, 60.9 mmol) was added. The brown, clear solution was stirred at rt overnight. Water (50 mL) was added and the mixture was stirred for 5 min. The resulting light brown precipitate was filtered and washed with water (3×). The resultant solid was dried under reduced pressure to afford 87A (7.39 g, 35.0 mmol, 74.6% yield). LC-MS Anal. Calc'd for $C_9H_{14}F_3NO$, 209.10. found [M+H] 210.1, $T_r$=0.81 min (Method D).

87B. N-(3,3,3-trifluoropropyl)cyclohexanamine

To a solution of 87A (2.8 g, 13.38 mmol) in tetrahydrofuran (29.2 ml) cooled to 0° C. was added borane-methyl sulfide complex in DCM (134 ml, 134 mmol). The reaction was heated at 50° C. overnight. The reaction was allowed to cool to rt, then further cooled to 0° C. in an ice bath. Methanol (21.66 ml, 535 mmol) was slowly added dropwise until evolution of gas ceased. The solvent was evaporated from the reaction mixture. Then, the crude material was taken up in MeOH (60 mL) and refluxed overnight to break up the borane complex. After 24 h, the reaction was allowed to cool to rt. The solvent was evaporated. The resulting residue was partitioned between EtOAc and sat. aq. $NaHCO_3$. Layers were separated. The aqueous phase was extracted with EtOAc (2×). The organic phases were combined, dried over $Na_2SO_4$, filtered, and concentrated to afford a cloudy oil. The crude material was dissolved in a minimal amount of hexanes and chromatographed. Purification of the crude material by silica gel chromatography gave 87A (2.13 g, 10.91 mmol, 82% yield) as a pale yellow oil. LC-MS Anal. Calc'd for $C_9H_{16}F_3N$, 195.12. found [M+H] 196.3, $T_r$=1.22 min (Method E).

87C. 4-bromo-N-cyclohexyl-2-nitro-N-(3,3,3-trifluoropropyl)aniline

A solution of 4-bromo-1-fluoro-2-nitrobenzene (0.406 ml, 3.34 mmol), 87B (0.738 ml, 4.01 mmol), and N,N-diisopropylethylamine (1.399 ml, 8.01 mmol) in NMP (1.012 ml) was heated at 150° C. for 21 h, then allowed to cool to rt. The reaction was partioned between EtOAc and $H_2O$. Layers were separated. The aqueous phase was extracted with EtOAc (3×). The combined organic phases were washed with $H_2O$ (2×), dried over $Na_2SO_4$, filtered, and concentrated to afford a dark brown residue. The crude material was dissolved in a minimal amount of $CH_2Cl_2$ and chromatographed. Purification of the crude material by silica gel chromatography gave 87C (909 mg, 2.300 mmol, 68.9% yield) as an orange residue. LC-MS Anal. Calc'd for $C_{15}H_{18}BrF_3N_2O_2$ 394.05. found [M+H] 395.1, $T_r$=2.43 min (Method E).

87D. 4-bromo-N1-cyclohexyl-N1-(3,3,3-trifluoropropyl)benzene-1,2-diamine

To a solution of ammonium chloride (0.738 g, 13.80 mmol) in water (1.376 ml) was added ethanol (9.63 ml). The reaction vessel was cooled to 0° C., then charged with zinc flake 325 mesh (1.239 g, 18.95 mmol). The mixture was treated with 87C (0.909 g, 2.300 mmol) in THF (8.6 mL). Then, the reaction mixture was allowed to warm to rt and stirred for 50 min. The reaction was filtered through Celite and the filter cake was washed with EtOAc and $CH_2Cl_2$. The filtrate was concentrated and the crude material was dissolved in a minimal amount of $CH_2Cl_2$ and chromatographed. Purification of the crude material by silica gel chromatography gave 87D (0.745 g, 1.938 mmol, 84% yield) as a red residue. LC-MS Anal. Calc'd for $C_{15}H_{20}BrF_3N_2$ 364.08. found [M+H]365.1, $T_r$=2.30 min (Method E).

87E. N1-cyclohexyl-4-(5,5-dimethyl-1,3,2-dioxaborinan-2-yl)-N1-(3,3,3-trifluoropropyl)benzene-1,2-diamine A suspension of potassium acetate (0.601 g, 6.12 mmol), 2-(2,2-dimethyl-1,3,5-dioxaborinan-5-yl)-5,5-dimethyl-1,3, 2-dioxaborinane (0.599 g, 2.65 mmol) and 87D (0.745 g, 2.040 mmol) in DMSO (3.05 ml) was degassed with $N_2$ for 10 min, then treated with $PdCl_2(dppf)$ (0.050 g, 0.061 mmol). The reaction was sparged with $N_2$ for an additional 10 min. The mixture was heated to 80° C. overnight, then allowed to cool to rt. The reaction was quenched with $H_2O$ and diluted with EtOAc. Layers were separated. The aqueous phase was extracted with EtOAc (3×). The combined organic phases were washed with $H_2O$ (3×), dried over $Na_2SO_4$, filtered, and concentrated to afford a black residue. The crude material was dissolved in a minimal amount of $CH_2Cl_2$ and chromatographed. Purification of the crude material by silica gel chromatography gave 87E (0.656 g, 80% yield) as a brown residue. LC-MS Anal. Calc'd for $C_{20}H_{30}BF_3N_2O_2$ 398.24. found [M+H]331.2 (mass of boronic acid), $T_r$=1.49 min (Method E).

87F. (1R,2S)-ethyl 2-(3-amino-4-(cyclohexyl(3,3,3-trifluoropropyl)amino)phenyl)cyclopropanecarboxylate A vial containing a mixture of 87E (0.293 g, 0.736 mmol), (1S,2S)-ethyl 2-iodocyclopropanecarboxylate (0.212 g, 0.883 mmol), which was obtained through chiral resolution following the procedure in Organic Process Research & Development 2004, 8, 353-359, and cesium carbonate (0.503 g, 1.545 mmol) in dioxane (1.886 ml) and water (0.943 ml) was degassed with $N_2$ for 10 min, then $PdCl_2$(dppf)-$CH_2Cl_2$Adduct (0.120 g, 0.147 mmol) was added and the resulting mixture was degassed for an additional 10 min. The solution was heated at 85° C. for 24 h, then allowed to cool to rt. The reaction was diluted with water and extracted with EtOAc (4×). The organic layers were combined, dried over over $Na_2SO_4$, filtered, and concentrated to afford a dark brown residue. The crude material was dissolved in a minimal amount of $CH_2Cl_2$ and chromatographed. Purification of the crude material by silica gel chromatography gave 87F (115.9 mg, 0.291 mmol, 39.5% yield) as a brown residue. LC-MS Anal. Calc'd for $C_{21}H_{29}F_3N_2O_2$ 398.22. found [M+H] 399.3, $T_r$=1.98 min (Method E).

87G. (1R,2S)-ethyl 2-(4-(cyclohexyl(3,3,3-trifluoropropyl)amino)-3-(3-(pyrimidin-5-yl)ureido)phenyl) cyclopropanecarboxylate To a solution of 87F (18.1 mg, 0.045 mmol) in THF (699 µl) was added 4-nitrophenyl carbonochloridate (9.61 mg, 0.048 mmol). The reaction was stirred at rt for 30 min. To this reaction were added pyrimidin-5-amine (12.96 mg, 0.136 mmol) and triethylamine (18.99 µl, 0.136 mmol). The reaction was heated at 50° C. overnight, then allowed to cool to rt. The solvent was evaporated with a stream of $N_2$ to give 87G. The crude product was used directly in the subsequent procedure. LC-MS Anal. Calc'd for $C_{26}H_{32}F_3N_5O_3$ 519.25. found [M+H] 520.3, $T_r$=2.26 min (Method E).

Example 87

(1R,2S)-2-(4-(cyclohexyl(3,3,3-trifluoropropyl) amino)-3-(3-(pyrimidin-5-yl)ureido)phenyl)cyclopropanecarboxylic acid To a solution of 87G (0.0236 g, 0.045 mmol) in tetrahydrofuran (0.101 ml) and MeOH (0.050 ml) was added lithium hydroxide as a 1.5 M aqueous solution (0.303 ml, 0.454 mmol). The mixture was heated at 50° C. overnight, then allowed to cool to rt. The reaction was neutralized with 1 N HCl (0.45 mL) and diluted with EtOAc. Layers were separated. The aqueous phase was extracted with EtOAc (3×). The organic phases were combined and the solvent was evaporated to give the crude product as a yellow residue. Purification by preparative HPLC afforded Example 87 (6.1 mg, 26% yield). LC-MS Anal. Calc'd for $C_{24}H_{28}F_3N_5O_3$ 491.21. found [M+H] 492.3, $T_r$=2.10 min (Method E).

Example 88

(1R,2S)-2-(4-(cyclohexyl(3,3,3-trifluoropropyl) amino)-3-(3-(p-tolyl)ureido)phenyl)cyclopropan- ecarboxylic acid

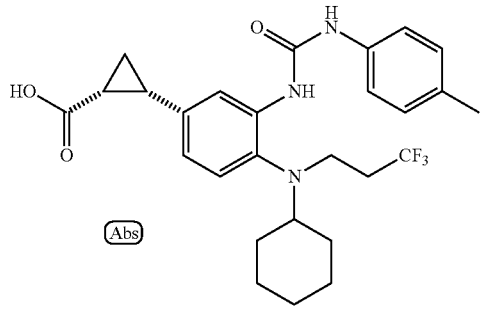

88A. (1R,2S)-ethyl 2-(4-(cyclohexyl(3,3,3-trifluoro- propyl)amino)-3-(3-(p-tolyl)ureido)phenyl)cyclopro- panecarboxylate To a solution of 87F (17.8 mg, 0.045 mmol) in THF (687 µl) was added 4-nitrophenyl carbonochloridate (9.45 mg, 0.047 mmol). The reaction was stirred at rt for 30 min. To this reaction were added p-toluidine (14.36 mg, 0.134 mmol) and triethylamine (18.68 µl, 0.134 mmol). The reaction was heated at 50° C. overnight, then allowed to cool to rt. The solvent was evaporated with a stream of $N_2$ to give 88A. The crude product was used directly in the subsequent procedure. LC-MS Anal. Calc'd for $C_{29}H_{36}F_3N_3O_3$ 531.27. found [M+H] 532.3, $T_r$=2.39 min (Method E).

Example 88

(1R,2S)-2-(4-(cyclohexyl(3,3,3-trifluoropropyl) amino)-3-(3-(p-tolyl)ureido)phenyl)cyclopropan- ecarboxylic acid To a solution of 88A (0.024 g, 0.045 mmol) in tetrahy- drofuran (0.100 ml) and MeOH (0.050 ml) was added lithium hydroxide as a 1.5 M aqueous solution (0.301 ml, 0.451 mmol). The mixture was heated at 50° C. overnight, then allowed to cool to rt. The reaction was neutralized with 1 N HCl (0.45 mL) and diluted with EtOAc. Layers were separated. The aqueous phase was extracted with EtOAc (3×). The organic phases were combined and the solvent was evaporated to give the crude product as a yellow residue. Purification by preparative HPLC afforded Example 88 (5.2 mg, 22% yield). LC-MS Anal. Calc'd for $C_{27}H_{32}F_3N_3O_3$ 503.24. found [M+H] 504.3, $T_r$=2.25 min (Method E).

Example 89

(1R,2S)-2-(3-(3-(2-cyanopyrimidin-5-yl)ureido)-4- (cyclohexyl(3,3,3-trifluoropropyl)amino)phenyl) cyclopropanecarboxylic acid

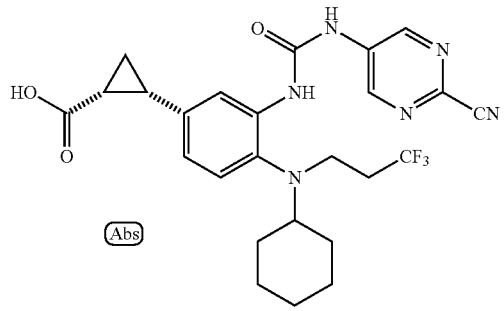

89A. (1R,2S)-2-(3-amino-4-(cyclohexyl(3,3,3-trif- luoropropyl)amino) phenyl)cyclopropanecarboxylic acid To a solution of 87F (0.0276 g, 0.069 mmol) in tetrahy- drofuran (0.154 ml) and MeOH (0.077 ml) was added lithium hydroxide as a 1.5 M aqueous solution (0.462 ml, 0.693 mmol). The mixture was heated at 50° C. Additional LiOH (0.79 mL of a 2 M solution) was added and the reaction was heated at 50° C. overnight, then allowed to cool to rt. The reaction was neutralized with 1 N HCl (0.69 mL) and diluted with EtOAc. Layers were separated. The aque- ous phase was extracted with EtOAc (5×). The organic phases were combined and the solvent was evaporated to give 89A as a residue. The crude product was used directly in the subsequent procedure. LC-MS Anal. Calc'd for $C_{19}H_{25}F_3N_2O_2$ 370.19. found [M+H] 371.3, $T_r$=1.89 min (Method E).

Example 89

(1R,2S)-2-(3-(3-(2-cyanopyrimidin-5-yl)ureido)-4- (cyclohexyl(3,3,3-trifluoropropyl)amino)phenyl) cyclopropanecarboxylic acid To a vial charged with 89A (0.026 g, 0.070 mmol) was added 5-isocyanatopyrimidine-2-carbonitrile (2.264 ml, 0.211 mmol) as a 0.093 M solution in $CH_2Cl_2$ and THF. The reaction was heated at 35° C. for 2 h, then allowed to cool to rt. The reaction was quenched with water and diluted with EtOAc. Layers were separated. The aqueous phase was extracted with EtOAc (3×). The organic phases were com- bined and the solvent was evaporated to give the crude product as a yellow residue. Purification by preparative HPLC afforded Example 89 (14.5 mg, 38% yield). LC-MS Anal. Calc'd for $C_{25}H_{27}F_3N_6O_3$ 516.21. found [M+H] 517.2, $T_r$=2.19 min (Method E).

Example 90

(1R,2S)-2-(4-(cyclohexyl(3,3,3-trifluoropropyl)amino)-3-(3-(5-methylisoxazol-3-yl)ureido)phenyl)cyclopropanecarboxylic acid

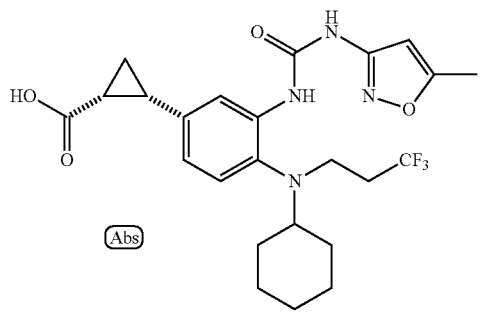

90A. (1R,2S)-ethyl 2-(4-(cyclohexyl(3,3,3-trifluoropropyl)amino)-3-(3-(5-methylisoxazol-3-yl)ureido)phenyl)cyclopropanecarboxylate To a solution of 87F (26.3 mg, 0.066 mmol) in THF (1015 µl) was added 4-nitrophenyl carbonochloridate (13.97 mg, 0.069 mmol). The reaction was stirred at rt for 30 min. To this reaction were added 5-methylisoxazol-3-amine (19.43 mg, 0.198 mmol) and triethylamine (27.6 µl, 0.198 mmol). The reaction was heated at 50° C. for 2 d, then allowed to cool to rt. The solvent was evaporated with a stream of $N_2$ to afford 90A. The crude product was used directly in the subsequent procedure. LC-MS Anal. Calc'd for $C_{26}H_{33}F_3N_4O_4$ 522.25. found [M+H]523.3, $T_r$=2.37 min (Method E).

Example 90

(1R,2S)-2-(4-(cyclohexyl(3,3,3-trifluoropropyl)amino)-3-(3-(5-methylisoxazol-3-yl)ureido)phenyl)cyclopropanecarboxylic acid To a solution of 90A (0.0345 g, 0.066 mmol) in tetrahydrofuran (0.147 ml) and MeOH (0.073 ml) was added lithium hydroxide as a 1.5 M aqueous solution (0.440 ml, 0.660 mmol). The mixture was heated at 50° C. overnight, then allowed to cool to rt. The reaction was neutralized with 1 N HCl (0.66 mL) and diluted with EtOAc. Layers were separated. The aqueous phase was extracted with EtOAc (3×). The organic phases were combined and the solvent was evaporated to give the crude product as a yellow residue. Purification by preparative HPLC afforded Example 90 (8.8 mg, 27% yield). LC-MS Anal. Calc'd for $C_{24}H_{29}F_3N_4O_4$ 494.21. found [M+H]495.3, $T_r$=2.21 min (Method E).

Example 91

(1S,2R)-2-(4-(cyclohexyl(3,3,3-trifluoropropyl)amino)-3-(3-(p-tolyl)ureido)phenyl)cyclopropanecarboxylic acid

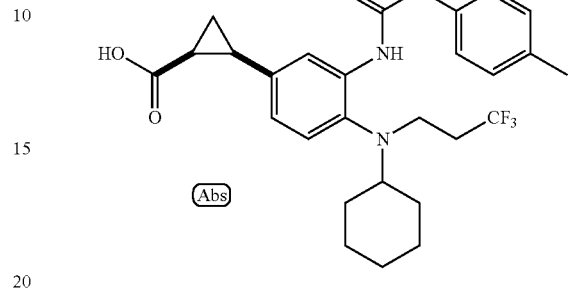

91A. (1S,2R)-ethyl 2-(3-amino-4-(cyclohexyl(3,3,3-trifluoropropyl)amino)phenyl)cyclopropanecarboxylate A vial containing a mixture of 87E (0.226 g, 0.567 mmol), (1R,2R)-ethyl 2-iodocyclopropanecarboxylate (0.163 g, 0.681 mmol), which was obtained through chiral resolution following the procedure in Organic Process Research & Development 2004, 8, 353-359, and cesium carbonate (0.388 g, 1.192 mmol) in dioxane (1.455 ml) and water (0.728 ml) was degassed with $N_2$ for 10 min, then $PdCl_2$(dppf)-$CH_2Cl_2$Adduct (0.093 g, 0.113 mmol) was added and the resulting mixture was degassed for an additional 10 min. The solution was heated at 85° C. for 24 h, then allowed to cool to rt. The reaction was diluted with water and extracted with EtOAc (4×). The organic layers were combined, dried over over $Na_2SO_4$, filtered, and concentrated to afford a dark brown residue. The crude material was dissolved in a minimal amount of $CH_2Cl_2$ and chromatographed. Purification of the crude material by silica gel chromatography gave 91A (115.6 mg, 0.290 mmol, 51.1% yield) as a brown residue. LC-MS Anal. Calc'd for $C_{21}H_{29}F_3N_2O_2$ 398.22. found [M+H] 399.3, $T_r$=1.98 min (Method E).

91B. (1S,2R)-ethyl 2-(4-(cyclohexyl(3,3,3-trifluoropropyl)amino)-3-(3-(p-tolyl)ureido)phenyl)cyclopropanecarboxylate To a solution of 91A (22.6 mg, 0.057 mmol) in THF (873 µl) was added 4-nitrophenyl carbonochloridate (12.00 mg, 0.060 mmol). The reaction was stirred at rt for 30 min. To this reaction were added p-toluidine (18.23 mg, 0.170 mmol) and triethylamine (23.72 µl, 0.170 mmol). The reaction was heated at 50° C. overnight, then allowed to cool to rt. The solvent was evaporated with a stream of $N_2$ to afford 91B. The crude product was used directly in the subsequent procedure. LC-MS Anal. Calc'd for $C_{29}H_{36}F_3N_3O_3$ 531.27. found [M+H] 532.3, $T_r$=2.38 min (Method E).

Example 91

(1S,2R)-2-(4-(cyclohexyl(3,3,3-trifluoropropyl)amino)-3-(3-(p-tolyl)ureido)phenyl)cyclopropanecarboxylic acid To a solution of 91B (0.0302 g, 0.057 mmol) in tetrahydrofuran (0.126 ml) and MeOH (0.063 ml) was added lithium hydroxide as a 1.5 M aqueous solution (0.379 ml, 0.568 mmol). The mixture was heated at 50° C. overnight, then allowed to cool to rt. The reaction was neutralized with 1 N HCl (0.57 mL) and diluted with EtOAc. Layers were separated. The aqueous phase was extracted with EtOAc (3×). The organic phases were combined and the solvent was evaporated to give the crude product as a yellow residue. Purification by preparative HPLC afforded Example 91 (10.3 mg, 33% yield). LC-MS Anal. Calc'd for $C_{27}H_{32}F_3N_3O_3$ 503.24. found [M+H] 504.3, $T_r$=2.24 min (Method E).

Example 92

(1S,2R)-2-(4-(cyclohexyl(3,3,3-trifluoropropyl) amino)-3-(3-(5-methylisoxazol-3-yl)ureido)phenyl) cyclopropanecarboxylic acid

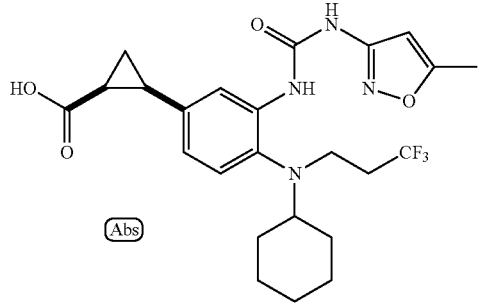

92A. (1S,2R)-ethyl 2-(4-(cyclohexyl(3,3,3-trifluoropropyl)amino)-3-(3-(5-methylisoxazol-3-yl)ureido) phenyl)cyclopropanecarboxylate To a solution of 91A (23 mg, 0.058 mmol) in THF (888 μl) was added 4-nitrophenyl carbonochloridate (12.22 mg, 0.061 mmol). The reaction was stirred at rt for 30 min. To this reaction were added 5-methylisoxazol-3-amine (16.99 mg, 0.173 mmol) and triethylamine (24.14 μl, 0.173 mmol). The reaction was heated at 50° C. for 2 d, then allowed to cool to rt. The solvent was evaporated with a stream of $N_2$ to afford 92A. The crude product was used directly in the subsequent procedure. LC-MS Anal. Calc'd for $C_{26}H_{33}F_3N_4O_4$ 522.25. found [M+H] 523.3, $T_r$=2.36 min (Method E).

Example 92

(1S,2R)-2-(4-(cyclohexyl(3,3,3-trifluoropropyl) amino)-3-(3-(5-methylisoxazol-3-yl)ureido)phenyl) cyclopropanecarboxylic acid To a solution of 92A (0.0302 g, 0.058 mmol) in tetrahydrofuran (0.128 ml) and MeOH (0.064 ml) was added lithium hydroxide as a 1.5 M aqueous solution (0.385 ml, 0.578 mmol). The mixture was heated at 50° C. overnight, then allowed to cool to rt. The reaction was neutralized with 1 N HCl (0.58 mL) and diluted with EtOAc. Layers were separated. The aqueous phase was extracted with EtOAc (3×). The organic phases were combined and the solvent was evaporated to give the crude product as a yellow residue. Purification by preparative HPLC afforded Example 92 (7.7 mg, 26% yield). LC-MS Anal. Calc'd for $C_{24}H_{29}F_3N_4O_4$ 494.21. found [M+H]495.2, $T_r$=2.22 min (Method E).

Example 93

(1R,2S)-2-(3-(3-(2-cyanopyrimidin-5-yl)ureido)-4-(cyclohexyl(isobutyl)amino)phenyl)cyclopropanecarboxylic acid

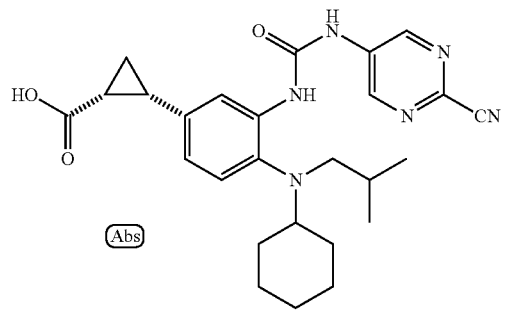

93A. (1R,2S)-2-(3-amino-4-(cyclohexyl(isobutyl) amino)phenyl) cyclopropanecarboxylic acid To a solution of 80E (0.0526 g, 0.147 mmol) in tetrahydrofuran (0.326 ml) and MeOH (0.163 ml) was added lithium hydroxide as a 1.5 M aqueous solution (0.978 ml, 1.467 mmol). The mixture was heated at 50° C. overnight. Additional LiOH (0.79 mL of a 2 M solution) was added and the reaction was heated at 50° C. overnight. The reaction allowed to cool to rt, then neutralized with 1 N HCl (1.5 mL) and diluted with EtOAc. Layers were separated. The aqueous phase was extracted with EtOAc (5×). The organic phases were combined and the solvent was evaporated to give 93A as a residue. The crude product was used directly in the subsequent procedure. LC-MS Anal. Calc'd for $C_{20}H_{30}N_2O_2$ 330.23. found [M+H]331.3, $T_r$=1.61 min (Method E).

Example 93

(1R,2S)-2-(3-(3-(2-cyanopyrimidin-5-yl)ureido)-4-(cyclohexyl(isobutyl)amino)phenyl)cyclopropanecarboxylic acid To a vial charged with 93A (0.024 g, 0.073 mmol) was added 5-isocyanatopyrimidine-2-carbonitrile (2.343 ml, 0.218 mmol) as a 0.093 M solution in $CH_2Cl_2$ and THF. The reaction was heated at 35° C. for 2 h, then allowed to cool to rt. The reaction was quenched with water and diluted with EtOAc. Layers were separated. The aqueous phase was extracted with EtOAc (3×). The organic phases were combined and the solvent was evaporated to give the crude product as a yellow residue. Purification by preparative HPLC afforded Example 93 (22.9 mg, 62%). LC-MS Anal. Calc'd for $C_{26}H_{32}N_6O_3$ 476.25. found [M+H] 477.3, $T_r$=2.04 min (Method E).

Example 94

(1R,2S)-2-(4-(cyclohexyhisobutyl)amino)-3-(3-(p-tolyl)ureido)phenyl) cyclopropanecarboxylic acid

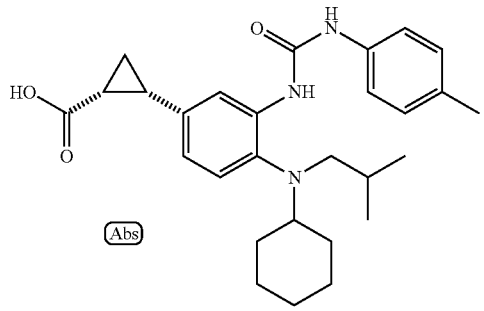

To a solution of 93A (0.024 g, 0.073 mmol) in tetrahydrofuran (0.147 ml) was added 1-isocyanato-4-methylbenzene (10.05 µl, 0.080 mmol). The reaction was heated at 35° C. for 2 h, then allowed to cool to rt. The reaction was quenched with water and diluted with EtOAc. Layers were separated. The aqueous phase was extracted with EtOAc (3×). The organic phases were combined and the solvent was evaporated to give the crude product as a residue. Purification by preparative HPLC afforded Example 94 (26 mg, 74% yield). LC-MS Anal. Calc'd for $C_{28}H_{37}N_3O_3$ 463.28. found [M+H] 464.3, $T_r$=2.07 min (Method E).

Example 95

(1S,2R)-2-(3-(3-(2-cyanopyrimidin-5-yl)ureido)-4-(cyclohexyl(isobutyl)amino)phenyl)cyclopropanecarboxylic acid

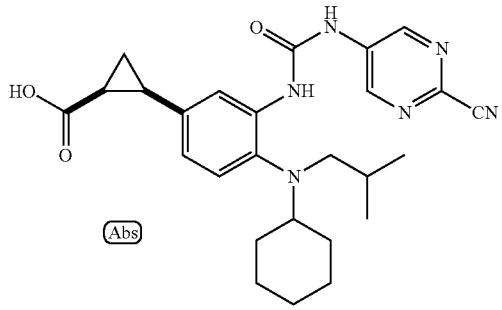

95A. (1S,2R)-ethyl 2-(4-(cyclohexyl(isobutyl)amino)-3-nitrophenyl) cyclopropanecarboxylate A vial containing a mixture of 80C, (1R,2R)-ethyl 2-iodocyclopropanecarboxylate (0.474 g, 1.977 mmol), which was obtained through chiral resolution following the procedure in Organic Process Research & Development 2004, 8, 353-359, and cesium carbonate (1.288 g, 3.95 mmol) in dioxane (4.83 ml) and water (2.413 ml) was degassed with $N_2$ for 10 min, then $PdCl_2$(dppf) (0.307 g, 0.377 mmol) was added and the resulting mixture was degassed for an additional 2 min. The solution was heated at 85° C. for 24 h, then allowed to cool to rt. The reaction was diluted with water and extracted with EtOAc (4×). The organic layers were combined, dried over over $Na_2SO_4$, filtered, and concentrated to afford a dark brown residue. The crude material was dissolved in a minimal amount of $CH_2Cl_2$ and chromatographed. Purification of the crude material by silica gel chromatography gave 95A (0.358 g, 0.921 mmol, 48.9% yield) as an orange residue. LC-MS Anal. Calc'd for $C_{22}H_{32}N_2O_4$ 388.50. found [M+H] 389.3, $T_r$=2.45 min (Method E).

95B. (1S,2R)-ethyl 2-(3-amino-4-(cyclohexyl(isobutyl)amino) phenyl) cyclopropanecarboxylate To a solution of ammonium chloride (0.296 g, 5.53 mmol) in water (0.551 ml) was added ethanol (3.86 ml). The reaction vessel was cooled to 0° C., then charged with zinc flake 325 mesh (0.496 g, 7.59 mmol). The mixture was treated with 95A (0.358 g, 0.921 mmol) in THF (0.83 mL). The reaction mixture was allowed to warm to rt and stirred for 30 min. The reaction was filtered through Celite and the filter cake was washed with EtOAc and $CH_2Cl_2$. The filtrate was concentrated and the crude material was dissolved in a minimal amount of $CH_2Cl_2$ and chromatographed. Purification of the crude material by silica gel chromatography gave 95B (275 mg, 0.759 mmol, 82% yield) as a colorless residue. LC-MS Anal. Calc'd for $C_{22}H_{34}N_2O_2$ 358.26. found [M+H] 359.3, $T_r$=1.84 min (Method E).

95C. (1S,2R)-2-(3-amino-4-(cyclohexyl(isobutyl)amino)phenyl) cyclopropanecarboxylic acid To a solution of 95B (0.0317 g, 0.088 mmol) in tetrahydrofuran (0.196 ml) and MeOH (0.098 ml) was added lithium hydroxide as a 1.5 M aqueous solution (0.589 ml, 0.884 mmol). The mixture was heated at 50° C. overnight. Additional LiOH (0.57 mL of a 2M solution) was added and the reaction was stirred at rt overnight. Reaction allowed to cool to rt. The reaction was neutralized with 1 N HCl (0.93 mL) and diluted with EtOAc. Layers were separated. The aqueous phase was extracted with EtOAc (5×). The organic phases were combined and the solvent was evaporated to give 95C as a residue. The crude product was used directly in the subsequent procedure. LC-MS Anal. Calc'd for $C_{20}H_{30}N_2O_2$ 330.23. found [M+H] 331.4, $T_r$=1.61 min (Method E).

Example 95

(1S,2R)-2-(3-(3-(2-cyanopyrimidin-5-yl)ureido)-4-(cyclohexyl(isobutyl)amino)phenyl)cyclopropanecarboxylic acid To a vial charged with 95C (0.029 g, 0.088 mmol) was added 5-isocyanatopyrimidine-2-carbonitrile (2.83 ml, 0.263 mmol) as a 0.093 M solution in $CH_2Cl_2$ and THF. The reaction was heated at 35° C. for 2 h, then allowed to cool to rt. The reaction was quenched with water and diluted with EtOAc. Layers were separated. The aqueous phase was extracted with EtOAc (3×). The organic phases were combined and the solvent was evaporated to give the crude product as a yellow residue. Purification by preparative HPLC afforded Example 95 (33.9 mg, 76% yield). LC-MS Anal. Calc'd for $C_{26}H_{32}N_6O_3$ 476.25. found [M+H] 447.3, $T_r$=2.04 min (Method E).

Example 96

(1R,2S)-2-(4-(cyclohexyhisobutyl)amino)-2-fluoro-5-(3-(5-methylisoxazol-3-yl)ureido)phenyl)cyclopropanecarboxylic acid

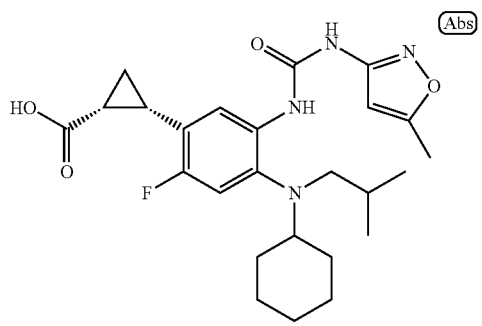 [SMILES: Cc1cc(NC(=O)Nc2cc([C@H]3C[C@H]3C(=O)O)c(F)cc2N(CC(C)C)C2CCCCC2)no1]

96A. 4-bromo-N-cyclohexyl-5-fluoro-N-isobutyl-2-nitroaniline

The title compound (2.30 g, 81%) was prepared following a procedure analogous to that for the synthesis of 45A, except that 1-bromo-2,4-difluoro-5-nitrobenzene (1.81 g, 7.59 mmol) was used instead of 4-bromo-1-fluoro-2-nitrobenzene. MS (ESI') m/z 373.3 (M+H)$^+$.

96B. 4-bromo-N$^1$-cyclohexyl-5-fluoro-N$^1$-isobutyl-benzene-1,2-diamine

To a mixture of 96A (1.00 g, 2.68 mmol) in EtOH (15 mL) and water (2 mL), under nitrogen atmosphere, was added ammonium chloride (0.86 g, 16.07 mmol). The mixture was stirred for 5 minutes before zinc (1.05 g, 16.07 mmol) was added. The reaction mixture was stirred for 18 hours before being diluted with CHCl$_3$ then filtered through a pad of Celite, which was then thoroughly rinsed with CHCl$_3$. The organic filtrates were combined and washed with water, then brine, before being dried (anhydrous sodium sulfate), filtered and concentrated in vacuo to afford a brown residue. Purification by flash chromatography afforded the title compound as a dark brown oil (0.81 g, 83%). MS(ESI$^+$) m/z 343.3 (M+H)$^+$.

96C. N$^1$-cyclohexyl-4-(5,5-dimethyl-1,3,2-dioxaborinan-2-yl)-5-fluoro-N$^1$-isobutylbenzene-1,2-diamine 96B (0.66 g, 1.93 mmol) was converted to the title compound (0.52 g, 72%), following a procedure analogous to that for the synthesis of Compound 1G of Example 1 Method B. MS(ESI$^+$) m/z 309.3 (M+H)$^+$ of boronic acid). $^1$H NMR (400 MHz, DMSO-d$_6$) δ 6.96 (d, J=6.6 Hz, 1H), 6.67 (d, J=11.4 Hz, 1H), 4.43 (s, 2H), 3.70 (s, 4H), 2.77-2.64 (m, 3H), 1.76-1.26 (m, 10H), 0.95 (s, 6H), 0.78 (d, J=6.6 Hz, 6H).

96D. (1R,2S)-ethyl 2-(5-amino-4-(cyclohexyl(isobutyl)amino)-2-fluorophenyl)cyclopropanecarboxylate To a sealable reaction vial containing 96C (0.26 g, 0.69 mmol), in dioxane (2 mL) and water (1 mL), was added (1S,2S)-ethyl 2-iodocyclopropanecarboxylate (0.20 g, 0.83 mmol), which was obtained through chiral resolution following the procedure in Organic Process Research & Development 2004, 8, 353-359, followed by Cs$_2$CO$_3$ (0.47 g, 1.45 mmol). The mixture was purged with Ar for 15 minutes before PdCl$_2$(dppf)-CH$_2$Cl$_2$ adduct (0.11 g, 0.14 mmol) was added. The reaction mixture was purged with Argon for another 5 minutes before the vial was capped and the reaction heated at 85° C. After 18 hours, the reaction was cooled to room temperature then partitioned between EtOAc and water. The layers were separated and the aqueous layer was thoroughly extracted with EtOAc. These organic extracts were combined with the original organic layer and were dried (anhydrous sodium sulfate), filtered and concentrated in vacuo to afford a dark brown oil. Purification by flash chromatography afforded the title compound as a gold oil (0.14 g, 53%). MS(ESI$^+$) m/z 377.4 (M+H)$^+$.

96E. (1R,2S)-2-(5-amino-4-(cyclohexyl(isobutyl)amino)-2-fluorophenyl)cyclopropanecarboxylic acid To a homogeneous mixture of 96D (0.14 g, 0.37 mmol) in anhydrous THF (0.8 mL) and MeOH (0.4 mL), in a sealable vial, was added a 1.5M aqueous solution of LiOH (2.5 mL, 3.75 mmol). The vial was capped and the resulting mixture was stirred at 50° C. for 46 hours. The mixture was cooled to room temperature then acidified to pH 6 with 1N HCl (aq). The resultant mixture was thoroughly extracted with EtOAc and the combined organic layers were concentrated in vacuo to afford the expected product as a residue (0.13 g, 100%), which was used without further purification. MS(ESI) m/z 349.3 (M+H)$^+$.

Example 96

(1R,2S)-2-(4-(cyclohexyl(isobutyl)amino)-2-fluoro-5-(3-(5-methylisoxazol-3-yl)ureido)phenyl)cyclopropanecarboxylic acid To a homogeneous mixture of 5-methylisoxazol-3-amine (11 mg, 0.11 mmol) in anhydrous THF (0.5 mL), in a sealable vial, was added 4-nitrophenyl carbonochloridate (27 mg, 0.13 mmol). The mixture was stirred at room temperature for one hour to afford 4-nitrophenyl (5-methylisoxazol-3-yl)carbamate. MS(ESI$^+$) m/z 264.1 (M+H)$^+$. The entire reaction mixture was used without further purification.

To a mixture of 96E (21 mg, 0.06 mmol) in DCM (2 mL), in a sealable vial, was added the 4-nitrophenyl (5-methylisoxazol-3-yl)carbamate reaction mixture (0.11 mmol), followed by TEA (0.02 mL, 0.14 mmol). The vial was capped and the mixture was stirred at room temperature for 10 days before being concentrated in vacuo to afford a residue. Purification by preparative HPLC afforded the title compound (5.1 mg, 18%). LC-MS Anal. Calc'd for C$_{25}$H$_{33}$FN$_4$O$_4$ 472.56. found [M+H] 473.3, T$_r$=2.04 min (Method E). $^1$HNMR (500 MHz, 1:1 MeOH-d$_4$/CDCl$_3$) δ 8.02-7.89 (m, 1H), 7.63 (s, 1H), 6.83 (d, J=10.9 Hz, 1H), 6.24 (br. s., 1H), 3.02 (s, 1H), 2.89 (s, 1H), 2.81 (br. s., 1H), 2.77-2.67 (m, 1H), 2.61 (m, 1H), 2.55-2.46 (m, 1H), 2.40 (s, 3H), 2.17-2.05 (m, 1H), 1.96-1.80 (m, 2H), 1.73 (d, J=9.9 Hz, 2H), 1.68-1.52 (m, 2H), 1.50-1.23 (m, 4H), 1.22-1.00 (m, 3H), 0.85 (m, 6H).

Example 97

(1R,2S)-2-(4-(cyclohexyhisobutyl)amino)-2-fluoro-5-(3-(3-methylisoxazol-5-yl)ureido)phenyl)cyclopropanecarboxylic acid

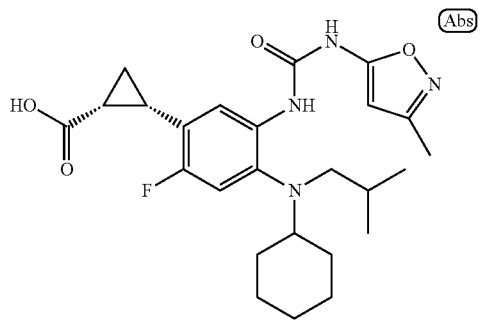 [SMILES: Cc1cc(NC(=O)Nc2cc([C@H]3C[C@H]3C(=O)O)c(F)cc2N(CC(C)C)C2CCCCC2)on1]

The title compound (1.5 mg, 5%) was prepared following a procedure analogous to that for the synthesis of Example 96, except that 3-methylisoxazol-5-amine (11 mg, 0.11 mmol) was used instead of 5-methylisoxazol-3-amine. LC-MS Anal. Calc'd for $C_{25}H_{33}FN_4O_4$ 472.56. found [M+H] 473.3, $T_r$=2.04 min (Method E). $^1$H NMR (1:1 MeOH-d$_4$/CDCl$_3$) δ 7.99 (s, 1H), 7.59 (s, 1H), 6.83 (d, J=10.9 Hz, 1H), 6.07 (s, 1H), 3.02 (s, 1H), 2.89 (s, 1H), 2.86-2.77 (m, 1H), 2.77-2.67 (m, 1H), 2.64-2.46 (m, 2H), 2.26 (s, 3H), 2.21-1.99 (m, 1H), 1.94-1.80 (m, 2H), 1.80-1.69 (m, 2H), 1.67-1.53 (m, 2H), 1.49-1.23 (m, 4H), 1.23-0.99 (m, 3H), 0.84 (d, J=6.4 Hz, 6H).

Example 98

(1R,2S)-2-(4-(cyclohexyl(isobutyl)amino)-2-fluoro-5-(3-(pyrimidin-5-yl)ureido)phenyl)cyclopropanecarboxylic acid

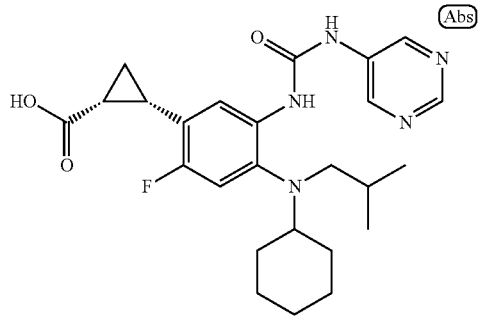 [SMILES: CC(C)CN(c1cc(F)c([C@H]2C[C@H]2C(=O)O)cc1NC(=O)Nc1cncnc1)C1CCCCC1]

The title compound (1.5 mg, 5%) was prepared following a procedure analogous to that for the synthesis of Example 96, except that pyrimidin-5-amine (11 mg, 0.12 mmol) was used instead of 5-methylisoxazol-3-amine. LC-MS Anal. Calc'd for $C_{25}H_{32}FN_5O_3$ 469.56. found [M+H] 470.3, $T_r$=2.04 min (Method E). $^1$H NMR (1:1 MeOH-d$_4$/CDCl$_3$) δ 7.99 (s, 1H), 7.90 (d, J=6.9 Hz, 1H), 7.60 (s, 2H), 6.85 (d, J=10.9 Hz, 1H), 3.02 (s, 1H), 2.89 (s, 1H), 2.81 (m, 1H), 2.79-2.72 (m, 1H), 2.72-2.48 (m, 3H), 2.13 (m, 1H), 1.96-1.83 (m, 2H), 1.82-1.70 (m, 2H), 1.68-1.54 (m, 2H), 1.51-1.25 (m, 4H), 1.24-1.01 (m, 3H), 0.86 (d, J=6.4 Hz, 6H).

Example 99

(1R,2S)-2-(4-(cyclohexyl(isobutyl)amino)-2-fluoro-5-(3-(p-tolyl)ureido)phenyl)cyclopropanecarboxylic acid

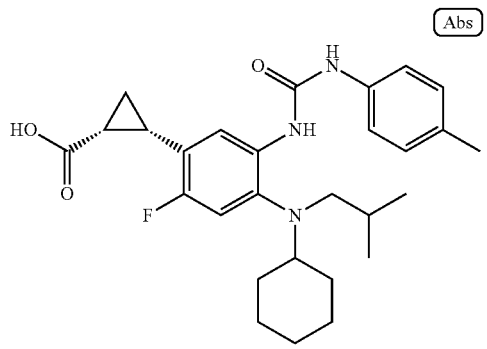 [SMILES: Cc1ccc(NC(=O)Nc2cc([C@H]3C[C@H]3C(=O)O)c(F)cc2N(CC(C)C)C2CCCCC2)cc1]

To a homogeneous mixture of 96E (21 mg, 0.06 mmol) in anhydrous THF (1 mL), in a sealable vial, was added 1-isocyanato-4-methylbenzene (14 mg, 0.11 mmol). The vial was sealed and the reaction mixture heated at 55° C. for two hours. After cooling to room temperature, the mixture was concentrated in vacuo to afford a residue which was purified by preparative HPLC to afford the title compound (18 mg, 59%). LC-MS Anal. Calc'd for $C_{28}H_{36}FN_3O_3$ 481.61. found [M+H] 482.3, $T_r$=2.04 min (Method E). $^1$H NMR (500 MHz, 1:1 MeOH-d$_4$/CDCl$_3$) δ 8.03-7.82 (m, 1H), 7.62 (s, 1H), 7.29 (d, J=7.9 Hz, 2H), 7.15 (d, J=7.9 Hz, 2H), 6.77 (m, 1H), 3.02 (s, 1H), 2.89 (s, 1H), 2.83-2.60 (m, 2H), 2.58-2.41 (m, 2H), 2.33 (s, 3H), 2.11 (m, 1H), 1.90-1.54 (m, 6H), 1.47-0.97 (m, 7H), 0.81 (m, 6H).

Example 100

(1R,2S)-2-(4-(cyclohexyl(isobutyl)amino)-5-(3-(4-ethoxyphenyl)ureido)-2-fluorophenyl)cyclopropanecarboxylic acid

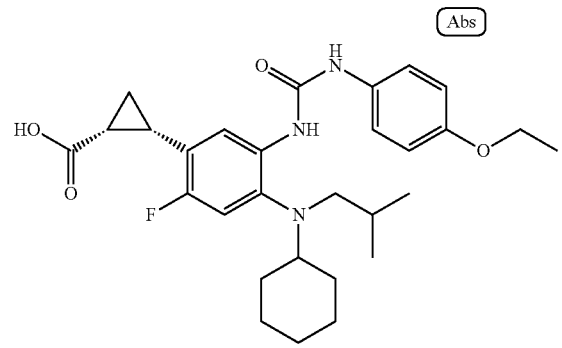 [SMILES: CCOc1ccc(NC(=O)Nc2cc([C@H]3C[C@H]3C(=O)O)c(F)cc2N(CC(C)C)C2CCCCC2)cc1]

The title compound (17 mg, 55%) was prepared following a procedure analogous to that for the synthesis of Example 96, except that 1-ethoxy-4-isocyanato-benzene (17 mg, 0.10 mmol) was used instead of 1-isocyanato-4-methylbenzene. LC-MS Anal. Calc'd for $C_{29}H_{38}FN_3O_4$ 511.63. found [M+H] 512.3, $T_r$=2.04 min (Method E). $^1$H NMR (500 MHz, 1:1 MeOH-d$_4$/CDCl$_3$) δ 8.03-7.90 (m, 1H), 7.63 (s, 1H), 7.28 (d, J=8.9 Hz, 2H), 6.96-6.85 (m, 2H), 6.77 (m, 1H), 4.04 (q, J=6.9 Hz, 2H), 3.02 (s, 1H), 2.89 (s, 1H), 2.79-2.58 (m, 2H), 2.57-2.36 (m, 2H), 2.10 (m, 1H), 1.79-1.49 (m, 6H), 1.47-1.30 (m, 5H), 1.29-0.94 (m, 5H), 0.78 (m, 6H).

Example 101

(1R,2S)-2-(5-(3-(benzo [d][1,3]dioxol-5-yl)ureido)-4-(cyclohexyl-(isobutyl)amino)-2-fluorophenyl)cyclopropanecarboxylic acid

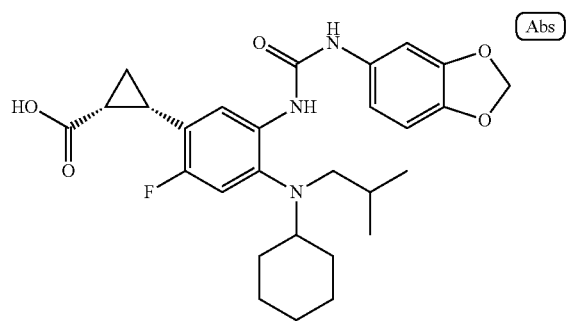 [SMILES: CC(C)CN(c1cc(F)c([C@H]2C[C@H]2C(=O)O)cc1NC(=O)Nc1ccc2c(c1)OCO2)C1CCCCC1]

The title compound (13 mg, 41%) was prepared following a procedure analogous to that for the synthesis of Example 96, except that 5-isocyanatobenzo[d]-[1,3]dioxole (19 mg, 0.12 mmol) was used instead of 1-isocyanato-4-methylbenzene. LC-MS Anal. Calc'd for $C_{28}H_{34}FN_3O_5$ 511.59. found [M+H] 512.3, $T_r$=2.04 min (Method E). $^1$H NMR (500 MHz, 1:1 MeOH-$d_4$/CDCl$_3$) δ 7.99-7.84 (m, 1H), 7.63 (s, 1H), 7.00 (s, 1H), 6.85-6.71 (m, 3H), 5.96 (s, 2H), 3.01 (s, 1H), 2.90 (s, 1H), 2.79-2.61 (m, 2H), 2.56-2.38 (m, 2H), 2.16-2.04 (m, 1H), 1.79-1.50 (m, 6H), 1.46-1.32 (m, 2H), 1.30-0.96 (m, 5H), 0.79 (dd, J=6.7, 2.7 Hz, 6H).

Example 102

(1S,2R)-2-(4-(cyclohexyl(isobutyl)amino)-2-fluoro-5-(3-(5-methylisoxazol-3-yl)ureido)phenyl)cyclopropanecarboxylic acid

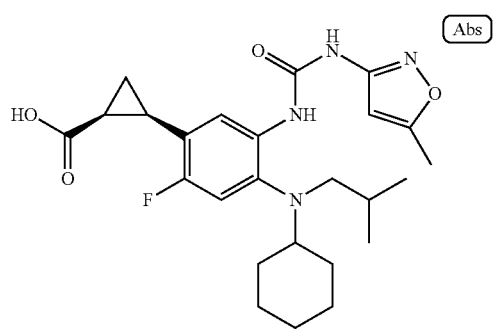 [SMILES: Cc1cc(NC(=O)Nc2cc([C@@H]3C[C@@H]3C(=O)O)c(F)cc2N(CC(C)C)C2CCCCC2)no1]

The title compound (3.0 mg, 10%) was prepared following a procedure analogous to that for the synthesis of Example 96, except that (1R,2R)-ethyl 2-iodocyclopropanecarboxylate (0.20 g, 0.83 mmol) was used instead of (1S,2S)-ethyl 2-iodocyclopropanecarboxylate used in 96D. LC-MS Anal. Calc'd for $C_{25}H_{33}FN_4O_4$ 472.56. found [M+H] 473.3, $T_r$=2.04 min (Method E). $^1$H NMR (500 MHz, 1:1 MeOH-$d_4$/CDCl$_3$) δ 8.01-7.91 (m, 1H), 7.62 (s, 1H), 6.83 (d, J=10.9 Hz, 1H), 6.23 (br. s., 1H), 3.02 (s, 1H), 2.86-2.77 (m, 2H), 2.77-2.68 (m, 1H), 2.60 (m, 1H), 2.51 (q, J=8.3 Hz, 1H), 2.40 (s, 3H), 2.16-2.05 (m, 1H), 1.96-1.79 (m, 2H), 1.73 (d, J=10.4 Hz, 2H), 1.66-1.52 (m, 2H), 1.50-1.23 (m, 4H), 1.20-0.99 (m, 3H), 0.89-0.79 (m, 6H).

Example 103

(1S,2R)-2-(4-(cyclohexyl(isobutyl)amino)-2-fluoro-5-(3-(pyrimidin-5-yl)ureido)phenyl)cyclopropanecarboxylic acid

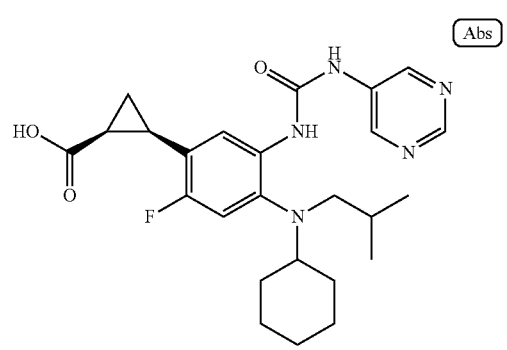 [SMILES: CC(C)CN(c1cc(F)c([C@@H]2C[C@@H]2C(=O)O)cc1NC(=O)Nc1cncnc1)C1CCCCC1]

The title compound (1.2 mg, 4%) was prepared following a procedure analogous to that for the synthesis of Example 102, except that pyrimidin-5-amine (11 mg, 0.12 mmol) was used instead of 5-methylisoxazol-3-amine. LC-MS Anal. Calc'd for $C_{25}H_{32}FN_5O_3$ 469.56. found [M+H] 470.3, $T_r$=2.04 min (Method E). $^1$H NMR (500 MHz, 1:1 MeOH-$d_4$/CDCl$_3$) δ 8.02-7.87 (m, 2H), 7.67 (s, 2H), 6.86 (d, J=11.4 Hz, 1H), 3.02 (s, 1H), 2.89 (s, 1H), 2.87-2.72 (m, 2H), 2.67-2.48 (m, 3H), 2.12 (d, J=5.9 Hz, 1H), 1.97-1.84 (m, 2H), 1.75 (m, 2H), 1.67-1.56 (m, 2H), 1.50-1.25 (m, 4H), 1.23-1.00 (m, 3H), 0.92-0.79 (m, 6H)

Example 104

(1S,2R)-2-(4-(cyclohexyhisobutyl)amino)-2-fluoro-5-(3-(p-tolyl)ureido)phenyl)cyclopropanecarboxylic acid

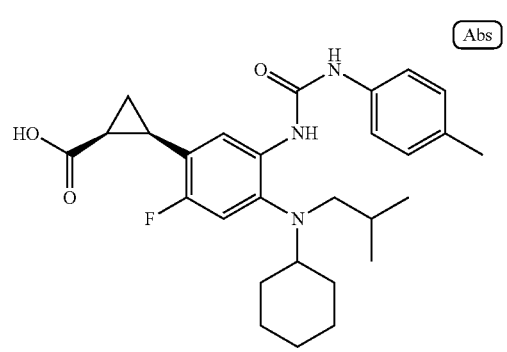 [SMILES: Cc1ccc(NC(=O)Nc2cc([C@@H]3C[C@@H]3C(=O)O)c(F)cc2N(CC(C)C)C2CCCCC2)cc1]

The title compound (13 mg, 42%) was prepared following a procedure analogous to that for the synthesis of Example 99, except that the enantiomer of 96E was used. LC-MS Anal. Calc'd for $C_{28}H_{36}FN_3O_3$ 481.61. found [M+H] 482.3, $T_r$=2.04 min (Method E). $^1$H NMR (500 MHz, 1:1 MeOH-$d_4$/CDCl$_3$) δ 7.90 (d, J=8.4 Hz, 1H), 7.62 (s, 1H), 7.29 (d, J=7.9 Hz, 2H), 7.14 (d, J=7.9 Hz, 2H), 6.78 (d, J=10.9 Hz, 1H), 3.02 (s, 1H), 2.89 (s, 1H), 2.79-2.70 (m, 1H), 2.70-2.61 (m, 1H), 2.54-2.44 (m, 2H), 2.32 (s, 3H), 2.14-2.03 (m, 1H), 1.77-1.51 (m, 6H), 1.45-1.32 (m, 2H), 1.31-0.97 (m, 5H), 0.80 (dd, J=6.4, 2.5 Hz, 6H).

Example 105

(1S,2R)-2-(4-(cyclohexyl(isobutyl)amino)-5-(3-(4-ethoxyphenyl)ureido)-2-fluorophenyl)cyclopropanecarboxylic acid

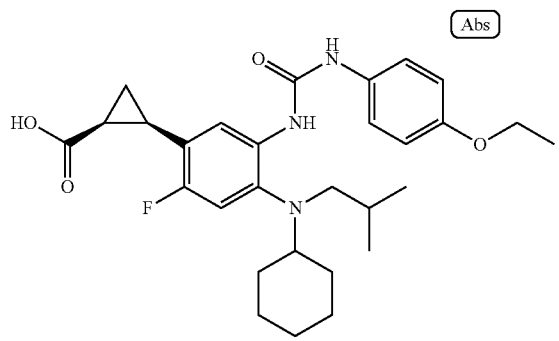 [SMILES: CCOc1ccc(NC(=O)Nc2cc([C@@H]3C[C@@H]3C(=O)O)c(F)cc2N(CC(C)C)C2CCCCC2)cc1]

The title compound (18 mg, 54%) was prepared following a procedure analogous to that for the synthesis of Example 100, except that the enantiomer of 96E was used. LC-MS Anal. Calc'd for $C_{29}H_{38}FN_3O_4$ 511.63. found [M+H] 512.3, $T_r$=2.04 min (Method E). $^1$H NMR (500 MHz, 1:1 MeOH-$d_4$/CDCl$_3$) δ 7.95 (d, J=7.9 Hz, 1H), 7.62 (s, 1H), 7.28 (d, J=8.9 Hz, 2H), 6.93-6.86 (m, 2H), 6.77 (d, J=10.9 Hz, 1H), 4.04 (q, J=6.9 Hz, 2H), 3.02 (s, 1H), 2.89 (s, 1H), 2.75-2.68 (m, 1H), 2.67-2.60 (m, 1H), 2.54-2.39 (m, 2H), 2.09 (m, 1H), 1.78-1.52 (m, 6H), 1.45-1.31 (m, 5H), 1.25-0.97 (m, 5H), 0.78 (dd, J=6.7, 4.2 Hz, 6H).

Example 106

(1S,2R)-2-(5-(3-(benzo [d][1,3]dioxol-5-yl)ureido)-4-(cyclohexyhisobutyl)amino)-2-fluorophenyl)cyclopropanecarboxylic acid

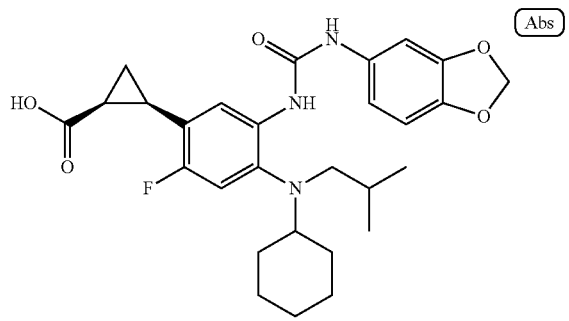 [SMILES: CC(C)CN(c1cc(F)c([C@@H]2C[C@@H]2C(=O)O)cc1NC(=O)Nc1ccc2c(c1)OCO2)C1CCCCC1]

The title compound (18 mg, 56%) was prepared following a procedure analogous to that for the synthesis of Example 101, except that the enantiomer of 96E was used. LC-MS Anal. Calc'd for $C_{28}H_{34}FN_3O_5$ 511.59. found [M+H] 512.3, $T_r$=2.04 min (Method E). $^1$H NMR (500 MHz, 1:1 MeOH-$d_4$/CDCl$_3$) δ 7.93 (d, J=7.9 Hz, 1H), 7.62 (s, 1H), 7.00 (s, 1H), 6.84-6.74 (m, 3H), 5.96 (s, 2H), 3.02 (s, 1H), 2.89 (s, 1H), 2.79-2.70 (m, 1H), 2.69-2.60 (m, 1H), 2.56-2.43 (m, 2H), 2.16-2.04 (m, 1H), 1.76-1.52 (m, 6H), 1.44-1.31 (m, 2H), 1.30-0.99 (m, 5H), 0.79 (dd, J=6.7, 2.7 Hz, 6H).

Example 107

(1R,2S)-2-(3-(2-(4-cyanophenyl)acetamido)-4-(cyclohexyl(3,3,3-trifluoropropyl)amino)phenyl)cyclopropanecarboxylic acid

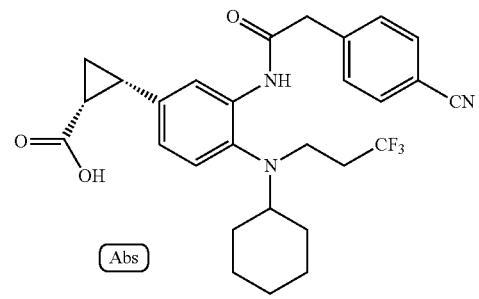 [SMILES: N#Cc1ccc(CC(=O)Nc2cc([C@H]3C[C@H]3C(=O)O)ccc2N(CCC(F)(F)F)C2CCCCC2)cc1]

107A. (1R,2S)-ethyl 2-(3-(2-(4-cyanophenyl)acetamido)-4-(cyclohexyl(3,3,3-trifluoropropyl)amino)phenyl)cyclopropanecarboxylate To a solution of 87F (26.1 mg, 0.066 mmol) in DMF (936 μl) at RT was added 2-(4-cyanophenyl)acetic acid (21.11 mg, 0.131 mmol), EDC (25.1 mg, 0.131 mmol), 1-Hydroxybenzotriazole hydrate (20.06 mg, 0.131 mmol), and Hunig's Base (22.88 μl, 0.131 mmol). The reaction was stirred at rt for 16 h. The reaction was quenched with 1 N NaOH and diluted with water. Layers were separated. The aqueous phase was extracted with EtOAc (2×). The organic phases were combined, washed with water (1×), brine (1×), dried over Na$_2$SO$_4$, filtered, and concentrated to afford a yellow residue. LC-MS Anal. Calc'd for $C_{30}H_{34}F_3N_3O_3$ 541.26. found [M+H] 542.2, $T_r$=2.26 min (Method G).

Example 107

(1R,2S)-2-(3-(2-(4-cyanophenyl)acetamido)-4-(cyclohexyl(3,3,3-trifluoropropyl)amino)phenyl)cyclopropanecarboxylic acid To a solution of 107A (35.5 mg, 0.066 mmol) in Tetrahydrofuran (146 μl) and MeOH (72.8 μl) was added 1.5 M lithium hydroxide aqueous solution (437 μl, 0.655 mmol). The mixture was heated at 50° C. overnight, then allowed to cool to rt. The crude material was purified via preparative HPLC to give Example 107 (2.7 mg, 5.05 umol, 27.3% yield). LC-MS Anal. Calc'd for $C_{28}H_{30}F_3N_3O_3$ 513.55. found [M+H] 513., $T_r$=1.78 min (Method G). $^1$H NMR (500 MHz, METHANOL-$d_4$) δ 8.32 (br. s., 1H), 7.76-7.66 (m, J=7.9 Hz, 2H), 7.57-7.47 (m, J=7.9 Hz, 2H), 7.08 (d, J=8.4 Hz, 1H), 7.01 (d, J=8.4 Hz, 1H), 3.83 (s, 2H), 3.14 (t, J=6.9 Hz, 2H), 2.62-2.52 (m, 1H), 2.48 (t, J=11.1 Hz, 1H), 2.06 (d, J=12.4 Hz, 1H), 1.98-1.78 (m, 2H), 1.68 (d, J=12.4 Hz, 2H), 1.63-1.52 (m, 4H), 1.39-1.30 (m, 1H), 1.13-0.91 (m, 5H).

Example 108

(1S,2R)-2-(3-(2-(4-cyanophenyl)acetamido)-4-(cyclohexyl(3,3,3-trifluoropropyl)amino)phenyl)cyclopropanecarboxylic acid

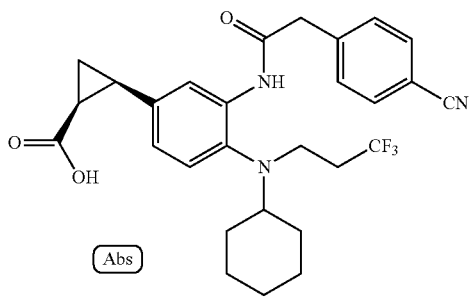 [SMILES: N#Cc1ccc(CC(=O)Nc2cc([C@@H]3C[C@@H]3C(=O)O)ccc2N(CCC(F)(F)F)C2CCCCC2)cc1]

108A. (1S,2R)-ethyl 2-(3-(2-(4-cyanophenyl)acetamido)-4-(cyclohexyl(3,3,3-trifluoropropyl)amino)phenyl)cyclopropanecarboxylate To a solution of 91A (22.7 mg, 0.057 mmol) in DMF (814 µl) at rt was added 2-(4-cyanophenyl)acetic acid (18.36 mg, 0.114 mmol), EDC (21.84 mg, 0.114 mmol), 1-Hydroxybenzotriazole hydrate (17.45 mg, 0.114 mmol), and Hunig's Base (19.90 µl, 0.114 mmol) The reaction was stirred at rt for 16 h. The reaction was quenched with 1 N NaOH and diluted with water. Layers were separated. The aqueous phase was extracted with EtOAc (2×). The organic phases were combined, washed with water (1×), brine (1×), dried over Na₂SO₄, filtered, and concentrated to afford a yellow residue. This material was purified via preparative HPLC to give 108A (11 mg, 0.020 mmol). LC-MS Anal. Calc'd for $C_{30}H_{34}F_3N_3O_3$ 541.26. found [M+H] 542.3, $T_r$=2.26 min (Method G).

Example 108

(1S,2R)-2-(3-(2-(4-cyanophenyl)acetamido)-4-(cyclohexyl(3,3,3-trifluoropropyl)amino)phenyl)cyclopropanecarboxylic acid To 108A (11 mg, 0.020 mmol) in MeOH (0.4 mL) and THF (0.3 mL) was added 2M LiOH aqueous solution (0.3 mL, 0.600 mmol). The mixture was stirred at rt for 6 h. The reaction was adjusted to pH 1 with 1N HCl, then the resulting solution was extracted with EtOAc. The organic phase was separated, washed with brine, dried over MgSO₄, filtered and concentrated. This crude material was purified by preparative HPLC to give Example 108 (2.1 mg, 3.93 umol, 19.3% yield). LC-MS Anal. Calc'd for $C_{28}H_{30}F_3N_3O_3$ 513.55. found [M+H] 513., $T_r$=1.78 min (Method G). ¹H NMR (500 MHz, METHANOL-d₄) δ 8.32 (br. s., 1H), 7.76-7.66 (m, J=7.9 Hz, 2H), 7.57-7.47 (m, J=7.9 Hz, 2H), 7.08 (d, J=8.4 Hz, 1H), 7.01 (d, J=8.4 Hz, 1H), 3.83 (s, 2H), 3.14 (t, J=6.9 Hz, 2H), 2.62-2.52 (m, 1H), 2.48 (t, J=11.1 Hz, 1H), 2.06 (d, J=12.4 Hz, 1H), 1.98-1.78 (m, 2H), 1.68 (d, J=12.4 Hz, 2H), 1.63-1.52 (m, 4H), 1.39-1.30 (m, 1H), 1.13-0.91 (m, 5H).

Example 109

(1R,2S)-2-(3-(2-(4-cyanophenyl)acetamido)-4-(cyclohexyhisobutyl)amino)phenyl)cyclopropanecarboxylic acid

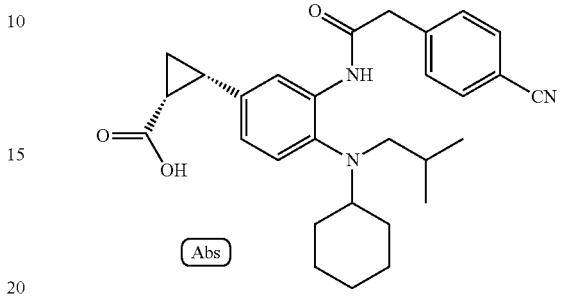

109A. (1R,2S)-ethyl 2-(3-(2-(4-cyanophenyl)acetamido)-4-(cyclohexyl(isobutyl)amino)phenyl)cyclopropanecarboxylate To a solution of 80E (29.5 mg, 0.082 mmol) in DMF (1029 µl) at rt was added 2-(4-cyanophenyl)acetic acid (26.5 mg, 0.165 mmol), EDC (31.5 mg, 0.165 mmol), 1-Hydroxybenzotriazole hydrate (25.2 mg, 0.165 mmol), and Hunig's Base (28.7 µl, 0.165 mmol). The reaction was stirred at rt for 16 h. The reaction was quenched with 1 N NaOH and diluted with water. Layers were separated. The aqueous phase was extracted with EtOAc (2×). The organic phases were combined, washed with water (1×), brine (1×), dried over Na₂SO₄, filtered, and concentrated to afford a yellow residue. The crude material was purified via preparative HPLC to give 109A (18 mg, 0.036 mmol, 45% yield). LC-MS Anal. Calc'd for $C_{31}H_{39}N_3O_3$ 501.30. found [M+H] 502.3, $T_r$=2.19 min (Method G).

Example 109

(1R,2S)-2-(3-(2-(4-cyanophenyl)acetamido)-4-(cyclohexyl(isobutyl)amino)phenyl)cyclopropanecarboxylic acid To 109A (18 mg, 0.036 mmol) in MeOH (0.4 mL) and THF (0.3 mL) was added 2M LiOH aqueous solution (0.3 mL, 0.600 mmol). The mixture was stirred at rt for 6 h. The reaction was adjusted to pH 1 with 1N HCl and then it was extracted with EtOAc. The organic phase was separated, washed with brine, dried over MgSO₄, filtered and concentrated. The crude material was purified via preparative HPLC to give Example 109 (5.4 mg, 10.9 umol, 30.5% yield). LC-MS Anal. Calc'd for $C_{29}H_{35}N_3O_3$ 473.3. found [M+H] 474.0, $T_r$=1.96 min (Method G). ¹H NMR (500 MHz, METHANOL-d₄) δ 8.31 (s, 1H), 7.78-7.67 (m, J=7.9 Hz, 2H), 7.54-7.47 (m, J=7.9 Hz, 2H), 7.06 (d, J=8.4 Hz, 1H), 6.97 (d, J=8.4 Hz, 1H), 3.83 (s, 2H), 2.69 (br. s., 2H), 2.61-2.54 (m, 1H), 2.33 (br. s., 1H), 2.04 (br. s., 1H), 1.67 (br. s., 2H), 1.65-1.42 (m, 4H), 1.36-1.19 (m, 2H), 1.11-0.90 (m, 5H), 0.76-0.69 (m, 6H).

Example 110

(1S,2R)-2-(3-(2-(4-cyanophenyl)acetamido)-4-(cyclohexyl(isobutyl)amino)phenyl)cyclopropanecarboxylic acid

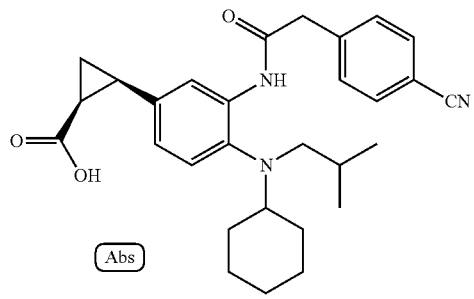 [SMILES: CC(C)CN(c1ccc([C@@H]2C[C@@H]2C(=O)O)cc1NC(=O)Cc1ccc(C#N)cc1)C1CCCCC1]

110A. (1S,2R)-ethyl 2-(3-(2-(4-cyanophenyl)acetamido)-4-(cyclohexyl(isobutyl)amino) phenyl)cyclopropanecarboxylate To a solution of 95B (28.5 mg, 0.079 mmol) in DMF (1 mL) at rt was added 2-(4-cyanophenyl)acetic acid (25.6 mg, 0.159 mmol), EDC (30.5 mg, 0.159 mmol), 1-Hydroxybenzotriazole hydrate (24.35 mg, 0.159 mmol), and Hunig's Base (0.028 mL, 0.159 mmol) The reaction was stirred at rt for 16 h. The reaction was quenched with 1 N NaOH and diluted with water. Layers were separated. The aqueous phase was extracted with EtOAc (2×). The organic phases were combined, washed with water (1×), brine (1×), dried over $Na_2SO_4$, filtered, and concentrated to afford a yellow residue. The crude material was purified via preparative HPLC to give 110A (13 mg, 0.026 mmol, 33% yield). LC-MS Anal. Calc'd for $C_{31}H_{39}N_3O_3$ 501.30. found [M+H] 502.3, $T_r$=2.16 min (Method G).

Example 110

(1S,2R)-2-(3-(2-(4-cyanophenyl)acetamido)-4-(cyclohexyl (isobutyl)amino)phenyl)cyclopropanecarboxylic acid To (1R,2S)-ethyl 2-(3-(2-(4-cyanophenyl) acetamido)-4-(cyclohexyl(isobutyl)amino)phenyl) cyclopropanecarboxylate (13 mg, 0.026 mmol)) in MeOH (0.4 mL) and THF (0.3 mL) was added 2M LiOH aqueous solution (0.3 mL, 0.600 mmol). The mixture was stirred at RT for 6 h. The reaction was adjusted to pH 1 with 1N HCl and then it was extracted with EtOAc. The organic phase was separated, washed with brine, dried over $MgSO_4$, filtered and concentrated. The crude material was purified via preparative HPLC to give Example 110 (1.3 mg, 2.7 umol, 10.4% yield). LC-MS Anal. Calc'd for $C_{29}H_{35}N_3O_3$ 473.3. found [M+H] 474.0, $T_r$=1.96 min (Method G). $^1$H NMR (500 MHz, METHANOL-$d_4$) δ 8.31 (s, 1H), 7.78-7.67 (m, J=7.9 Hz, 2H), 7.54-7.47 (m, J=7.9 Hz, 2H), 7.06 (d, J=8.4 Hz, 1H), 6.97 (d, J=8.4 Hz, 1H), 3.83 (s, 2H), 2.69 (br. s., 2H), 2.61-2.54 (m, 1H), 2.33 (br. s., 1H), 2.04 (br. s., 1H), 1.67 (br. s., 2H), 1.65-1.42 (m, 4H), 1.36-1.19 (m, 2H), 1.11-0.90 (m, 5H), 0.76-0.69 (m, 6H).

Example 111

(1R,2S)-2-(4-(cyclohexyl(4,4,4-trifluoro-2-methylbutyl)amino)-3-(3-(p-tolyl)ureido)phenyl)cyclopropanecarboxylic acid

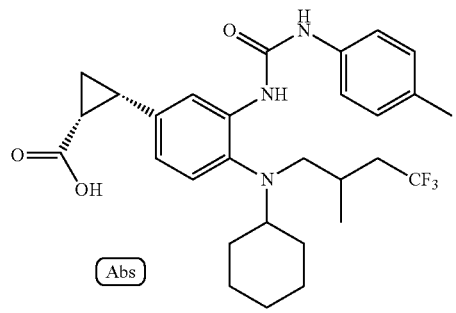 [SMILES: Cc1ccc(NC(=O)Nc2cc([C@H]3C[C@H]3C(=O)O)ccc2N(CC(C)CC(F)(F)F)C2CCCCC2)cc1]

Preparation 111A: Racemic N-(4,4,4-trifluoro-2-methylbutyl)cyclohexanamine

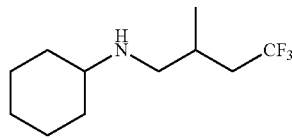

To a solution of N-cyclohexyl-4,4,4-trifluoro-2-methylbutanamide (2.2 g, 9.27 mmol) in THF (100 mL) at room temperature was added a solution of LAH (13.91 mL, 27.8 mmol) resulting in gas evolution. The mixture was then heated to reflux for 6 hours, cooled to rt and then to 0° C. in an ice bath. 1 mL of water was carefully added, followed by 1 mL of NaOH, 3 mL of sat aq $NH_4Cl$. The resulting mixture was stirred at 0° C. for 30 minutes and then filtered through Celite rinsing with EtOAc. Concentration in vacuo gave the crude Preparation 111A (1.88 g, 8.25 mmol, 89% yield) as a yellow oil. LC-MS Anal. Calc'd for $C_{11}H_{20}F_3N$, 223.15. found [M+H] 224.2, $T_r$=0.62 min (Method D). The crude material was taken on without further purification.

Preparation 111B: Racemic 4-bromo-N-cyclohexyl-2-nitro-N-(4,4,4-trifluoro-2-methylbutyl)aniline

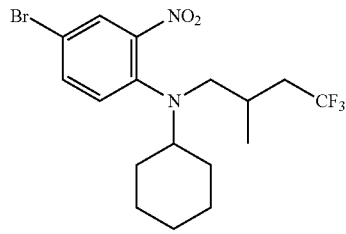 [SMILES: CC(CN(c1ccc(Br)cc1N)C1CCCCC1)CC(F)(F)F]

4-bromo-1-fluoro-2-nitrobenzene (2.168 g, 9.85 mmol) was mixed with Preparation 111A (2.0 g, 8.96 mmol) in a pressure vial with a stir bar. The viscous suspension was then heated at 130° C. for 48 hours. LC-MS showed an ~1:1 mixture of SM and desired product. The mixture was then cooled to RT, diluted with DCM and purified via ISCO machine (80 g column, 40 mL/min, 0-10% EtOAc/hexanes over 20 minutes, rt=11 minutes) to give Preparation 111B (2.21 g, 4.12 mmol, 46.0% yield) as a yellow oil. The purity was determined to be ~79% with some unreacted fluorobenzene present. LC-MS Anal. Calc'd for $C_{17}H_{22}BrF_3N_2O_2$ 422.08. found [M+H] 423.3, 425.3, $T_r$=1.29 min. (Method D).

Preparation 111C: Racemic 4-bromo-N1-cyclohexyl-N1-(4,4,4-trifluoro-2-methylbutyl)benzene-1,2-diamine

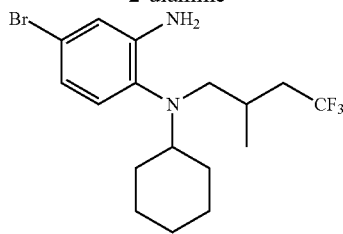

Preparation 111C was prepared by the procedure described in Example 87D utilizing example 111B. LC-MS Anal. Calc'd for $C_{17}H_{24}BrF_3N_2$ 392.11. found [M+H] 393.3, 396.3, $T_r$=1.24 min. (Method D).

Preparation 111D: Racemic N1-cyclohexyl-4-(5,5-dimethyl-1,3,2-dioxaborinan-2-yl)-N1-(4,4,4-trifluoro-2-methylbutyl)benzene-1,2-diamine

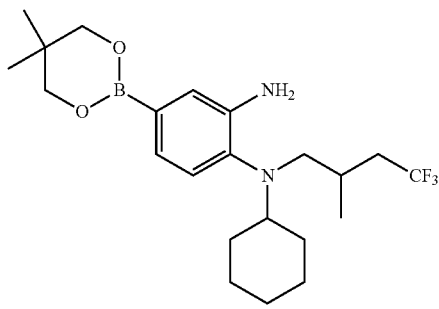 [SMILES: CC(CN(c1ccc(B2OCC(C)(C)CO2)cc1N)C1CCCCC1)CC(F)(F)F]

Preparation 111D was prepared by the procedure described in Example 87E utilizing Preparation 111C. LC-MS Anal. Calc'd for $C_{22}H_{34}BF_3N_2O_2$ 426.27. found [M+H] 359.1 (boronic acid), $T_r$=1.62 min. Method C).

Preparation 111E: (1R,2S)-ethyl 2-(3-amino-4-(cyclohexyl(4,4,4-trifluoro-2-methylbutyl)amino)phenyl) cyclopropanecarboxylate, mixture of diastereomers

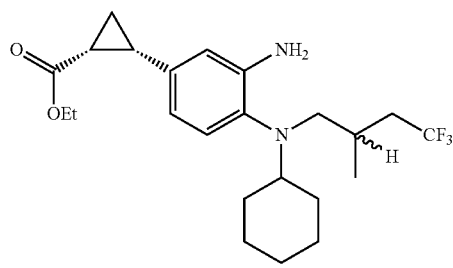 [SMILES: CCOC(=O)[C@@H]1C[C@@H]1c1ccc(N(CC(C)CC(F)(F)F)C2CCCCC2)c(N)c1]

Preparation 111E was prepared by the procedure described in Example 87F utilizing preparation 111D and (1S,2S)-ethyl 2-iodocyclopropanecarboxylate. Isolated as a mixture of diastereomers. LC-MS Anal. Calc'd for $C_{23}H_{33}F_3N_2O_2$ 426.25. found [M+H] 427.41, $T_r$=1.02 min (Method D).

Preparation 111F: (1R,2S)-ethyl 2-(4-(cyclohexyl(4,4,4-trifluoro-2-methylbutyl)amino)-3-(3-(p-tolyl) ureido)phenyl)cyclopropanecarboxylate, mixture of diastereomers

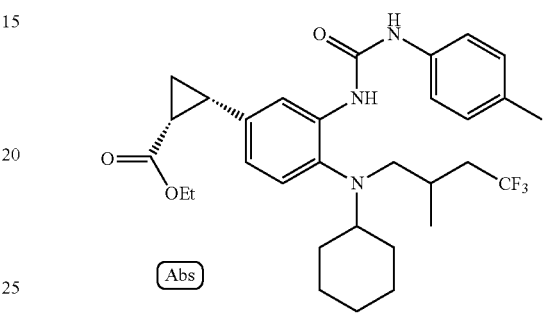

To a solution of Preparation 111E (30 mg, 0.070 mmol) in THF (1 mL) at RT was added 4-nitrophenyl carbonochloridate (14.89 mg, 0.074 mmol). The reaction was stirred at RT for 2 h, then p-toluidine (22.61 mg, 0.211 mmol) was added. The reaction was heated at 50° C. for 16 h, then cooled to RT and diluted with MeOH. The crude material was purified with prep HPLC (Waters Xbridge C18 19×100 mm), 20 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 220 to give Preparation 111F (20 mg, 0.035 mmol, 50.3% yield) as a mixture of diastereomers and as an off-white solid. LC-MS Anal. Calc'd for $C_{31}H_{40}F_3N_3O_3$ 559.30. found [M+H] 560.5, $T_r$=1.18 min (Method D).

Example 111

(1R,2S)-2-(4-(cyclohexyl(4,4,4-trifluoro-2-methylbutyl)amino)-3-(3-(p-tolyl)ureido)phenyl)cyclopropanecarboxylic acid, mixture of diastereomers To Preparation 111F (20 mg, 0.036 mmol) at RT was added MeOH (0.5 mL) and THF (0.2 mL) followed by a 1.3M LiOH solution (0.550 mL, 0.715 mmol). The mixture was stirred at 50° C. for 16 h, then allowed to cool to rt. The mixture was adjusted to pH 1 with 1N HCl, then diluted with EtOAc. The organic phase was separated and washed with brine, dried over $MgSO_4$, filtered and concentrated to give the crude material. The crude material was purified via preparative LC/MS with the following conditions: Column: Waters XBridge C18, 19×100 mm, 5-um particles; Guard Column: Waters XBridge C18, 19×10 mm, 5-um particles; Mobile Phase A: 5:95 acetonitrile:water with 10-mM ammonium acetate; Mobile Phase B: 95:5 acetonitrile:water with 10-mM ammonium acetate; Gradient: 44-84% B over 10 minutes, then a 5-minute hold at 100% B; Flow: 20 mL/min. Fractions containing the desired product were combined and dried via centrifugal evaporation to afford the title compound as a mixture of diastereomers (7.5 mg, 0.014 mmol, 39% yield). LC-MS Anal. Calc'd for $C_{29}H_{36}F_3N_3O_3$ 531.271. found [M+H] 532.25, $T_r$=1.92 min (Method D).

Examples 112-113

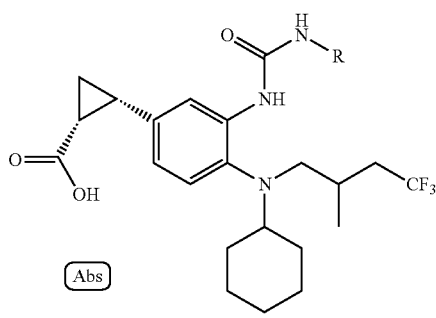

Examples 112-113 were obtained following the procedure of Preparation 111F utilizing the corresponding aniline followed by the saponification step described in Example 111, all isolated as a mixture of diastereomers

| Ex. No. | Name | R | $Tr^{method}_D$ (min) | (M + H)⁺ |
|---|---|---|---|---|
| 112 | (1R,2S)-2-(4-(cyclohexyl(4,4,4-trifluoro-2-methylbutyl)amino)-3-(3-(pyrimidin-5-yl)ureido)phenyl)cyclopropanecarboxylic acid | pyrimidin-5-yl | 1.78 | 520.0 |
| 113 | (1R,2S)-2-(4-(cyclohexyl(4,4,4-trifluoro-2-methylbutyl)amino)-3-(3-(5-methylisoxazol-3-yl)ureido)phenyl)cyclopropanecarboxylicacid | 5-methylisoxazol-3-yl | 2.02 | 523.15 |

Example 114

(1S,2R)-2-(4-(cyclohexyl(4,4,4-trifluoro-2-methylbutyl)amino)-3-(3-(p-tolyl)ureido)phenyl)cyclopropanecarboxylic acid, mixture of diastereomers

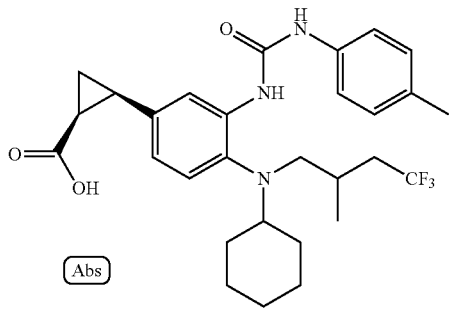 [SMILES: Cc1ccc(NC(=O)Nc2cc([C@@H]3C[C@@H]3C(=O)O)ccc2N(CC(C)CC(F)(F)F)C2CCCCC2)cc1]

Preparation 114A (1S,2R)-ethyl 2-(3-amino-4-(cyclohexyl(4,4,4-trifluoro-2-methylbutyl)amino)phenyl) cyclopropanecarboxylate (Mixture of Diastereomers)

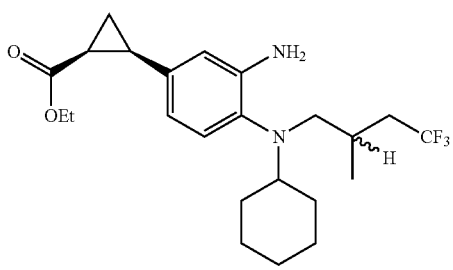 [SMILES: CCOC(=O)[C@H]1C[C@H]1c1ccc(N(CC(C)CC(F)(F)F)C2CCCCC2)c(N)c1]

Preparation 114A was prepared by the procedure described in Example 87F utilizing preparation 111D and (1R,2R)-ethyl 2-iodocyclopropanecarboxylate. Isolated as a mixture of diastereomers. LC-MS Anal. Calc'd for $C_{23}H_{33}F_3N_2O_2$ 426.25. found [M+H] 427.41, $T_r$=1.03 min. (Method D).

Preparation 114B (1S,2R)-ethyl 2-(4-(cyclohexyl(4,4,4-trifluoro-2-methylbutyl)amino)-3-(3-(p-tolyl)ureido)phenyl)cyclopropanecarboxylate (Mixture of Diastereomers)

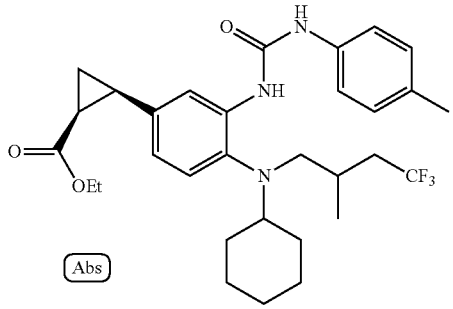

To a solution of Preparation 114A (30 mg, 0.070 mmol) in THF (1 mL) at RT was added 4-nitrophenyl carbonochloridate (14.89 mg, 0.074 mmol). The reaction was stirred at RT for 2 h, then p-toluidine (22.61 mg, 0.211 mmol) was added. The reaction was heated at 50° C. for 16 h, then cooled to RT and diluted with MeOH. The crude material was purified with prep HPLC (Waters Xbridge C18 19×100 mm), 20 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 220 to give Preparation 114B (20 mg, 0.036 mmol, 50.8% yield) as a mixture of diastereomers and as an off-white solid. LC-MS Anal. Calc'd for $C_{31}H_{40}F_3N_3O_3$ 559.30. found [M+H] 560.4, $T_r$=1.19 min (Method D).

Example 114

(1S,2R)-2-(4-(cyclohexyl(4,4,4-trifluoro-2-methyl-butyl)amino)-3-(3-(p-tolyl)ureido)phenyl)cyclopropanecarboxylic acid, (Mixture of Diastereomers)

To Preparation 114A (20 mg, 0.036 mmol) at RT was added MeOH (0.5 mL) and THF (0.2 mL), followed by a 1.3M LiOH solution (0.550 mL, 0.715 mmol). The mixture was stirred at 50° C. for 16 h, then cooled to RT. The mixture was adjusted to pH 1 with 1N HCl, then diluted with EtOAc. The organic phase was separated and washed with brine, dried over $MgSO_4$, filtered and concentrated to give the crude material. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 15 minutes, then a 5-minute hold at 100% B; Flow: 20 mL/min. Fractions containing the desired product were combined and dried via centrifugal evaporation to afford the title compound as a mixture of diastereomers (10 mg, 0.019 mmol, 53% yield). LC-MS Anal. Calc'd for $C_{29}H_{36}F_3N_3O_3$ 531.27. found [M+H] 532.25, $T_r$=1.92 min (Method D).

Examples 115-116

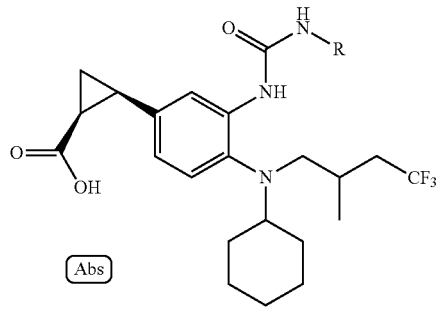

Examples 115-116 were obtained following the procedure of Preparation 114B utilizing the corresponding aniline followed by the saponification step described in Example 114, all isolated as a mixture of diastereomers

| Ex. No. | Name | R | $Tr^{Method\ M}$ (min) | $(M + H)^+$ |
|---|---|---|---|---|
| 115 | (1S,2R)-2-(4-(cyclohexyl(4,4,4-trifluoro-2-methylbutyl)amino)-3-(3-(pyrimidin-5-yl)ureido)phenyl)cyclopropanecarboxylic acid | pyrimidin-5-yl | 1.78 | 520.0 |
| 116 | (1S,2R)-2-(4-(cyclohexyl(4,4,4-trifluoro-2-methylbutyl)amino)-3-(3-(5-methylisoxazol-3-yl)ureido)phenyl)cyclopropanecarboxylic acid | 5-methylisoxazol-3-yl | 2.02 | 523.15 |

Example 117

(1R,2S)-2-(4-(diisobutylamino)-3-(2-(4-fluorophenyl)acetamido)phenyl)cyclopropanecarboxylic acid

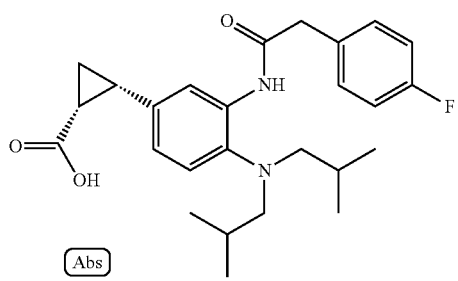 [SMILES: CC(C)CN(CC(C)C)c1ccc([C@H]2C[C@H]2C(=O)O)cc1NC(=O)Cc1ccc(F)cc1]

Example 117 was prepared following the procedure for Example 60 using the corresponding acid. LC-MS Anal. Calc'd for $C_{26}H_{33}FN_2O_3$ 440.25. found [M+H] 441.3, $T_r$=2.11 min (Method M). $^1$H NMR (500 MHz, DMSO-$d_6$) δ 8.74 (s, 1H), 8.16 (s, 1H), 7.36 (dd, J=8.4, 5.9 Hz, 2H), 7.23-7.06 (m, 3H), 6.89 (dd, J=8.4, 1.5 Hz, 1H), 3.72 (s, 2H), 2.02-1.91 (m, 1H), 1.53 (dt, J=13.4, 6.7 Hz, 2H), 1.41-1.33 (m, 1H), 1.24 (td, J=7.9, 4.5 Hz, 1H), 0.82-0.71 (m, 12H).

Example 118

(1R,2S)-2-(4-(diisobutylamino)-3-(2-(6-methylpyridin-3-yl)acetamido)phenyl)cyclopropanecarboxylic acid

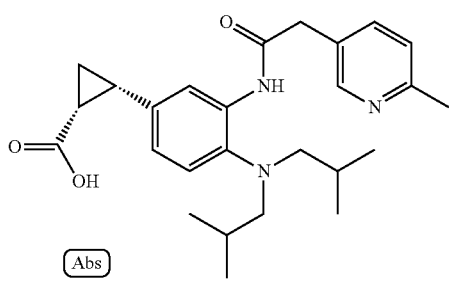 [SMILES: Cc1ccc(CC(=O)Nc2cc([C@H]3C[C@H]3C(=O)O)ccc2N(CC(C)C)CC(C)C)cn1]

Example 118 was prepared following the procedure for Example 60 using the corresponding acid. LC-MS Anal. Calc'd for $C_{26}H_{35}N_3O_3$ 437.27. found [M+H] 438.3, $T_r$=1.44 min (Method M). $^1$H NMR (500 MHz, DMSO-$d_6$) δ 8.81 (s, 1H), 8.43-8.30 (m, 1H), 8.13 (s, 1H), 7.62 (dd, J=7.9, 2.0 Hz, 1H), 7.23 (d, J=7.9 Hz, 1H), 7.17 (d, J=7.9 Hz, 1H), 6.98-6.87 (m, 1H), 3.72 (s, 2H), 2.46-2.36 (m, 3H), 2.02-1.91 (m, 1H), 1.54 (dt, J=13.4, 6.7 Hz, 2H), 1.41-1.31 (m, 1H), 1.24 (dt, J=8.1, 4.1 Hz, 1H), 0.89-0.75 (m, 13H).

Example 119

(1R,2S)-2-(3-(2-(4-chlorophenyl)acetamido)-4-(diisobutylamino)phenyl)cyclopropanecarboxylic acid

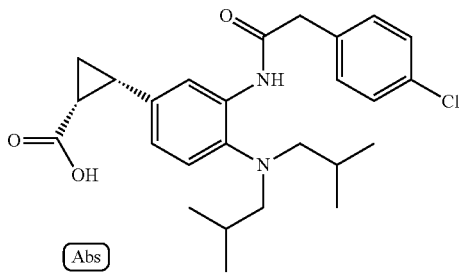 [SMILES: CC(C)CN(CC(C)C)c1ccc([C@H]2C[C@H]2C(=O)O)cc1NC(=O)Cc1ccc(Cl)cc1]

Example 119 was prepared following the procedure for Example 60 using the corresponding acid. LC-MS Anal. Calc'd for $C_{26}H_{33}ClN_2O_3$ 456.22. found [M+H] 457.3, $T_r$=2.25 min (Method M). $^1$H NMR (500 MHz, DMSO-$d_6$) δ 8.74 (s, 1H), 8.15 (s, 1H), 7.44-7.39 (m, 2H), 7.39-7.31 (m, 2H), 7.15 (d, J=7.9 Hz, 1H), 6.90 (dd, J=7.9, 1.5 Hz, 1H), 3.74 (s, 2H), 2.01-1.90 (m, 1H), 1.53 (dt, J=13.4, 6.7 Hz, 2H), 1.41-1.33 (m, 1H), 1.24 (dt, J=8.1, 4.1 Hz, 1H), 0.82-0.72 (m, 13H).

Example 120

(1R,2S)-2-(3-(2-(4-cyanophenyl)acetamido)-4-(diisobutylamino)phenyl)cyclopropanecarboxylic acid

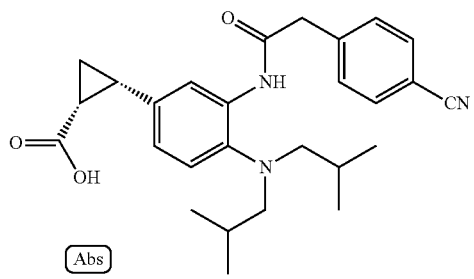 [SMILES: CC(C)CN(CC(C)C)c1ccc([C@H]2C[C@H]2C(=O)O)cc1NC(=O)Cc1ccc(C#N)cc1]

Example 120 was prepared following the procedure for Example 60 using the corresponding acid. LC-MS Anal. Calc'd for $C_{27}H_{33}N_3O_3$ 447.25. found [M+H] 448.3, $T_r$=1.97 min (Method M). $^1$H NMR (500 MHz, DMSO-$d_6$) δ 8.81 (s, 1H), 8.10 (s, 1H), 7.88-7.81 (m, J=7.9 Hz, 2H), 7.62-7.50 (m, J=8.4 Hz, 2H), 7.15 (d, J=7.9 Hz, 1H), 6.97-6.78 (m, 1H), 3.86 (s, 2H), 2.43 (d, J=8.4 Hz, 1H), 2.00-1.91 (m, 1H), 1.54 (dt, J=13.1, 6.8 Hz, 2H), 1.38-1.30 (m, 1H), 1.24-1.14 (m, 1H), 0.82-0.72 (m, 12H).

Example 121

(1R,2S)-2-(4-(diisobutylamino)-3-(2-(4-methoxyphenyl) acetamido)phenyl)cyclopropanecarboxylic acid

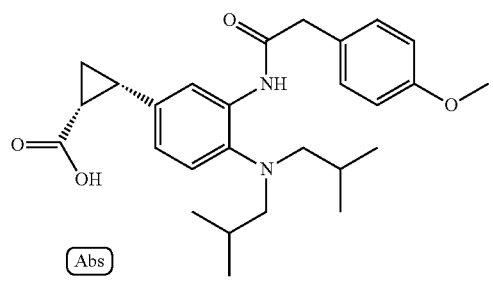 [SMILES: COc1ccc(CC(=O)Nc2cc([C@H]3C[C@H]3C(=O)O)ccc2N(CC(C)C)CC(C)C)cc1]

Example 121 was prepared following the procedure for Example 60 using the corresponding acid. LC-MS Anal. Calc'd for $C_{27}H_{36}N_2O_4$ 452.27. found [M+H] 453.3, $T_r$=2.05 min (Method M). $^1$H NMR (500 MHz, DMSO-$d_6$) δ 8.67 (s, 1H), 8.19 (s, 1H), 7.23 (d, J=8.9 Hz, 2H), 7.14 (d, J=8.4 Hz, 1H), 6.93-6.79 (m, 3H), 3.74 (s, 3H), 2.50-2.46 (m, 5H), 2.01-1.90 (m, 1H), 1.50 (dt, J=13.4, 6.7 Hz, 2H), 1.42-1.35 (m, 1H), 1.24 (td, J=8.2, 4.5 Hz, 1H), 0.78-0.71 (m, 12H).

Example 122

(1R,2S)-2-(4-(cyclohexyl(4,4,4-trifluoro-2-methylbutyl)amino)-3-(2-(p-tolyl)acetamido)phenyl)cyclopropanecarboxylic acid (Mixture of Diastereomers)

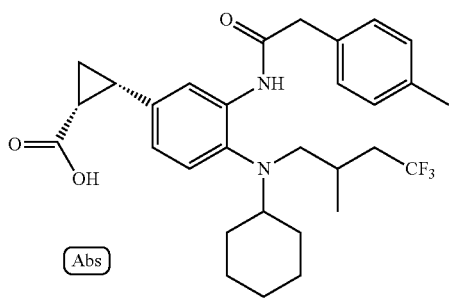 [SMILES: Cc1ccc(CC(=O)Nc2cc([C@H]3C[C@H]3C(=O)O)ccc2N(CC(C)CC(F)(F)F)C2CCCCC2)cc1]

Preparation 122A: (1R,2S)-ethyl 2-(4-(cyclohexyl(4,4,4-trifluoro-2-methylbutyl)amino)-3-(2-(p-tolyl)acetamido)phenyl)cyclopropanecarboxylate, (Mixture of Diastereomers)

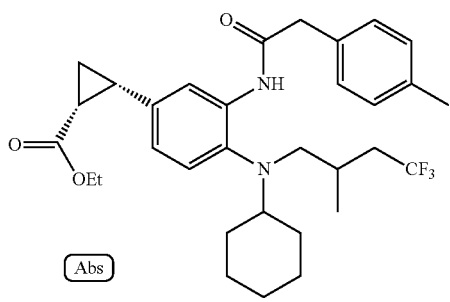 [SMILES: CCOC(=O)[C@@H]1C[C@@H]1c1ccc(N(CC(C)CC(F)(F)F)C2CCCCC2)c(NC(=O)Cc2ccc(C)cc2)c1]

To a solution of Preparation 111E (30 mg, 0.070 mmol) in DMF (1 mL) at RT was added 2-(p-tolyl)acetic acid (21.13 mg, 0.141 mmol), EDC (27.0 mg, 0.141 mmol), 1-Hydroxybenzotriazole hydrate (21.54 mg, 0.141 mmol) and Hunig's Base (0.025 mL, 0.141 mmol). The reaction was stirred at RT for 16 h, then diluted with MeOH and the crude material was purified by preparative HPLC (Waters Xbridge C18 19×100 mm), 20 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 220 to give Preparation 122A as a mixture of diastereomers (20 mg, 0.036 mmol, 50.9% yield) as an off-white solid. LC-MS Anal. Calc'd for $C_{32}H_{41}F_3N_2O_3$ 558.31. found [M+H] 559.4, $T_r$=1.28 min (Method D).

Example 122

(1R,2S)-2-(4-(cyclohexyl(4,4,4-trifluoro-2-methylbutyl)amino)-3-(2-(p-tolyl)acetamido)phenyl)cyclopropanecarboxylic acid (Mixture of Diastereomers)

To Preparation 122A (20 mg, 0.036 mmol) at RT was added MeOH (0.5 mL) and THF (0.2 mL), followed by 1.3M LiOH solution (0.550 mL, 0.715 mmol). The mixture was stirred at 50° C. for 16 h, then cooled to RT. The mixture was adjusted to pH 1 with 1N HCl, then diluted with EtOAc. The organic phase was separated and washed with brine, dried over MgSO₄, filtered and concentrated to give the crude material. The crude material was purified via preparative LC/MS with the following conditions: Column: Waters XBridge Shield RP18, 19×250 mm, 5-um particles; Guard Column: Waters XBridge C18, 19×10 mm, 5-um particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation to afford the title compound as a mixture of diastereomers (11.8 mg, 0.022 mmol, 62%). LC-MS Anal. Calc'd for $C_{30}H_{37}F_3N_2O_3$ 530.28. found [M+H] 531.2, $T_r$=2.47 min (Method M). ¹H NMR (500 MHz, METHANOL-d₄) δ 8.46-8.29 (m, 1H), 7.21 (s, 3H), 7.03 (d, J=7.9 Hz, 1H), 6.98-6.87 (m, 1H), 3.72 (s, 1H), 3.39-3.24 (m, 3H), 2.57 (q, J=8.4 Hz, 1H), 2.36 (s, 2H), 2.19 (t, J=11.1 Hz, 1H), 2.09-1.98 (m, 1H), 1.64-1.57 (m, 2H), 1.54 (br. s., 1H), 1.45 (br. s., 1H), 1.34 (td, J=8.2, 5.0 Hz, 1H), 1.04-0.91 (m, 3H), 0.91-0.76 (m, 4H).

Example 123

(1S,2R)-2-(4-(cyclohexyl(4,4,4-trifluoro-2-methylbutyl)amino)-3-(2-(p-tolyl)acetamido)phenyl)cyclopropanecarboxylic acid, mixture of diastereomers

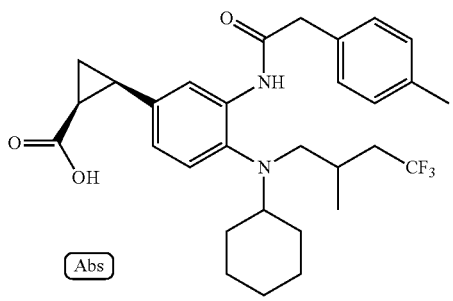 [SMILES: CCOC(=O)[C@H]1C[C@H]1c1ccc(N(CC(C)CC(F)(F)F)C2CCCCC2)c(NC(=O)Cc2ccc(C)cc2)c1]

Preparation 123A: (1S,2R)-ethyl 2-(4-(cyclohexyl(4,4,4-trifluoro-2-methylbutyl)amino)-3-(2-(p-tolyl)acetamido)phenyl)cyclopropanecarboxylate, (Mixture of Diastereomers)

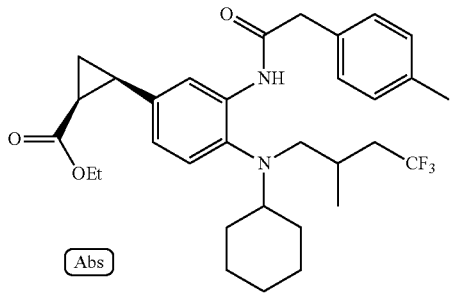

To a solution of Preparation 114A (30 mg, 0.070 mmol) in DMF (1 mL) at RT was added 2-(p-tolyl)acetic acid (21.13 mg, 0.141 mmol), EDC (27.0 mg, 0.141 mmol), 1-Hydroxybenzotriazole hydrate (21.54 mg, 0.141 mmol) and Hunig's Base (0.025 mL, 0.141 mmol). The reaction was stirred at RT for 16 h, then diluted with MeOH and the crude material was purified by preparative HPLC (Waters Xbridge C18 19×100 mm), 20 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 220 to give Preparation 123A as a mixture of diastereomers (16 mg, 0.029 mmol, 40.7% yield) as an off-white solid. LC-MS Anal. Calc'd for $C_{32}H_{41}F_3N_2O_3$ 558.31. found [M+H] 559.4, $T_r$=1.28 min (Method M).

Example 123

(1S,2R)-2-(4-(cyclohexyl(4,4,4-trifluoro-2-methylbutyl)amino)-3-(2-(p-tolyl)acetamido)phenyl)cyclopropanecarboxylic acid To Preparation 123A (20 mg, 0.036 mmol) at RT was added MeOH (0.5 mL) and THF (0.2 mL), followed by a 1.3M LiOH solution (0.550 mL, 0.715 mmol). The mixture was stirred at 50° C. for 16 h, then cooled to RT. The mixture was adjusted to pH 1 with 1N HCl, then diluted with EtOAc. The organic phase was separated and washed with brine, dried over $MgSO_4$, filtered and concentrated to give the crude material. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 5-minute hold at 100% B; Flow: 20 mL/min. Fractions containing the desired product were combined and dried via centrifugal evaporation to afford the title compound as a mixture of diastereomers (7.9 mg, 0.015 mmol, 41% yield). LC-MS Anal. Calc'd for $C_{30}H_{37}F_3N_2O_3$ 530.28. found [M+H] 531.2, $T_r$=2.47 min (Method M). $^1$H NMR (500 MHz, METHANOL-$d_4$) δ 8.46-8.29 (m, 1H), 7.21 (s, 3H), 7.03 (d, J=7.9 Hz, 1H), 6.98-6.87 (m, 1H), 3.72 (s, 1H), 3.39-3.24 (m, 3H), 2.57 (q, J=8.4 Hz, 1H), 2.36 (s, 2H), 2.19 (t, J=11.1 Hz, 1H), 2.09-1.98 (m, 1H), 1.64-1.57 (m, 2H), 1.54 (br. s., 1H), 1.45 (br. s., 1H), 1.34 (td, J=8.2, 5.0 Hz, 1H), 1.04-0.91 (m, 3H), 0.91-0.76 (m, 4H).

Example 124

2-(4-(diisobutylamino)-3-(3-o-tolylureido)phenyl) cyclopropanecarboxylic acid

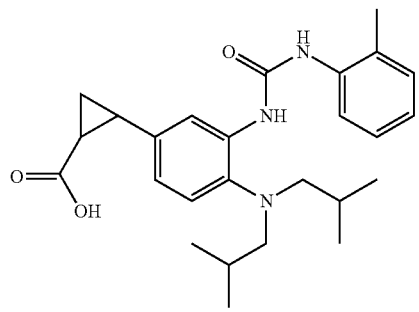 [SMILES: Cc1ccccc1NC(=O)Nc1cc(C2CC2C(=O)O)ccc1N(CC(C)C)CC(C)C]

124A. Ethyl 2-(4-(diisobutylamino)-3-(3-o-tolylureido)phenyl) cyclopropanecarboxylate A round bottom flask was charged with 1D (30.2 mg, 0.091 mmol) in THF (454 μl). 1-isocyanato-2-methylbenzene (18.14 mg, 0.136 mmol) was added and the reaction mixture was stirred at rt for 60 min. Excess THF was removed in vacuo. The crude product was used as is in the next reaction. LC-MS Anal. Calc'd for $C_{28}H_{39}N_3O_3$ 465.63. found [M+H] 466.3. $T_r$=1.04 min (Method D).

Example 124

2-(4-(diisobutylamino)-3-(3-o-tolylureido)phenyl) cyclopropanecarboxylic acid

To a round bottom flask charged with 124A (42.4 mg, 0.091 mmol) was added THF (1083 μl). A solution of lithium hydroxide (10.90 mg, 0.455 mmol) in water (1084 μl, 60.2 mmol) was added. The reaction mixture was stirred at rt overnight and heated at 50° C. for 3 h. Ethanol (1 mL) and 1 N NaOH (1 mL) was added. After heating at 50° C. overnight, ethanol and THF were removed in vacuo. 1N aqueous HCl was added and the solid product was collected by filtration. The crude solid was purified by preparative HPLC to give example 124 (6.6 mg, 0.015 mmol, 16%) LC-MS Anal. Calc'd for $C_{26}H_{35}N_3O_3$ 437.57. found [M+H] 438.0. $T_r$=2.20 min (Method L). $^1$H NMR (500 MHz, METHANOL-$d_4$) δ ppm 7.95 (1H, br. s.), 7.35 (1H, d, J=5.95 Hz), 7.20 (1H, d, J=7.43 Hz), 7.17 (1H, t, J=7.43 Hz), 7.08-7.13 (1H, m), 7.01 (1H, d, J=7.93 Hz), 6.88 (1H, d, J=7.43 Hz), 2.53-2.59 (1H, m), 2.46-2.53 (4H, m), 2.03 (1H, d, J=5.45 Hz), 1.53-1.65 (3H, m), 1.31 (1H, d, J=3.47 Hz), 0.75 (12H, d, J=5.94 Hz)

Example 125

(1S,2R)-2-(4-(diisobutylamino)-3-(3-(p-tolyl)ureido)phenyl)-N-(methylsulfonyl)cyclopropanecarboxamide

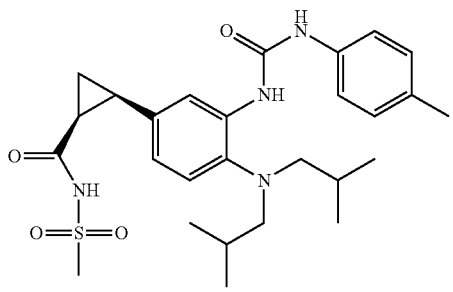 [SMILES: Cc1ccc(NC(=O)Nc2cc([C@@H]3C[C@@H]3C(=O)NS(C)(=O)=O)ccc2N(CC(C)C)CC(C)C)cc1]

To a solution of example 1, enantiomer 2 (20 mg, 0.046 mmol) in DMF (1 mL) was added DMAP (41.9 mg, 0.343 mmol), then EDC (88 mg, 0.457 mmol) and methanesulfonamide (65.2 mg, 0.686 mmol). The mixture was stirred at room temperature for 18 h. The reaction was filtered and purified via preparative LC/MS: Column: Waters XBridge C18, 19×150 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 15 minutes, then a 5-minute hold at 100% B; Flow: 20 mL/min. Fractions containing the desired product were combined and dried via centrifugal evaporation to gave the title compound (1 mg, 1.943 μmol, 4.25% yield). LC-MS Anal. Calc'd for $C_{27}H_{38}N_4O_4S$ 514.26. found [M+H] 515.4, $T_r$=0.98 min (Method B). $^1$H NMR (500 MHz, METHANOL-$d_4$) δ 7.85 (d, J=2.0 Hz, 1H), 7.29 (d, J=7.9 Hz, 2H), 7.12 (d, J=7.9 Hz, 2H), 7.05 (d, J=8.4 Hz, 1H), 6.89 (d, J=1.5 Hz, 1H), 2.69 (s, 3H), 2.57 (d, J=7.4 Hz, 5H), 2.31 (s, 3H), 2.19-2.05 (m, 1H), 1.85-1.74 (m, 1H), 1.69-1.55 (m, 2H), 1.34-1.20 (m, 1H), 0.82 (dd, J=6.7, 1.7 Hz, 12H).

Example 126

(1S,2R)—N-(cyclopropylsulfonyl)-2-(4-(diisobutylamino)-3-(3-(p-tolyl)ureido)phenyl)cyclopropanecarboxamide

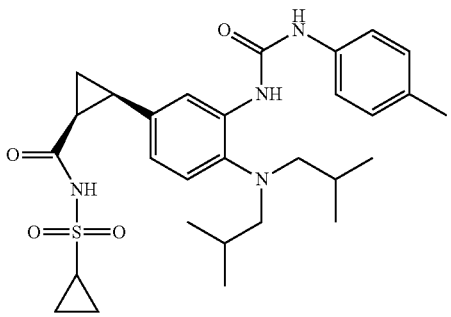 [SMILES: Cc1ccc(NC(=O)Nc2cc([C@@H]3C[C@@H]3C(=O)NS(=O)(=O)C3CC3)ccc2N(CC(C)C)CC(C)C)cc1]

Example 126 was prepared following the procedure for Example 125 using the corresponding sulfonyl chloride. LC-MS Anal. Calc'd for $C_{29}H_{40}N_4O_4S$ 540.27. found [M+H] 541.1, $T_r$=1.00 min (Method B). $^1$H NMR (500 MHz, METHANOL-$d_4$) δ 7.92-7.87 (m, 1H), 7.30 (d, J=8.4 Hz, 2H), 7.12 (d, J=7.9 Hz, 2H), 7.05 (s, 1H), 6.92-6.85 (m, 1H), 2.66-2.61 (m, 1H), 2.58 (d, J=7.4 Hz, 4H), 2.50-2.42 (m, 1H), 2.31 (s, 3H), 2.18-2.09 (m, 1H), 1.83-1.74 (m, 1H), 1.68-1.55 (m, 2H), 1.37-1.27 (m, 1H), 1.21-1.12 (m, 1H), 1.01-0.92 (m, 1H), 0.83 (dd, J=6.7, 1.2 Hz, 12H), 0.79-0.73 (m, 1H), 0.72-0.62 (m, 1H).

Example 127

(1S,2R)-2-(4-((S)-1-phenylpropoxy)-3-(3-(p-tolyl)ureido) phenyl)cyclopropanecarboxylic acid

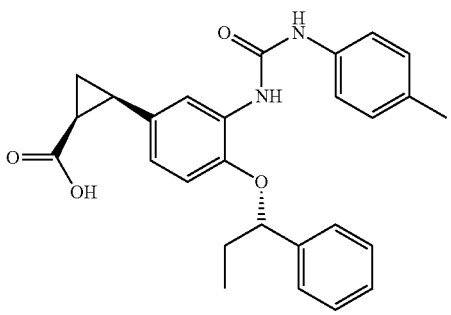

Examples 127 was prepared following the procedure for Example 47 using chiral SFC (Method H), analytical chiral HPLC $T_r$=11.344 min (Method J). LC-MS Anal. Calc'd for $C_{27}H_{28}N_2O_4$ 444.20. found [M+H] 445.22, $T_r$=3.59 min (Method A). $^1$H NMR (400 MHz, CHLOROFORM-d) δ 8.19 (br. s., 1H), 7.94 (br. s., 1H), 7.49 (s, 1H), 7.34-7.24 (m, 3H), 7.19-7.07 (m, 4H), 7.00 (d, J=8.1 Hz, 2H), 6.75 (d, J=8.1 Hz, 1H), 6.51 (d, J=8.4 Hz, 1H), 4.91 (t, J=6.3 Hz, 1H), 2.49 (q, J=8.3 Hz, 1H), 2.34 (s, 3H), 2.11 (d, J=7.0 Hz, 1H), 1.82-1.65 (m, 2H), 1.50 (q, J=5.6 Hz, 1H), 1.30-1.20 (m, 1H), 0.74 (t, J=7.4 Hz, 3H).

Example 128

(1R,2S)-2-(4-((R)-1-phenylpropoxy)-3-(3-(p-tolyl)ureido) phenyl)cyclopropanecarboxylic acid

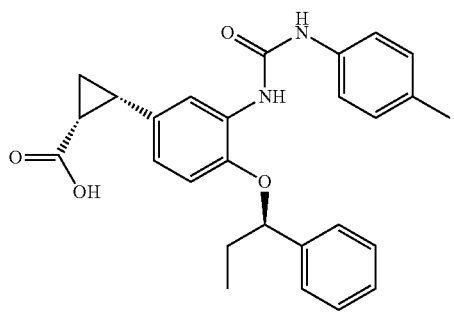 [SMILES: CC[C@@H](Oc1ccc([C@H]2C[C@H]2C(=O)O)cc1NC(=O)Nc1ccc(C)cc1)c1ccccc1]

Example 128 was prepared following the procedure for Example 47 using chiral SFC (Method H), analytical chiral HPLC $T_r$=15.532 min (Method J) LC-MS Anal. Calc'd for $C_{27}H_{28}N_2O_4$ 444.20. found [M+H] 445.23, $T_r$=3.60 min (Method A). $^1$H NMR (400 MHz, CHLOROFORM-d) δ 8.09 (br. s., 1H), 7.66 (br. s., 1H), 7.41 (br. s., 1H), 7.26-7.19 (m, 2H), 7.16-7.02 (m, 6H), 6.76 (d, J=8.1 Hz, 1H), 6.52 (d, J=8.4 Hz, 1H), 4.91 (t, J=6.3 Hz, 1H), 2.47 (q, J=8.1 Hz, 1H), 2.30 (s, 3H), 2.06 (d, J=5.1 Hz, 1H), 1.74 (qt, J=13.8, 6.8 Hz, 2H), 1.51 (d, J=5.9 Hz, 1H), 1.31-1.16 (m, 1H), 0.76 (t, J=7.4 Hz, 3H).

Example 129

(1R,2S)-2-(4-(cyclohexyl(isobutyl)amino)-3-(3-(3-methylisoxazol-5-yl)ureido)phenyl)cyclopropanecarboxylic acid

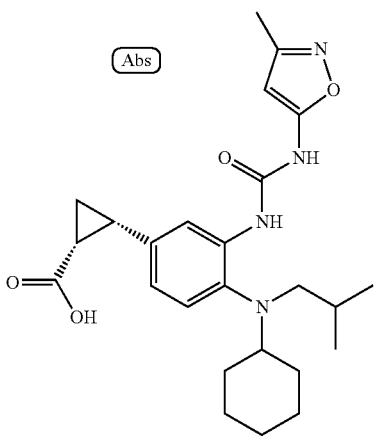 [SMILES: Cc1cc(NC(=O)Nc2cc([C@H]3C[C@H]3C(=O)O)ccc2N(CC(C)C)C2CCCCC2)on1]

To a solution of triphosgene (74.5 mg, 0.251 mmol) in THF (2 mL) was added 3-methylisoxazol-5-amine (61.6 mg, 0.628 mmol) and Hunig's Base (0.219 mL, 1.255 mmol). After stirring for 1 h, 80E (45 mg, 0.126 mmol) in THF (2.000 mL) was added. The resulting solution was stirred at rt for 1 h, then heated at 60° C. for 1.5 h. After removing solvent in vacuo purification of the crude via silica gel chromatography (0-70% EtOAc in Hexanes, 12 g) gave 40 mg ester. This was dissolved in THF (1 mL), then sodium hydroxide (0.377 mL, 0.377 mmol) was added. A precipitate formed, then MeOH (~1 mL) was added. Most of the MeOH and THF was then removed in vacuo and the crude material was diluted with 2 mL of water. The pH was adjusted to ~4 using 1N HCl. The aqueous phase was then extracted with EtOAc (3×10 mL) and the combined organic phase was washed with brine, dried with $Na_2SO_4$, filtered and concentrated. Purification via preparative HPLC gave the title compound (30 mg, 0.066 mmol, 52.6% yield) as a white solid. LC-MS Anal. Calc'd for $C_{25}H_{34}N_4O_4$ 454.26. found [M+H] 455.19, $T_r$=3.24 min (Method A). $^1$H NMR (500 MHz, DMSO-$d_6$) δ 8.47 (d, J=2.0 Hz, 1H), 7.89-7.80 (m, 2H), 7.15 (dd, J=14.9, 8.4 Hz, 2H), 6.85 (dd, J=7.9, 2.0 Hz, 1H), 3.11-3.03 (m, 1H), 2.63 (d, J=6.9 Hz, 4H), 2.48-2.41 (m, 2H), 2.40 (s, 3H), 1.62 (dquin, J=13.4, 6.7 Hz, 2H), 1.19 (d, J=6.9 Hz, 3H), 0.85 (d, J=6.4 Hz, 12H).

Example 130

Racemic (1S,2R)-2-(4-(diisobutylamino)-3-(3-p-tolylureido)phenyl)cyclopentanecarboxylic acid

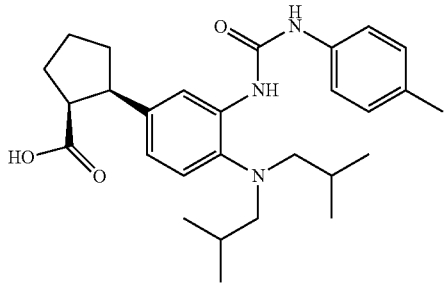 [SMILES: Cc1ccc(NC(=O)Nc2cc([C@@H]3CCC[C@@H]3C(=O)O)ccc2N(CC(C)C)CC(C)C)cc1]

130A: methyl 2-(4-(diisobutylamino)-3-(3-p-tolylureido)phenyl)cyclopent-1-enecarboxylate To a stirring solution of methyl cyclopent-1-enecarboxylate (9.63 mg, 0.076 mmol), 1-(5-bromo-2-(diisobutylamino)phenyl)-3-p-tolylurea (30 mg, 0.069 mmol), palladium(II) acetate (0.467 mg, 2.081 μmol), and tri-o-tolylphosphine (2.112 mg, 6.94 μmol) in DMF (Volume: 2 mL) at was degassed 3× via a freeze pump thaw process under an atmosphere of nitrogen. At this point TEA (0.015 mL, 0.104 mmol) was added and the reaction was heated to 100° C. for 24 hours. The mixture was then cooled to RT and concentrated in vacuo. Purification by preparative HPLC gave title compound (5.6 mg, 0.012 mmol, 16.6% yield) as a white solid. LC-MS Anal. Calc'd for $C_{29}H_{39}N_3O_3$ 477.64. found [M+H] 478.3, $T_r$=2.32 min (Method E).

Example 130

Racemic (1S,2R)-2-(4-(diisobutylamino)-3-(3-p-tolylureido)phenyl)cyclopentanecarboxylic acid To a stirring solution °Pd/C (1.969 mg, 0.019 mmol) and methyl 2-(4-(diisobutylamino)-3-(3-p-tolylureido)phenyl) cyclopent-1-enecarboxylate (0.088 g, 0.185 mmol) in DCM (1 mL) and MeOH (1.000 mL) at rt was added a ballon of hydrogen gas. The system was allowed to stir at room temperature for 2 hours. The mixture was then purged with $N_2$ and filtered thru celite. Concentration in vacuo afforded the saturated intermediate. The crude material was taken on without purification. The crude material was dissolved in tetrahydrofuran (2 mL) and MeOH (0.400 mL) at rt and sodium hydroxide (4.00 mg, 0.100 mmol) was added. The system was sealed and purged with N2 and heated to 60° C. for 16 hours. The mixture was then cooled to RT, neutralized with 1 N HCl and extracted thrice with EtOAc. The combined organics were dried over MgSO4, filtered and concentrated in vacuo. Purification by preparative HPLC afforded the title compound (4.8 mg, 0.002 mmol, 10% yield) as a white solid. LC-MS Anal. Calc'd for $C_{28}H_{39}N_3O_3$ 465.6. found [M+H] 466.0, $T_r$=3.040 min (Method E).

Evaluation of Biological Activity

Exemplary compounds were tested for inhibition of IDO activity. Experimental procedures and results are provided below.

IDO Kynurenine Assay with Human IDO1/HEK293 Cells

Human IDO1/HEK293 cells were seeded at 10,000 cells per 50 uL per well with RPMI/phenol red free media contains 10% FBS in a 384-well black wall clear bottom tissue culture plate (Matrix Technologies LLC) 125 nL of certain concentration of compound was then added to each well using ECHO liquid handling systems. The cells were incubated for 20 hours in 37° C. incubator with 5% $CO_2$.

The compound treatments were stopped by adding Trichloroacetic Acid (Sigma-Aldrich) to a final concentration at 0.2%. The cell plate was further incubated at 50° C. for 30 minute. The equal volume supernatant (20 uL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Results of the IDO assays are shown in the table below. HEK Human IDO-1

| Example # | HEK Human IDO-1 $IC_{50}$ (nM) |
|---|---|
| 1J | 8 |
| ent-1J | 2 |
| 5 | 941 |
| 6 | 148 |
| 9 | 97 |
| 14 | 86 |
| 15 | 541 |
| 19 | 442 |
| 20 | 61 |
| 30 | 6 |
| 31 | 4 |
| 34 | 2 |
| 36 | 7 |
| 37 | 7 |

-continued

| Example # | HEK Human IDO-1 IC$_{50}$ (nM) |
|---|---|
| 43 | 88 |
| 60 | 21 |
| 63 | 262 |
| 67 | 23 |
| 71 | 519 |
| 72 | 200 |
| 73 | 527 |
| 75 | 787 |
| 76 | 338 |
| 77 | 64 |
| 87 | 994 |
| 117 | 97 |
| 118 | 126 |
| 129 | 0.5 |

What is claimed is:
1. A compound of formula (I)

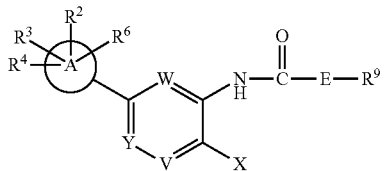

where
X is

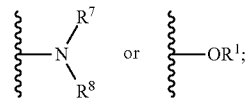

E is NH or CH$_2$;
W is CR$^{10}$;
Y is CR$^{11}$;
V is CR$^{12}$;

is C$_3$-C$_8$ cycloalkyl;
R$^1$ is C$_1$-C$_{10}$ alkyl optionally substituted with halo or phenyl wherein said phenyl may be optionally substituted with halo;
R$^2$ is COOH, heteroaryl or CONHSO$_2$R$^{14}$;
R$^3$ is H, C$_1$-C$_{10}$ alkyl or halo;
R$^4$ is H, C$_1$-C$_{10}$ alkyl, or halo;
R$^6$ is H;
R$^7$ and R$^8$ are independently selected from the group consisting of C$_1$-C$_{10}$ alkyl optionally substituted with halo or phenyl, wherein said phenyl may be optionally substituted with halo, C$_1$-C$_{10}$ alkoxy, C$_1$-C$_{10}$-alkoxy-C$_1$-C$_{10}$-alkyl, C$_3$-C$_8$ cycloalkyl, aryl optionally substituted with halo;
R$^9$ is aryl, C$_1$-C$_{10}$ alkylaryl, C$_3$-C$_8$ cycloalkylaryl, C$_1$-C$_{10}$ alkoxyaryl, C$_1$-C$_{10}$ alkyl heteroaryl, heteroaryl, or

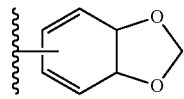

wherein R$^9$ may be substituted with at least one alkyl, halo, alkoxy, CN, or haloalkyloxy;
R$^{10}$ is H or halo;
R$^{11}$ is H or halo; and
R$^{12}$ is H, C$_1$-C$_{10}$ alkyl, or C$_2$-C$_{10}$ alkenyl;
R$^{14}$ is CF$_3$, C$_3$-C$_8$ cycloalkyl or C$_1$-C$_{10}$ alkyl;
and/or a stereoisomer, tautomer or a pharmaceutically acceptable salt thereof.

2. The compound according to claim 1 wherein

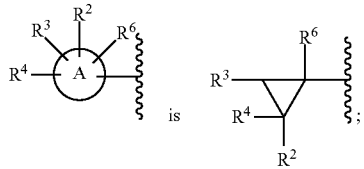

X is NR$^7$R$^8$;
E is NH;
R$^2$ is COOH,

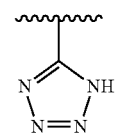

or CONHSO$_2$R$^{14}$;
R$^3$ is H or C$_1$-C$_6$ alkyl;
R$^4$ is H, C$_1$-C$_6$ alkyl, or halo;
R$^6$ is H;
R$^7$ and R$^8$ are independently selected from C$_1$-C$_6$ alkyl, C$_1$-C$_6$ alkoxy, C$_3$-C$_8$ cycloalkyl, or C$_1$-C$_6$-alkoxy-C$_1$-C$_6$-alkyl;
R$^{10}$ is H;
R$^{11}$ is halo or H; and
R$^{12}$ is H;
R$^{14}$ is CF$_3$ C$_3$-C$_6$ cycloalkyl or C$_1$-C$_6$ alkyl;
and/or a stereoisomer, tautomer or a pharmaceutically acceptable salt thereof.

3. The compound according to claim 1 wherein

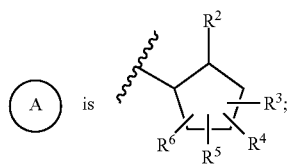

E is NH;
X is

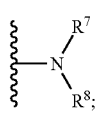

$R^2$ is COOH;
$R^3$, $R^4$, $R^5$ and $R^6$ are H;
$R^7$ and $R^8$ are independently selected from $C_1$-$C_{10}$ alkyl;
$R^9$ is $C_1$-$C_{10}$ alkylaryl;
and/or a stereoisomer, tautomer or a pharmaceutically acceptable salt thereof.

4. The compound according to claim 3 wherein $R^7$ and $R^8$ are each

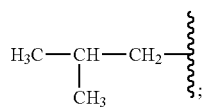

and
$R^9$ is

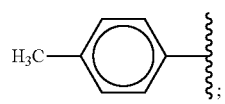

and/or a stereoisomer, tautomer or a pharmaceutically acceptable salt thereof.

5. The compound according to claim 1 wherein

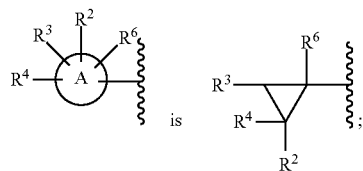

X is $OR^1$;
E is NH;
$R^2$ is COOH,

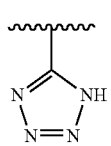

or —$CONHSO_2R^{14}$;
$R^3$, $R^4$, $R^5$ and $R^6$ are H;
$R^1$ is aryl-$C_1$-$C_6$-alkyl or $C_1$-$C_6$ alkyl wherein $R^1$ may be optionally substituted with halo;
$R^9$ is aryl or $C_1$-$C_6$ alkylaryl wherein $R^9$ may be substituted with at least one alkyl, halo, alkoxy, CN, or haloalkyloxy;
$R^{12}$ is H, $C_1$-$C_6$ alkyl, $C_2$-$C_6$ alkenyl, or halo;
and/or a stereoisomer, tautomer or a pharmaceutically acceptable salt thereof.

6. The compound according to claim 1 wherein E is $CH_2$;

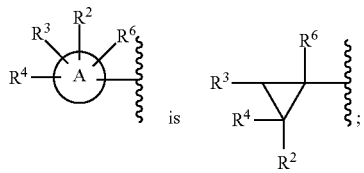

X is —$NR^7R^8$;
$R^2$ is COOH; and
$R^7$ and $R^8$ are independently selected from $C_1$-$C_6$ alkyl;
and/or a stereoisomer, tautomer or a pharmaceutically acceptable salt thereof.

7. The compound according to claim 6 wherein
$R^2$ is COOH;
$R^7$ and $R^8$ are each

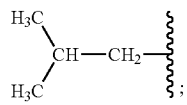

and
$R^9$ is

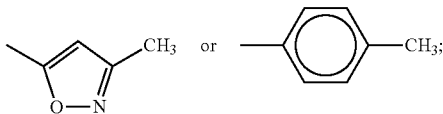

and/or a stereoisomer, tautomer or a pharmaceutically acceptable salt thereof.

8. The compound according to claim 1 wherein the $IC_{50}$ in the HEK Human IDO-1 assay is <10 nM.

9. A pharmaceutical composition comprising one or more compounds according to claim 1 and a pharmaceutically acceptable carrier or diluent.

10. A method of inhibiting the activity of indoleamine 2,3-dioxygenase comprising contacting said indoleamine 2,3-dioxygenase with a compound according to claim 1, or a pharmaceutically acceptable salt thereof.

11. The compound of claim 1, or a pharmaceutically acceptable salt thereof, selected from the group consisting of:
(1R,2S)-2-(4-(cyclohexyl(4,4,4-trifluoro-2-methylbutyl) amino)-3-(2-(p-tolypacetamido)phenyl)cyclopropanecarboxylic acid;
(1S,2R)-2-(4-(cyclohexyl(4,4,4-trifluoro-2-methylbutyl) amino)-3-(2-(p-tolypacetamido)phenyl)cyclopropanecarboxylic acid, mixture of diastereomers;
2-(4-(diisobutylamino)-3-(3-o-tolylureido)phenyl) cyclopropanecarboxylic acid;
(1S,2R)-2-(4-(diisobutylamino)-3-(3-(p-tolyl)ureido)phenyl)-N-(methylsulfonyl)cyclopropanecarboxamide;
(1S,2R)—N-(cyclopropylsulfonyl)-2-(4-(diisobutylamino)-3-(3-(p-tolyl)ureido)phenyl)cyclopropanecarboxamide;
(1S,2R)-2-(4-((S)-1-phenylpropoxy)-3-(3-(p-tolyl) ureido) phenyl)cyclopropanecarboxylic acid;
(1R,2S)-2-(4-((R)-1-phenylpropoxy)-3-(3-(p-tolyl) ureido) phenyl)cyclopropanecarboxylic acid;

(1R,2S)-2-(4-(cyclohexyl(isobutyl)amino)-3-(3-(3-methylisoxazol-5-yl)ureido)phenyl)cyclopropanecarboxylic acid; and (1S,2R)-2-(4-(diisobutylamino)-3-(3-p-tolylureido)phenyl)cyclopentanecarboxylic acid.

* * * * *

UNITED STATES PATENT AND TRADEMARK OFFICE
CERTIFICATE OF CORRECTION

PATENT NO. : 9,675,571 B2
APPLICATION NO. : 14/776035
DATED : June 13, 2017
INVENTOR(S) : James Aaron Balog et al.

It is certified that error appears in the above-identified patent and that said Letters Patent is hereby corrected as shown below:

In the Claims

Claim 1, Column 147, Line 56 (approx.), delete "$CONHSO_2R^{14}$;" and insert -- —$CONHSO_2R^{14}$; --, therefor.

Claim 1, Column 147, Line 65, delete "halo;" and insert -- halo; and --, therefor.

Claim 3, Column 148, Line 42 (approx.), delete "$CONHSO_2R^{14}$;" and insert -- —$CONHSO_2R^{14}$; --, therefor.

Claim 3, Column 148, Line 54, delete "$CF_3$" and insert -- $CF_3$, --, therefor.

Claim 20, Column 150, Line 52, delete "(p-tolypacetamido)" and insert -- (p-tolyl)acetamido) --, therefor.

Claim 20, Column 150, Line 55, delete "(p-tolypacetamido)" and insert -- (p-tolyl)acetamido) --, therefor.

Claim 20, Column 150, Line 61, delete "(1S,2R)—N-" and insert -- (1S,2R)-N- --, therefor.

Signed and Sealed this
Twenty-third Day of January, 2018

Joseph Matal
*Performing the Functions and Duties of the
Under Secretary of Commerce for Intellectual Property and
Director of the United States Patent and Trademark Office*